United States Patent
Shiraishi et al.

(10) Patent No.: US 12,121,991 B2
(45) Date of Patent: Oct. 22, 2024

(54) PROCESSING APPARATUS, AND MANUFACTURING METHOD OF MOVABLE BODY

(71) Applicant: NIKON CORPORATION, Tokyo (JP)

(72) Inventors: Masayuki Shiraishi, Kumagaya (JP); Shigeki Egami, Tokyo (JP); Yoshio Kawabe, Kumagaya (JP); Yosuke Tatsuzaki, Kumagaya (JP); Yuichi Shibazaki, Kumagaya (JP)

(73) Assignee: NIKON CORPORATION, Tokyo (JP)

(*) Notice: Subject to any disclaimer, the term of this patent is extended or adjusted under 35 U.S.C. 154(b) by 1074 days.

(21) Appl. No.: 16/756,604

(22) PCT Filed: Oct. 25, 2017

(86) PCT No.: PCT/JP2017/038563
§ 371 (c)(1),
(2) Date: Jul. 1, 2020

(87) PCT Pub. No.: WO2019/082313
PCT Pub. Date: May 2, 2019

(65) Prior Publication Data
US 2020/0353560 A1    Nov. 12, 2020

(51) Int. Cl.
*B23K 26/04* (2014.01)

(52) U.S. Cl.
CPC .................. *B23K 26/04* (2013.01)

(58) Field of Classification Search
CPC ............... B23K 26/04; B23K 26/0643; B23K 26/0673; B23K 26/032; B23K 2103/50; B23K 2103/32; A61B 5/1077; A61B 2090/06
See application file for complete search history.

(56) References Cited

U.S. PATENT DOCUMENTS

| | | | |
|---|---|---|---|
| 4,994,639 A | 2/1991 | Dickinson et al. | |
| 10,112,257 B1 | 10/2018 | Thomas et al. | |
| 2004/0061149 A1 | 4/2004 | Uyumonji et al. | |
| 2009/0007933 A1 | 1/2009 | Thomas et al. | |
| 2012/0314224 A1* | 12/2012 | Luellau ............... | A61B 5/1077 356/601 |
| 2013/0337187 A1 | 12/2013 | Reh et al. | |
| 2014/0242285 A1 | 8/2014 | Pettersson et al. | |

(Continued)

FOREIGN PATENT DOCUMENTS

| | | |
|---|---|---|
| JP | S59-87993 A | 5/1984 |
| JP | S63-108981 A | 5/1988 |

(Continued)

OTHER PUBLICATIONS

Machine Translation of Yamaoka (JP 2008119718), performed on Jan. 24, 2024 (Year: 2008).*

(Continued)

*Primary Examiner* — Brian W Jennison
(74) *Attorney, Agent, or Firm* — Oliff PLC

(57) ABSTRACT

A processing apparatus has: a light irradiation apparatus that irradiates a surface of an object with a processing light; and a measurement apparatus that measures a position of an irradiation area, which is formed on the surface of the object by the light irradiation apparatus, relative to the object.

78 Claims, 62 Drawing Sheets

(56) References Cited

U.S. PATENT DOCUMENTS

2015/0211083 A1* 7/2015 Gabilondo ............ F16C 41/008
  219/121.73
2017/0139328 A1 5/2017 Shibazaki
2017/0144255 A1 5/2017 Song

FOREIGN PATENT DOCUMENTS

| | | |
|---|---|---|
| JP | H02-229687 A | 9/1990 |
| JP | 2005-169397 A | 6/2005 |
| JP | 2008-119718 A | 5/2008 |
| JP | 2015-532686 A | 11/2015 |
| JP | 2016-013571 A | 1/2016 |
| JP | 2016-034659 A | 3/2016 |
| JP | 2016-221561 A | 12/2016 |
| WO | 2014/037281 A2 | 3/2014 |

OTHER PUBLICATIONS

Apr. 29, 2022 Office Action issued in Chinese Patent Application No. 201780096203.7.
Sep. 9, 2022 Office Action in Brazilian Patent Application No. BR112020007946-4.
Sep. 14, 2022 Office Action issued in U.S. Appl. No. 16/756,898.
Jul. 23, 2021 Office Action issued in Chinese Patent Application No. 201780096203.7.
Feb. 21, 2023 Office Action issued in Chinese Patent Application No. 201780096203.7.
Mar. 6, 2022 Office Action issued in Japanese Patent Application No. 2019-549752.
Sep. 7, 2021 Office Action issued in Japanese Patent Application No. 2019-549752.
Jun. 11, 2021 Search Report issued in European Patent Application No. 17930028.0.
Jul. 5, 2022 Office Action issued in Japanese Patent Application No. 2019-549752.
Jan. 30, 2023 Office Action issued in U.S. Appl. No. 16/756,898.
Dec. 12, 2017 Written Opinion issued in International Patent Application No. PCT/JP2017/038563.
Apr. 11, 2023 Office Action issued in European Patent Application No. 17 930 028.0.
Apr. 10, 2023 Office Action issued in Brazilian Patent Application No. BR112020007946-4.
Jun. 13, 2023 Office Action issued in U.S. Appl. No. 16/756,898.
Dec. 14, 2023 Office Action issued in U.S. Appl. No. 16/756,898.
Dec. 20, 2023 Office Action issued in Canadian Patent Application No. 3,080,282.
May 21, 2024 Office Action issued in U.S. Appl. No. 16/756,898.

* cited by examiner

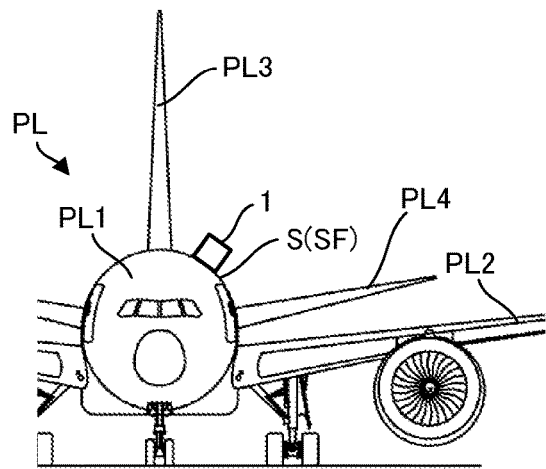
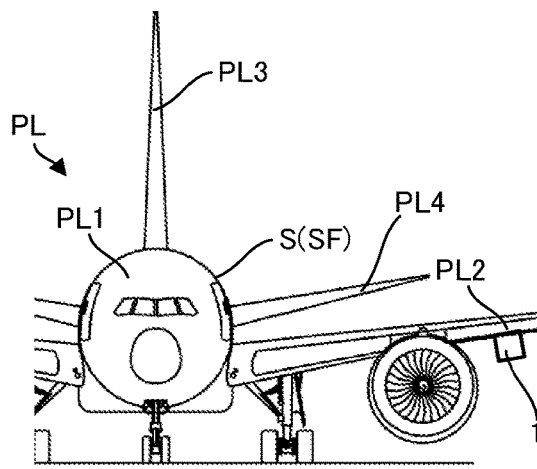
FIG. 6A
FIG. 6B
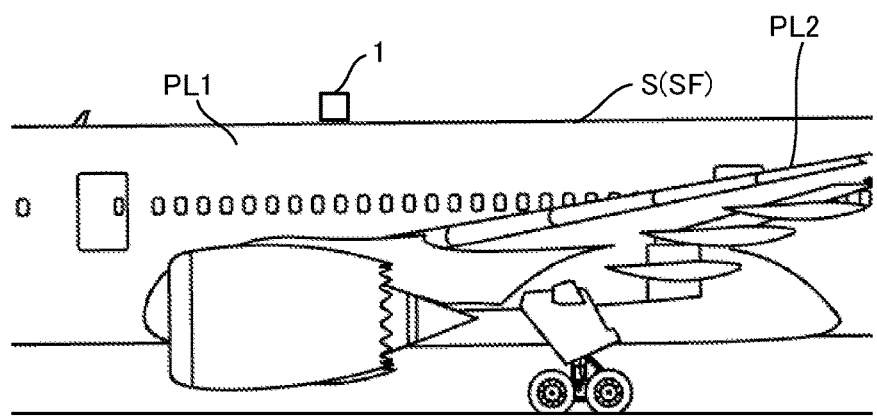
FIG. 6C

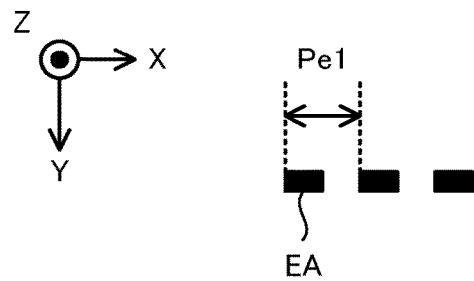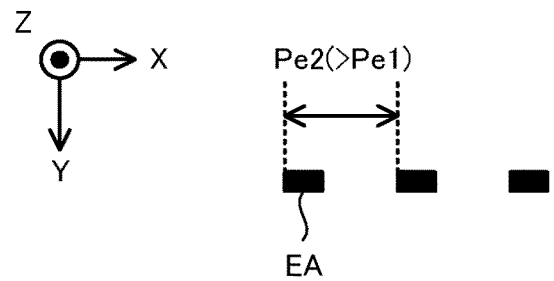
FIG. 47A          FIG. 47B
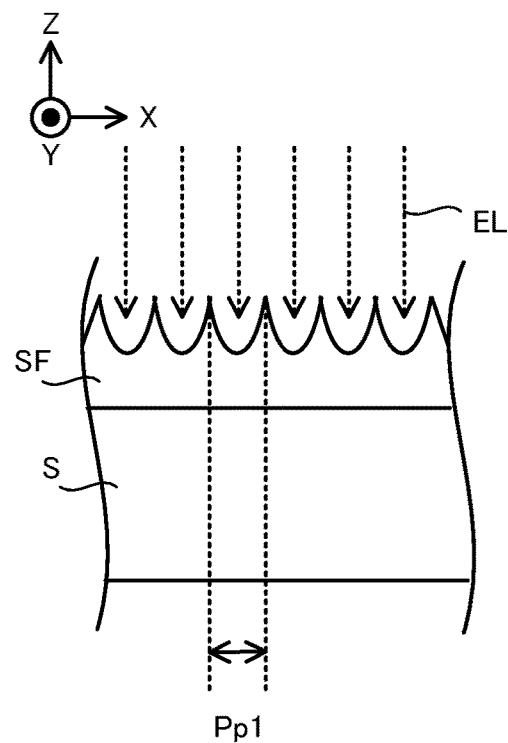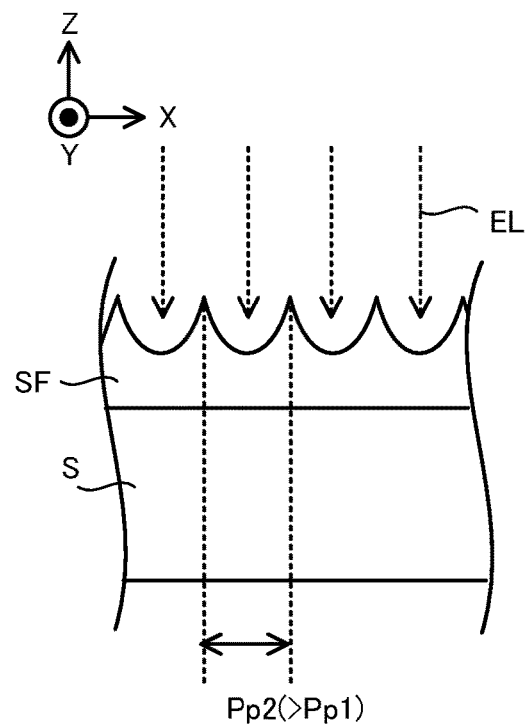
FIG. 47C          FIG. 47D

PROCESSING APPARATUS, AND MANUFACTURING METHOD OF MOVABLE BODY

TECHNICAL FIELD

The present invention relates to a processing apparatus that is configured to process an object by irradiating it with a processing light, and a manufacturing method of manufacturing a movable body.

BACKGROUND ART

A Patent Literature 1 discloses, as a processing apparatus that is configured to process an object, a processing apparatus that forms a structure by irradiating a surface of an object with a laser beam to reduce a resistance of the surface. The processing apparatus is required to form the structure at the object properly.

CITATION LIST

Patent Literature

Patent Literature 1: U.S. Pat. No. 4,994,639B

SUMMARY OF INVENTION

A first aspect provide a processing apparatus that is provided with: a light irradiation apparatus that irradiates a surface of an object with a processing light; and a control apparatus that controls the light irradiation apparatus by using an information relating to a characteristic of the surface of the object.

A second aspect provides a processing apparatus that is provided with: a light irradiation apparatus that irradiates a surface of an object with a processing light; a second measurement apparatus that measures a characteristic of the surface of the object; and a control apparatus that controls the light irradiation apparatus by using a measured result of the second measurement apparatus.

A third aspect provides a processing apparatus that is provided with: a light irradiation apparatus that irradiates a surface of an object with a processing light; and a control apparatus that controls the light irradiation apparatus based on a state of the surface of the object.

A fourth aspect provides a processing apparatus that is provided with: a light irradiation apparatus that irradiates a surface of an object with a processing light; and a third measurement apparatus that measures a characteristic of a sample structure that is at least a part of a structure formed by an irradiation of the processing light from the light irradiation apparatus.

A fifth aspect provides a manufacturing method of a movable body that moves in a fluid, the manufacturing method includes: irradiating a surface of an object with a processing light; changing an irradiation state of the processing light by using an information relating to a characteristic of the surface of the object; and forming a structure at the surface of the object by changing a thickness of a part of the surface of the object by the irradiation of the processing light to the surface of the object.

A sixth aspect provides a manufacturing method of a movable body that moves in a fluid, the manufacturing method includes: irradiating a surface of an object with a processing light; changing an irradiation state of the processing light by using an information relating to a characteristic of the surface of the object; and forming a structure at the surface of the object by removing a part of the surface of the object by the irradiation of the processing light to the surface of the object.

A seventh aspect provides a manufacturing method of a movable body that moves in a fluid, the manufacturing method includes: irradiating a surface of an object with a processing light; measuring a characteristic of the surface of the object; changing an irradiation state of the processing light by using a measured result of the characteristic; and forming a structure at the surface of the object by changing a thickness of a part of the surface of the object by the irradiation of the processing light to the surface of the object.

An eighth aspect provides a manufacturing method of a movable body that moves in a fluid, the manufacturing method includes: irradiating a surface of an object with a processing light; measuring a characteristic of the surface of the object; changing an irradiation state of the processing light by using a measured result of the characteristic; and forming a structure at the surface of the object by removing a part of the surface of the object by the irradiation of the processing light to the surface of the object.

A ninth aspect provides a manufacturing method of a movable body that moves in a fluid, the manufacturing method includes: irradiating a surface of an object with a processing light; forming a structure at the surface of the object by changing a thickness of a part of the surface of the object by the irradiation of the processing light to the surface of the object; and measuring a characteristic of a sample structure that is at least a part of a structure formed by an irradiation of the processing light.

A tenth aspect provides a manufacturing method of a movable body that moves in a fluid, the manufacturing method includes: irradiating a surface of an object with a processing light; forming a structure at the surface of the object by removing a part of the surface of the object by the irradiation of the processing light to the surface of the object; and measuring a characteristic of a sample structure that is at least a part of a structure formed by an irradiation of the processing light.

Figures 2A, 2B:
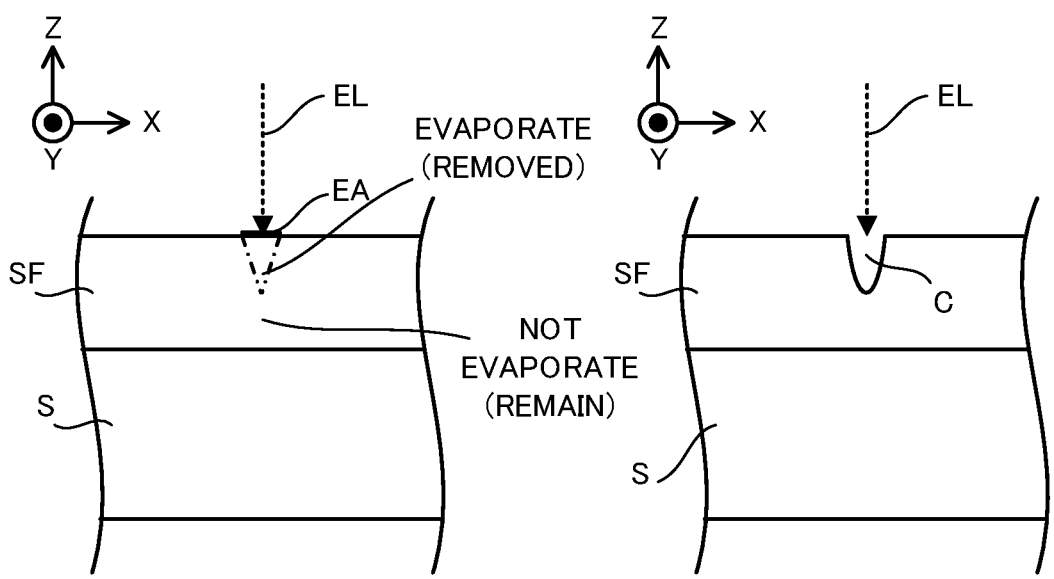

Each of FIG. 2A to FIG. 2B is a cross-sectional view that schematically illustrates an aspect of a processing of a coat of paint formed on a surface of a processing target object.

Figure 3A:
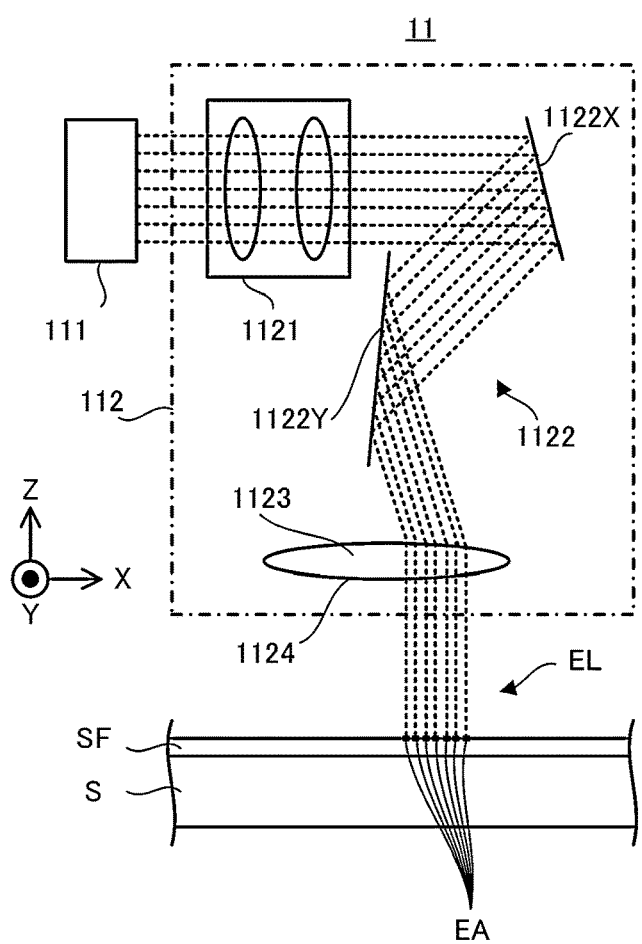
Figure 3B:
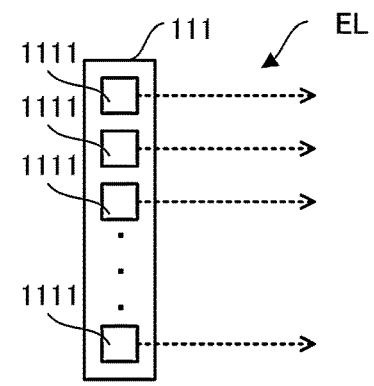
Figure 3C:
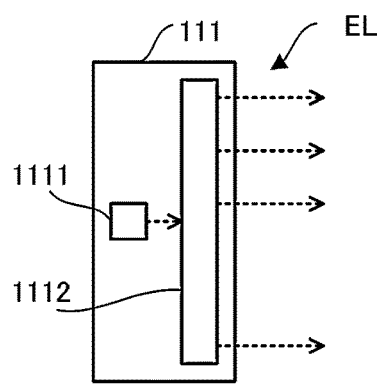
Figure 3D:
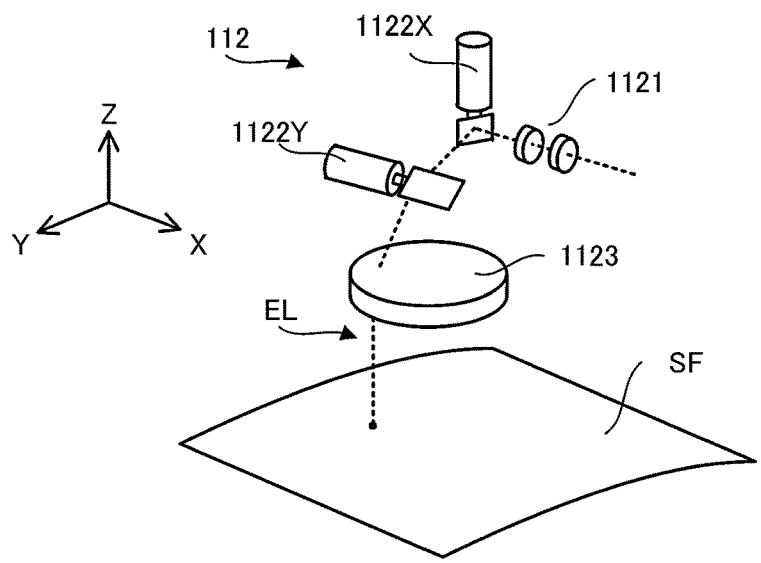

FIG. 3A is a cross-sectional view that schematically illustrates a light irradiation apparatus of the processing apparatus in the present embodiment, each of FIG. 3B and FIG. 3C is a cross-sectional view that illustrates a structure of a light source system of the light irradiation apparatus and FIG. 3D is a perspective view that schematically illustrates other example of an optical system of the light irradiation apparatus.

Figure 4:
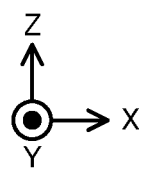
Figure 4:
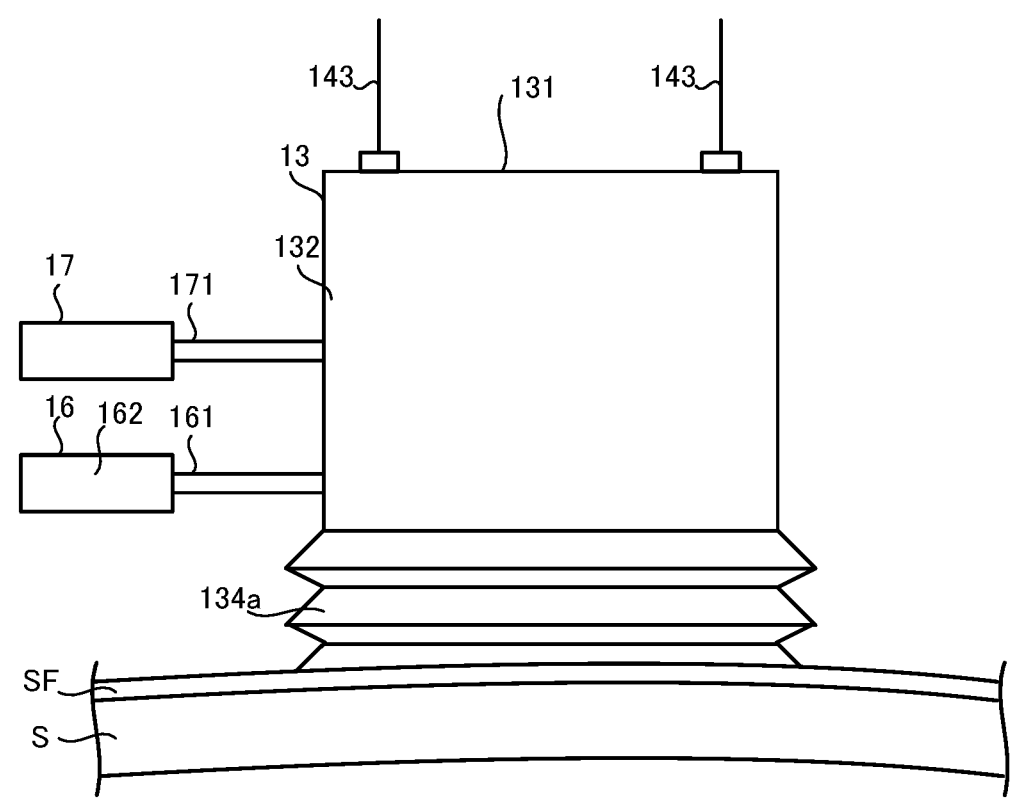

FIG. 4 is a side view that illustrates a housing apparatus.

Figure 5A:
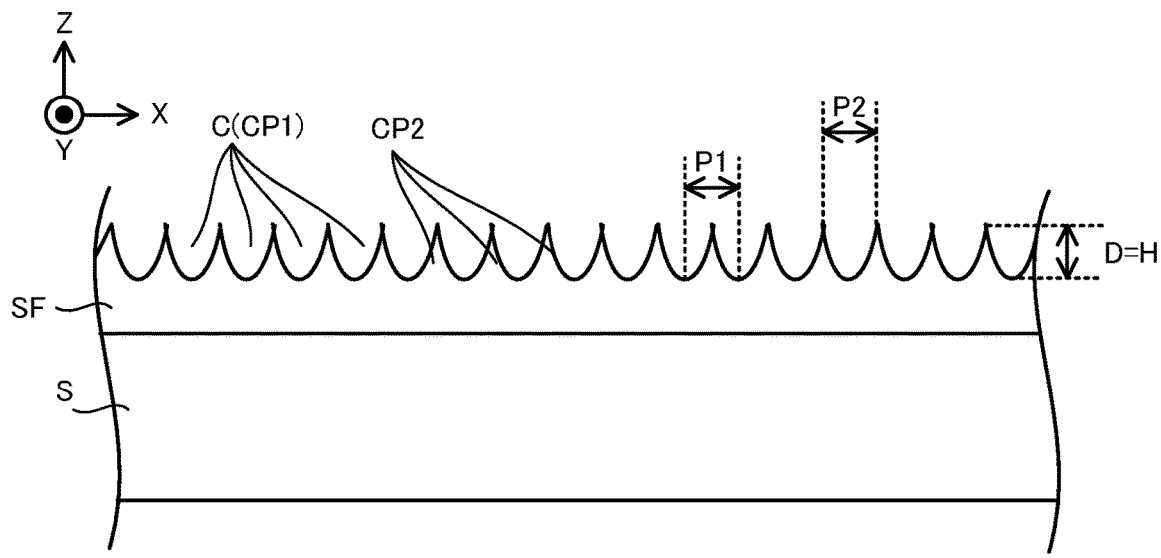
Figure 5B:
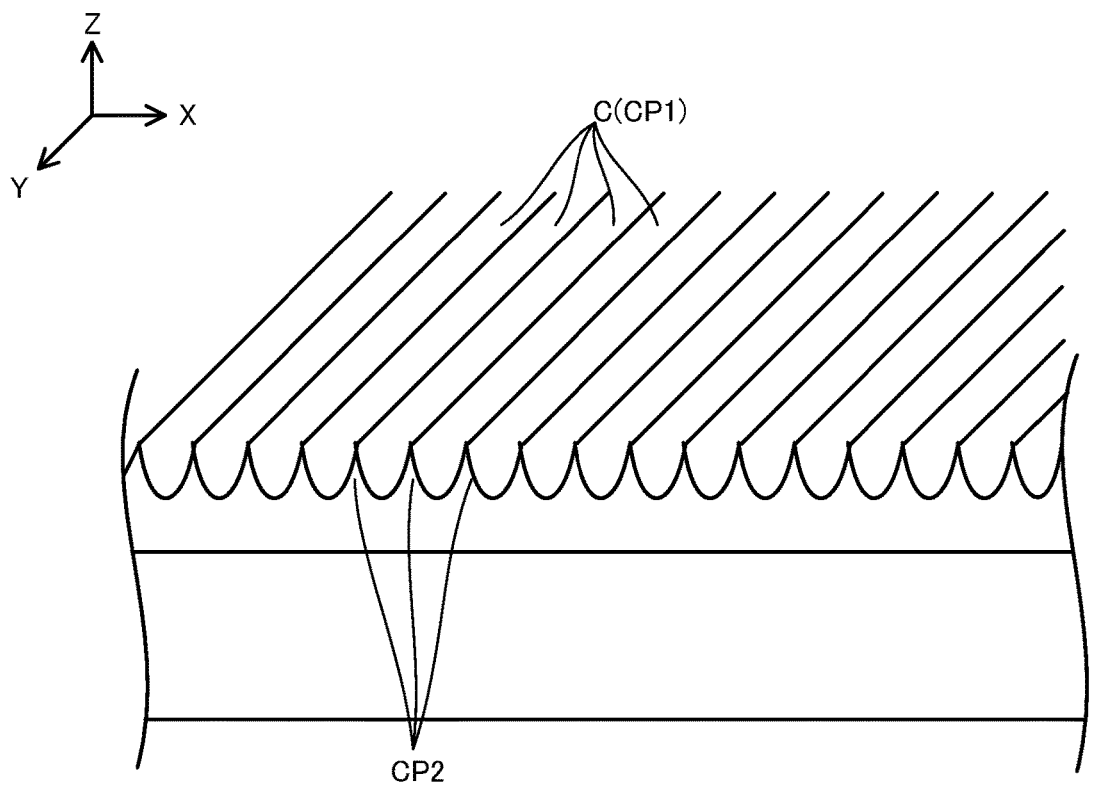

FIG. 5A is a cross-sectional view that illustrates a cross-sectional surface of a riblet structure formed by the processing apparatus in the present embodiment and FIG. 5B is a perspective view that illustrates a cross-sectional surface of a riblet structure formed by the processing apparatus in the present embodiment.

Each of FIG. 6A and FIG. 6B is a front view that illustrates an airplane that is one example of the processing target object at which the riblet structure is formed and FIG.

6C is a side view that illustrates the airplane that is one example of the processing target object at which the riblet structure is formed.

Figure 7:
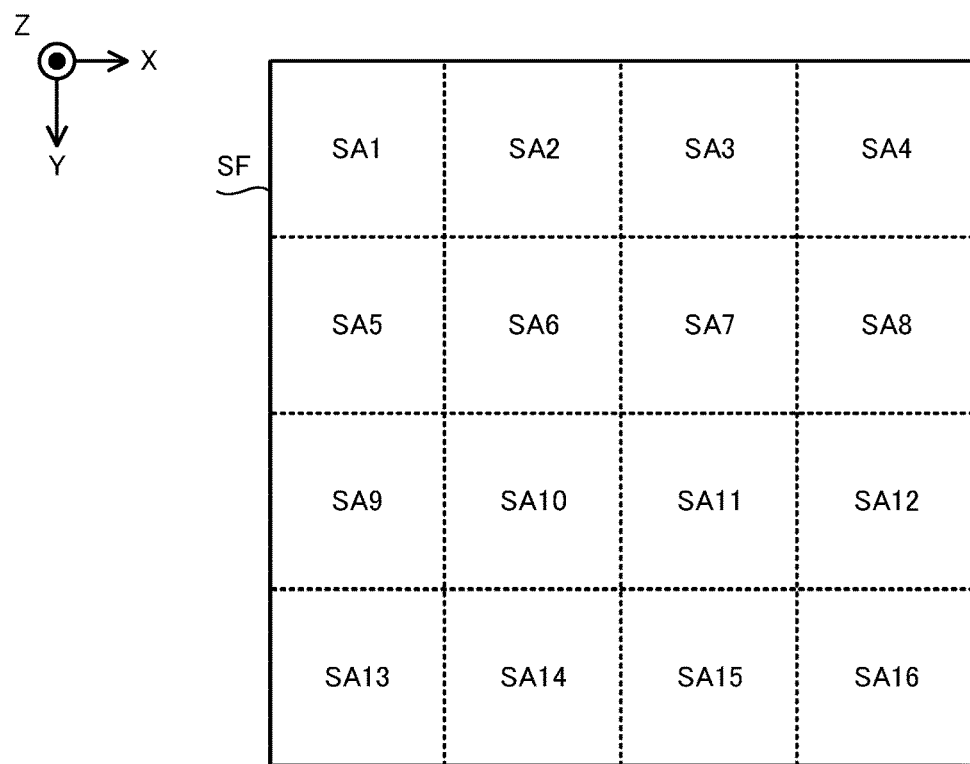

FIG. 7 is a plan view that illustrates a plurality of unit processing areas that are set on a surface of the coat SF of paint.

Figure 8:
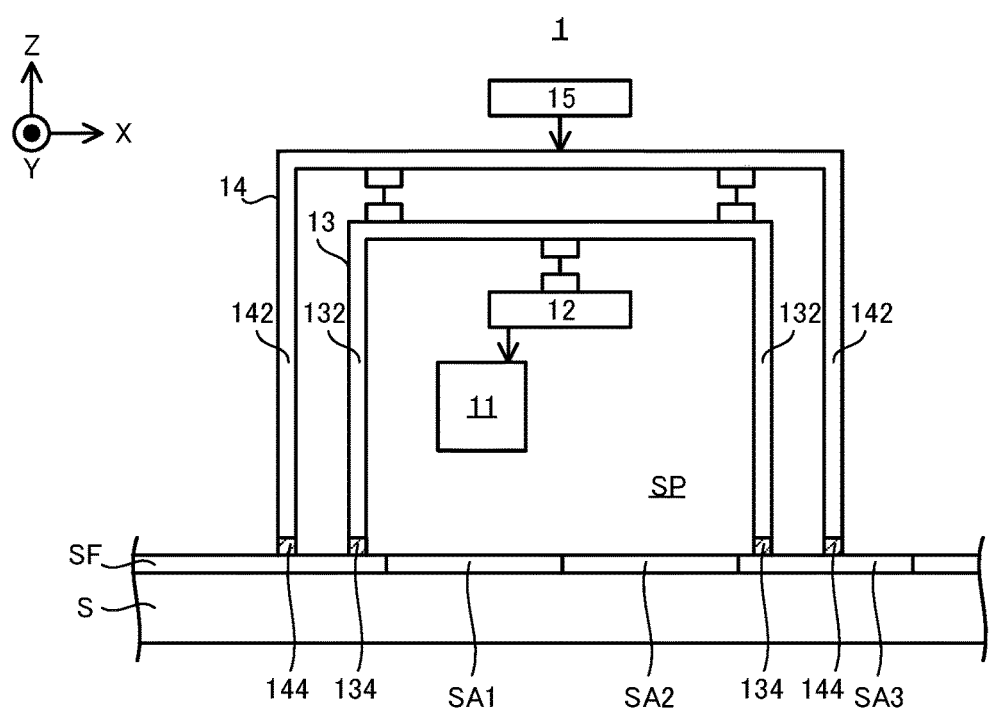

FIG. 8 is a cross-sectional view that illustrates the processing apparatus that performs one step of a processing operation for forming the riblet structure.

Figure 9A:
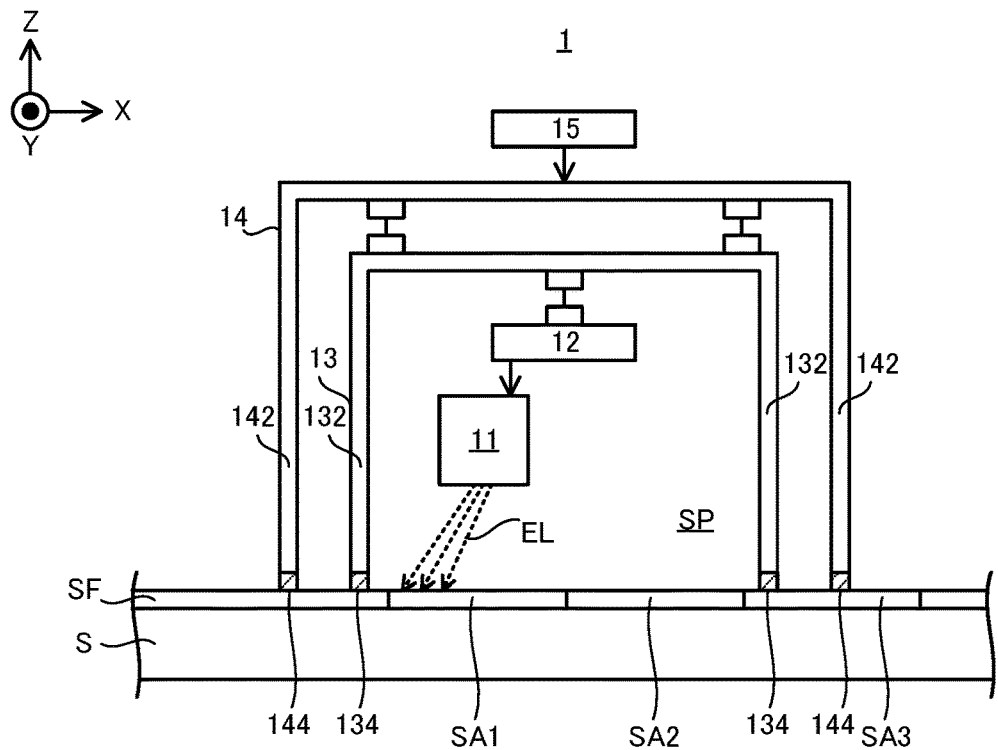
Figure 9B:
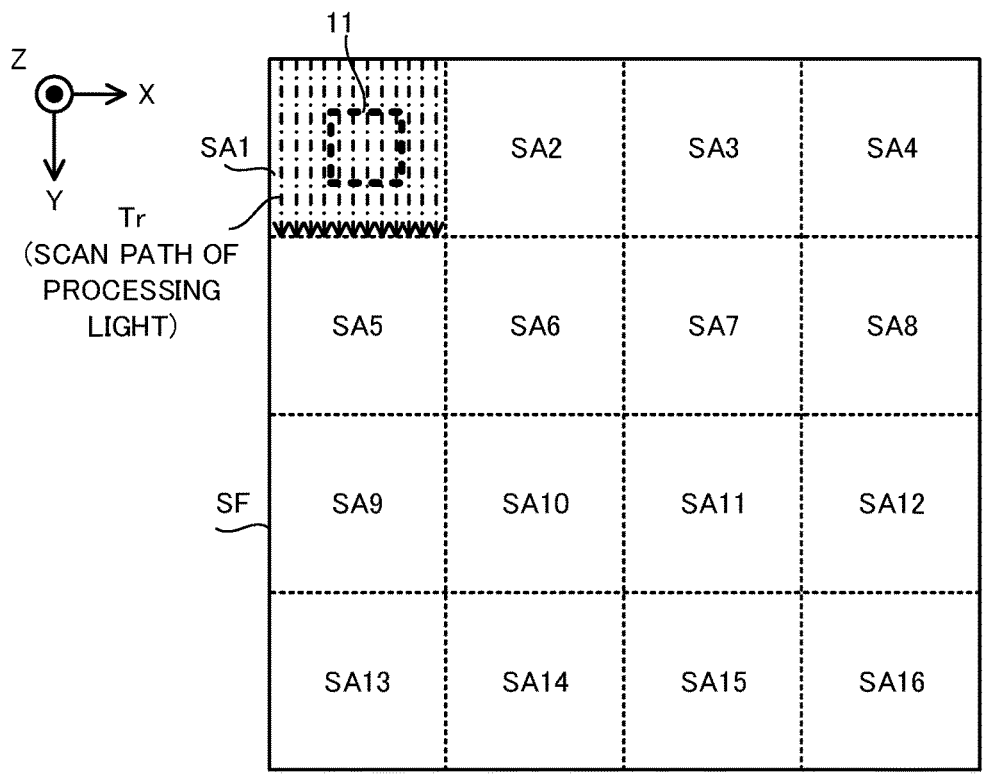

FIG. 9A is a cross-sectional view that illustrates the processing apparatus that performs one step of the processing operation for forming the riblet structure and FIG. 9B is a plane view that illustrates the surface of the coat of paint on which one step of the processing operation illustrated in FIG. 9A is performing.

Figure 10:
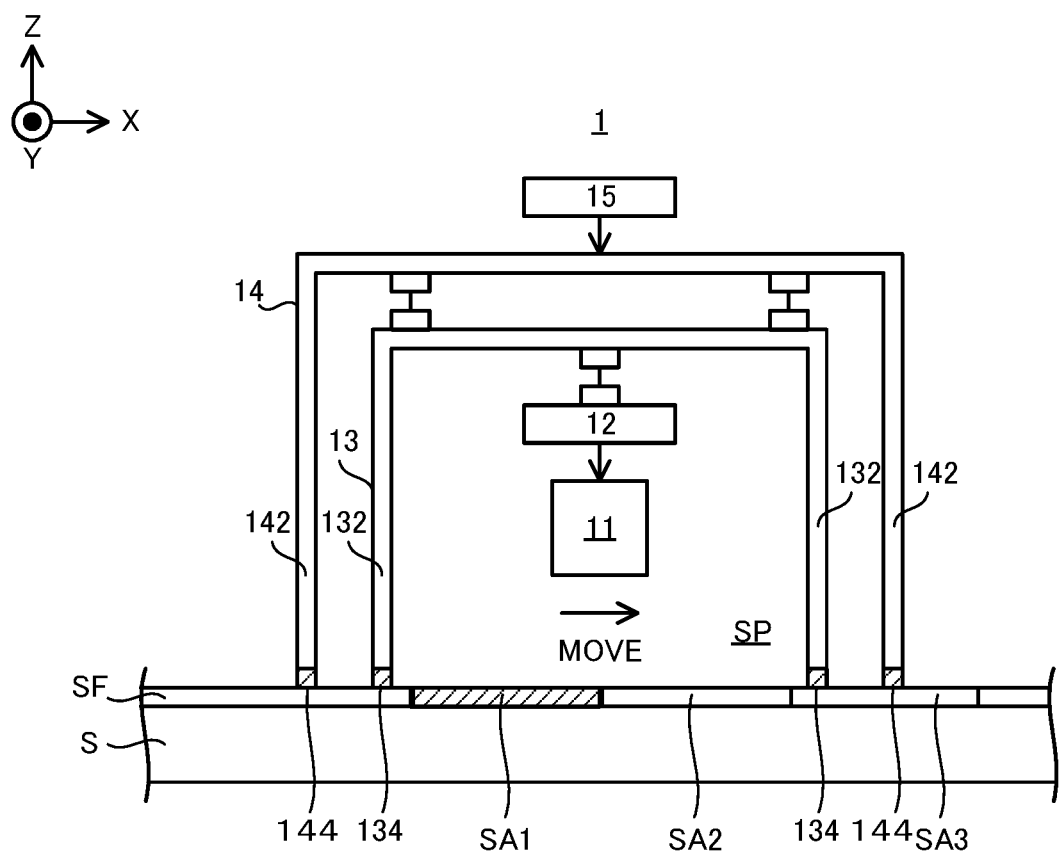

FIG. 10 is a cross-sectional view that illustrates the processing apparatus that performs one step of the processing operation for forming the riblet structure.

Figure 11A:
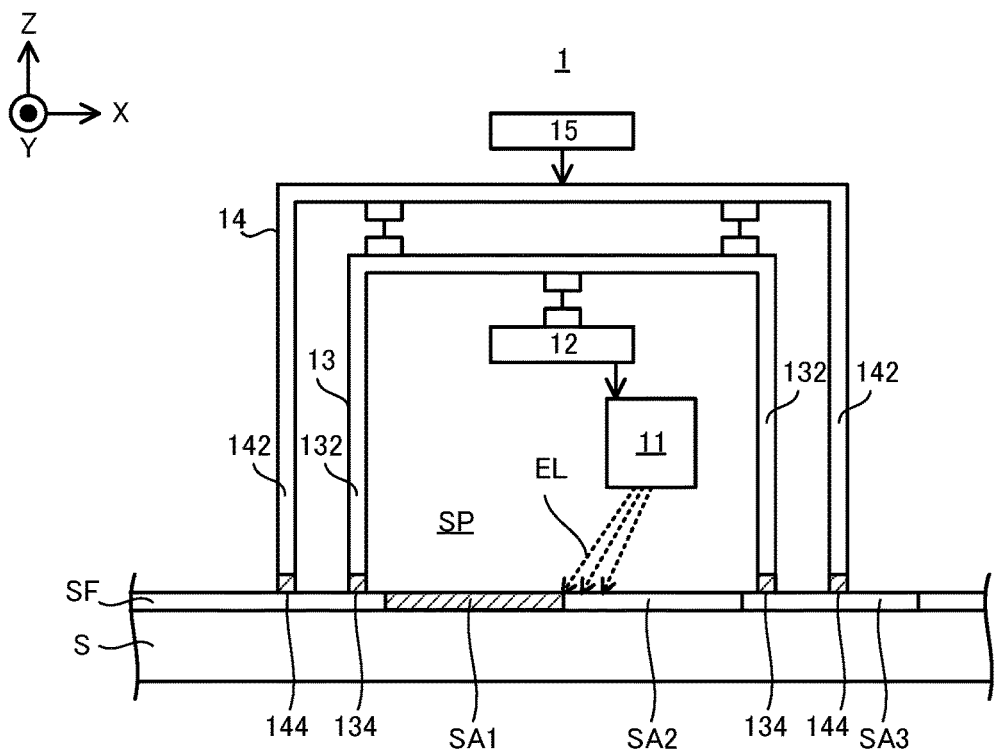
Figure 11B:
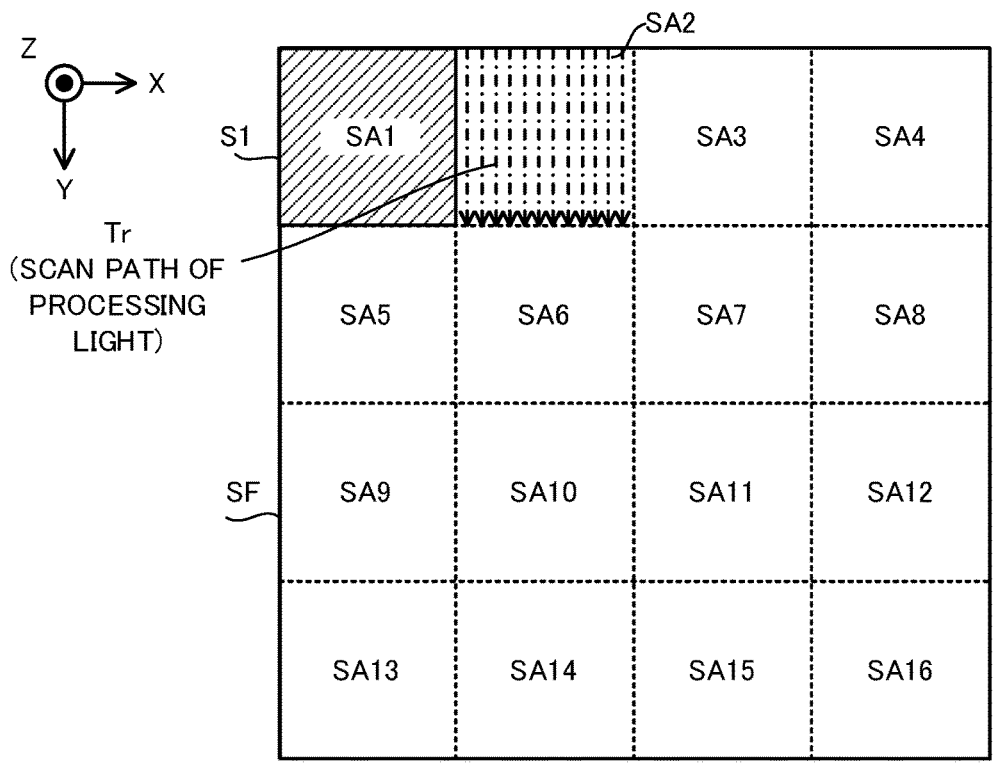

FIG. 11A is a cross-sectional view that illustrates the processing apparatus that performs one step of the processing operation for forming the riblet structure and FIG. 11B is a plane view that illustrates the surface of the coat of paint on which one step of the processing operation illustrated in FIG. 11A is performing.

Figure 12:
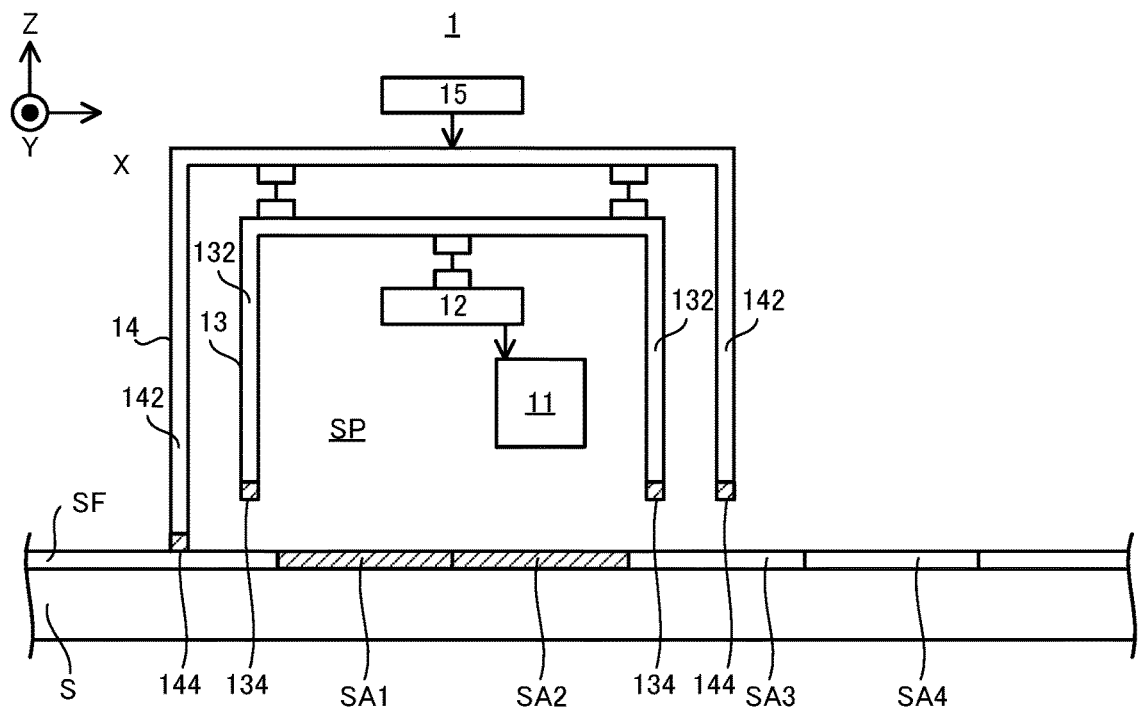

FIG. 12 is a cross-sectional view that illustrates the processing apparatus that performs one step of the processing operation for forming the riblet structure.

Figure 13:
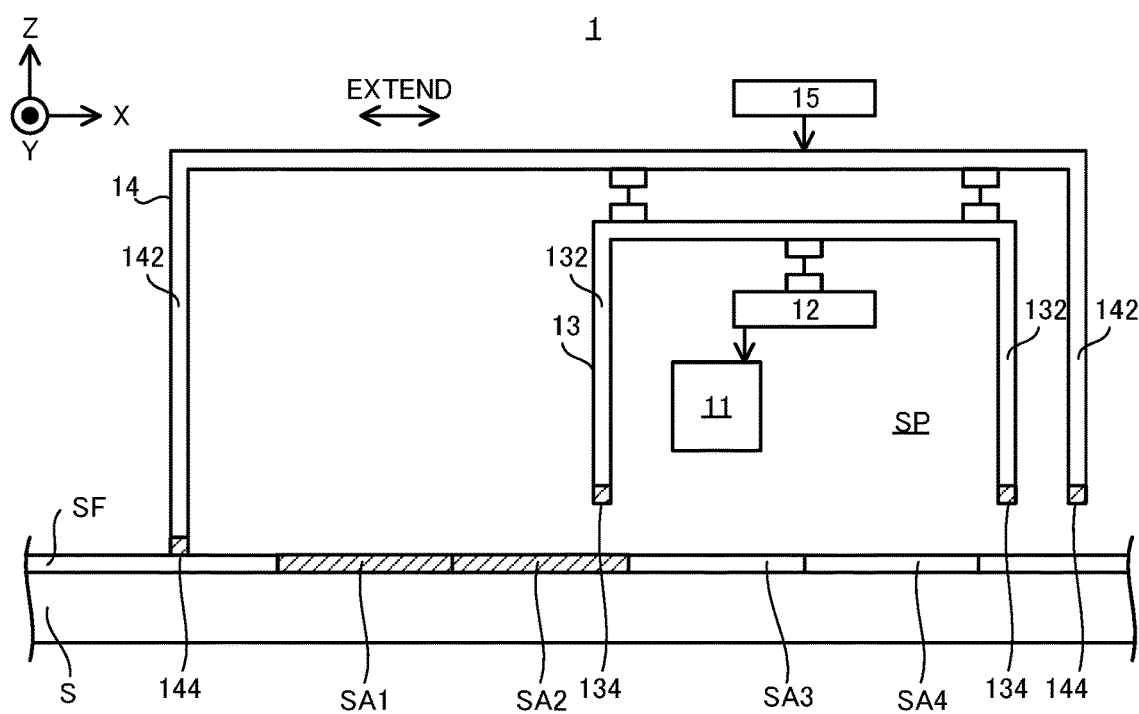

FIG. 13 is a cross-sectional view that illustrates the processing apparatus that performs one step of the processing operation for forming the riblet structure.

Figure 14:
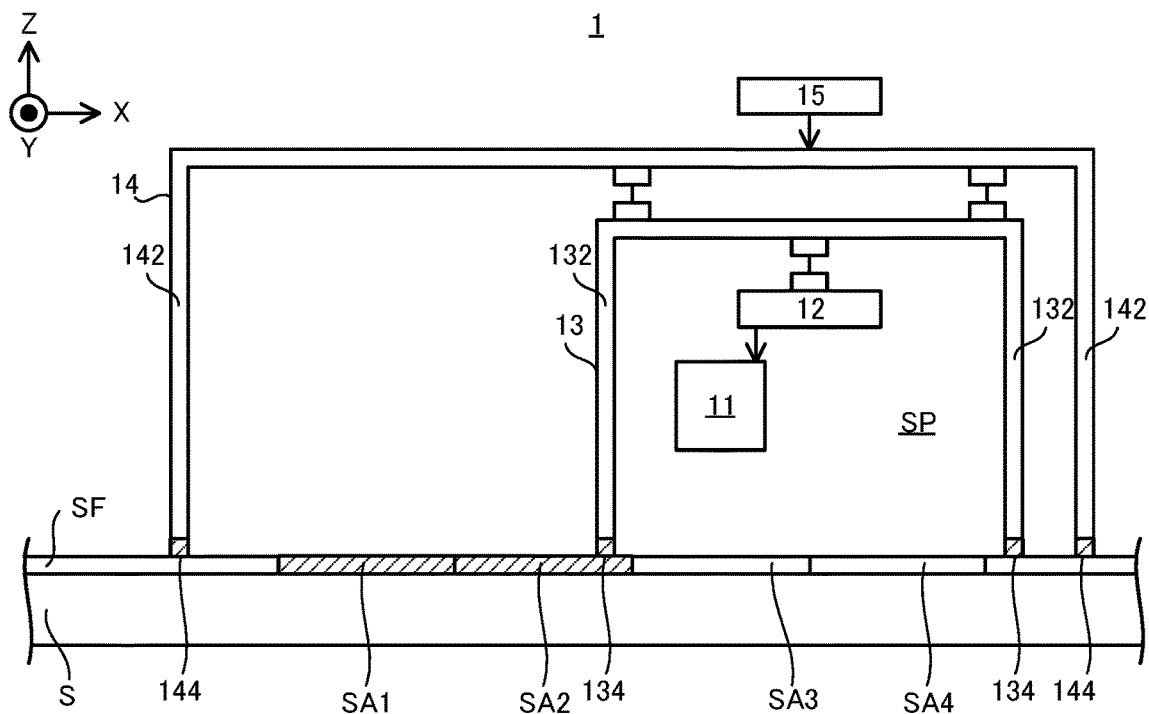

FIG. 14 is a cross-sectional view that illustrates the processing apparatus that performs one step of the processing operation for forming the riblet structure.

Figure 15:
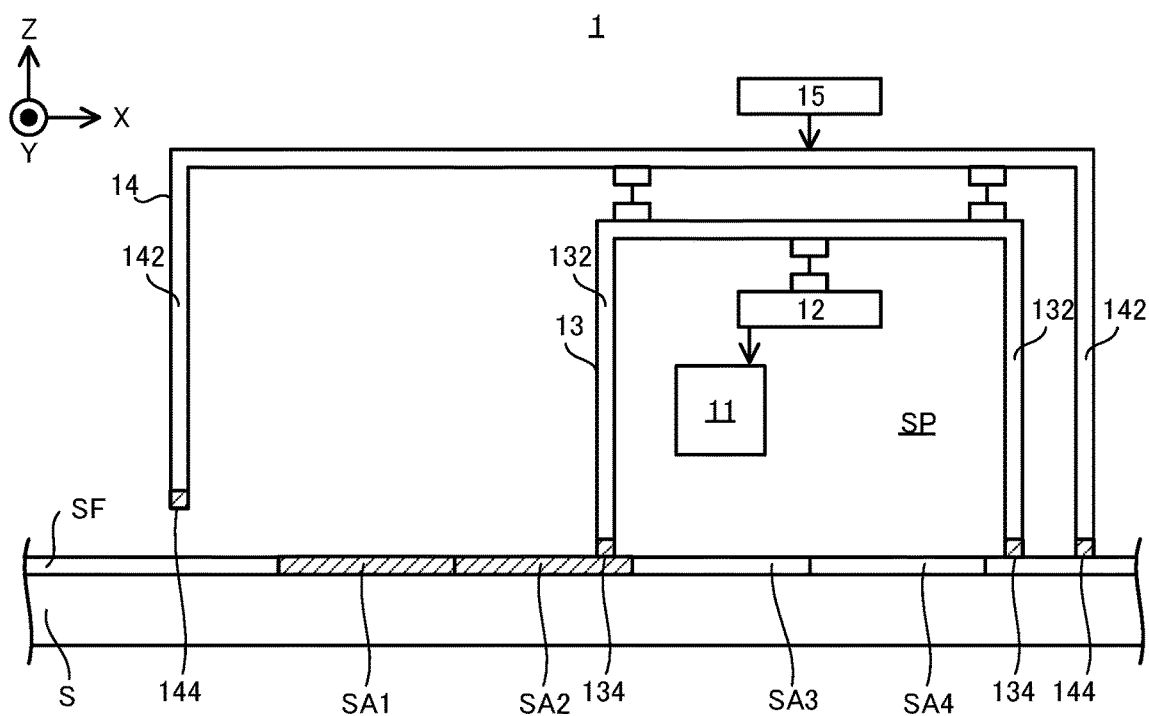

FIG. 15 is a cross-sectional view that illustrates the processing apparatus that performs one step of the processing operation for forming the riblet structure.

Figure 16:
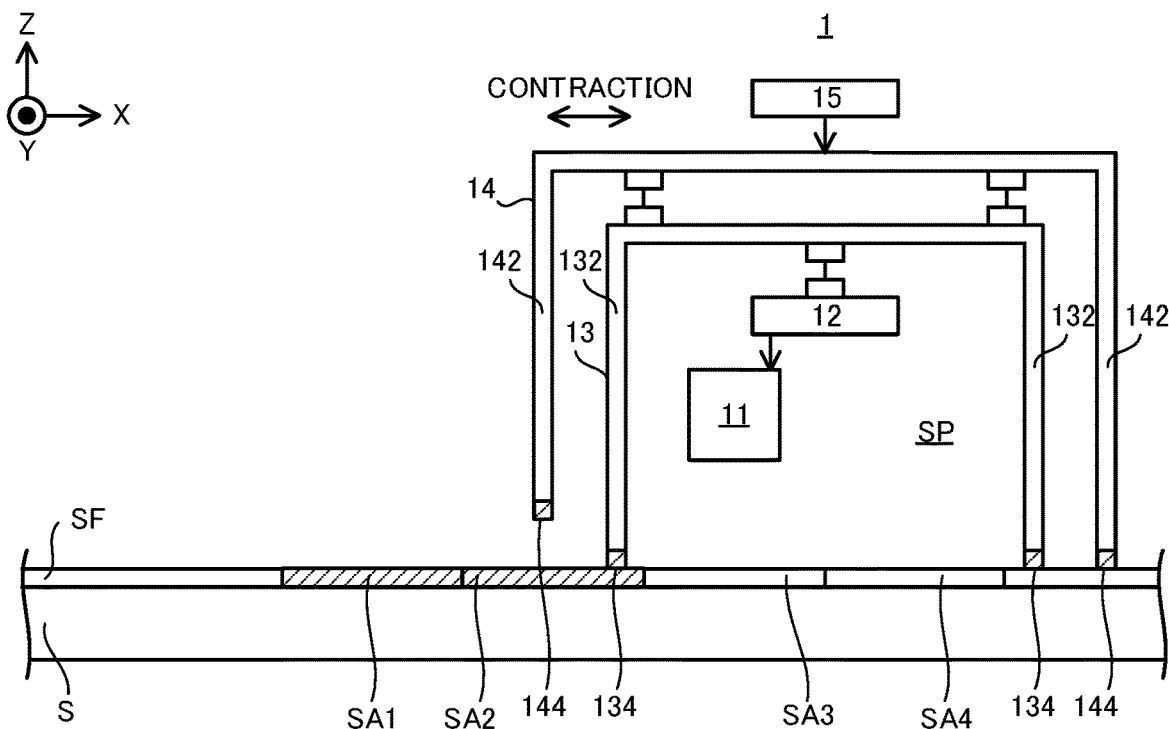

FIG. 16 is a cross-sectional view that illustrates the processing apparatus that performs one step of the processing operation for forming the riblet structure.

Figure 17:
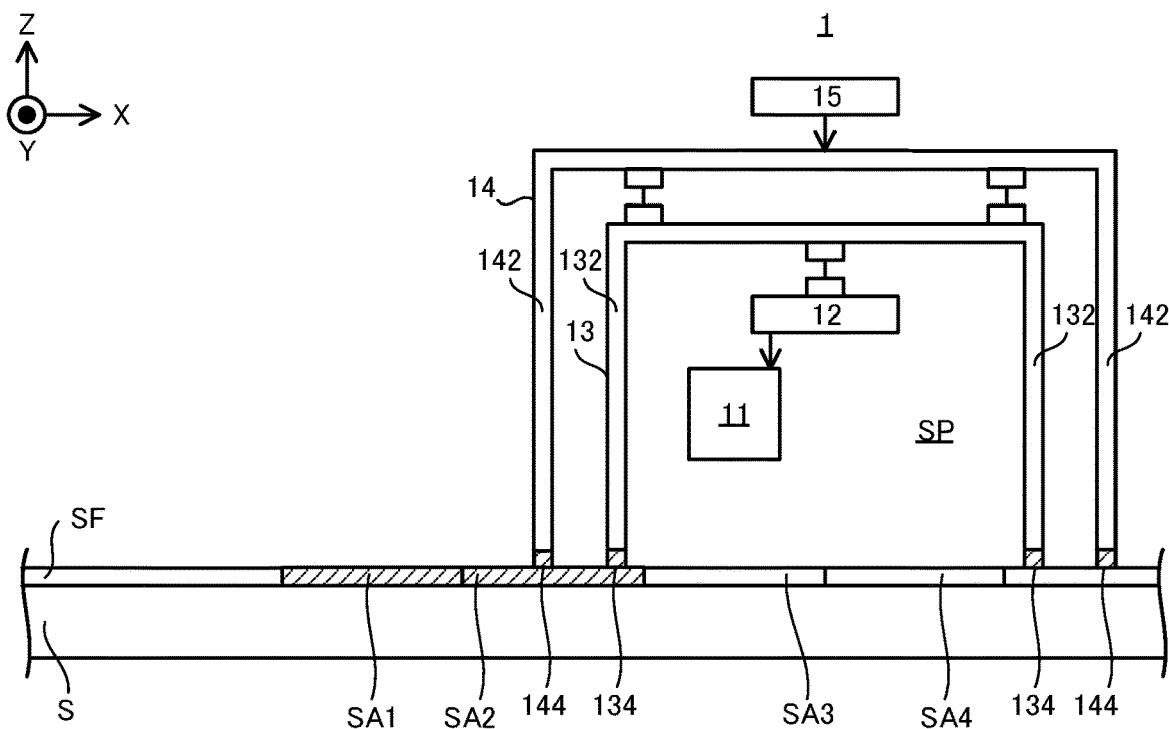

FIG. 17 is a cross-sectional view that illustrates the processing apparatus that performs one step of the processing operation for forming the riblet structure.

Figure 18:
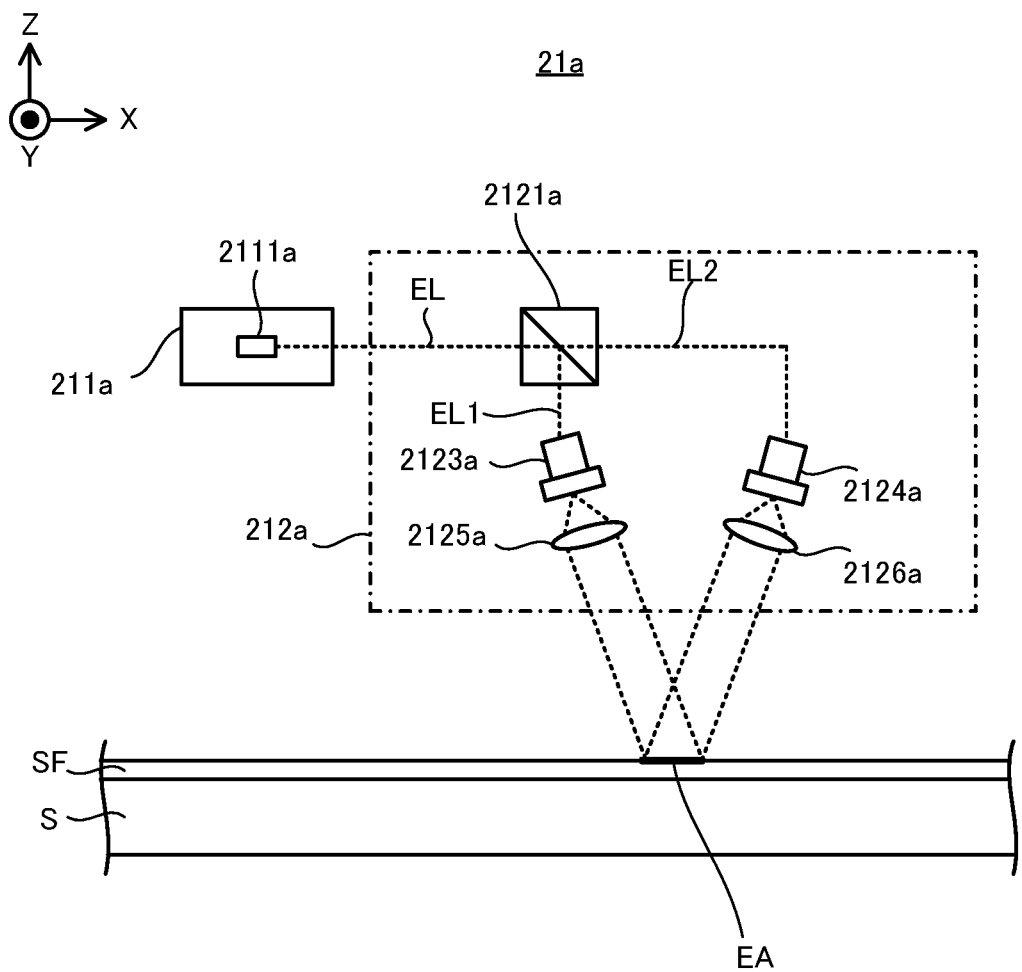

FIG. 18 is a cross-sectional view that schematically illustrates other example of the light irradiation apparatus.

Figure 19:
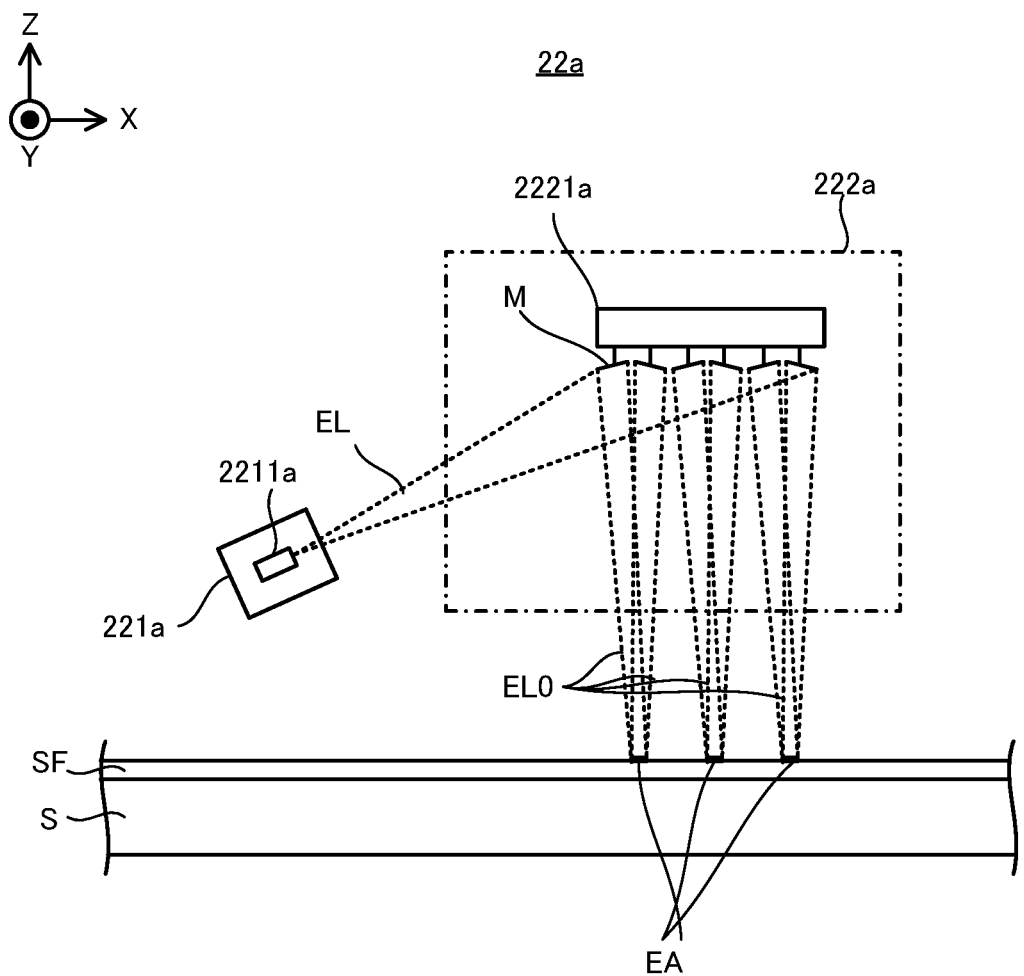

FIG. 19 is a cross-sectional view that schematically illustrates other example of the light irradiation apparatus.

Figure 20:
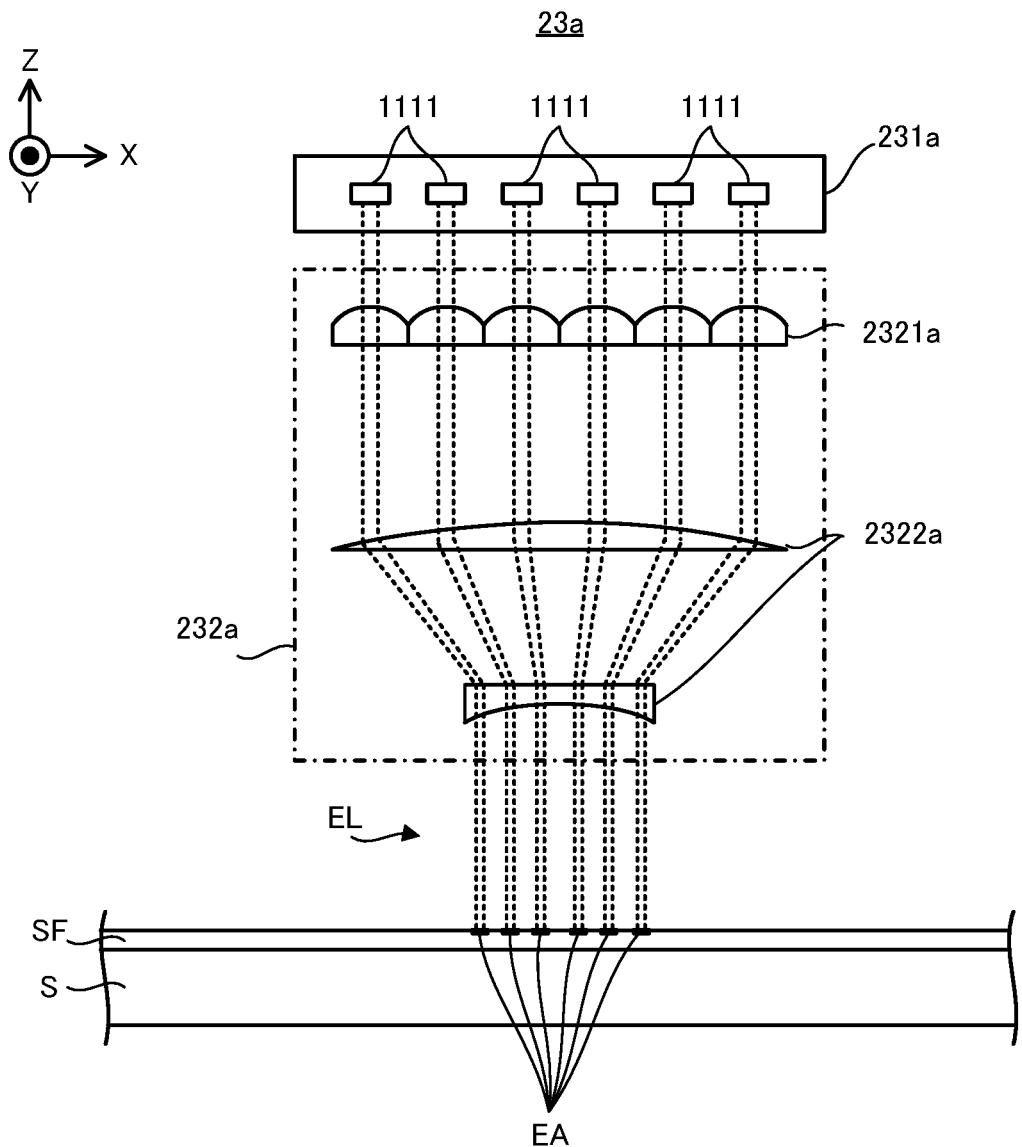

FIG. 20 is a cross-sectional view that schematically illustrates other example of the light irradiation apparatus.

Figure 21:
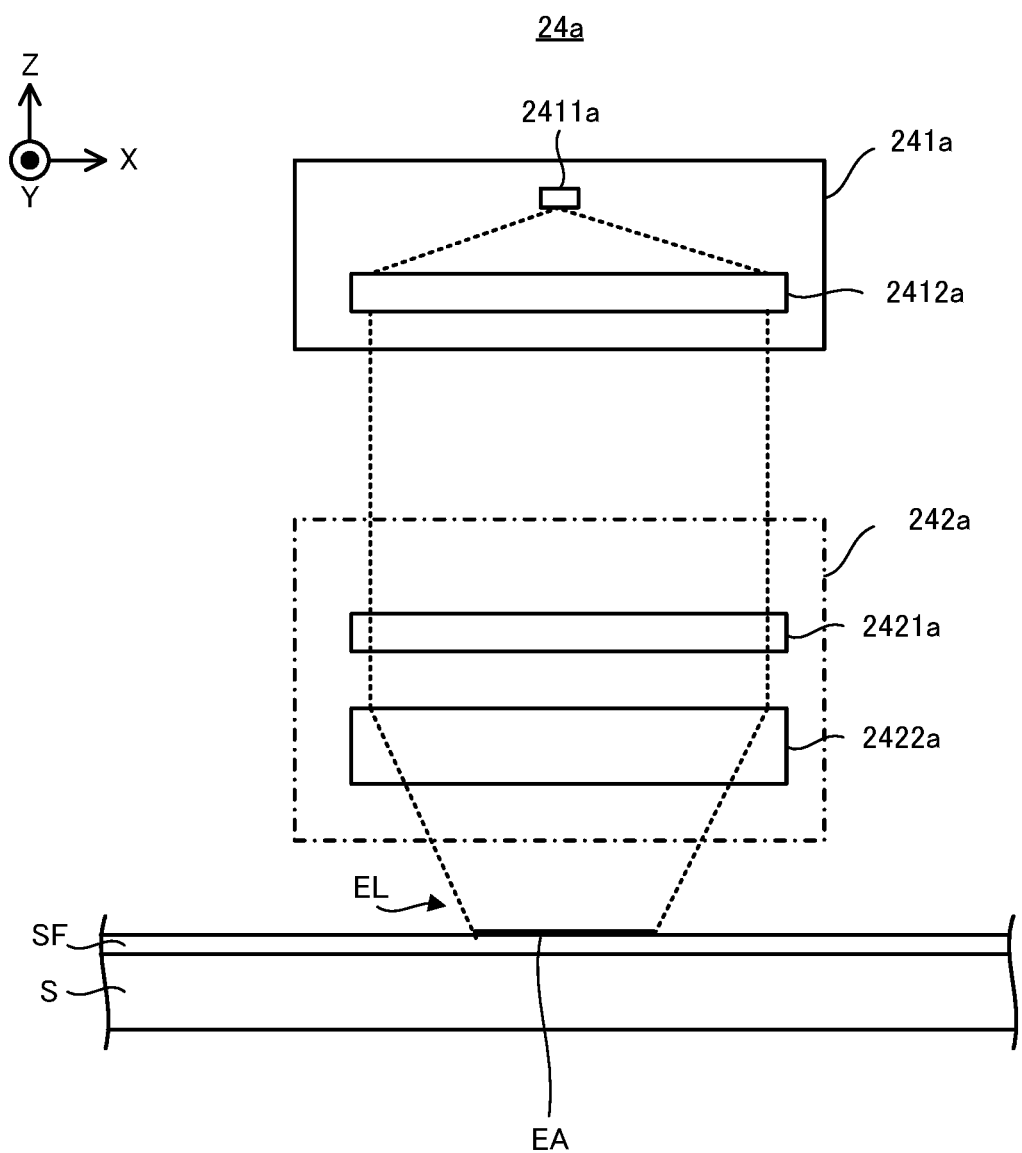

FIG. 21 is a cross-sectional view that schematically illustrates other example of the light irradiation apparatus.

Figure 22:
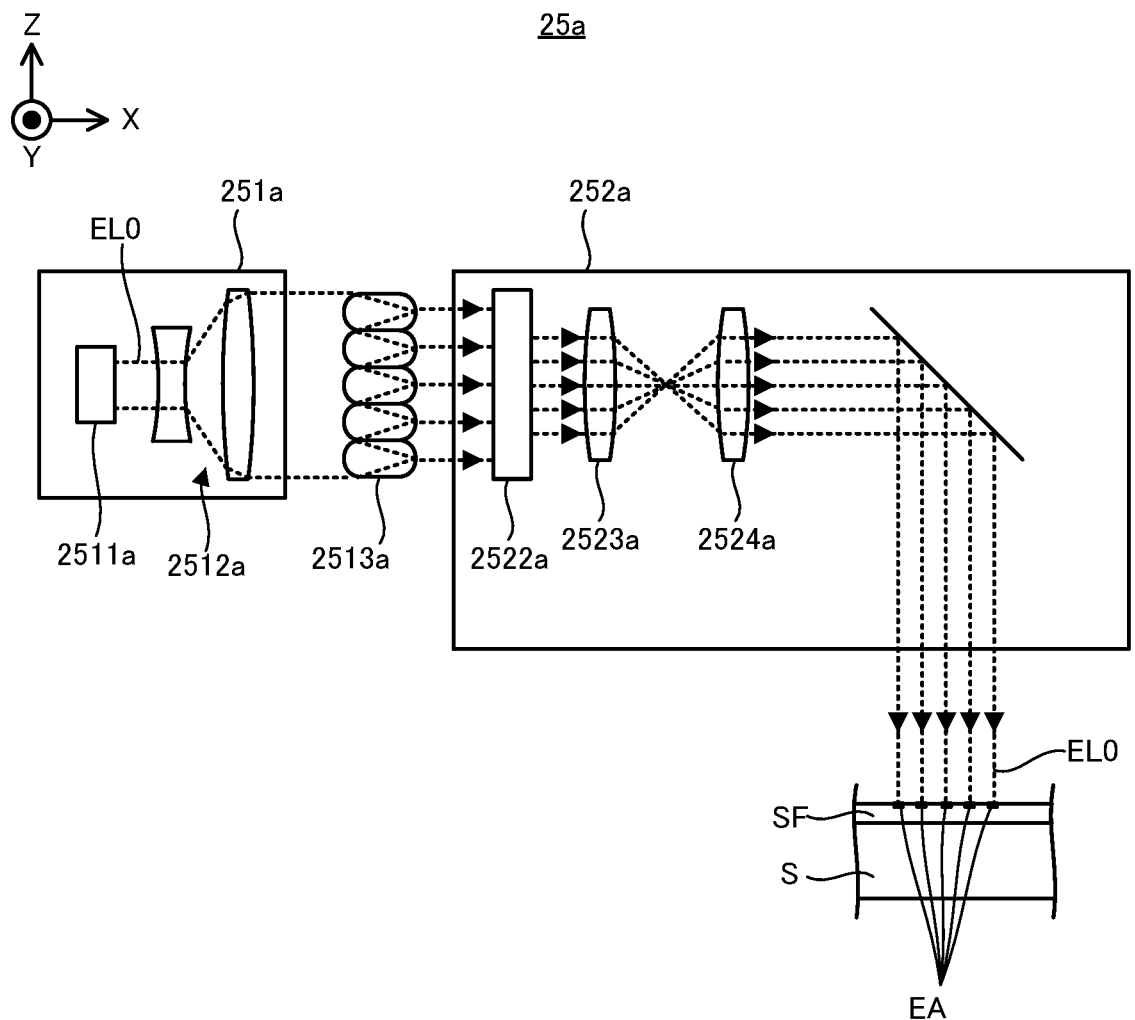

FIG. 22 is a cross-sectional view that schematically illustrates other example of the light irradiation apparatus.

Figure 23:
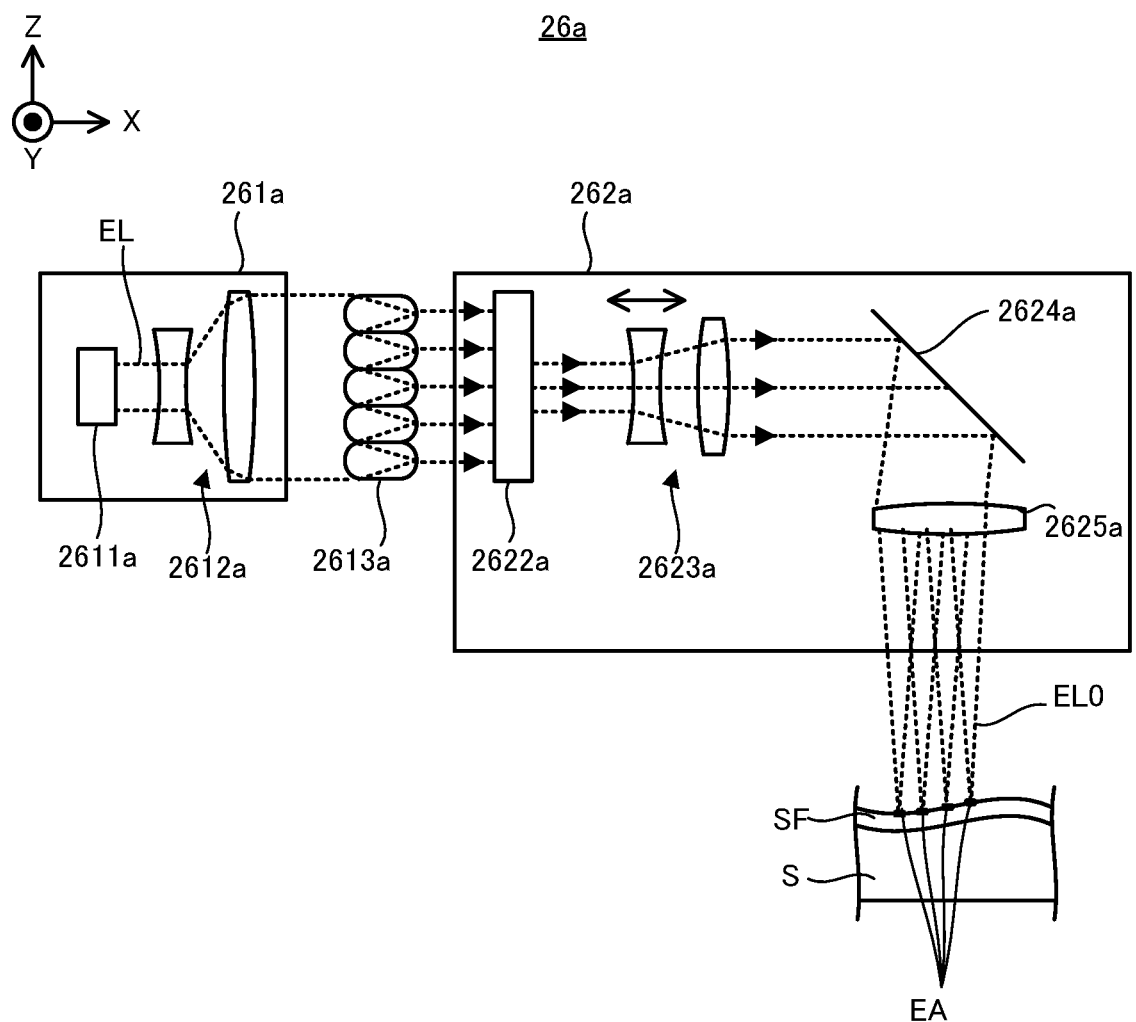

FIG. 23 is a cross-sectional view that schematically illustrates other example of the light irradiation apparatus.

Figure 24:
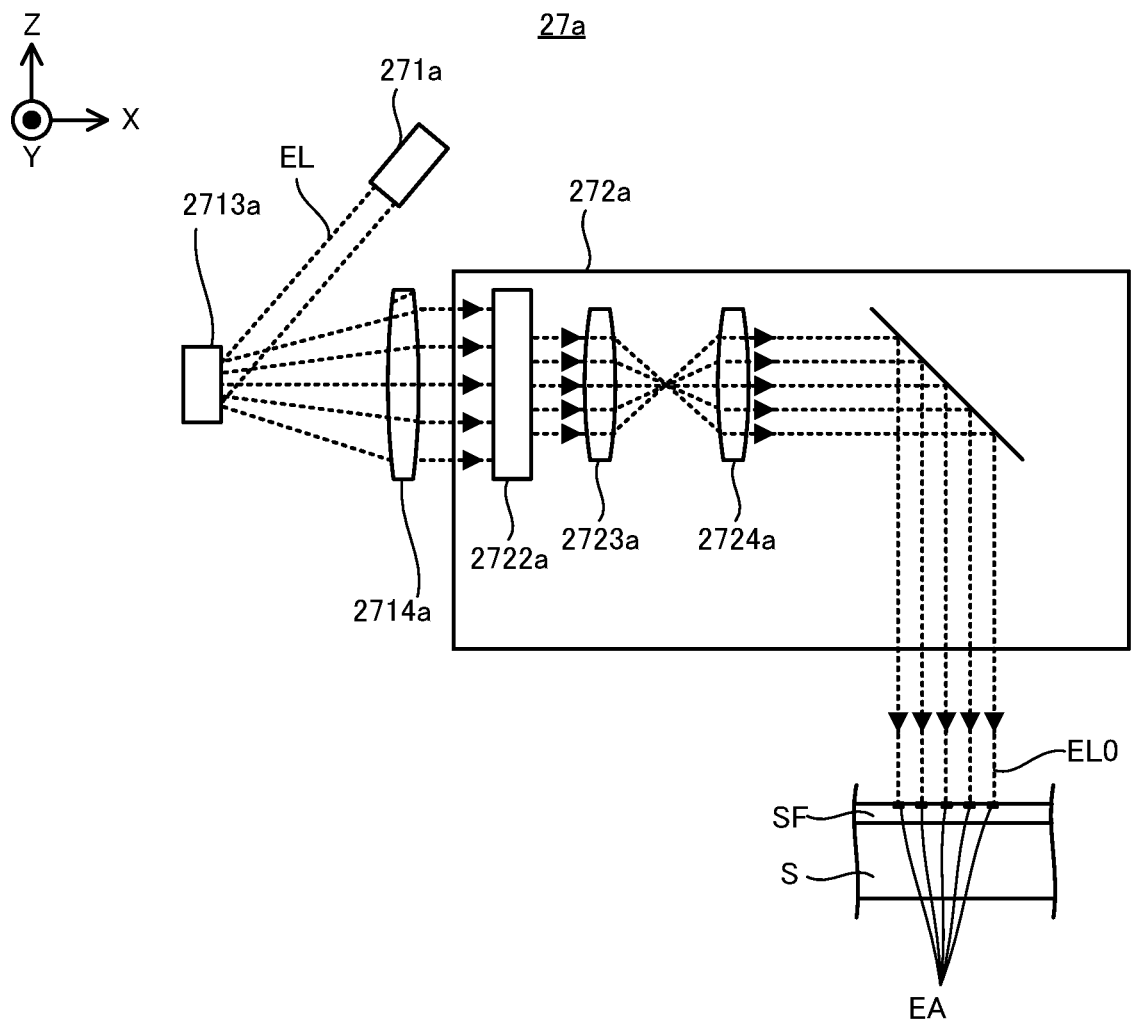

FIG. 24 is a cross-sectional view that schematically illustrates other example of the light irradiation apparatus.

Figure 25:
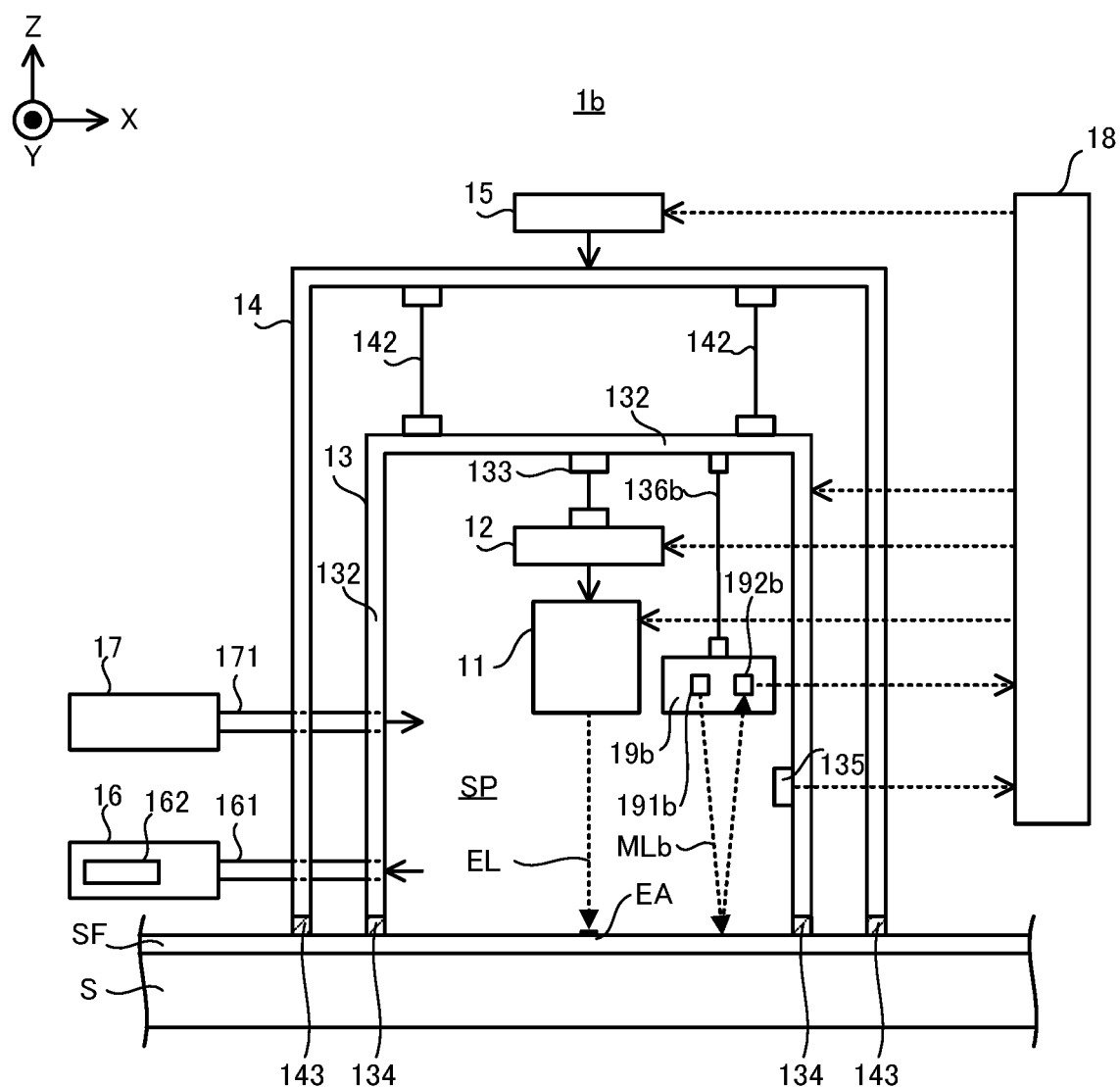

FIG. 25 is a cross-sectional view that schematically illustrates an entire structure of a processing apparatus in a second modified example.

Figure 26A:
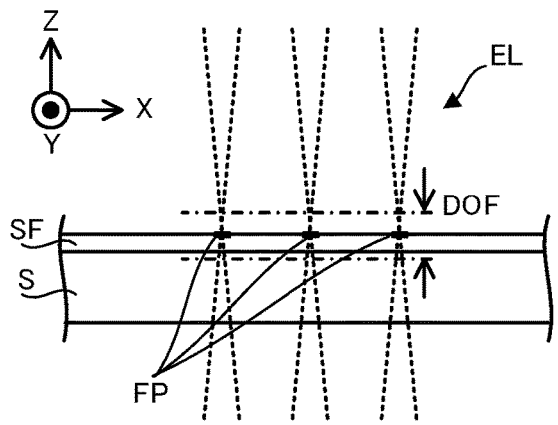
Figure 26B:
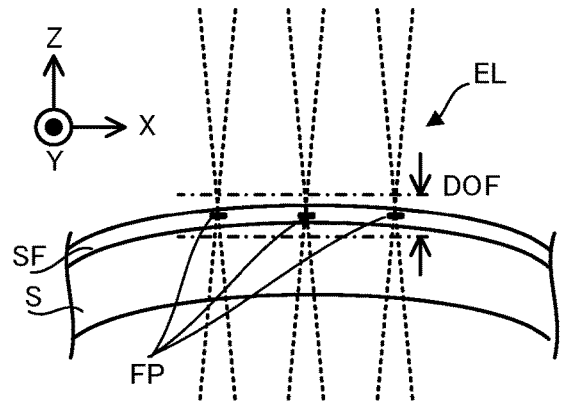
Figure 26C:
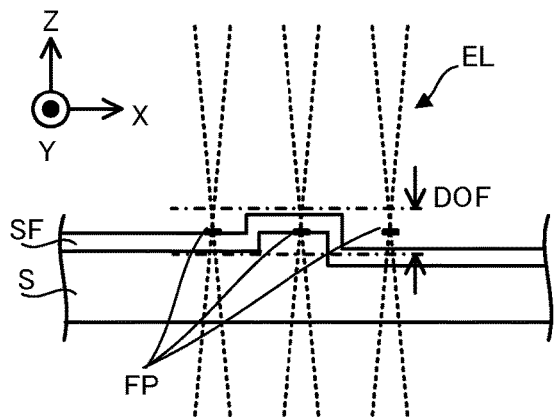
Figure 26D:
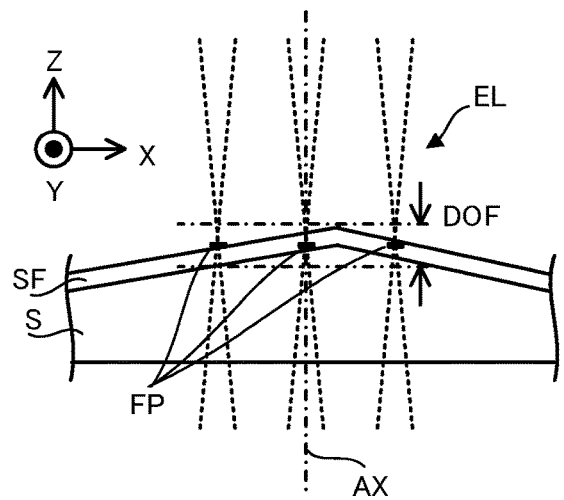

FIG. 26A is a cross-sectional view that illustrates an aspect in which the surface of the coat of paint is positioned within a range of a depth of focus of the optical system when the surface of the coat of paint is a flat surface, FIG. 26B is a cross-sectional view that illustrates an aspect in which the surface of the coat of paint is positioned within the range of the depth of focus of the optical system when the surface of the coat of paint is a curved surface, FIG. 26C is a cross-sectional view that illustrates an aspect in which the surface of the coat of paint is positioned within the range of the depth of focus of the optical system when there is a concavity and/or convexity at the surface of the coat of paint and FIG. 26D is a cross-sectional view that illustrates an aspect in which the surface of the coat of paint is positioned within the range of the depth of focus of the optical system when the surface of the coat of paint is inclined with respect to an optical axis of the optical system.

Figure 27:
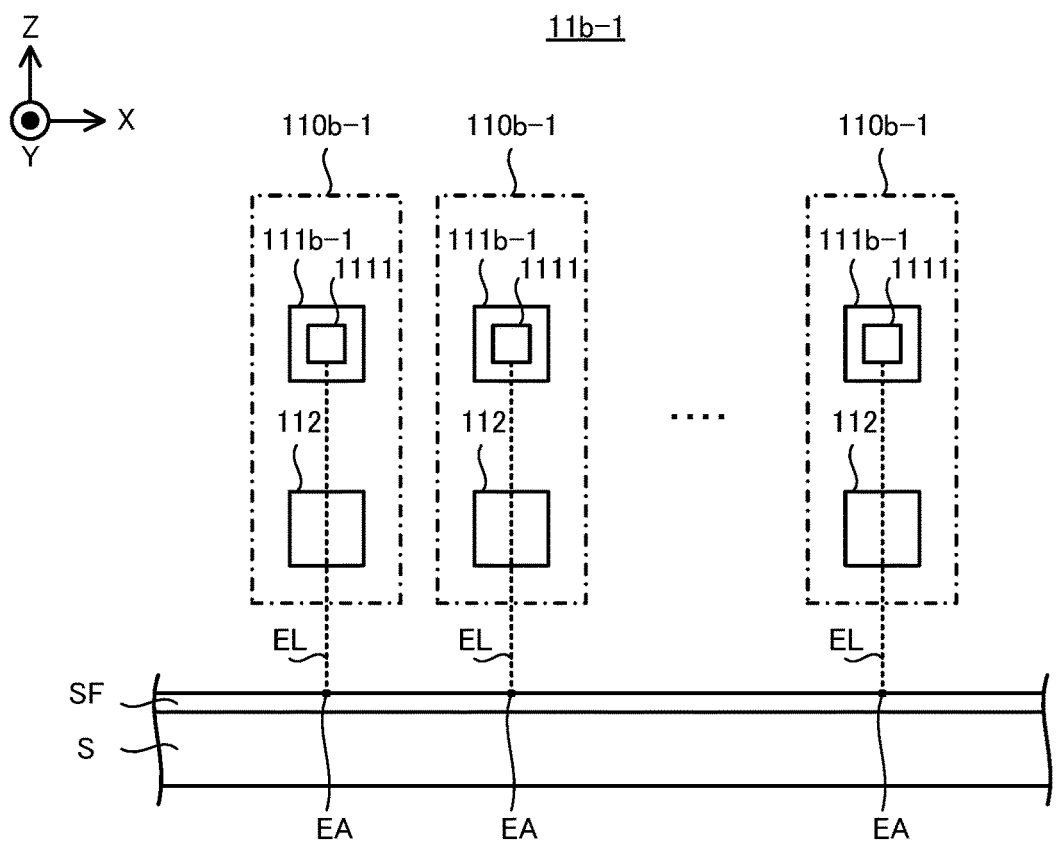

FIG. 27 is a cross-sectional view that schematically illustrates the light irradiation apparatus that is configured to adjust light concentration positions of a plurality of processing lights individually.

Figure 28:
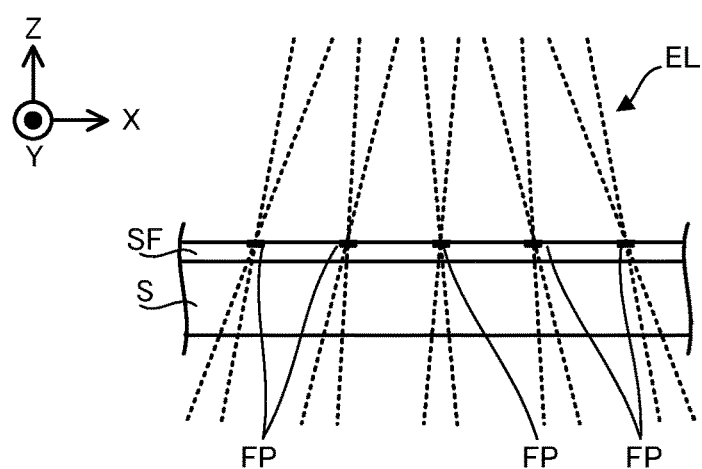

FIG. 28 is a cross-sectional view that illustrates an aspect of an irradiation of the plurality of processing lights when the optical system is an optical system that is not telecentric at the coat of paint side.

Figure 29A:
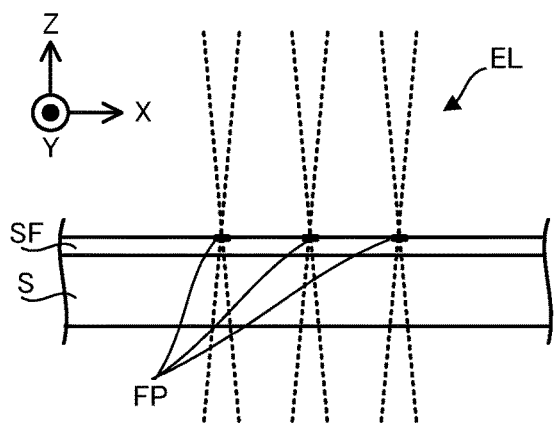
Figure 29B:
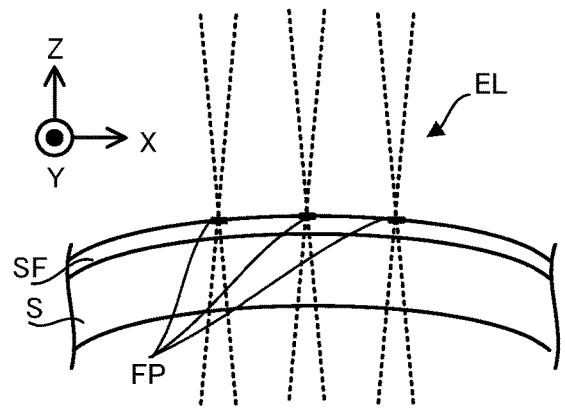
Figure 29C:
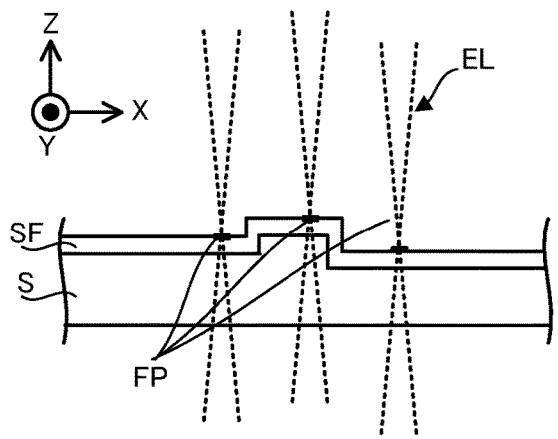
Figure 29D:
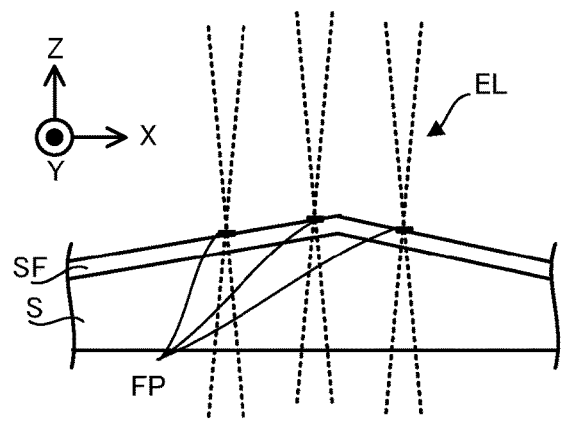

FIG. 29A is a cross-sectional view that illustrates an aspect in which the light concentration positions of the plurality of processing lights are located at the surface of the coat of paint when the surface of the coat of paint is a flat surface, FIG. 29B is a cross-sectional view that illustrates an aspect in which the light concentration positions of the plurality of processing lights are located at the surface of the coat of paint when the surface of the coat of paint is a curved surface, FIG. 29C is a cross-sectional view that illustrates an aspect in which the light concentration positions of the plurality of processing lights are located at the surface of the coat of paint when there is a concavity and/or convexity at the surface of the coat of paint and FIG. 29D is a cross-sectional view that illustrates an aspect in which the light concentration positions of the plurality of processing lights are located at the surface of the coat of paint when the surface of the coat of paint is inclined with respect to the optical axis of the optical system.

Figure 30A:
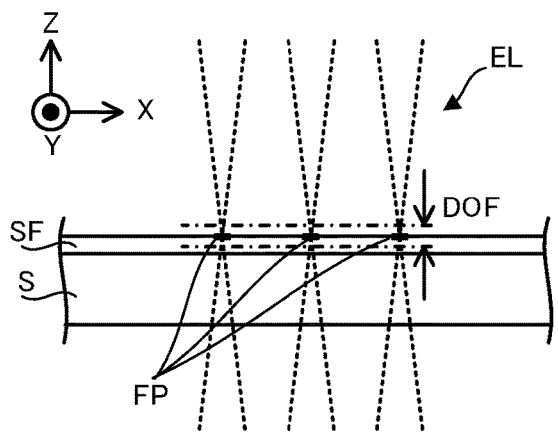
Figure 30B:
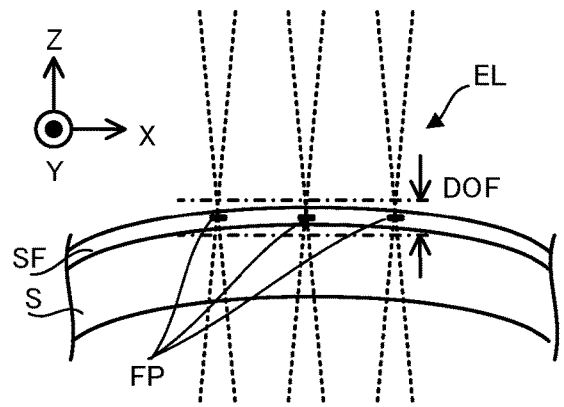
Figure 30C:
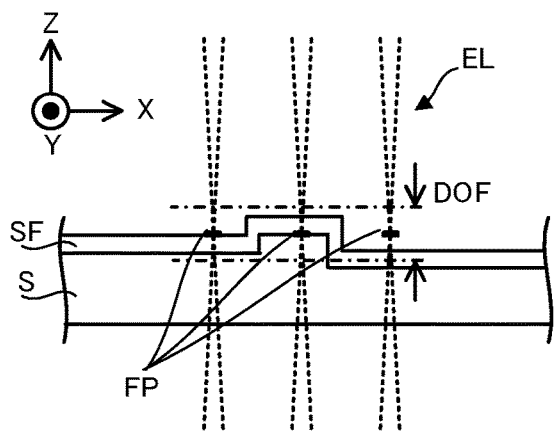
Figure 30D:
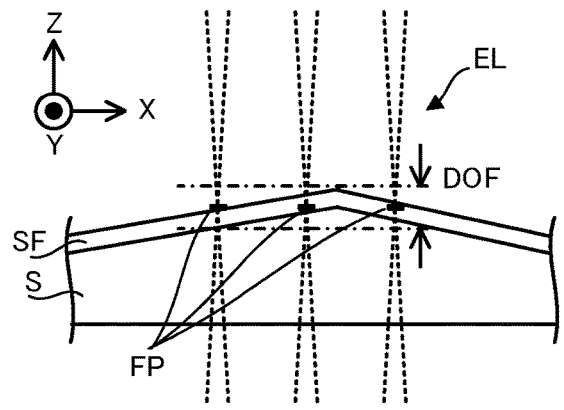

FIG. 30A is a cross-sectional view that illustrates the range of the depth of focus of the optical system that is set to include the surface of the coat of paint when the surface of the coat of paint is a flat surface, FIG. 30B is a cross-sectional view that illustrates the range of the depth of focus of the optical system that is set to include the surface of the coat of paint when the surface of the coat of paint is a curved surface, FIG. 30C is a cross-sectional view that illustrates the range of the depth of focus of the optical system that is set to include the surface of the coat of paint when there is a concavity and/or convexity at the surface of the coat of paint and FIG. 30D is a cross-sectional view that illustrates the range of the depth of focus of the optical system that is set to include the surface of the coat of paint when the surface of the coat of paint is inclined with respect to the optical axis of the optical system.

Figure 31A:
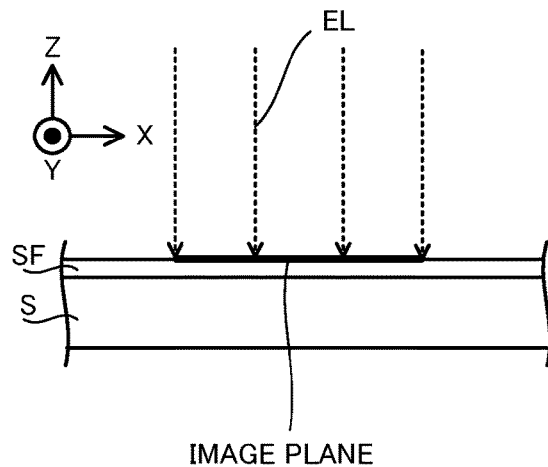
Figure 31B:
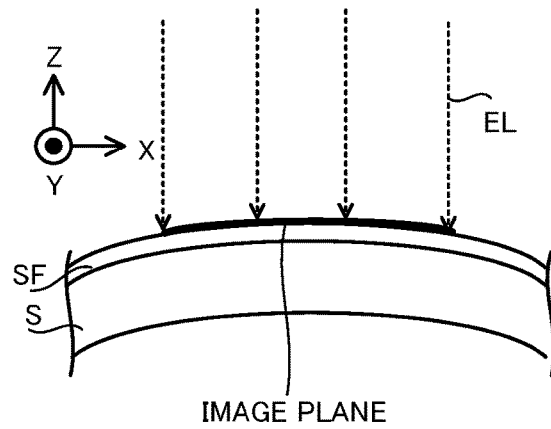
Figure 31C:
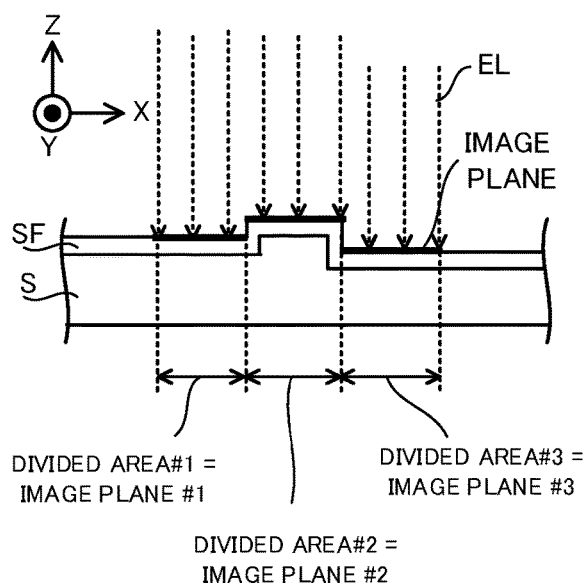
Figure 31D:
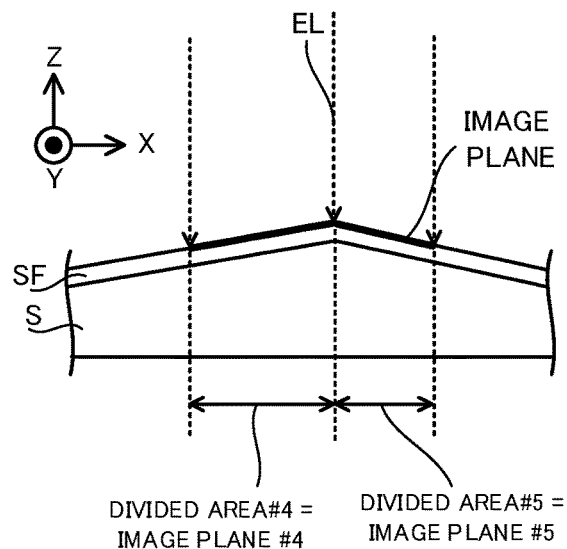

FIG. 31A is a cross-sectional view that illustrates an image plane that is set to be coincident with the surface of the coat of paint when the surface of the coat of paint is a flat surface, FIG. 31B is a cross-sectional view that illustrates an image plane that is set to be coincident with the surface of the coat SF of paint when the surface of the coat of paint is a curved surface, FIG. 31C is a cross-sectional view that illustrates an image plane that is set to be coincident with the surface of the coat SF of paint when there is a concavity and/or convexity at the surface of the coat of paint and FIG. 31D is a cross-sectional view that illustrates an image plane that is set to be coincident with the surface of the coat SF of paint when the surface of the coat of paint is inclined with respect to the optical axis of the optical system.

Figure 32A:
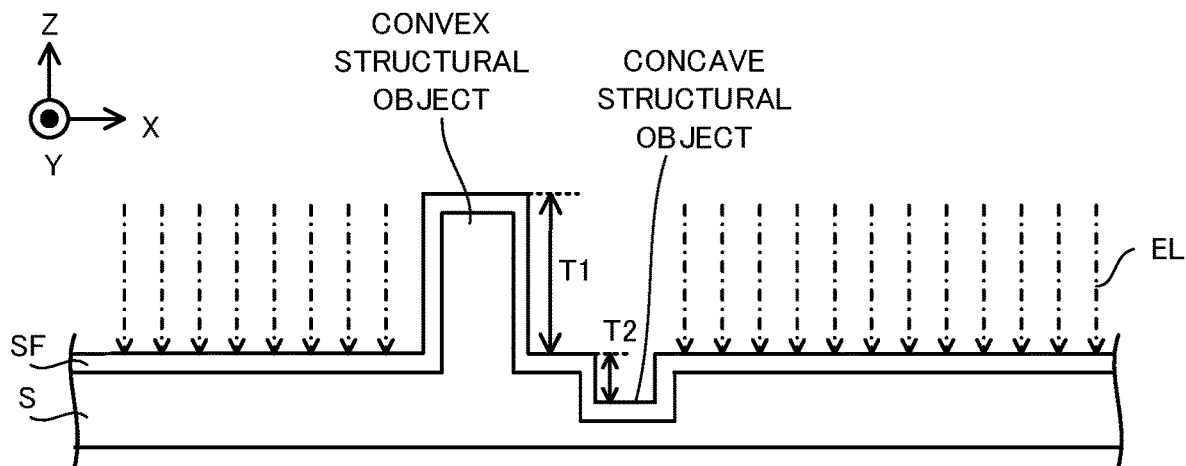
Figure 32B:
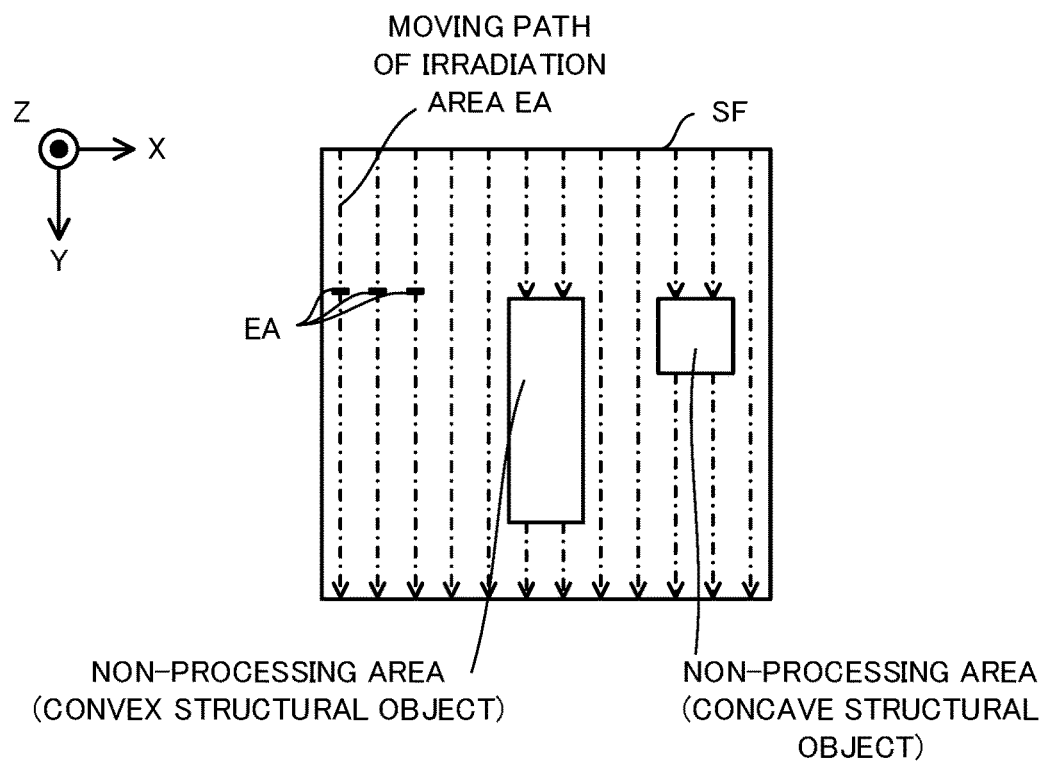

FIG. 32A is a cross-sectional view that illustrates a non-processing area and FIG. 32B is a plan view that illustrates the non-processing area.

Figure 33A:
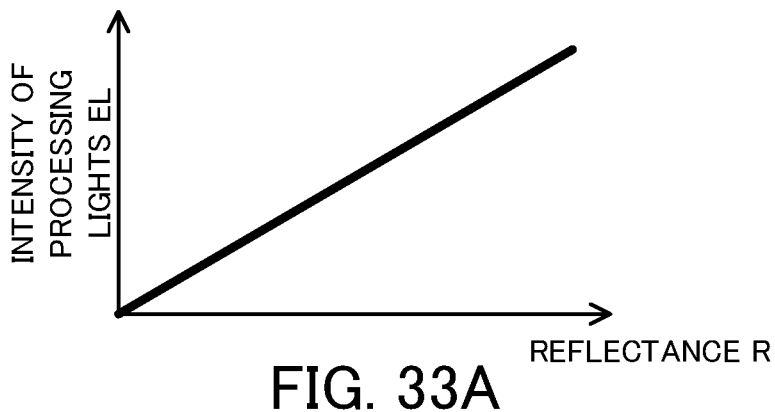
Figure 33B:
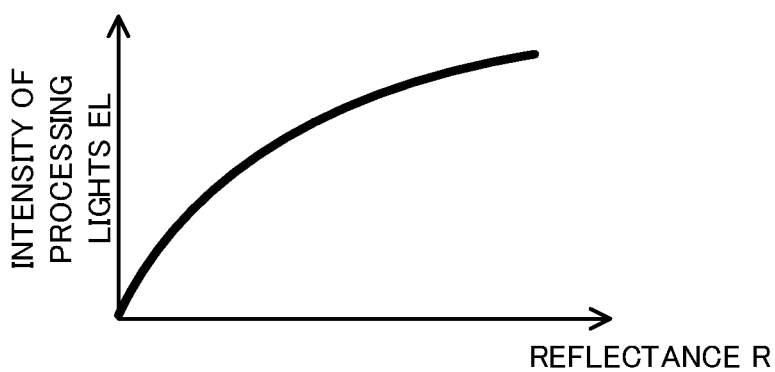
Figure 33C:
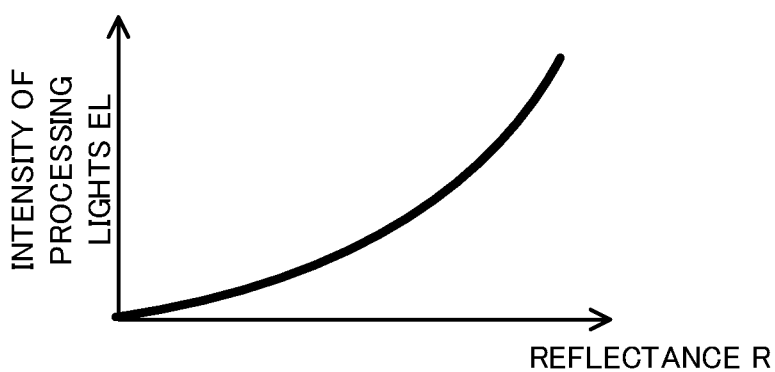

Each of FIG. 33A to FIG. 33C is a graph that illustrates a relationship between a reflectance of the coat of paint to the processing light and an intensity of the processing light that is set by a control apparatus.

Figure 34A:
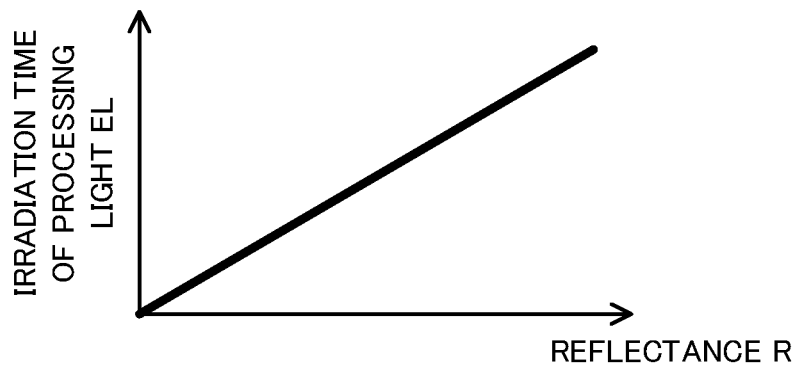
Figure 34B:
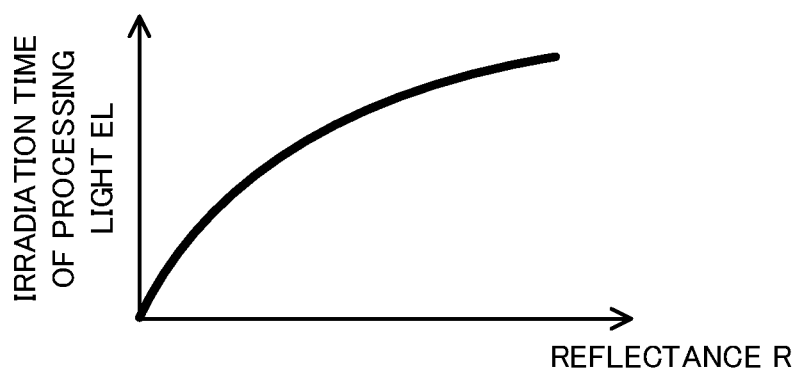
Figure 34C:
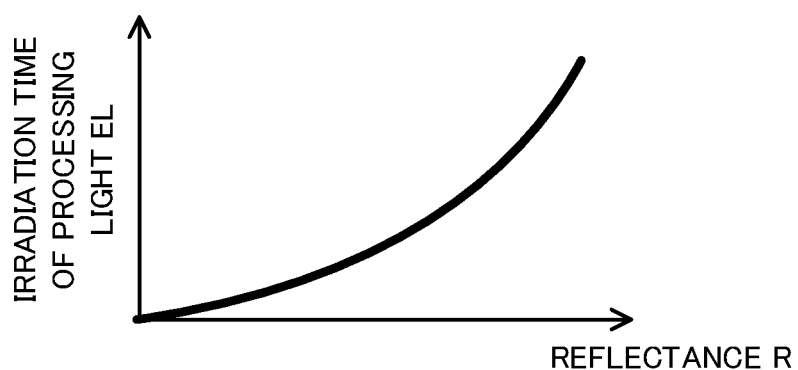

Each of FIG. 34A to FIG. 34C is a graph that illustrates a relationship between the reflectance of the coat of paint to the processing light and an irradiation time of the processing light that is set by a control apparatus.

Figure 35:
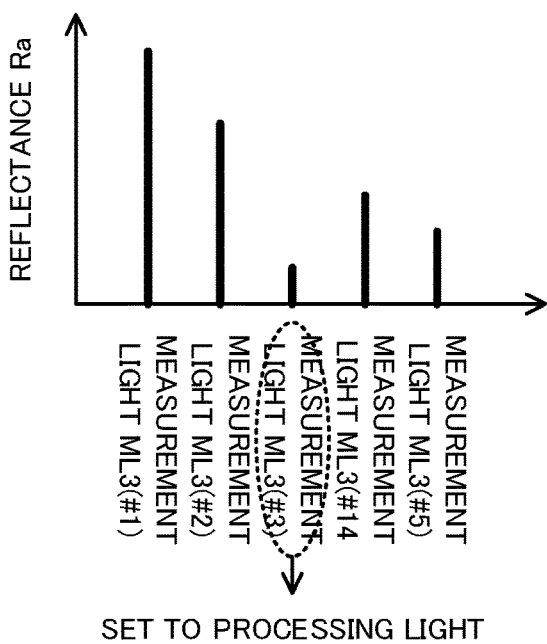

FIG. 35 is a graph that illustrates the reflectance of the coat of paint to a plurality of measurement light having different wavelengths, respectively.

Figure 36:
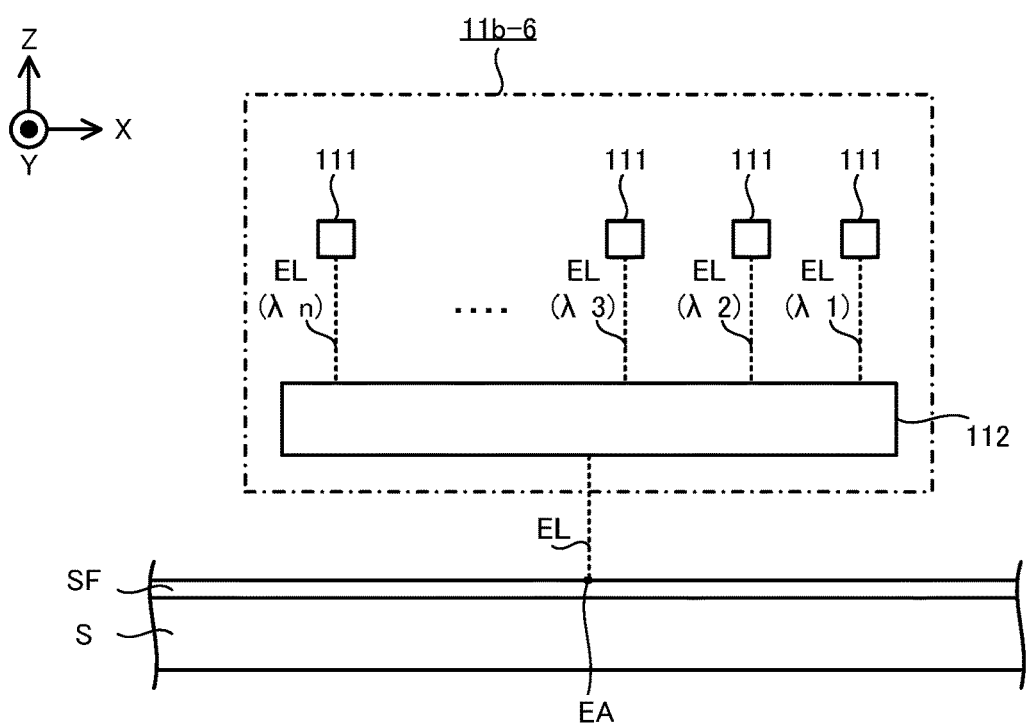

FIG. 36 is a cross-sectional view that schematically illustrates a light irradiation apparatus having a plurality of light source systems.

Figure 37:
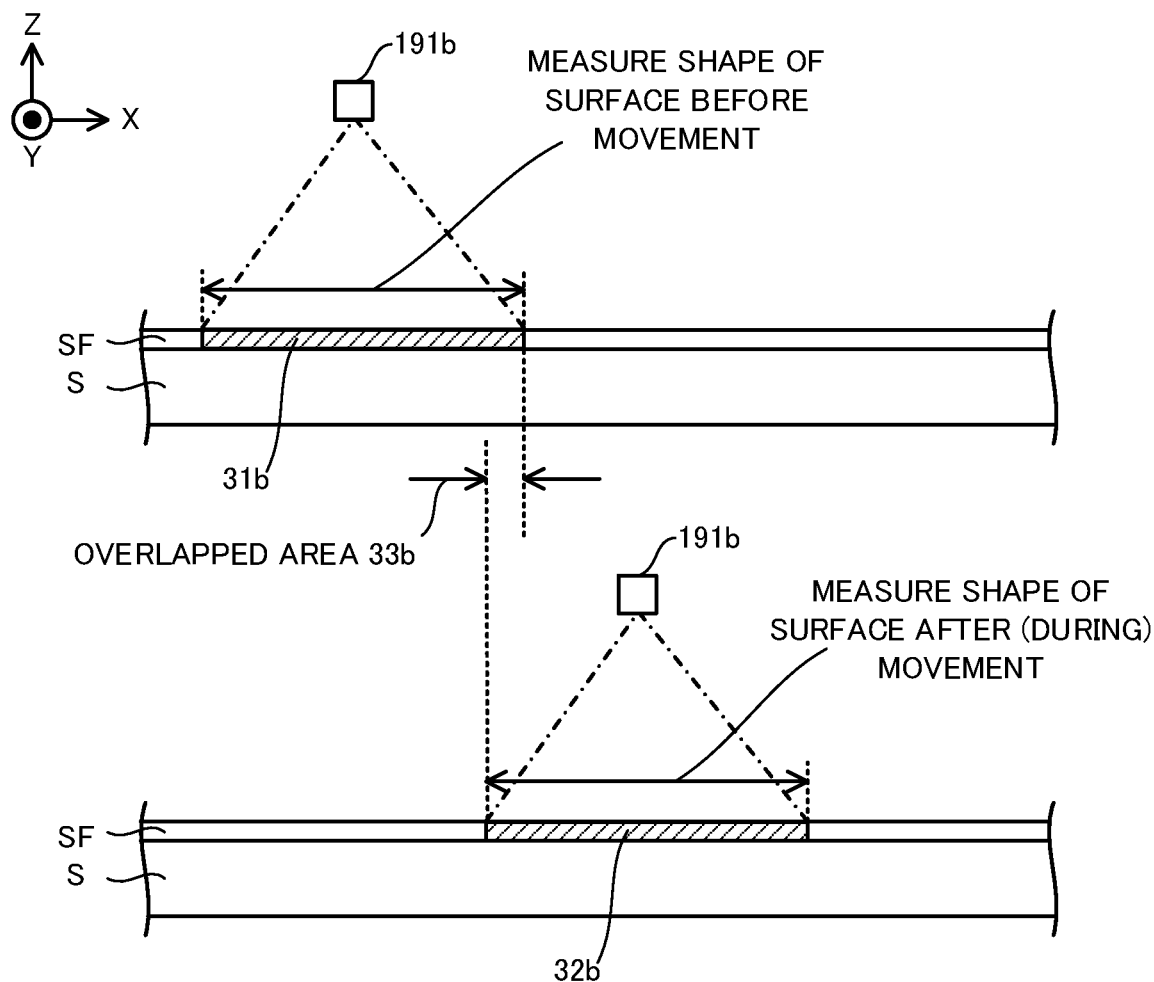

FIG. 37 is a cross-sectional view that illustrates a range at which a surface characteristic measurement apparatus measures a shape of the surface of the coat of paint when the light irradiation apparatus moves relative to the coat SF of paint.

Figure 38:
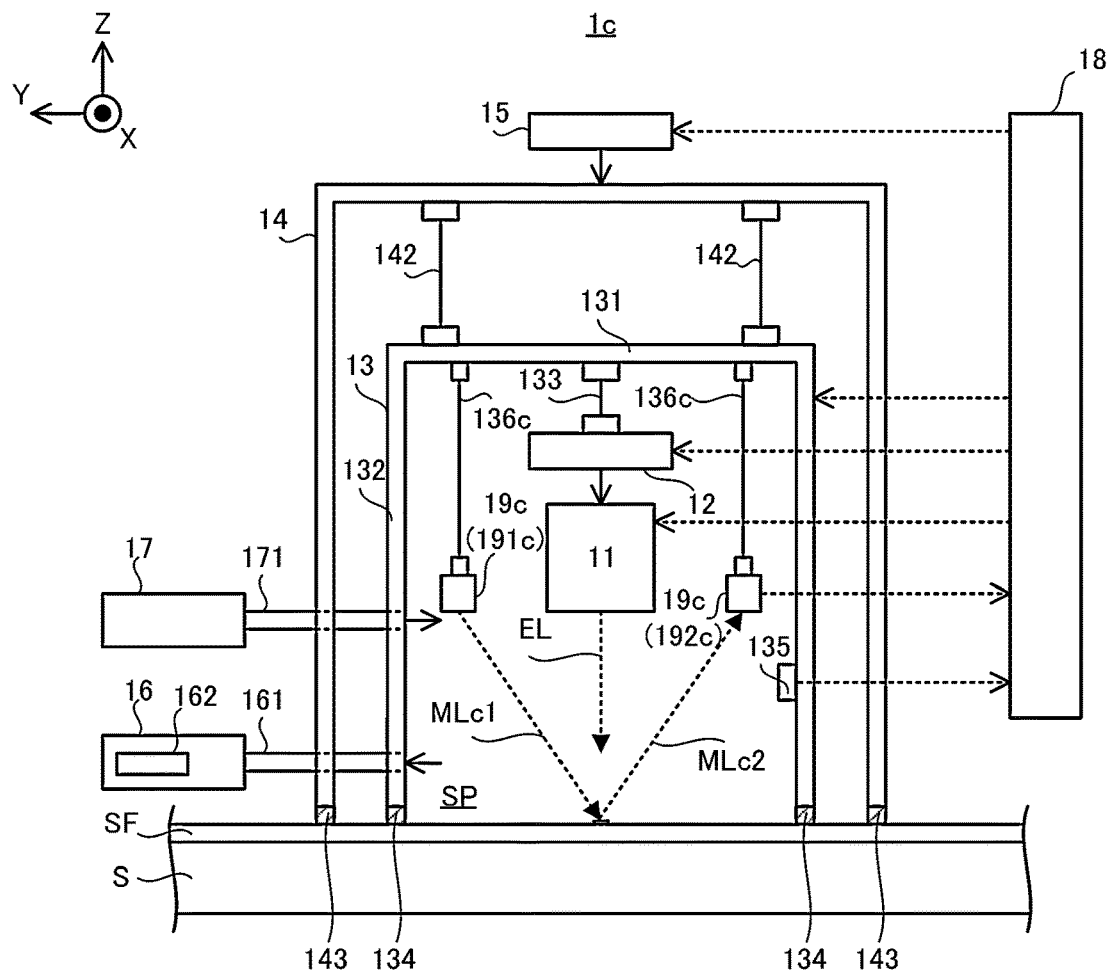

FIG. 38 is a cross-sectional view that schematically illustrates an entire structure of a processing apparatus in a third modified example.

Figure 39:
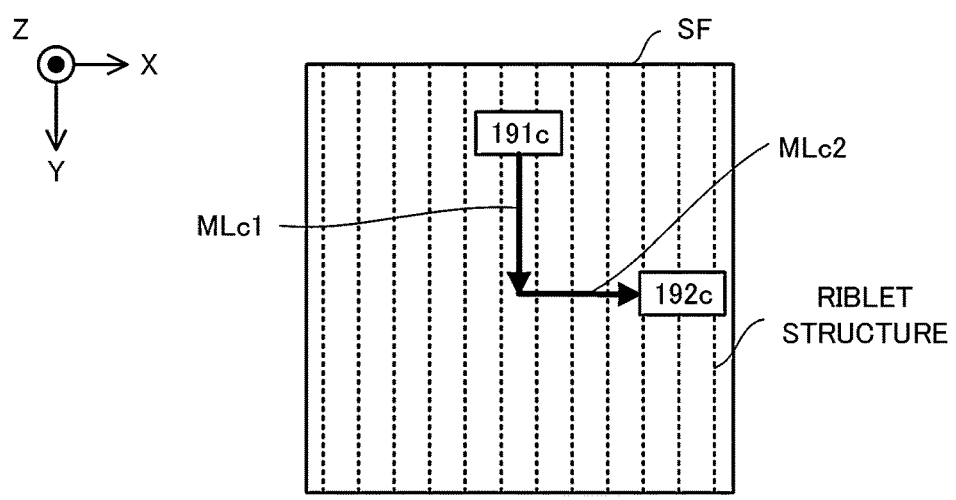

FIG. 39 is a plan view that illustrates a positional relationship between a projection apparatus of a structure measurement apparatus and a detection apparatus.

Figure 40:
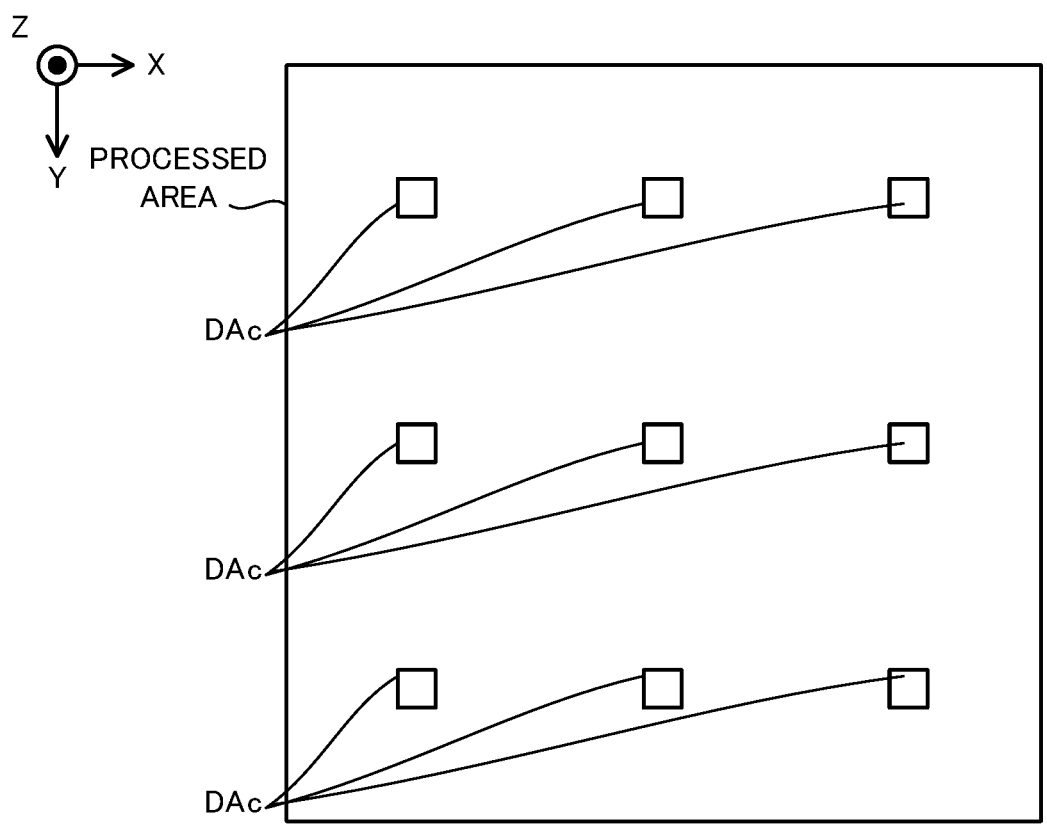

FIG. 40 is a plan view that illustrates a sample area at which the structure measurement apparatus measures a characteristic of the riblet structure.

Figure 41A:
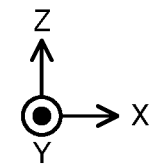
Figure 41A:
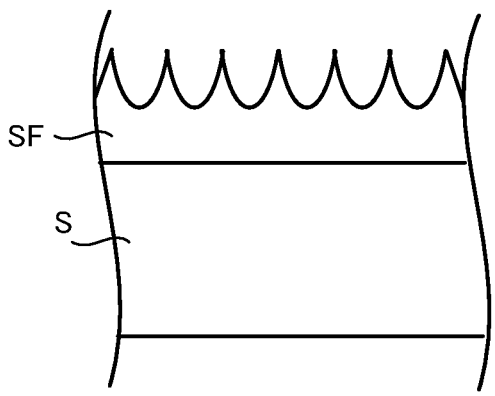
Figure 41B:
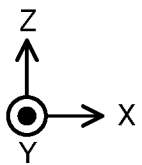
Figure 41B:
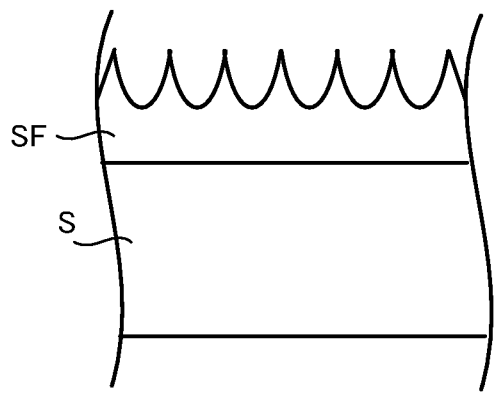
Figure 41C:
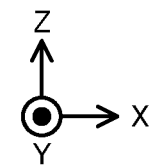
Figure 41C:
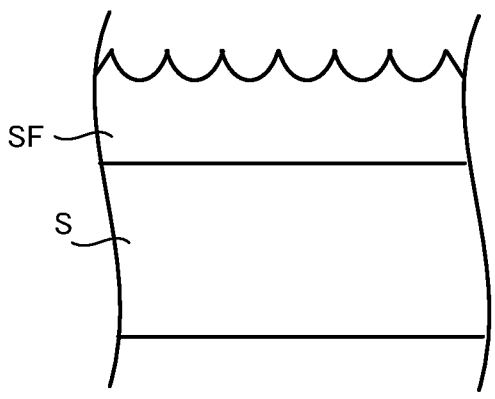
Figure 41D:
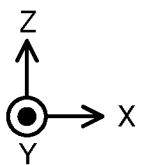
Figure 41D:
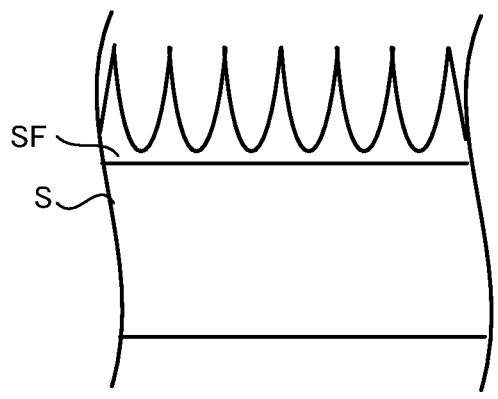

FIG. 41A is a cross-sectional view that illustrates an ideal riblet structure which the processing apparatus should form, FIG. 41B is a cross-sectional view that illustrates a riblet structure a size of which is same as a size of the ideal riblet structure, FIG. 41C is a cross-sectional view that illustrates a riblet structure a size of which is smaller than the size of the ideal riblet structure and FIG. 41D is a cross-sectional view that illustrates a riblet structure a size of which is larger than the size of the ideal riblet structure.

Figure 42A:
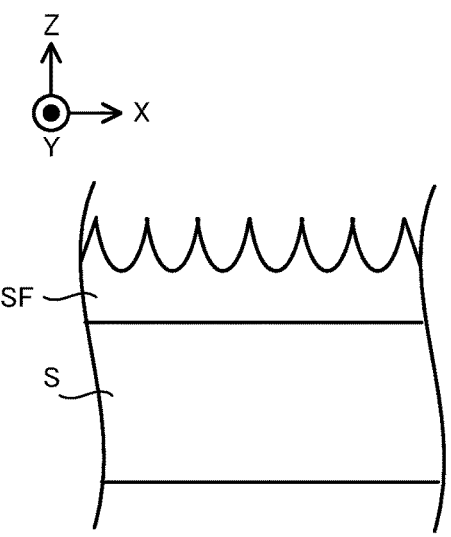
Figure 42B:
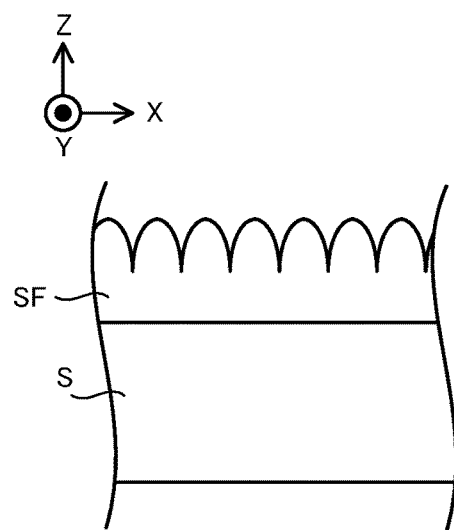

FIG. 42A is a cross-sectional view that illustrates a riblet structure a shape of which is same as a shape of the ideal riblet structure and FIG. 42B is a cross-sectional view that illustrates a riblet structure a shape of which is different from the shape of the ideal riblet structure.

Figure 43:
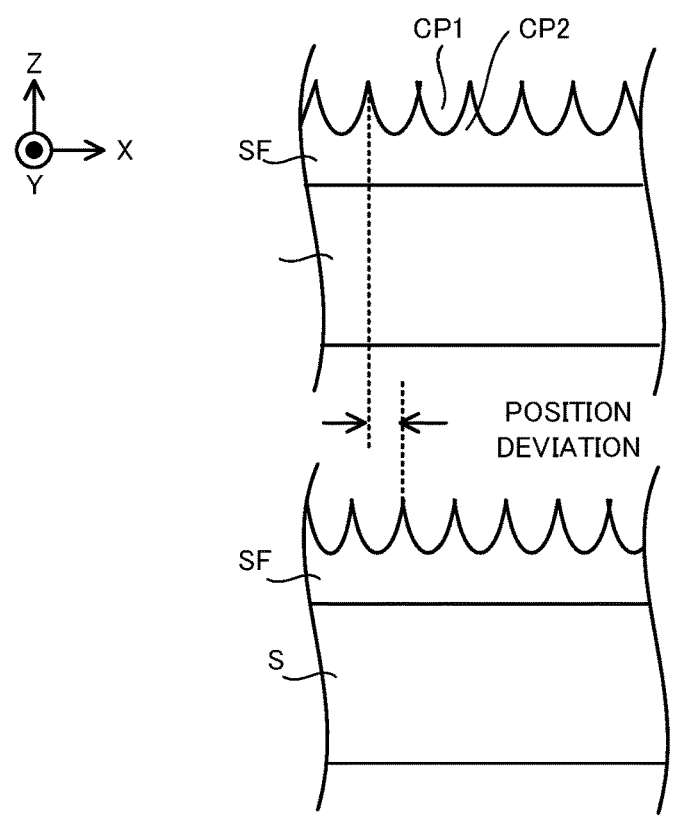

FIG. 43 (upper part) is a cross-sectional view that illustrates a riblet structure including a concave structure at a position that is same as a position of the concave structure constituting the ideal riblet structure and FIG. 43 (lower part) is a cross-sectional view that illustrates a riblet structure including the concave structure at a position that is different from the position of the concave structure constituting the ideal riblet structure.

Figure 44A:
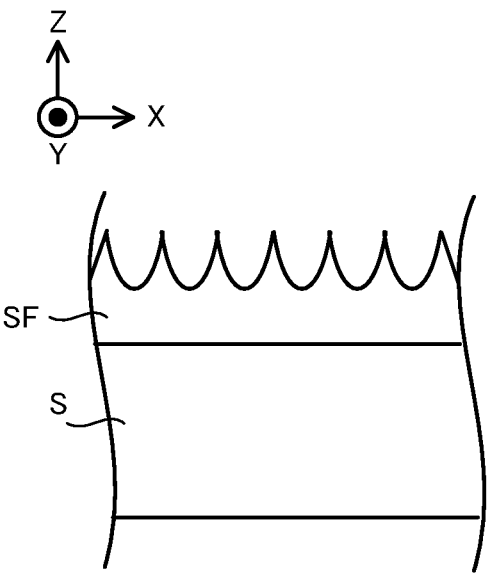
Figure 44B:
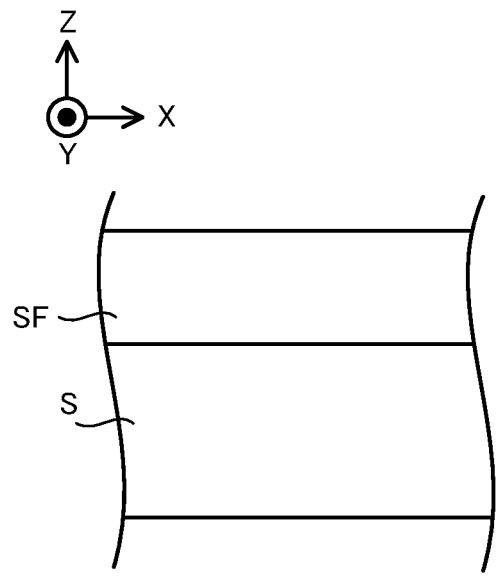

FIG. 44A is a cross-sectional view that illustrates the sample area in which the riblet structure is formed and FIG. 44B is a cross-sectional view that illustrates the sample area in which the riblet structure is not formed.

Figure 45A:
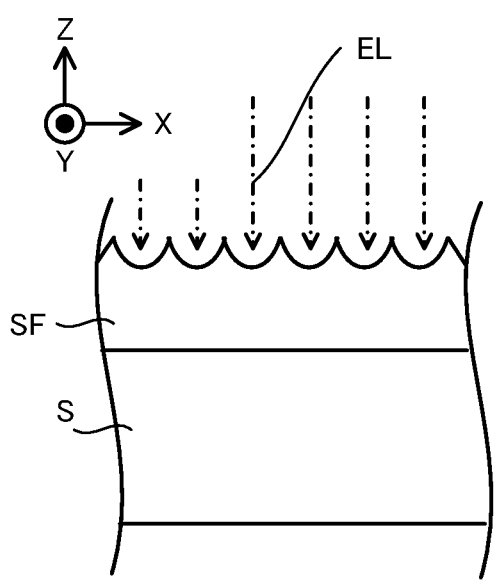
Figure 45B:
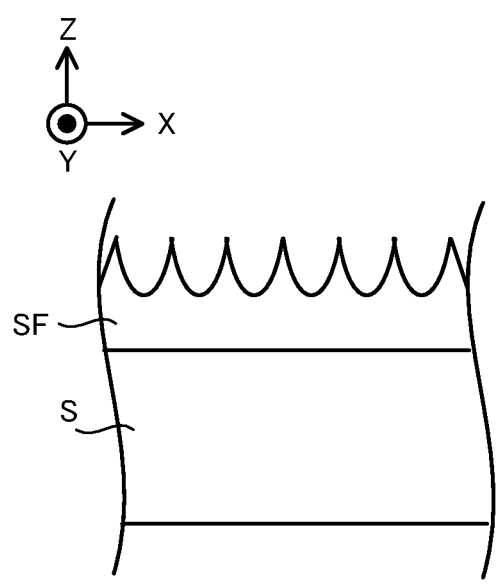

FIG. 45A is a cross-sectional view that illustrates an aspect in which the riblet structure having a size smaller than an ideal size is irradiated with the processing light for modifying the riblet structure and FIG. 45B is a cross-sectional view that illustrates the modified riblet structure.

Figure 46:
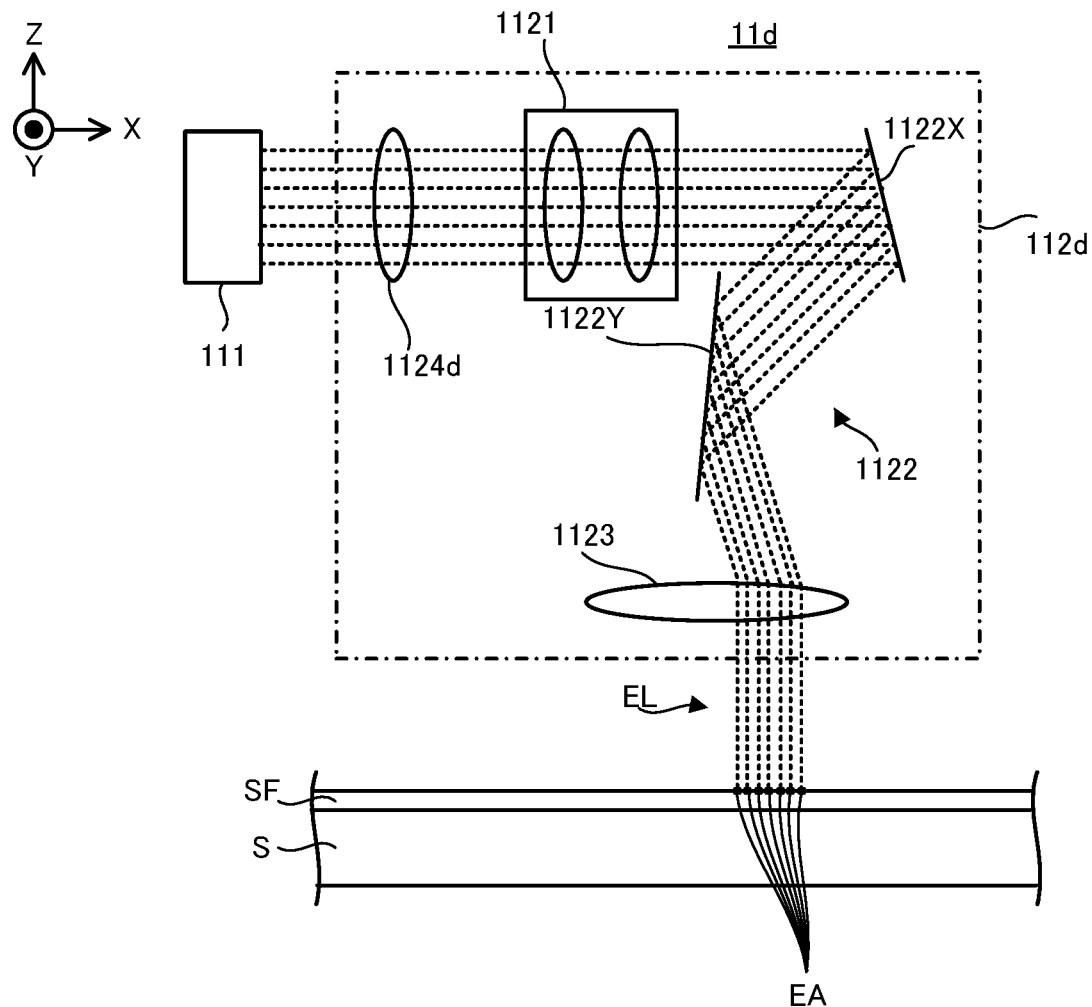

FIG. 46 is a cross-sectional view that schematically illustrates a structure of a light irradiation apparatus of a processing apparatus in a fourth modified example.

FIG. 47A and FIG. 47B are plan views that illustrate plurality of irradiation areas having different arrangement pitches, respectively, and FIG. 47C and FIG. 47D are cross-sectional views that illustrate the riblet structures formed by irradiating the plurality of irradiation areas illustrated in FIG. 47A and FIG. 47B with the plurality of processing lights, respectively.

Figure 48A:
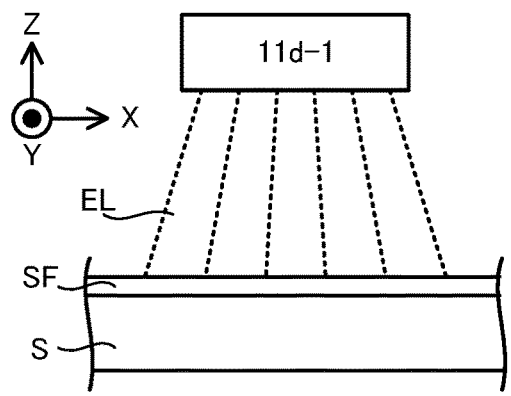
Figure 48B:
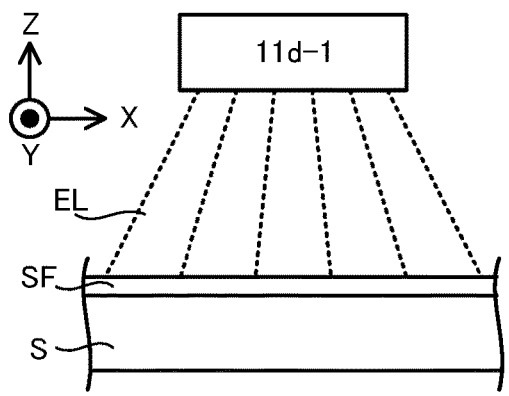
Figure 48C:
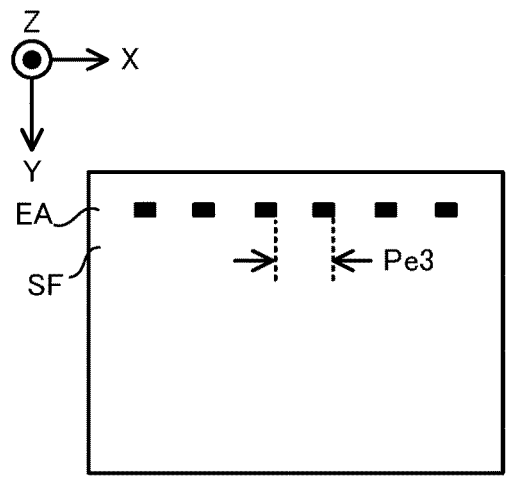
Figure 48D:
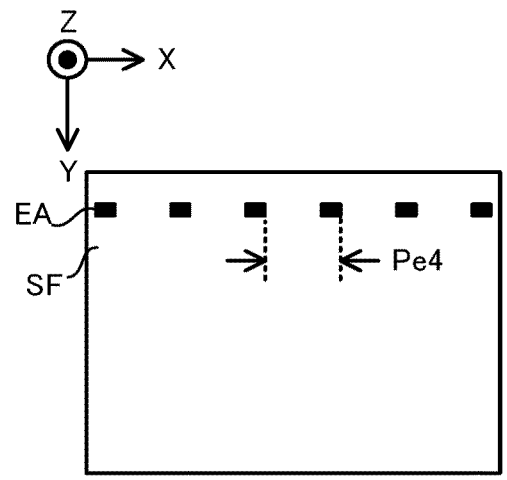

FIG. 48A and FIG. 48B are plan views that illustrate the plurality of processing lights having different relative angles, respectively, and FIG. 48C and FIG. 48D are plan views that illustrate the plurality of irradiation areas that are irradiated with the plurality of processing lights illustrated in FIG. 48A and FIG. 48B, respectively.

Figure 49A:
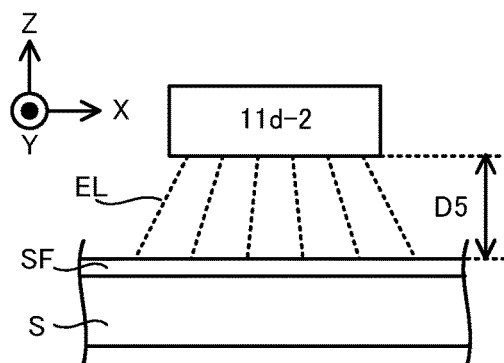
Figure 49B:
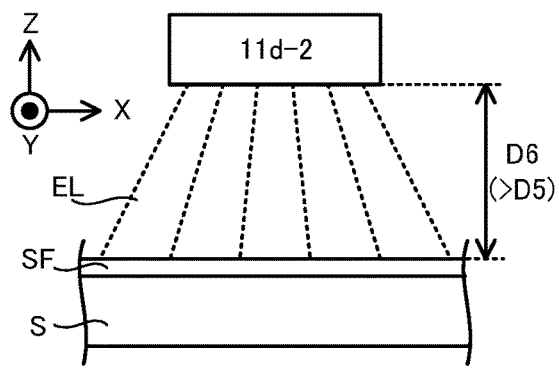
Figure 49C:
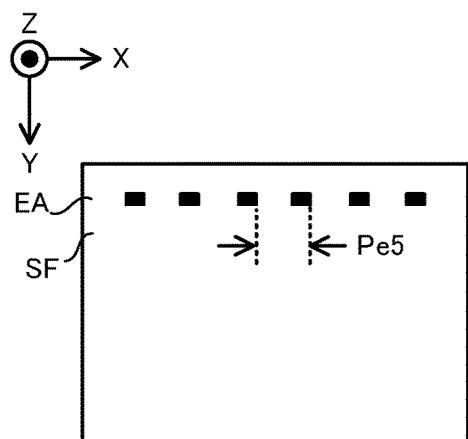
Figure 49D:
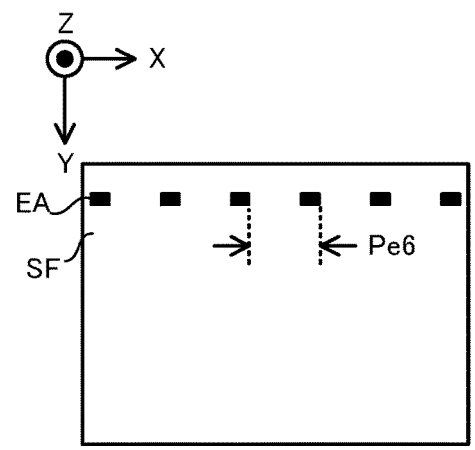

FIG. 49A and FIG. 49B are plan views that illustrate the plurality of processing lights irradiated by the light irradiation apparatuses between which distances from the coat SF of paint are different, respectively, and FIG. 49C and FIG. 49D are plan views that illustrate the plurality of irradiation areas that are irradiated with the plurality of processing lights illustrated in FIG. 49A and FIG. 49B, respectively.

Figure 50A:
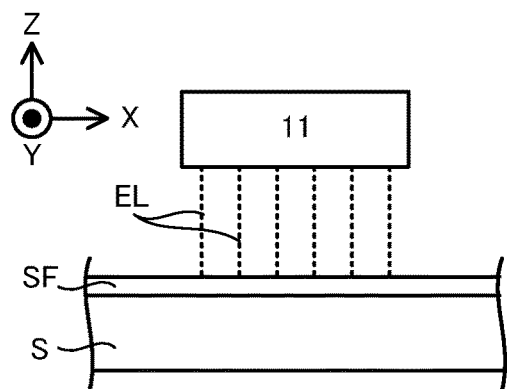
Figure 50C:
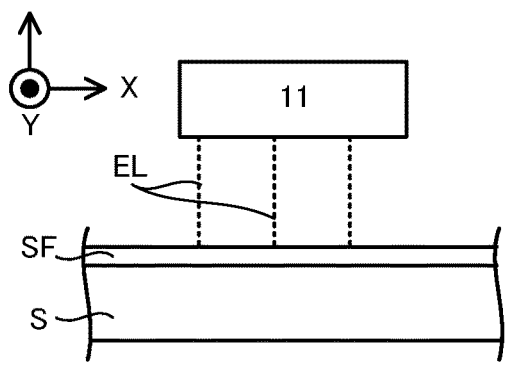
Figure 50B:
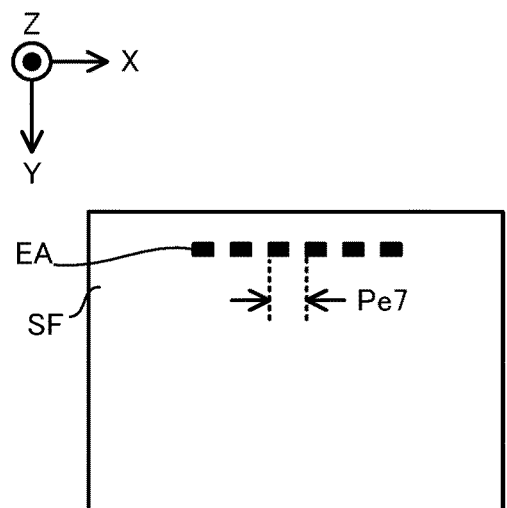
Figure 50D:
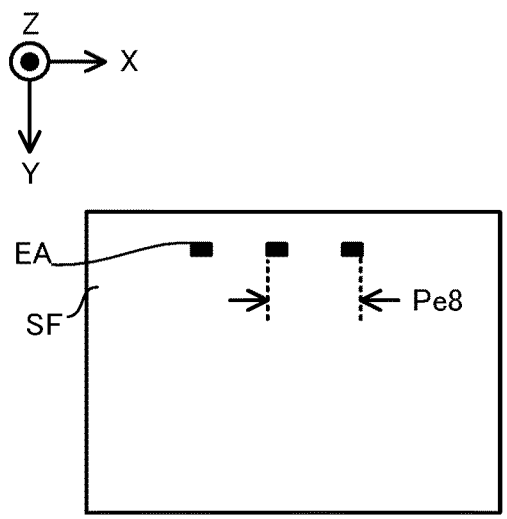

FIG. 50A and FIG. 50C are plan views that illustrate the plurality of processing lights irradiated by the light irradiation apparatuses between which the number of the light source for irradiating with the processing light are different from each other, respectively, and FIG. 50B and FIG. 50D are plan views that illustrate the plurality of irradiation areas that are irradiated with the plurality of processing lights illustrated in FIG. 50A and FIG. 50C, respectively.

Figure 51A:
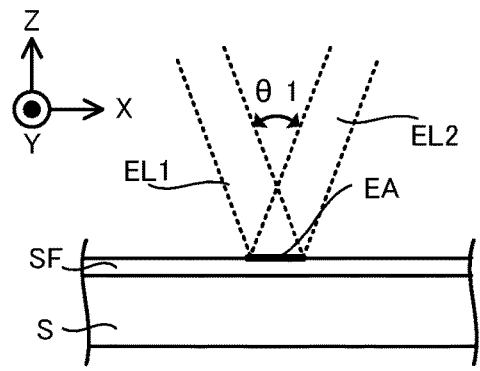
Figure 51C:
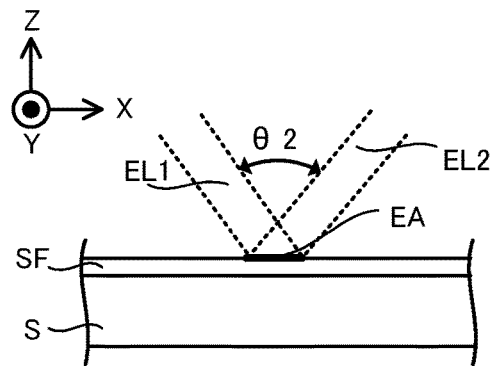
Figure 51B:
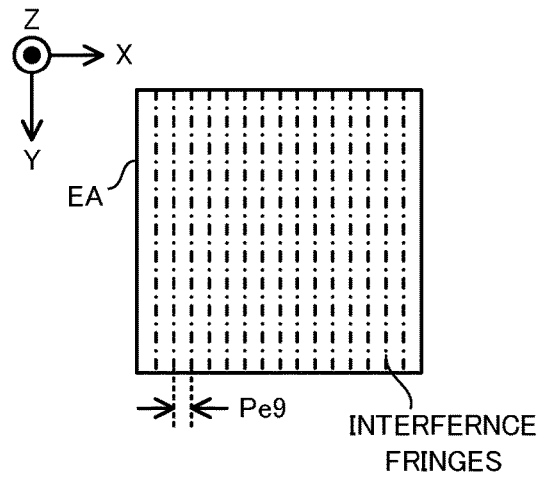
Figure 51D:
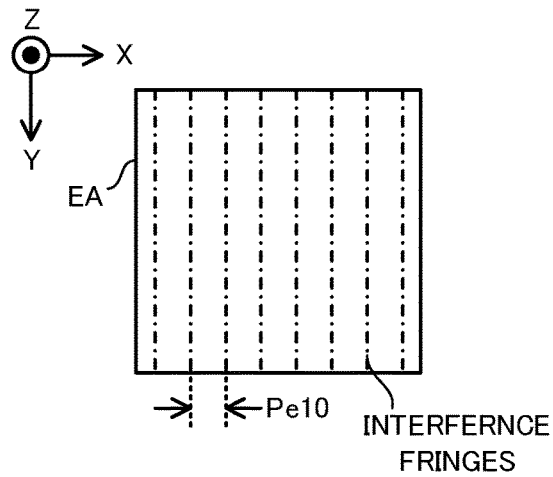

FIG. 51A and FIG. 51C are plan views that illustrate first and second divided lights having different intersecting angles, respectively, and FIG. 51B and FIG. 51D are plan views that illustrate interference fringes formed on the surface of the coat of paint by an interference of the first and second divided lights illustrated in FIG. 51A and FIG. 51C, respectively.

Figure 52:
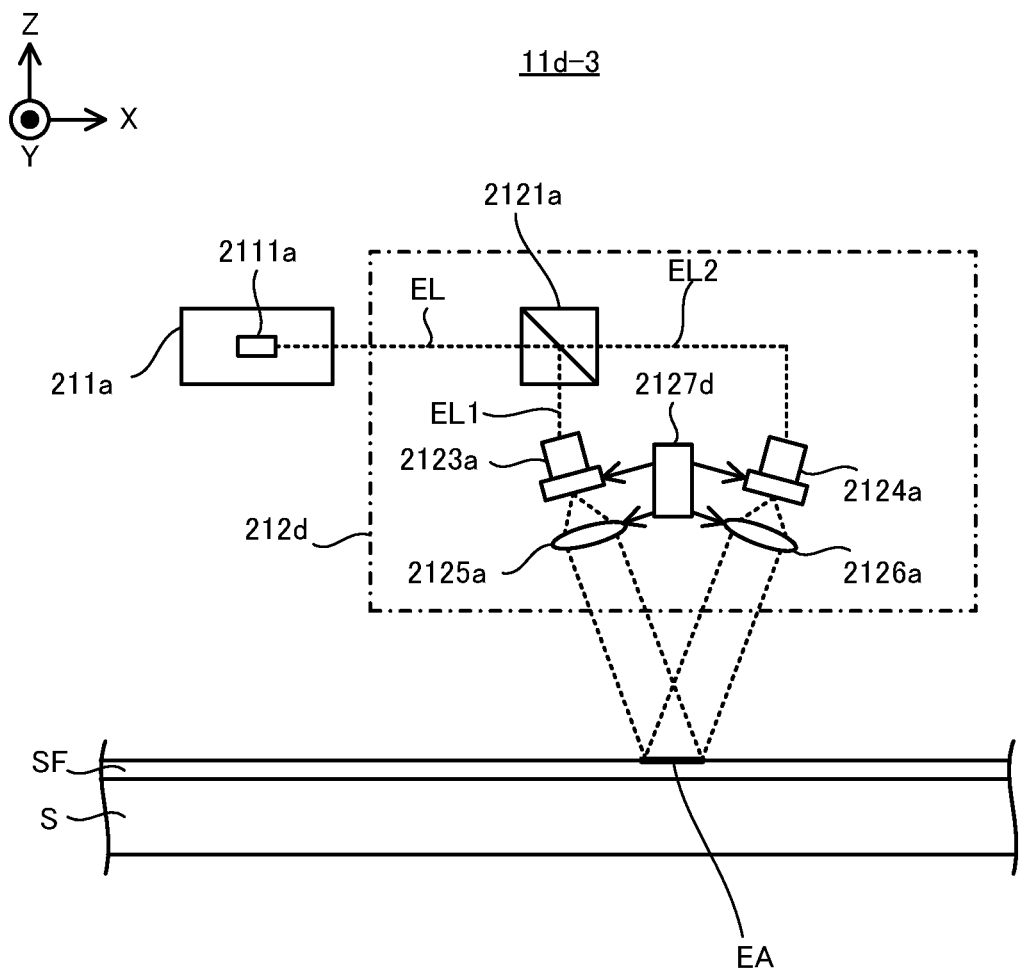

FIG. 52 is a cross-sectional views that illustrates a light irradiation apparatus that is configured to adjust the intersecting angle of the first and second divided light.

Figure 53:
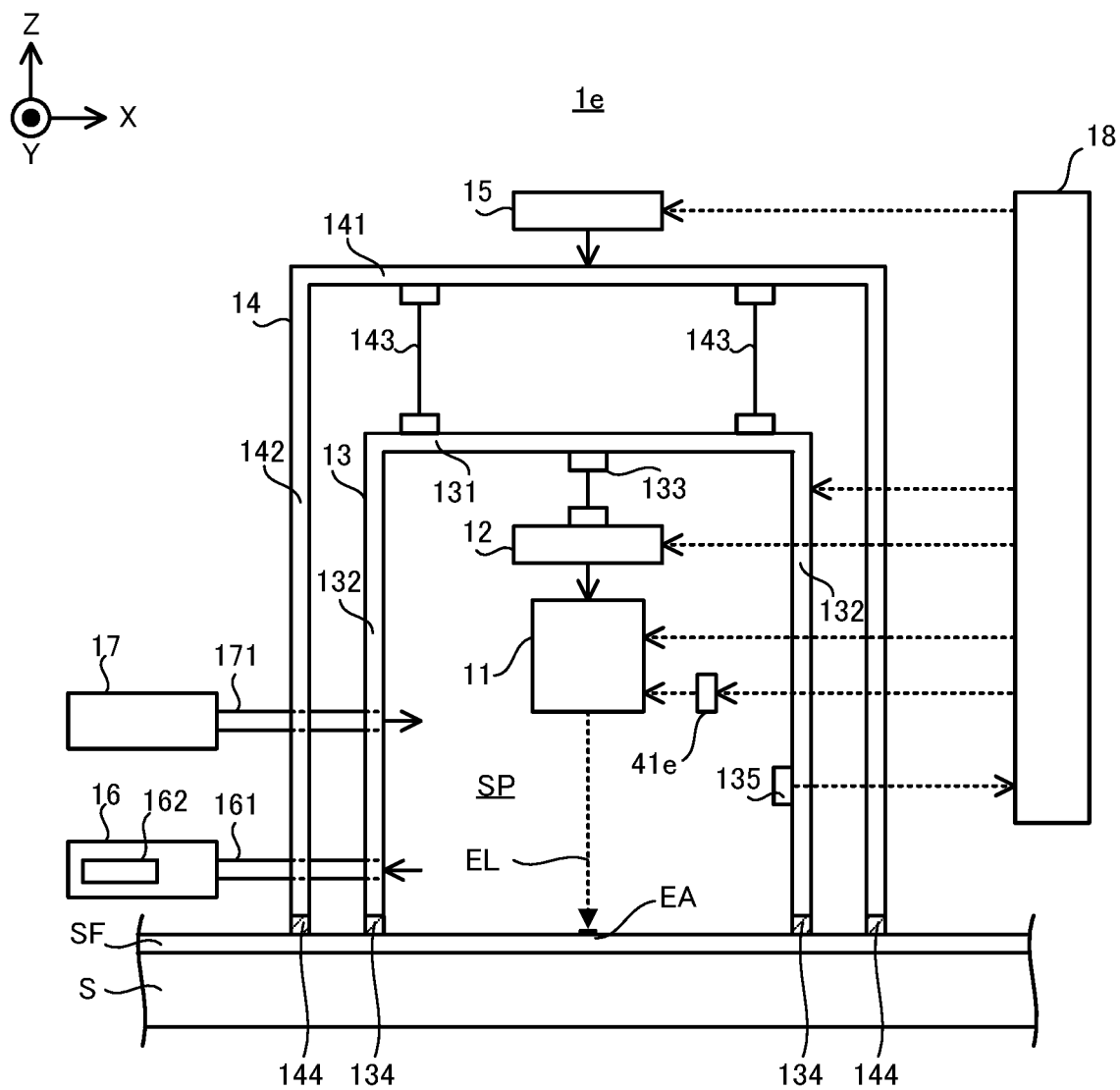

FIG. 53 is a cross-sectional view that schematically illustrates an entire structure of a processing apparatus in a fifth modified example.

Figure 54A:
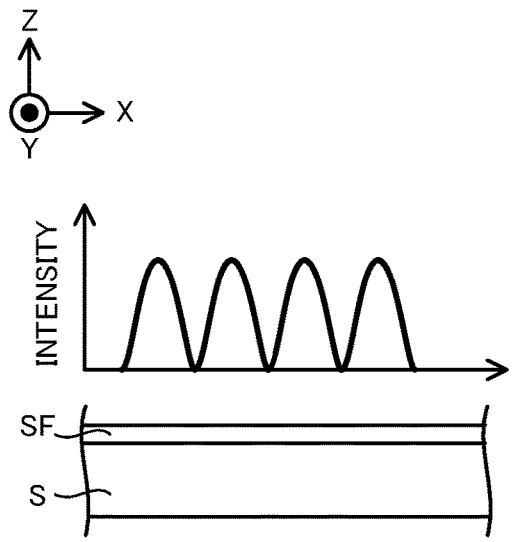
Figure 54C:
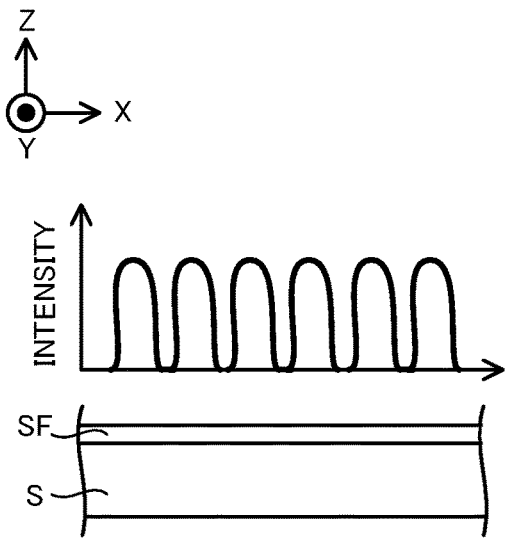
Figure 54B:
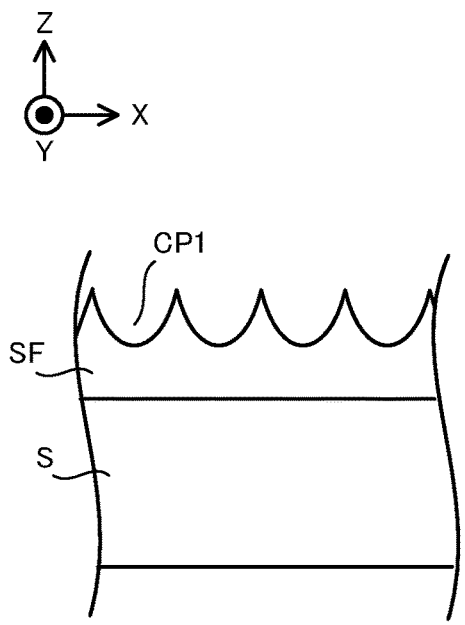
Figure 54D:
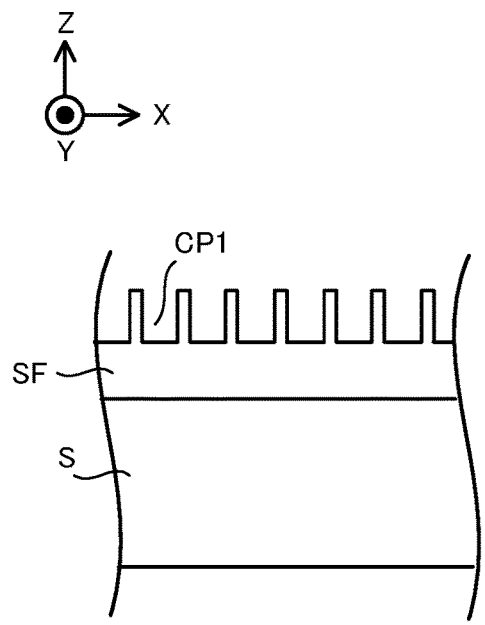

Each of FIG. 54A and FIG. 54C is a plan view that illustrates an intensity distribution on the surface of the coat of paint and FIG. 54B and FIG. 54D are cross-sectional views that illustrate the riblet structure formed by the irradiation of the plurality of processing lights having the intensity distributions illustrated in FIG. 54A and FIG. 54C, respectively.

Figure 55A:
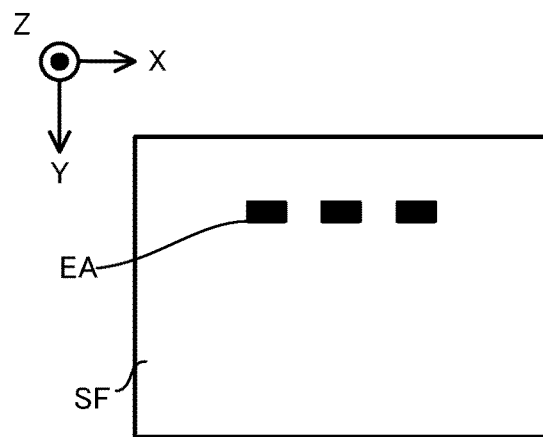
Figure 55C:
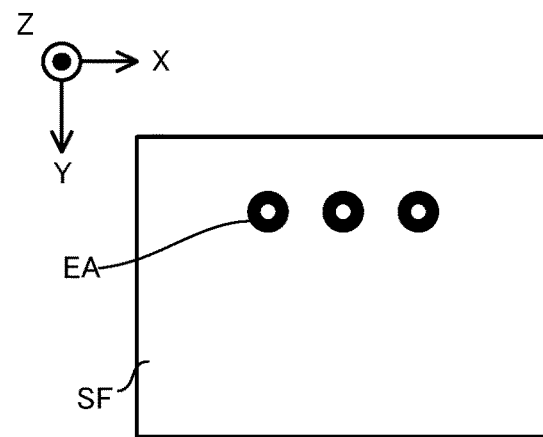
Figure 55B:
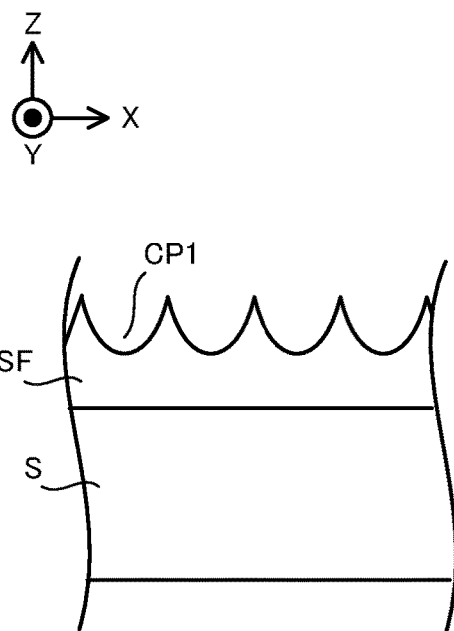
Figure 55D:
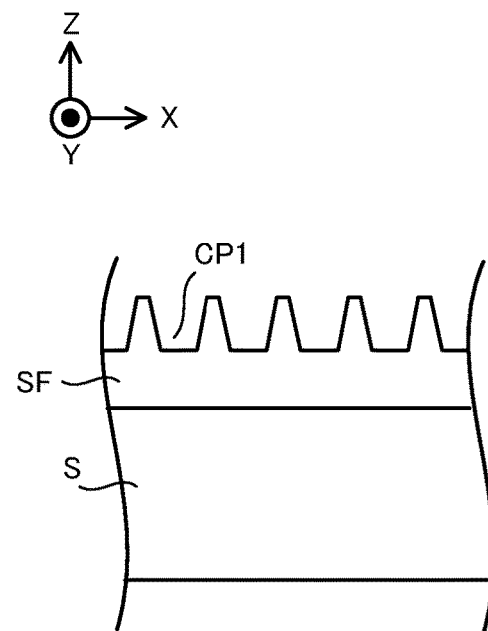

FIG. 55A and FIG. 55C are cross-sectional views that illustrate the plurality of irradiation areas having different shapes, respectively, and FIG. 55B and FIG. 55D are cross-sectional views that illustrate the riblet structures formed by irradiating the plurality of irradiation areas having shapes illustrated in FIG. 55A and FIG. 55C with the plurality of processing lights, respectively.

Figure 56A:
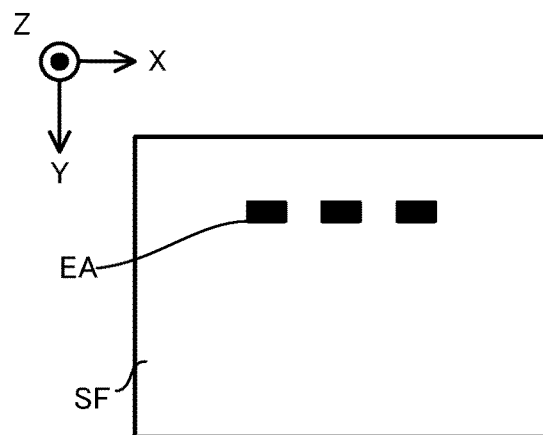
Figure 56C:
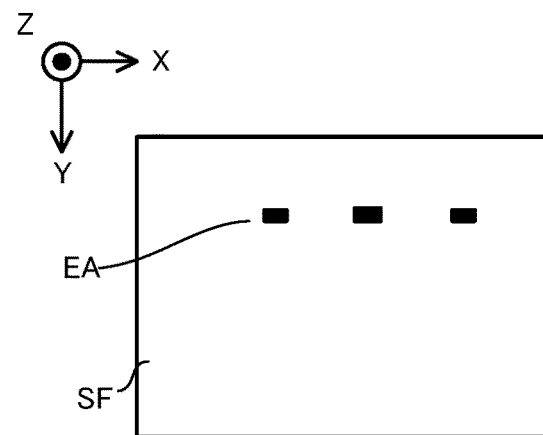
Figure 56B:
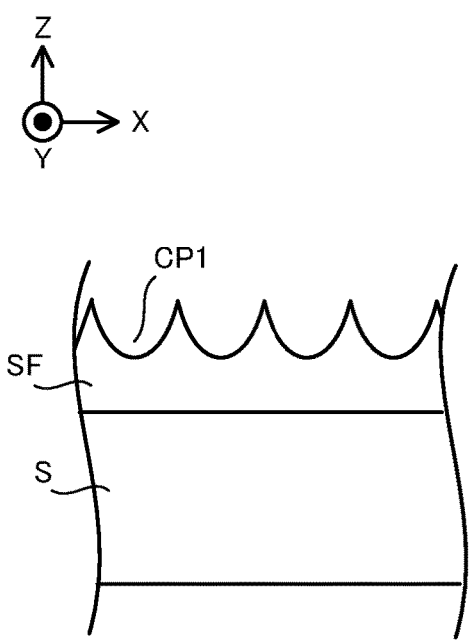
Figure 56D:
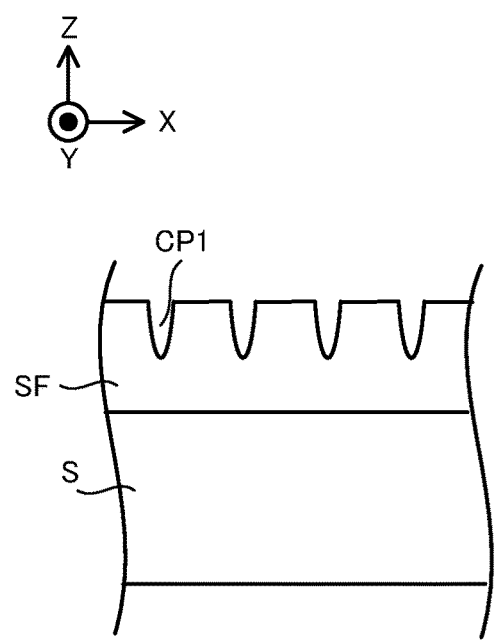

FIG. 56A and FIG. 56C are cross-sectional views that illustrate the plurality of irradiation areas having different sizes, respectively, and FIG. 56B and FIG. 56D are cross-sectional views that illustrate the riblet structures formed by irradiating the plurality of irradiation areas having sizes illustrated in FIG. 56A and FIG. 56C with the plurality of processing lights, respectively.

Figure 57A:
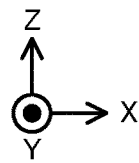
Figure 57A:
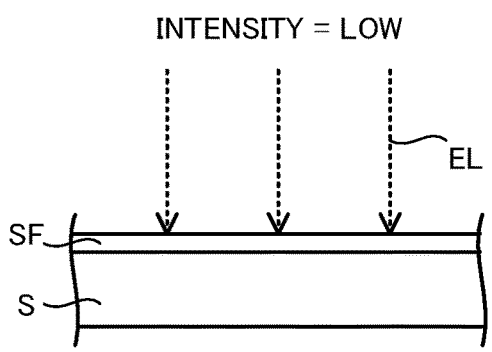
Figure 57C:
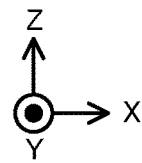
Figure 57C:
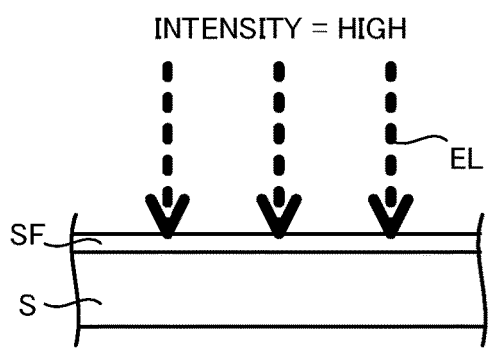
Figure 57B:
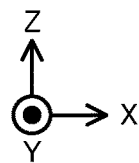
Figure 57B:
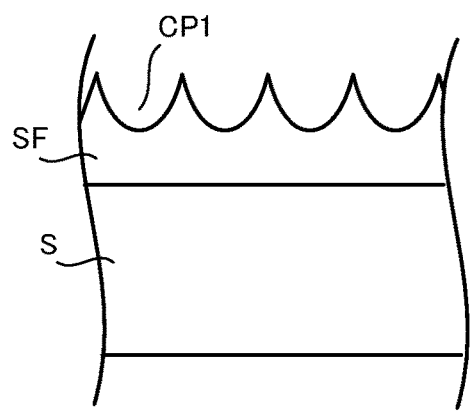
Figure 57D:
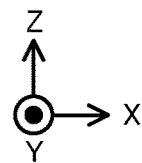
Figure 57D:
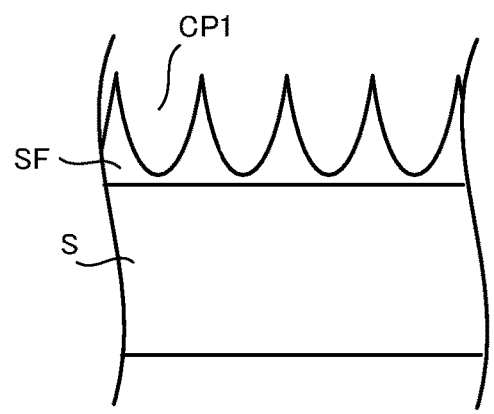

FIG. 57A and FIG. 57C are cross-sectional view that illustrate the plurality of processing lights having different intensities, respectively, and FIG. 57B and FIG. 57D are cross-sectional views that illustrate the riblet structure formed by the irradiation of the plurality of processing lights having the intensities illustrated in FIG. 57A and FIG. 57C, respectively.

Figure 58A:
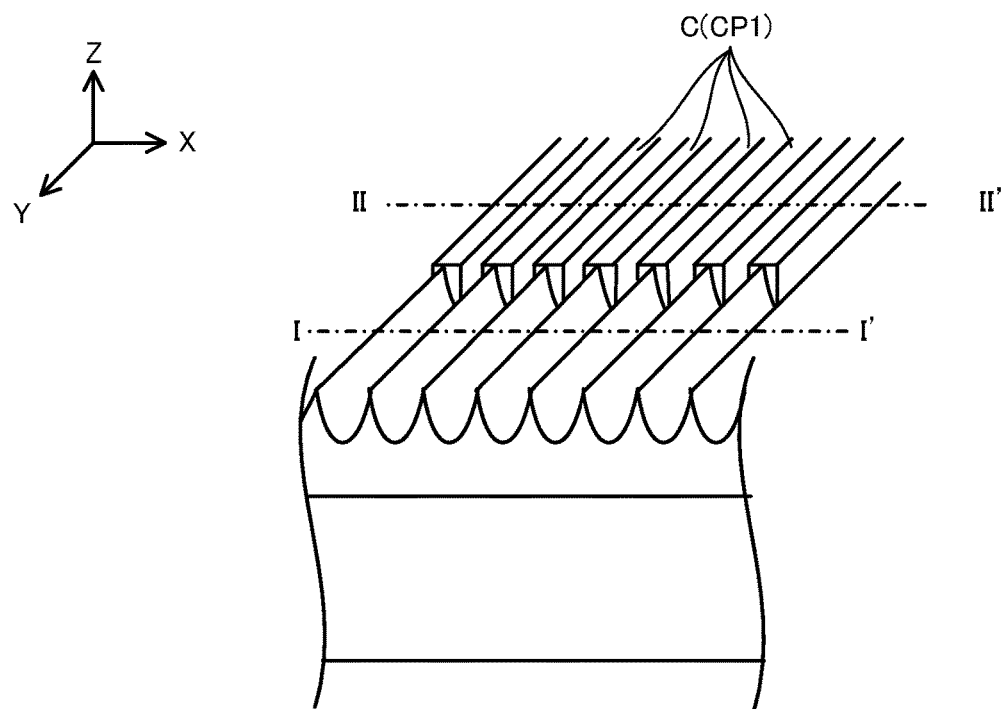
Figures 58B, 58C:
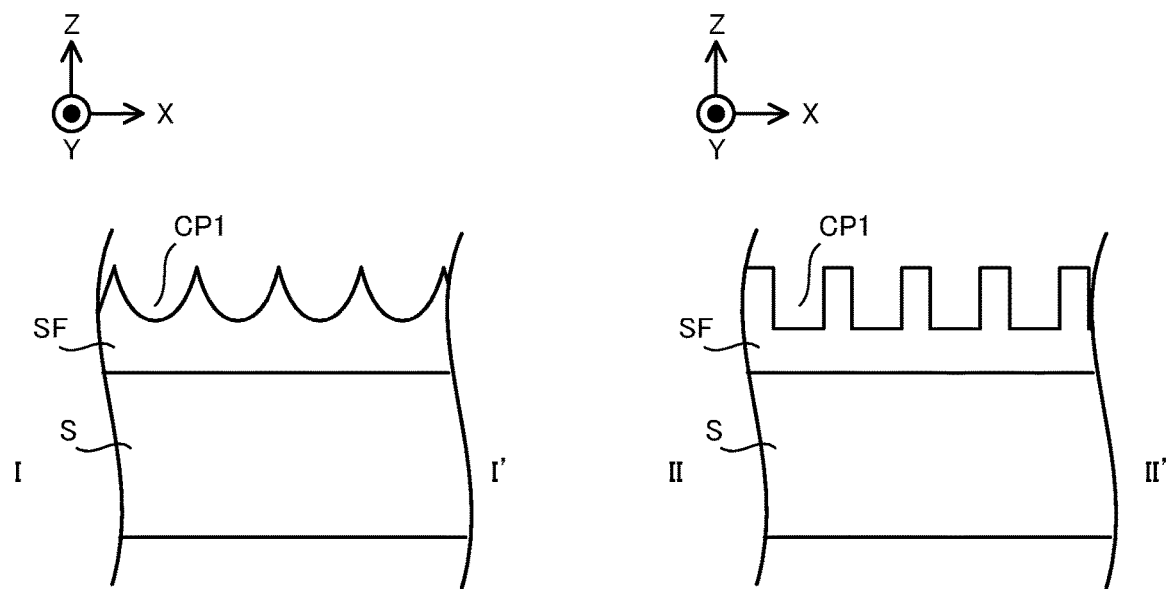

FIG. 58A is a perspective view that illustrates the riblet structure in which a shape of the cross-sectional surface of the concave structure changes along an extending direction, FIG. 58B is a I-I' cross-sectional surface in FIG. 58A and FIG. 58C is a II-II' cross-sectional surface in FIG. 58A.

Figure 59A:
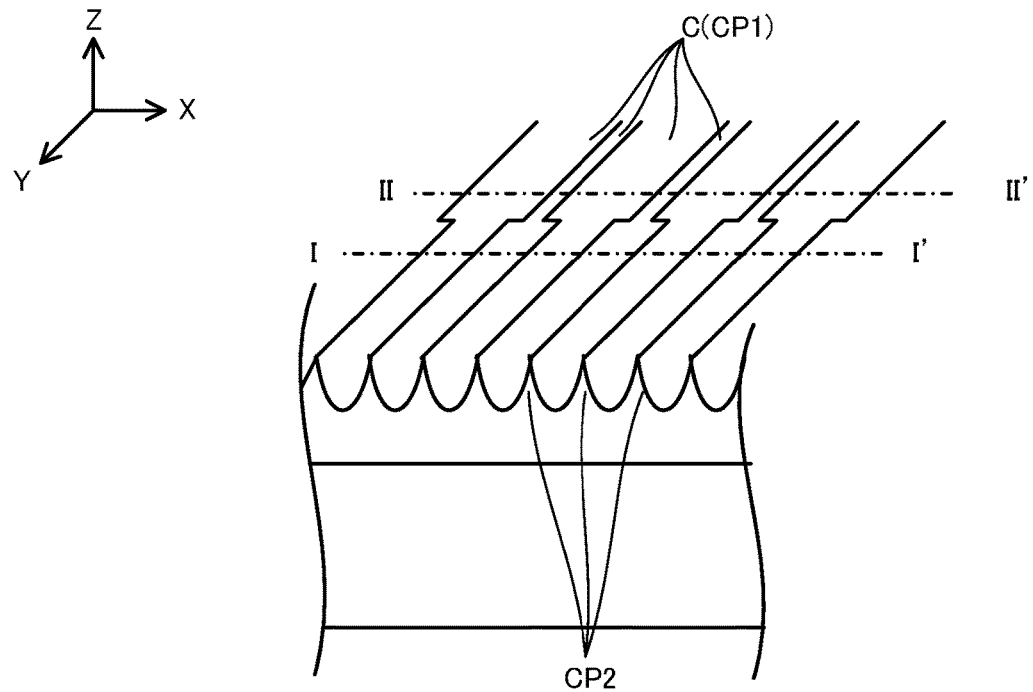
Figures 59B, 59C:
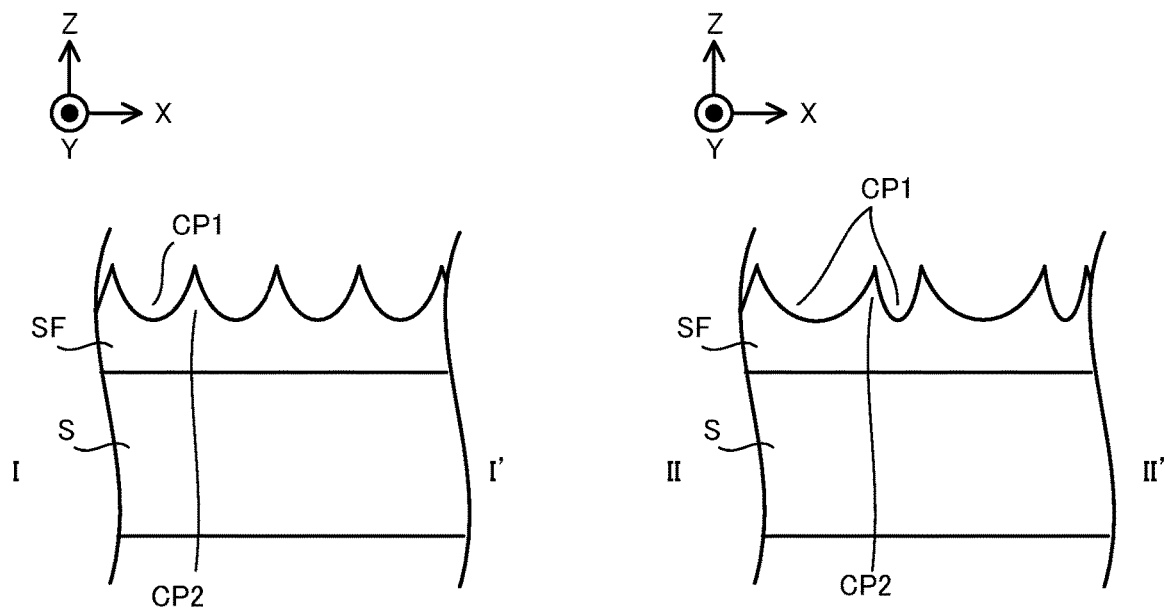

FIG. 59A is a perspective view that illustrates the riblet structure in which a width of the concave structure changes along the extending direction, FIG. 59B is a I-I' cross-sectional surface in FIG. 54A and FIG. 59C is a II-II' cross-sectional surface in FIG. 59A.

Figure 60:
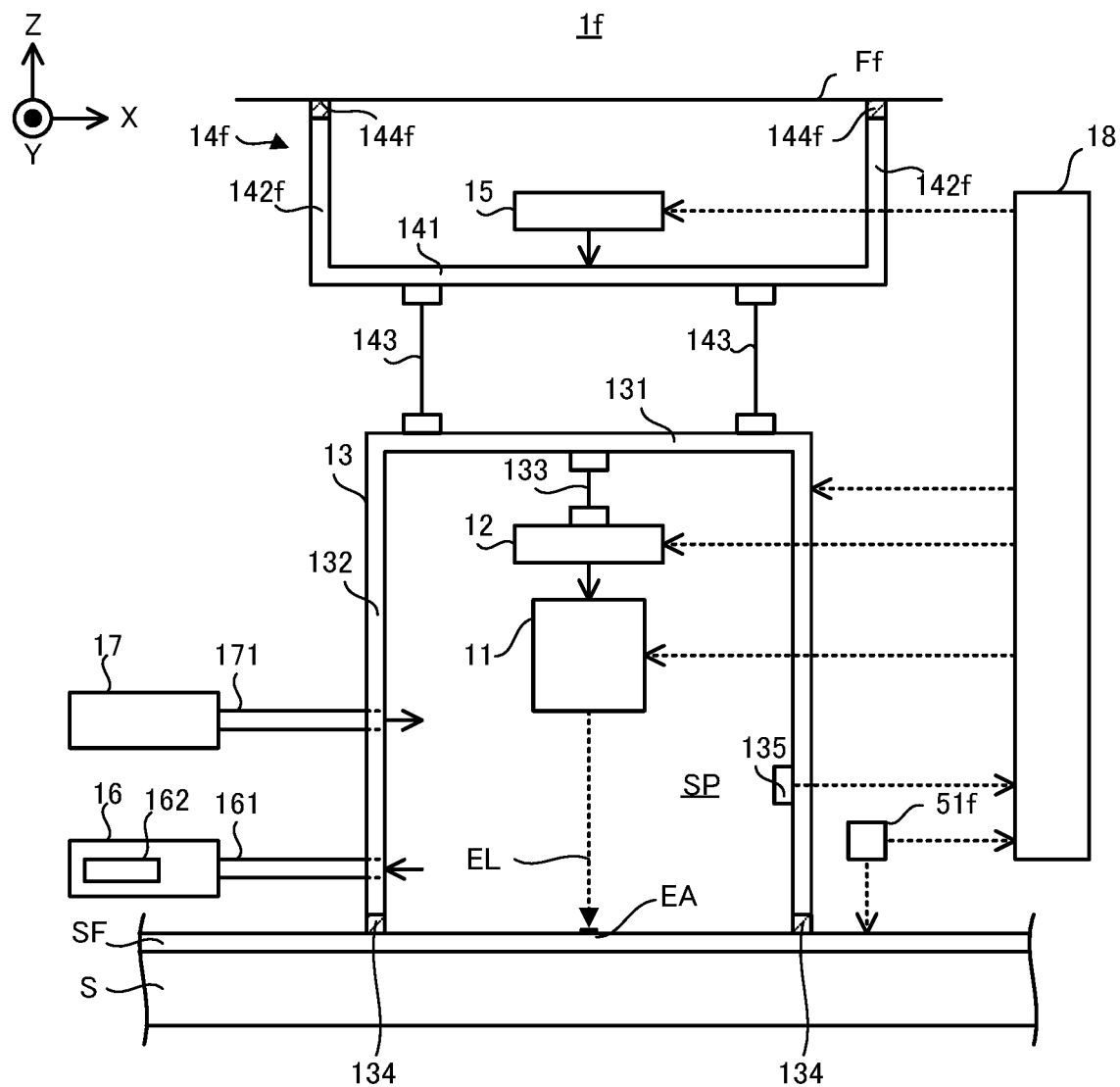

FIG. 60 is a cross-sectional view that schematically illustrates an entire structure of a processing apparatus in a sixth modified example.

Figure 61:
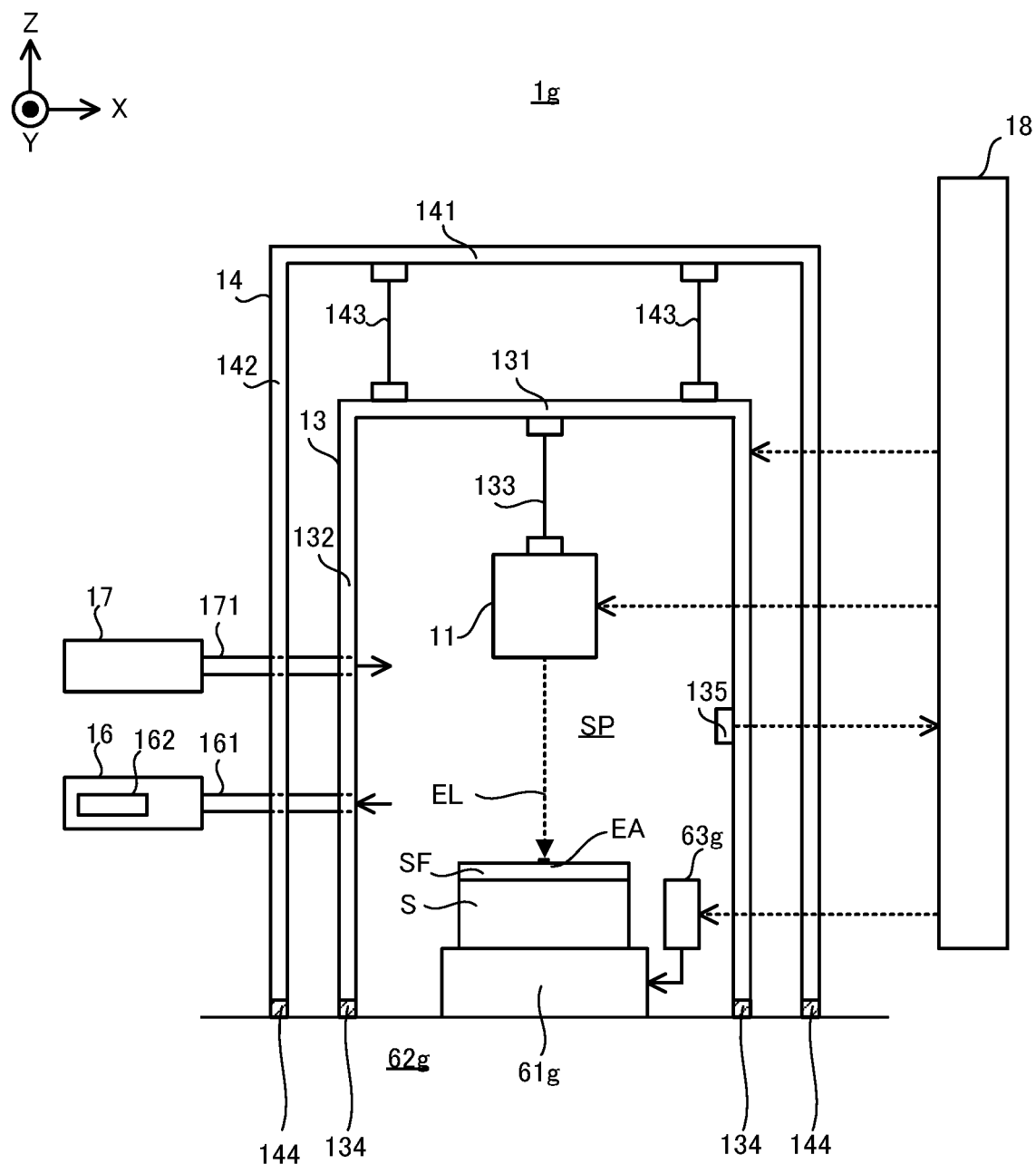

FIG. 61 is a cross-sectional view that schematically illustrates an entire structure of a processing apparatus in a seventh modified example.

Figure 62:
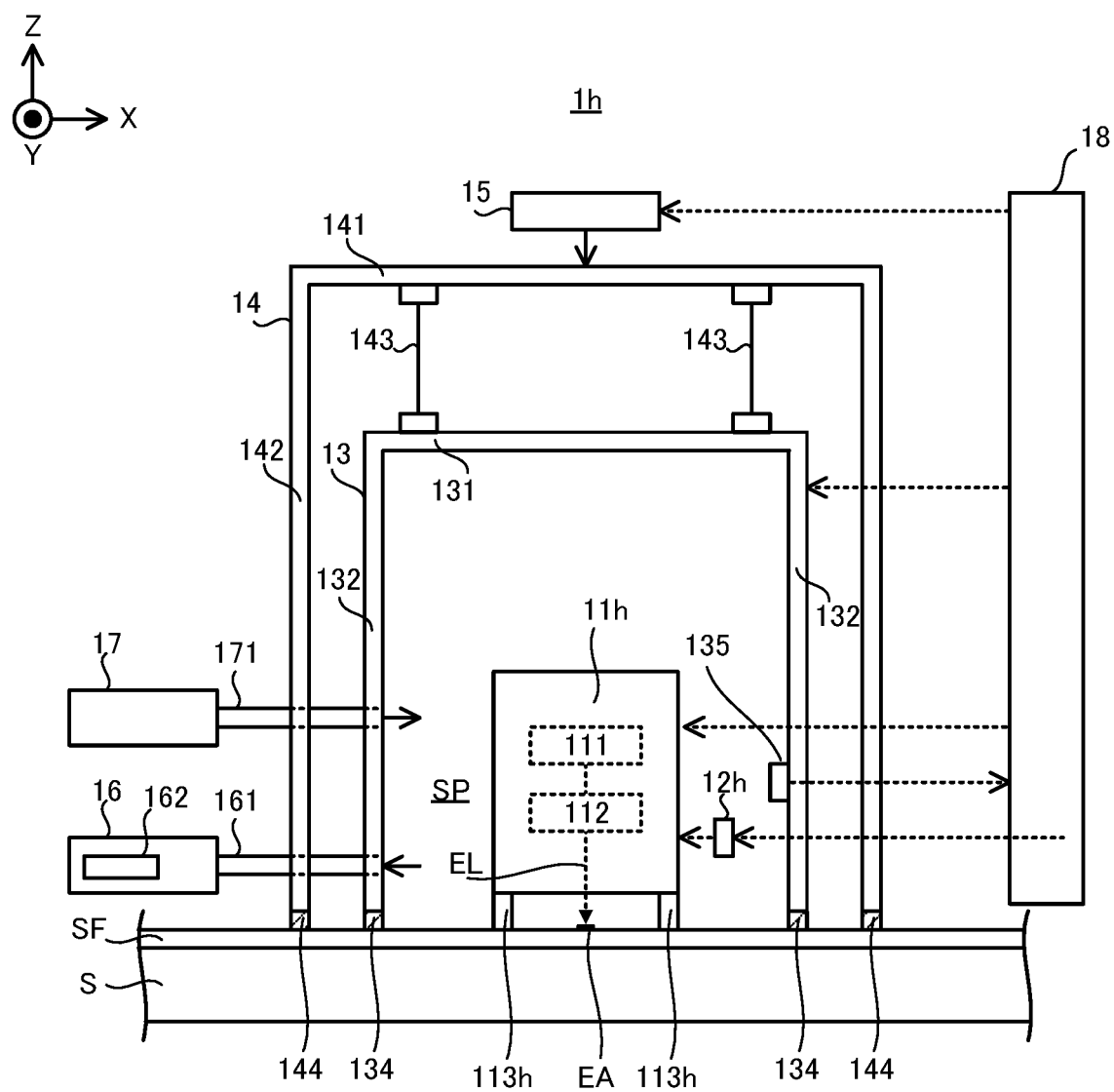

FIG. 62 is a cross-sectional view that schematically illustrates an entire structure of a processing apparatus in an eighth modified example.

Figure 63:
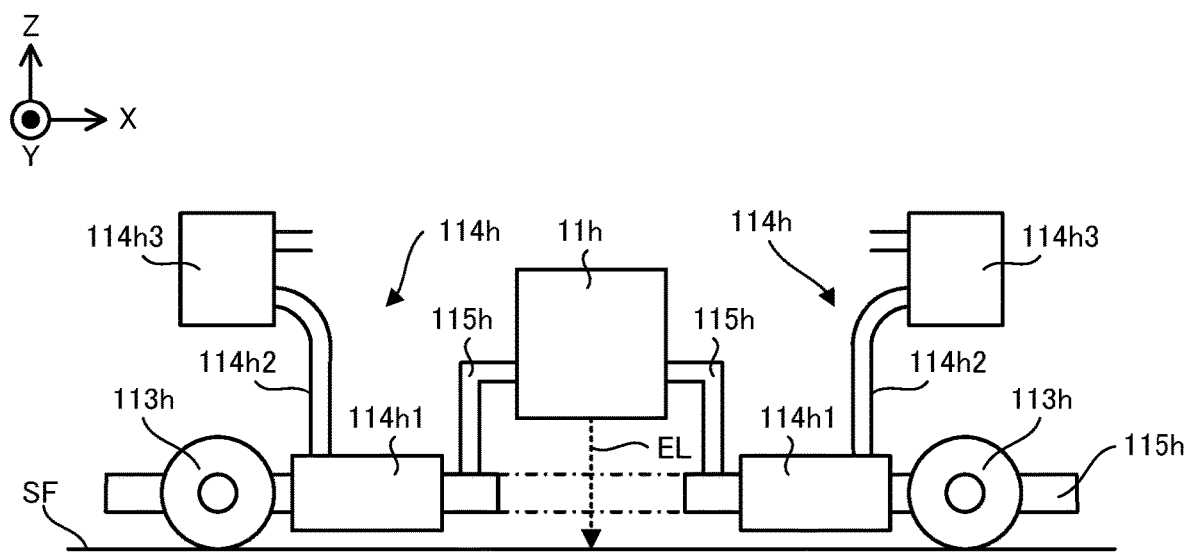

FIG. 63 is a cross-sectional view that illustrates one example of a structure of a suction part that allows the light irradiation apparatus to be disposed at the coat of paint.

Figure 64:
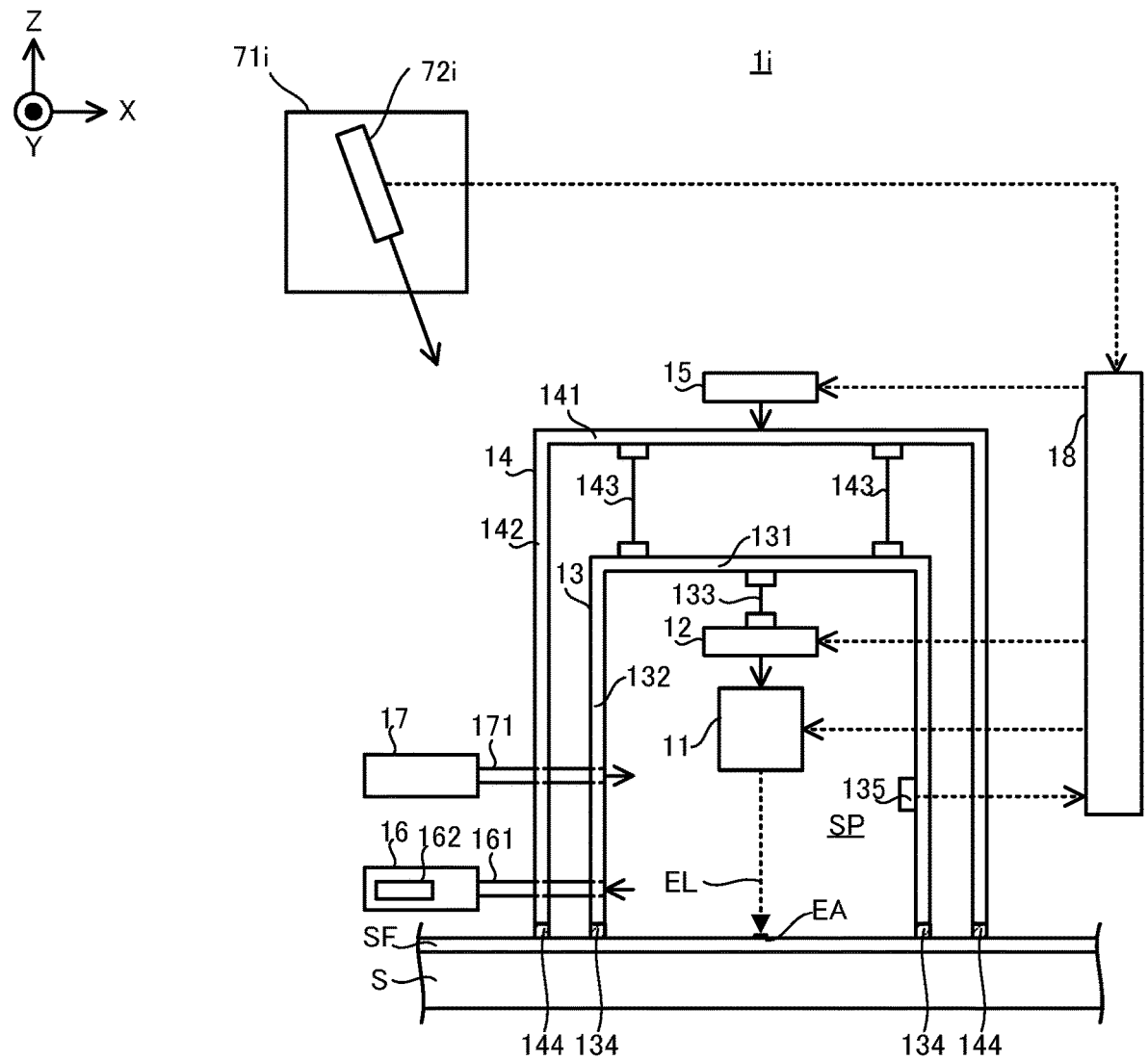

FIG. 64 is a cross-sectional view that schematically illustrates an entire structure of a processing apparatus in a ninth modified example.

Figure 65:
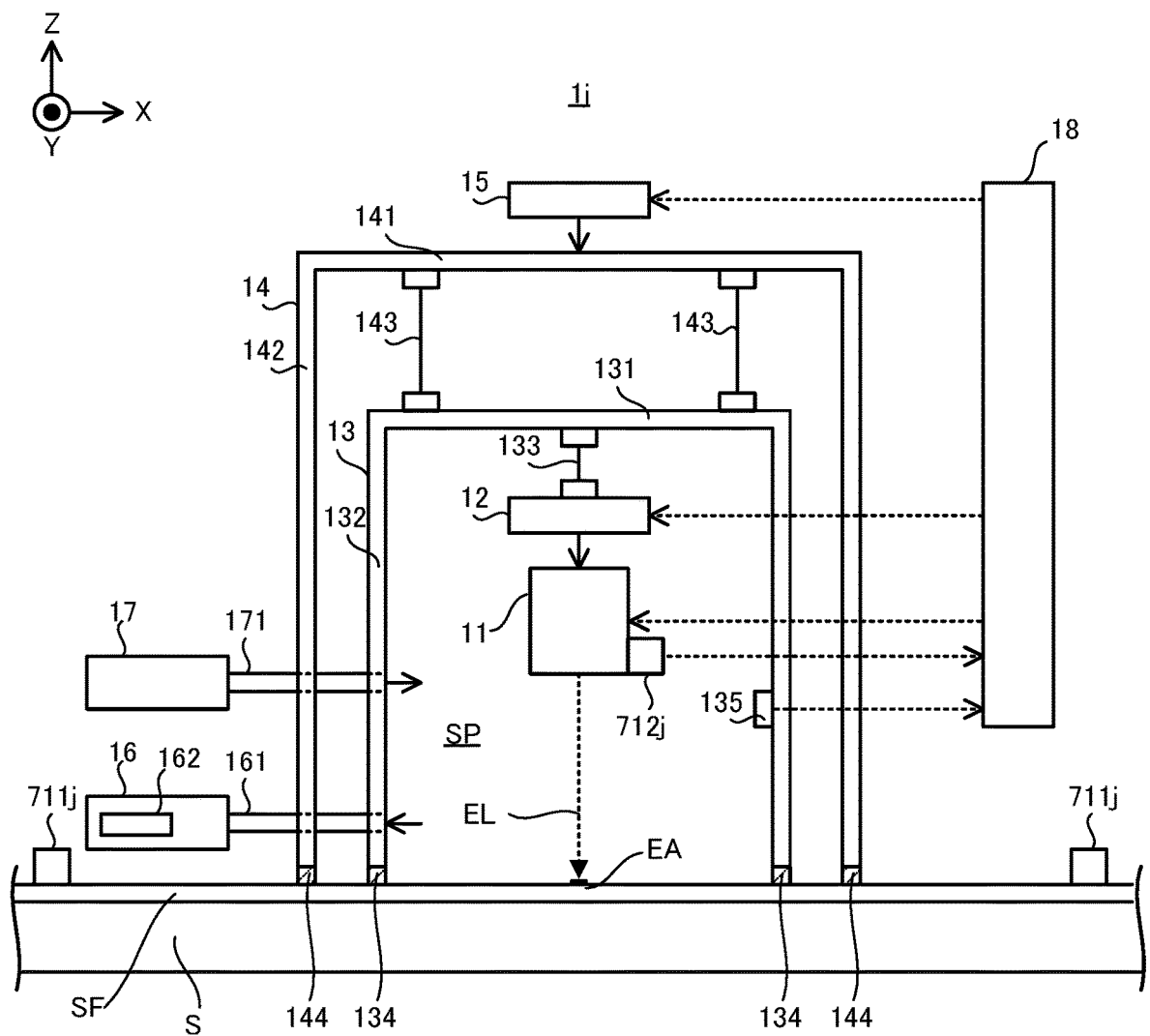

FIG. 65 is a cross-sectional view that schematically illustrates an entire structure of a processing apparatus in a tenth modified example.

Figure 66A:
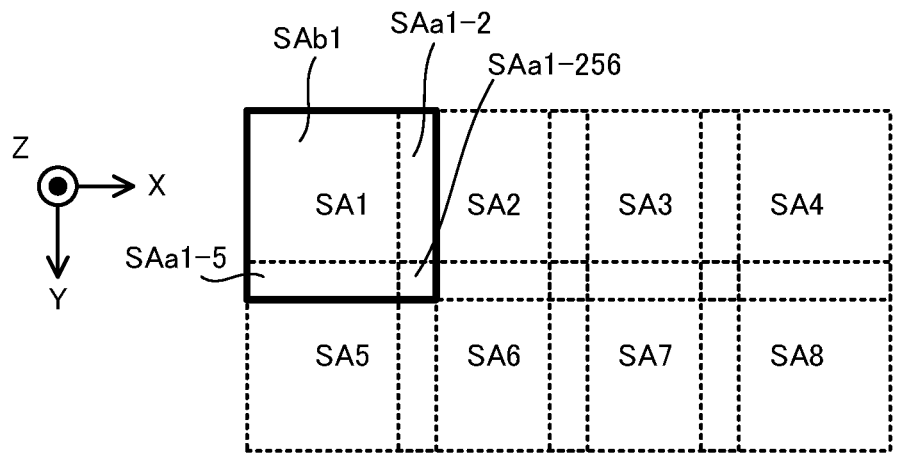
Figure 66B:
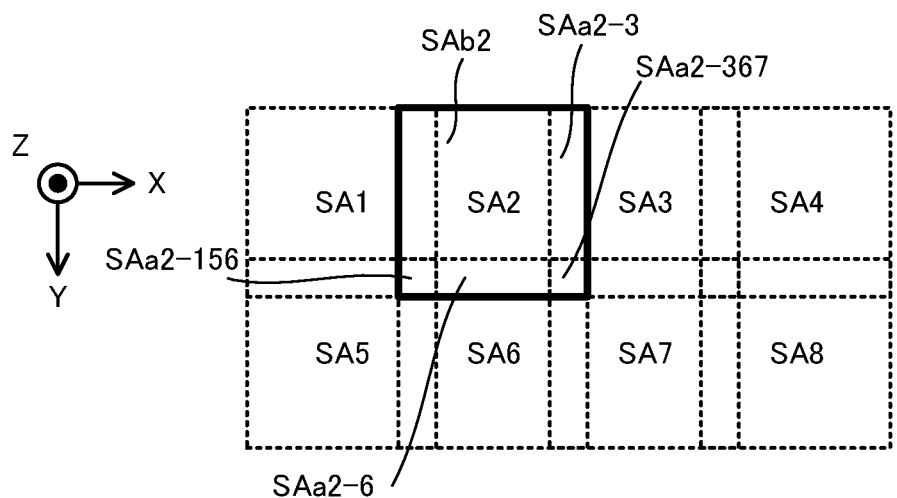

Each of FIG. 66A and FIG. 66B is a plan view that illustrates a unit processing area that is partially overlapped with an adjacent another unit processing area.

Figure 67:
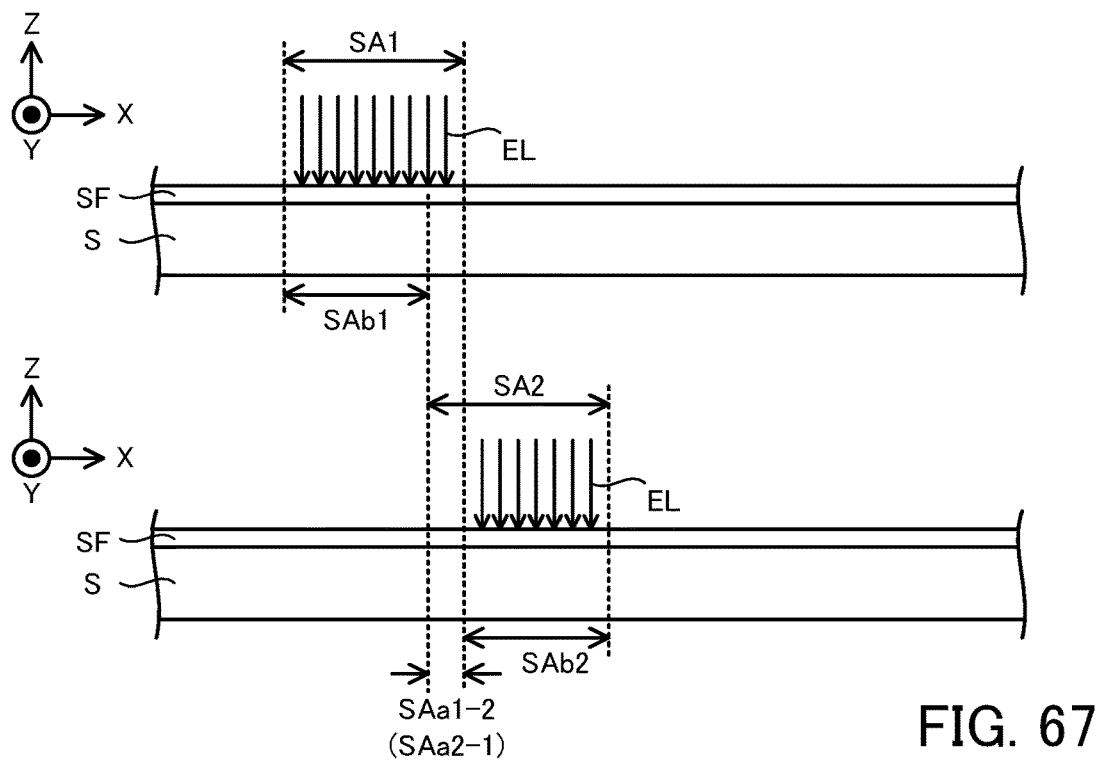

FIG. 67 is a cross-sectional view that illustrates an aspect of the irradiation of the processing light to the adjacent two unit processing areas.

Figure 68:
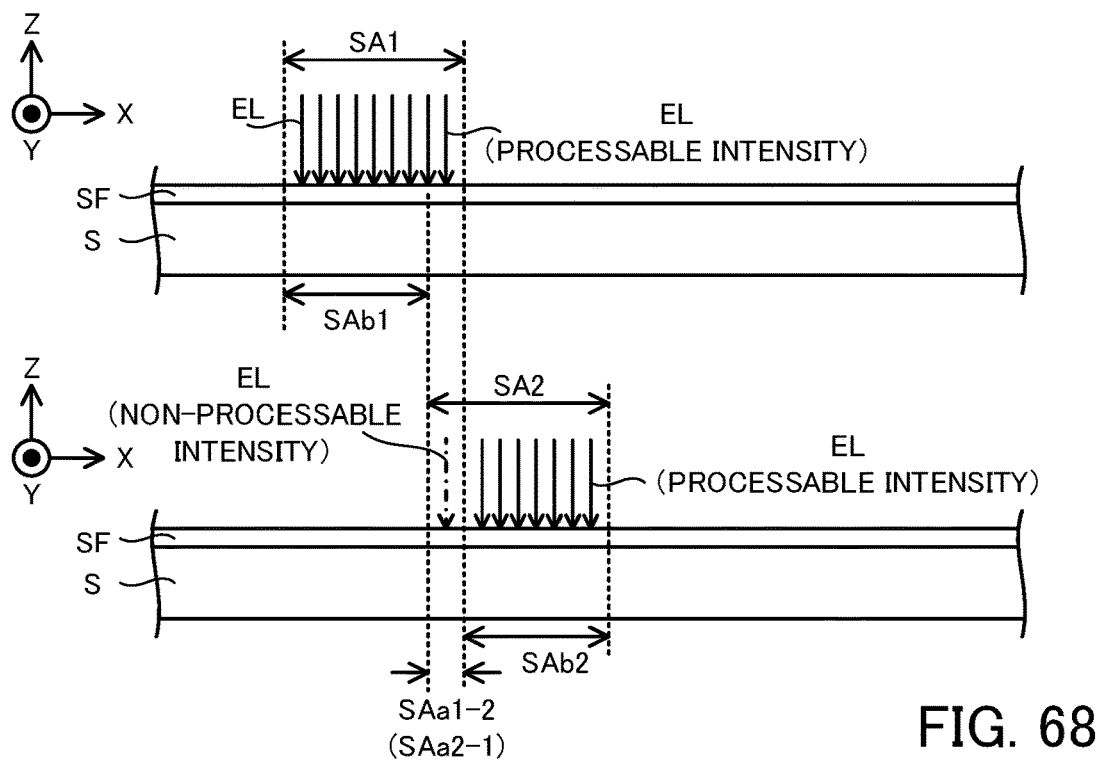

FIG. 68 is a cross-sectional view that illustrates an aspect of the irradiation of the processing light to the adjacent two unit processing areas.

Figure 69:
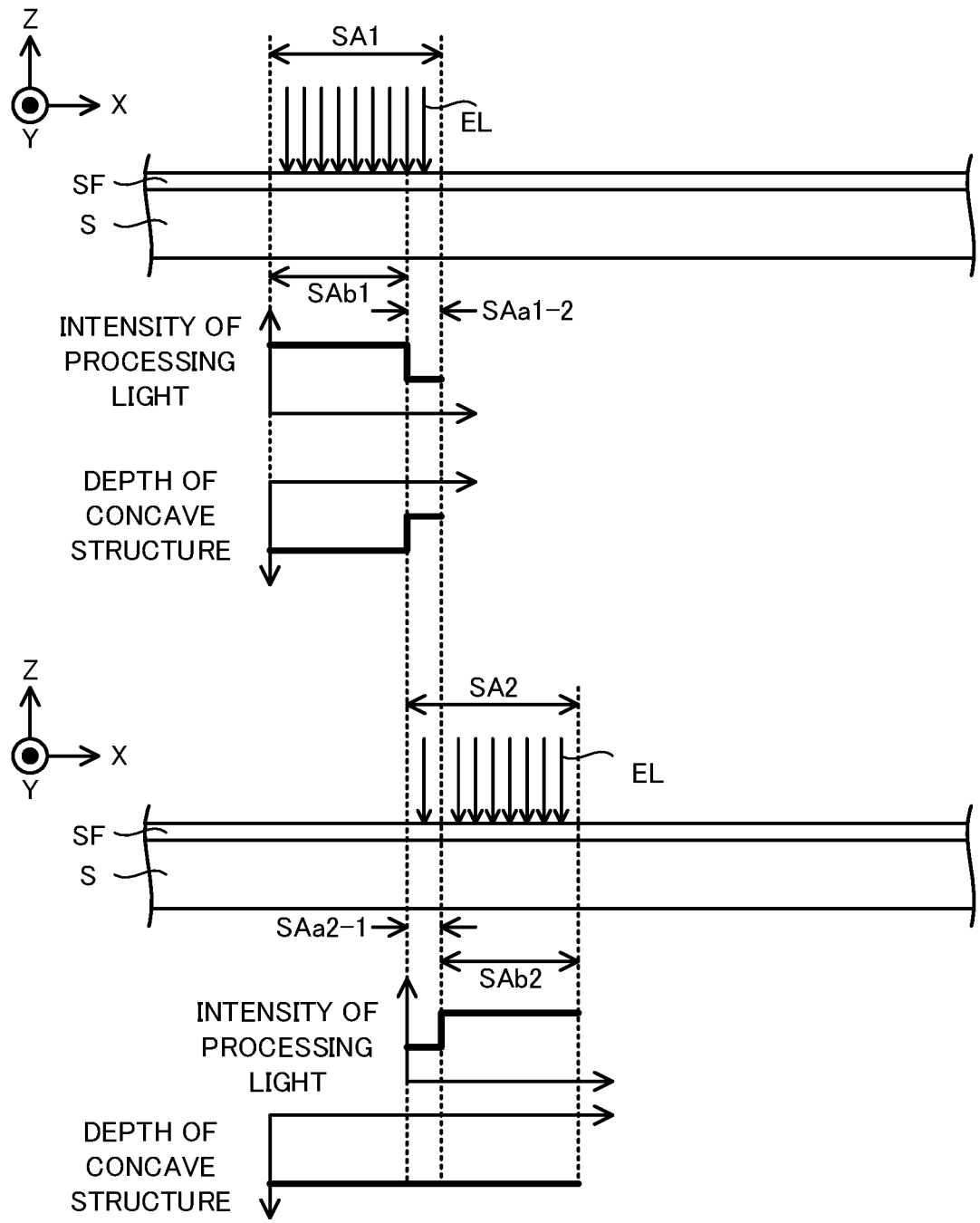

FIG. 69 is a cross-sectional view that illustrates the intensity of the processing light with which the adjacent two unit processing areas are irradiated.

Figure 70:
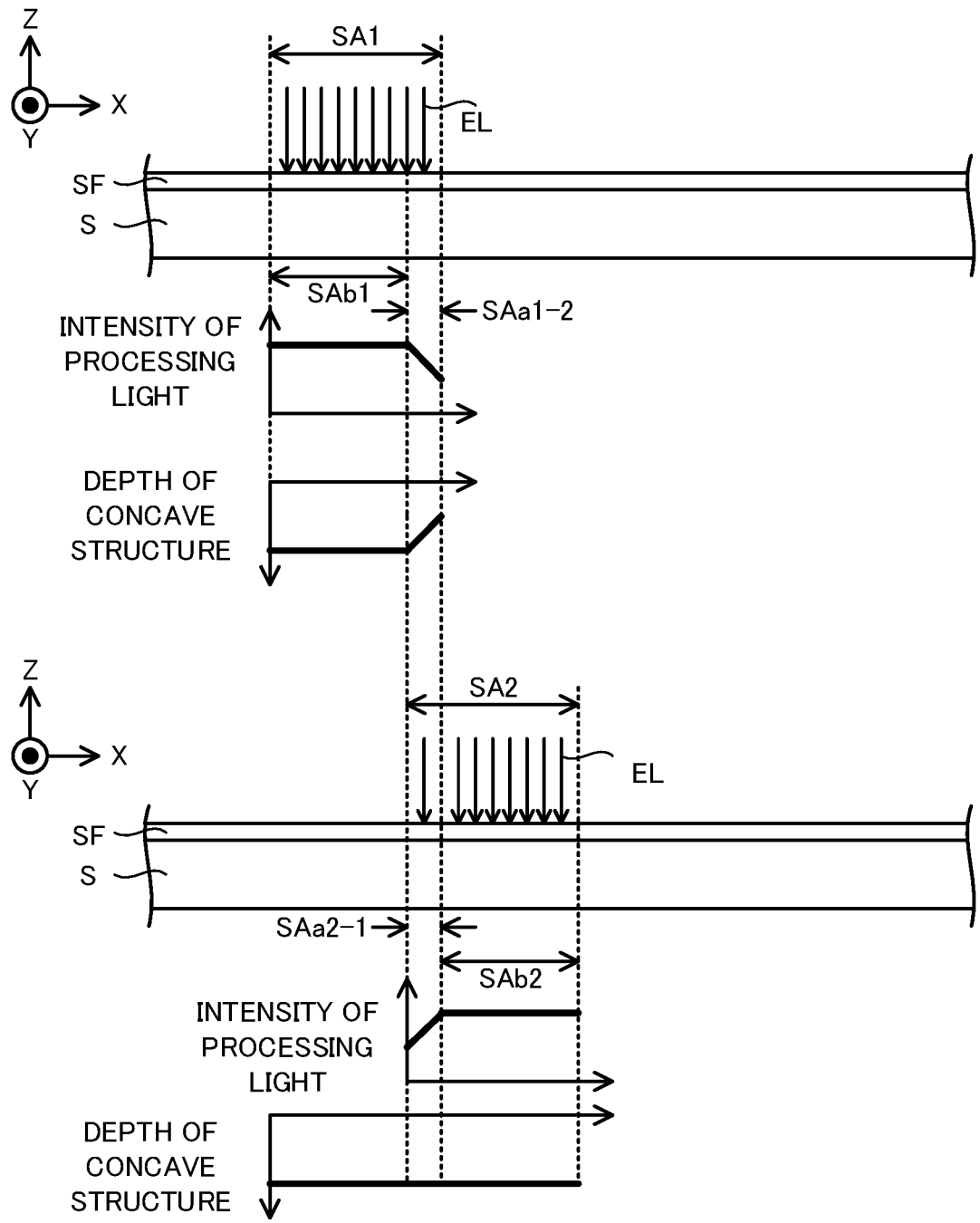

FIG. 70 is a cross-sectional view that illustrates the intensity of the processing light with which the adjacent two unit processing areas are irradiated.

Figure 71A:
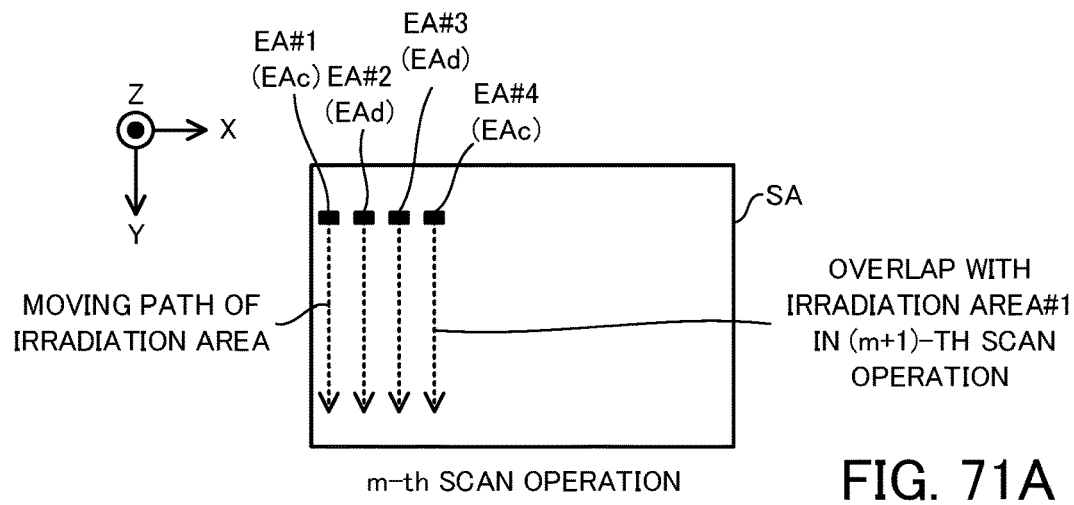
Figure 71B:
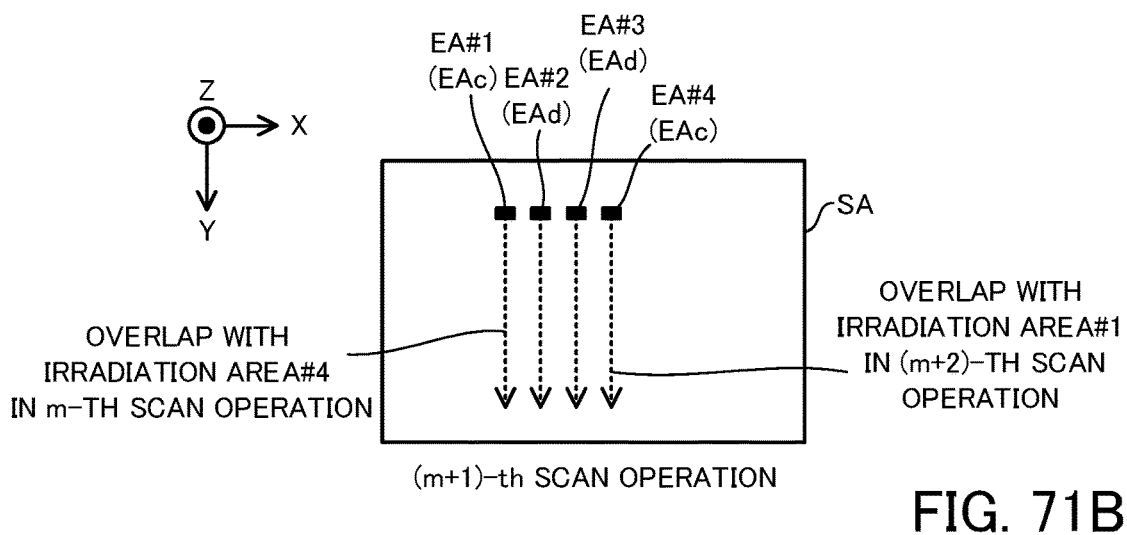
Figure 71C:
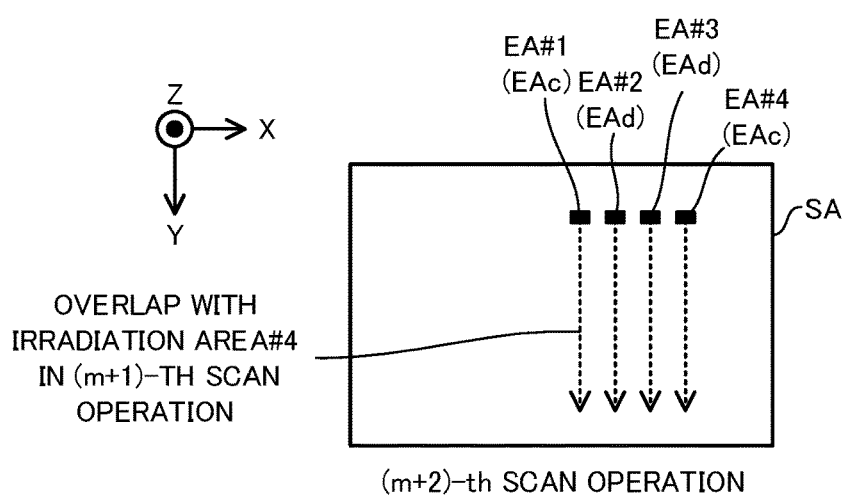

Each of FIG. 71A to FIG. 71C is a plan view that illustrates an area at which the plurality of irradiation areas moves by a single scan operation.

Figure 72A:
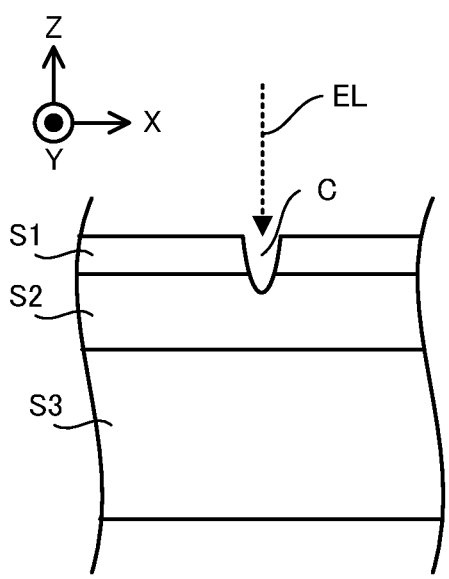
Figure 72B:
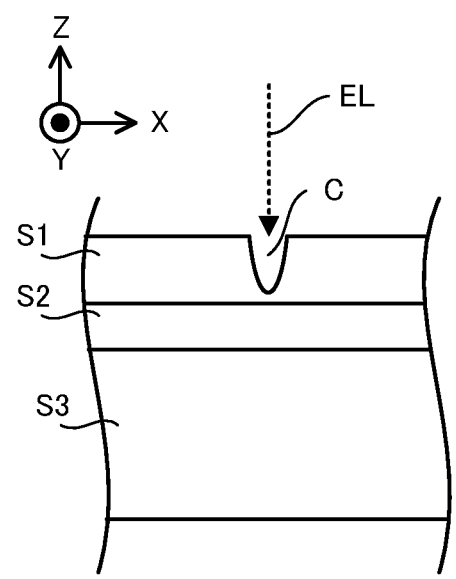

Each of FIG. 72A to FIG. 72B is a cross-sectional view that illustrates a structural object in which a plurality of layers are laminated.

DESCRIPTION OF EMBODIMENTS

Next, with reference to drawings, embodiments of the present invention will be described. However, the present invention is not limited to the below described embodiments.

(1) STRUCTURE OF PROCESSING APPARATUS 1

Figure 1:
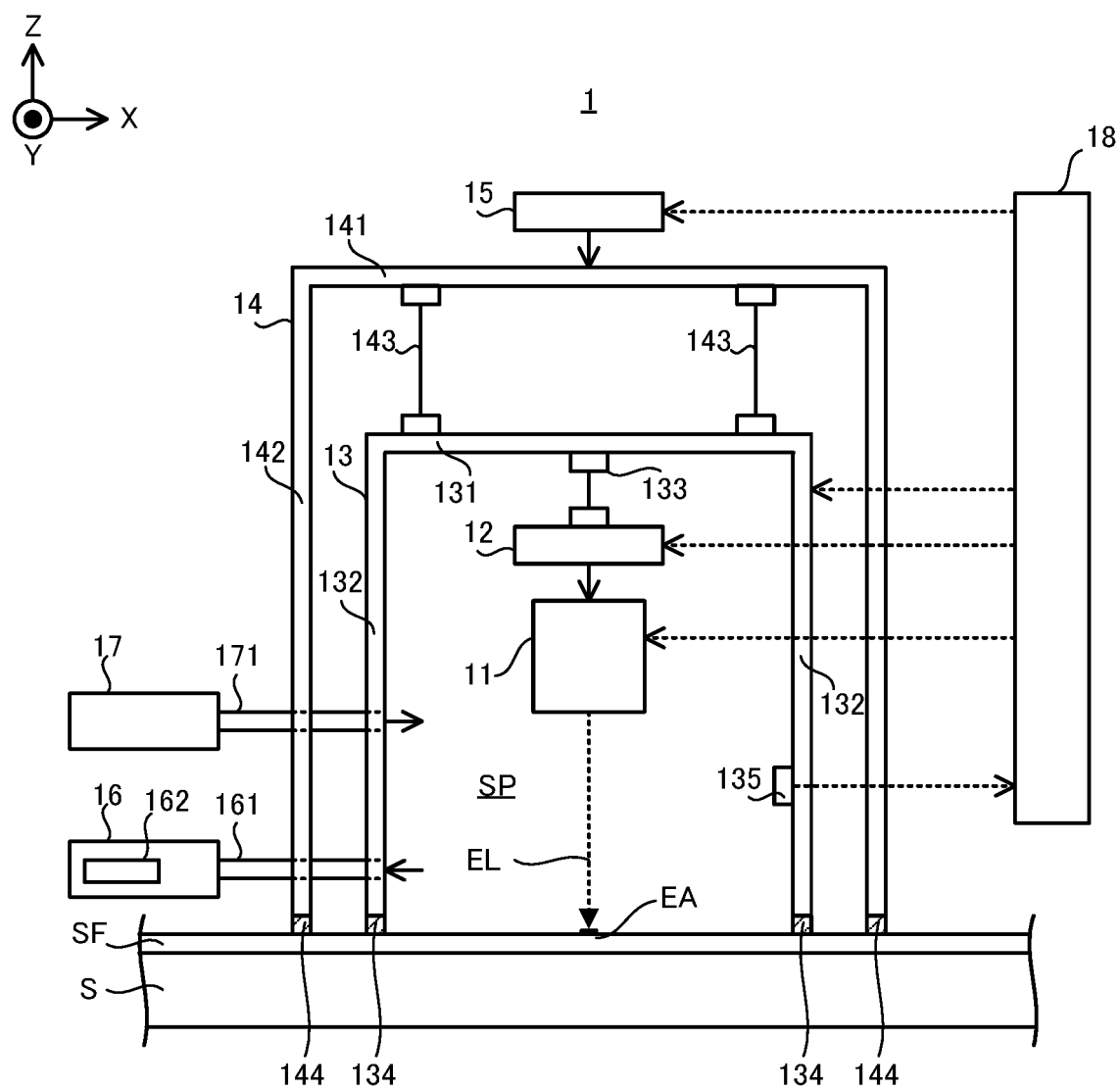
FIG. 1 is a cross-sectional view that schematically illustrates an entire structure of a processing apparatus in the present embodiment.

Firstly, with reference to FIG. 1, a structure of a processing apparatus 1 in the present embodiment will be described. FIG. 1 is a cross-sectional view that schematically illustrates the structure of the processing apparatus 1 in the present embodiment. Note that the structure of the processing apparatus 1 will be described in an XYZ rectangular coordinate system that is defined by a X axis, a Y axis and a Z axis that are perpendicular to one another in the below described description. An X axis and a Y axis are directions along a horizontal direction and a Z axis is a direction perpendicular to the X axis and the Y axis. Although the processing apparatus 1 is disposed on a processing target object S having a surface along the horizontal plane in FIG. 1, the processing apparatus 1 is not necessarily disposed on the processing target object S having the surface along the horizontal plane. For example, as described later in detail with reference to FIG. 6 and so on, the processing apparatus 1 is sometimes disposed on a processing target object S having a surface intersecting with the horizontal plane and is sometimes suspended from the processing target object S. In this case, the X axis and the Y axis may be defined as directions along the surface of the processing target object S.

As illustrated in FIG. 1, the processing apparatus 1 processes a coat SF of paint that is formed on a surface of the processing target object S. The processing target object S may be a metal, may be an alloy (for example, a duralumin and the like), may be a resin (for example, CFRP (Carbon Fiber Reinforced Plastic) and the like), may be a glass or may be an object that is made from any other material, for example. The coat SF of paint is a film that covers the surface of the processing target object S. A thickness of the coat SF of paint is several microns to several hundred microns, for example, however, may be any other size. A painting material that constitutes the coat SF of paint may include a resin painting material (for example, at least one of a polyurethane type of painting material, a vinyl type of painting material, a silicon type of painting material and an epoxy type of painting material) or may include any other type of painting material, for example.

The processing apparatus 1 irradiates the coat SF of paint with a processing light EL in order to process the coat SF of paint. The processing light EL may be any type of light, as long as the coat SF of paint is processed by irradiating the coat SF of paint with it. As one example, the processing light EL may be a laser light. Moreover, the processing light EL may be a light having any wavelength, as long as the coat SF of paint is processed by irradiating the coat SF of paint with it. The present embodiment will be described by using an example in which the processing light EL is an invisible light (for example, at least one of an infrared light, an ultraviolet light and the like). However, the processing light EL may be a visible light.

The processing apparatus 1 irradiates an irradiation area EA set (in other words, formed) on the surface of the coat SF of paint with the processing light EL. As illustrated in FIG. 2A, when the irradiation area EA is irradiated with the processing light EL, a part of the coat SF of paint that overlaps with the irradiation area EA (namely, the coat of paint that is located at an −Z side of the irradiation area EA) evaporates by the processing light EL. Here, all of the coat SF of paint that overlaps with the irradiation area EA does not evaporate along a thickness direction of the coat SF of paint. Namely, a part of the coat SF of paint that overlaps with the irradiation area EA (specifically, a part of the coat SF of paint that is relatively close to the irradiation area EA) evaporates and other part of the coat SF of paint that overlaps with the irradiation area EA (specifically, a part of the coat SF of paint that is relatively far away from the irradiation area EA) does not evaporate along the thickness direction of the coat SF of paint. In other words, the coat SF of paint evaporates so that the processing target object S is not exposed from the coat SF of paint. As a result, the coat SF of paint is removed at a part at which the coat SF of paint evaporates. On the other hand, the coat SF of paint remains as it is at a part at which the coat SF of paint does not evaporate. Namely, as illustrated in FIG. 2B, the coat SF of paint is partially removed at a part that is irradiated with the processing light EL. As a result, as illustrated in FIG. 2B, the thickness of the coat SF of paint is thinner in the part that is irradiated with the processing light EL, compared to a part that is not irradiated with the processing light EL. In other words, as illustrated in FIG. 2B, there are the coat SF of paint that is relatively thick because it is not irradiated with the processing light EL and the coat SF of paint that is relatively thin because it is irradiated with the processing light EL on the surface of the processing target object S. Namely, the thickness of the coat SF of paint is adjusted at least partially by an irradiation of the processing light EL. As a result, a concave part (in other words, a groove part) C corresponding to the part at which the coat SF of paint is relatively thin is formed on the surface of the coat SF of paint. Therefore, "an operation for processing the coat SF of paint" in the present embodiment includes an operation for adjusting the thickness of the coat SF of paint, an operation for removing a part of the coat SF of paint and an operation for forming the concave part C at the coat SF of paint. Moreover, an energy of the processing light EL with which the coat SF of paint is irradiated is determined so that the irradiation of the processing light EL does not affect the processing target object S. In other words, the energy of the processing light EL is determined so that the irradiation of the processing light EL affects only the coat SF of paint.

The coat SF of paint evaporate by absorbing the processing light EL. Namely, the coat SF of paint is decomposed photochemically, for example, and removed by means of the energy of the processing light EL being transmitted to the coat SF of paint. Incidentally, when the processing light EL is the laser light, a phenomenon in which the coat SF of paint is decomposed photochemically and removed by means of the energy of the processing light EL being transmitted to the coat SF of paint is sometimes referred to as a laser ablation. Thus, the coat SF of paint includes a material that is allowed to absorb the processing light EL. Specifically, the coat SF of paint may include a material in which an absorptance relating to the processing light EL (namely, an absorptance relating to a light having a wavelength that is different from a wavelength range of the visible light) is equal to or higher than a first absorption threshold value, for example. This material may be a coloring matter.

When the coat SF of paint includes the coloring matter, the coloring matter may a coloring matter that takes on a predetermined color when it is irradiated with the visible light. As a result, the coat SF of paint including this coloring matter takes on the predetermined color. In this case, the coloring matter may have a characteristic that the absorptance of a first light component having a wavelength that is allowed to be recognized by a human as the predetermined colored light when it is reflected by the coat SF of paint among a wavelength range of the visible light is different from the absorptance of a second light component of the visible light other than the first light component so that the coat SF of paint takes on the predetermined color. For example, the coloring matter may have a characteristic that the absorptance of the first light component is lower than the absorptance of the second light component. For example, the coloring matter may have a characteristic that the absorptance of the first light component is equal to or lower than a predetermined second absorption threshold value (note that the second absorption threshold value is lower than the first absorption threshold value) and the absorptance of the second light component is equal to or higher than a predetermined third absorption threshold value (note that the third absorption threshold value is higher than the second absorption threshold value). As one example of the coloring matter that is allowed to absorb the processing light EL being the invisible light to a certain degree and that takes on the predetermined color, there is a near infrared absorption coloring matter manufactured by Spectrum Info Ltd located in Kiev in Ukraine (as one example, a tetrafluoro boronated 4-((E)-2-{(3E)-2-chloro-3-[2-(2,6-diphenyl-4H-thiopyran-4-ylidene) ethylidene] cyclohexa-1-yen-1-yl} vinyl)-2,6-diphenylthiopyrylium).

Alternatively, when the coat SF of paint includes the coloring matter, the coloring matter may a coloring matter that is transparent to the visible light. As a result, the coat SF of paint including this coloring matter is a transparent film (what we call a clear coat). In this case, the coloring matter may have a characteristic that it does not absorb the visible light much (namely, reflects to a certain degree) so that the coat SF of paint is transparent. For example, the coloring matter may have a characteristic that the absorptance of the visible light is lower than a predetermined fourth absorption threshold value. As one example of the coloring matter that is allowed to absorb the processing light EL being the invisible light to a certain degree and that is transparent to the visible light, there is a near infrared absorption coloring matter manufactured by Spectrum Info Ltd located in Kiev in Ukraine (as one example, a tetrafluoro boronated 6-chloro-2-[(E)-2-(3-{(E)-2-[6-chloro-1-ethylbenzo [cd] indole-2(1H)-ylidene]ethylidene}-2-phenyl-1-cyclopentene-1-yl) ethenyl]-1-ethylbenzo [cd]-indolium).

Again in FIG. 1, in order to process the coat SF of paint, the processing apparatus 1 is provided with a light irradiation apparatus 11, a driving system 12, a housing apparatus 13, a support apparatus 14, a driving system 15, an exhaust apparatus 16, a gas supply apparatus 17 and a control apparatus 18.

The light irradiation apparatus 11 is configured to irradiate the coat SF of paint with the processing light EL under the control of the control apparatus 18. In order to emit the processing light EL, the light irradiation apparatus 11 is provided with a light source system 111 that is configured to emit the processing light EL and an optical system 112 that guides the processing light EL emitted from the light source system 111 to the coat SF of paint as illustrated in FIG. 3A.

The light source system 111 emits a plurality of processing lights EL at the same time, for example. Thus, the light source system 111 is provided with a plurality of light sources 1111 as illustrated in FIG. 3B. The plurality of light sources 1111 are arranged in a line at regular intervals. Each light source 1111 emits a pulsed light as the processing light EL. When a light emitting time width (hereinafter, it is referred to as a "pulse width") of the pulsed light is shorter, a processing accuracy (for example, a forming accuracy of a riblet structure described later) improves. Therefore, each light source 1111 may emit the pulsed light having a relatively short pulse width as the processing light EL. For example, each light source 1111 may emit the pulsed light having the pulse width that is equal to or shorter than 1000 nanoseconds as the processing light EL. Alternatively, the light source system 111 may be provided with single light source 1111 and a divide device 1112 that divides the light from the single light source 1111 into the plurality of processing lights EL, as illustrated in FIG. 3C. A plurality of emitting ports from which the plurality of processing lights EL divided by the divide device 1112, respectively, are arranged in a line at regular intervals. At least one of an optical fiber coupler and a waveguide splitter is one example of the divide device 1112. Note that at least one of a lens-array, a diffractive optical element, a spatial light modulator and the like may be used as the divide device 1112, as described later.

The optical system 112 is provided with a focusing lens 1121, a Galvano mirror 1122 and a fθ lens 1123. The coat SF of paint is irradiated with the plurality of processing lights EL through the focusing lens 1121, the Galvano mirror 1122 and the fθ lens 1123.

The focusing lens 1121 is an optical element that is constructed from one or more lens and that is for adjusting light concentration positions of the plurality of processing lights EL (namely, a focus position of the optical system 112) by adjusting a position of at least one lens thereof along an optical axis direction. The Galvano mirror 1122 deflects the plurality of processing lights EL so that the surface of the coat SF of paint is swept with the plurality of processing lights EL (namely, the plurality of irradiation areas EA that are irradiated with the plurality of processing lights EL, respectively, moves on the surface of the coat SF of paint). The Galvano mirror 1122 is provided with a X scanning mirror 1122X and a Y scanning mirror 1122Y. The X scanning mirror 1122X reflects the plurality of processing lights EL to the Y scanning mirror 1122Y. The X scanning mirror 1122X is configured to swing or rotate in the θY direction (namely, in a rotational direction around the Y axis). Due to the swing or the rotation of the X scanning mirror 1122X, the surface of the coat SF of paint is swept with the plurality of processing lights EL along the X axis direction. Due to the swing or the rotation of the X scanning mirror 1122X, the plurality of irradiation areas EA moves on the coat SF of paint along the X axis direction. The X scanning mirror 1122X changes a relative position relationship between the plurality of irradiation areas EA and the coat SF of paint along the X axis direction. The Y scanning mirror 1122Y reflects the plurality of processing lights EL to the fθ lens 1123. The Y scanning mirror 1122Y is configured to swing or rotate in the θX direction (namely, in a rotational direction around the X axis). Due to the swing or the rotation of the Y scanning mirror 1122Y, the surface of the coat SF of paint is swept with the plurality of processing lights EL along the Y axis direction. Due to the swing or the rotation of the Y scanning mirror 1122X, the plurality of irradiation areas EA moves on the coat SF of paint along the Y axis direction. The Y scanning mirror 1122Y changes a relative position relationship between the plurality of irradiation areas EA and the coat SF of paint along the Y axis direction. The fθ lens 1123 is an optical element for focuses the plurality of processing lights EL from the Galvano mirror 1122 on the coat SF of paint.

The fθ lens 1123 is a terminal optical element that is disposed at the most light emitting side of the optical system 112 (in other word, that is closest to the coat SF of paint or that is disposed at an end of an optical path of the plurality of processing lights EL) among the optical element(s) of the optical system 112. The fθ lens 1123 is configured to be attachable to and detachable from the optical system 112. As a result, new fθ lens 1123 is allowed to be attached to the optical system 112 after old fθ lens 1123 is detached from the optical system 112. However, when the optical system 112 is provided with an optical element (for example, a cover lens) that is disposed at more emitting side than the fθ lens 1123, this optical element is the terminal optical element and this optical element is configured to be attachable to and detachable from the optical system 112.

Traveling directions of the plurality of processing lights EL from the optical system 112 is parallel to each other, for example. As a result, in the present embodiment, the coat SF of paint is irradiated with the plurality of processing lights EL traveling directions of which are parallel to each other at the same time. Namely, the plurality of irradiation areas EA are set on the coat SF of paint at the same time. Thus, a throughput relating to the processing of the coats SF of paint improves compared to the case where the coat SF of paint is irradiated with the single processing light EL. Note that the optical system 112 may be configured so that all optical elements (for example, the focusing lens 1121, the Galvano mirror 1122 and the fθ lens 1123) are not on the same plane as illustrated in FIG. 3D.

Again in FIG. 1, the driving system 12 moves the light irradiation apparatus 11 relative to the coat SF of paint (namely, relative to the processing target object S on the surface of which the coat SF of paint is formed) under the control of the control apparatus 18. Namely, the driving system 12 moves the light irradiation apparatus 11 relative to the coat SF of paint so as to change a relative positional relationship between the light irradiation apparatus 11 and the coat SF of paint. When the relative positional relationship between the light irradiation apparatus 11 and the coat SF of paint is changed, a relative positional relationship between the plurality of irradiation areas EA that are irradiated with the plurality of processing lights EL, respectively, and the coat SF of paint is also changed. Thus, it can be said that the driving system 12 moves the light irradiation apparatus 11 relative to the coat SF of paint so as to change the relative positional relationship between the plurality of irradiation areas EA and the coat SF of paint. The driving system 12 may move the light irradiation apparatus 11 along the surface of the coat SF of paint. In an example illustrated in FIG. 1, the surface of the coat SF of paint is a plane that is parallel to at least one of the X axis and the Y axis, and thus, the driving system 12 may move the light irradiation apparatus 11 along at least one of the X axis and the Y axis. As a result, the irradiation areas EA moves on the coat SF of paint along at least one of the X axis and the Y axis. The driving system 12 may move the light irradiation apparatus 11 along the thickness direction of the coat SF of paint (namely, a direction that intersects with the surface of the coat SF of paint). In the example illustrated in FIG. 1, the thickness direction of the coat SF of paint is a direction along the Z axis, and thus, the driving system 12 may move the light irradiation apparatus 11 along the Z axis. The driving system 12 may move the light irradiation apparatus 11 along the θX direction, the θY direction and the θZ direction in addition to at least one of the X axis, the Y axis and the Z axis.

The driving system 12 supports the light irradiation apparatus 11 and moves the supporting light irradiation apparatus 11. In which case, the driving system 12 is provided with a first supporting member that supports the light irradiation apparatus 11 and a first moving mechanism that moves the first supporting member, for example.

The housing apparatus 13 is provided with a top member 131 and a partition member 132. The top member 131 is disposed at the +Z side than the light irradiation apparatus 11. The top member 131 is a plate-like member along the XY plane. The top member 131 supports the driving system 12 through a supporting member 133. The partition member 132 is disposed at (or near) an outer rim of a surface at the −Z side of the top member 131. The partition member 132 is a pipe-like (for example, a cylinder-like or rectangular pipe-like) member that extends from the top member 131 toward the −Z side. A space surrounded by the top member 131 and the partition member 132 is a containing space SP in which the light irradiation apparatus 11 and the driving system 12 are housed. Therefore, the above described driving system 12 moves the light irradiation apparatus 11 in the hosing space SP. Moreover, the containing space SP includes a space between the light irradiation apparatus 11 and the coat SF of paint (especially, a space including the optical path of the processing lights EL). More specifically, the containing space SP includes a space between the terminal optical element (for example, fθ lens 1123) of the light irradiation apparatus 11 and the coat SF of paint (especially, the space including the optical path of the processing lights EL).

Each of the top member 131 and the partition member 132 is a member that is configured to shield the processing light EL. Namely, each of the top member 131 and the partition member 132 is opaque to the wavelength of the processing light EL. As a result, the processing light EL propagating in the containing space SP does not leak outside the containing space SP (namely, outside the housing apparatus 13). Note that each of the top member 131 and the partition member 132 may be a member that is configured to fade the processing light EL. Namely, each of the top member 131 and the partition member 132 is translucent to the wavelength of the processing light EL. Moreover, each of the top member 131 and the partition member 132 is a member that does not allow unnecessary substance that is generated by the irradiation of the processing light EL to pass therethrough (namely, that is configured to shield). Fume of the coat SF of paint is one example of the unnecessary substance. As a result, the unnecessary substance that is generated in the containing space SP does not leak outside the containing space SP (namely, outside the housing apparatus 13).

An end part (specifically, an end part at the coat SF of paint side and an end part at the −Z side in the example illustrated in FIG. 1) 134 of the partition member 132 is allowed to contact with the surface of the coat SF of paint. When the end part 134 contacts with the coat SF of paint, the housing apparatus 13 (namely, the top member 131 and the partition member 132) maintains a sealability of the containing space SP with the coat SF of paint. The end part 134 is configured to change a shape thereof (especially, a shape of a contact surface (the surface at the −Z side in the example illustrated in FIG. 1) of the end part 134 that contacts with the coat SF of paint, the same applies to the below described description) in accordance with a shape of the surface of the coat SF of paint when it contacts with the coat SF of paint. For example, when the end part 134 contacts with the coat SF of paint the surface of which is a planar shape, the shape of the end part 134 becomes a planar shape as with the coat SF of paint. For example, when the end part 134 contacts with the coat SF of paint the surface of which is a curved shape, the shape of the end part 134 becomes a curved shape as with the coat SF of paint. As a result, the sealability of the containing space SP improves, compared to the case where the end part 134 is not configured to change the shape thereof in accordance with the shape of the surface of the coat SF of paint. The end part 134 that is made from a member having an elasticity such as a gum (in other words, a flexible member) is one example of the end part 134 that is configured to change the shape. Note that a bellows-like end part 134a that is a structure having an elasticity as illustrated in FIG. 4 may be used as the end part 134 that is configured to change the shape, for example.

Return to FIG. 1, the end part 134 is configured to attach to the coat SF of paint in a state where it contacts with the coat SF of paint. For example, the end part 134 may be provided with a suction mechanism that is configured to suck the coat SF of paint. When the end part 134 attaches to the coat SF of paint, the sealability of the containing space SP improves more, compared to the case where the end part 134 does not attach to the coat SF of paint. However, the end part 134 may not be configured to adhere to the coat SF of paint. Even in this case, the sealability of the containing space SP is maintained to a certain degree as long as the end part 134 contacts with the coat SF of paint.

The partition member 132 is a member that is configured to extend and contract along the Z axis by a non-illustrated driving system (for example, an actuator) that operates under the control of the control apparatus 18. For example, the partition member 132 may be a bellows-like member (what we call a bellows). In this case, the partition member 132 is configured to extend and contract due to the expansion and the contraction of the bellows-like part. Alternatively, the partition member 132 may be provided with a telescopic pipe in which a plurality of hollow cylindrical members having different diameters, respectively, are combined, for example. In this case, the partition member 132 is configured to extend and contract due to a relative movement of the plurality of cylindrical members. A state of the partition member 132 is allowed to be set to at least a first expansion state in which the partition member 132 extends along the Z axis and a size thereof in the Z axis direction is relatively long and a first contraction state in which the partition member 132 contracts along the Z axis and the size thereof in the Z axis direction is relatively short. When the partition member 132 is in the first expansion state, the end part 134 is allowed to contact with the coat SF of paint. On the other hand, when the partition member 132 is in the first contraction state, the end part 134 does not contact with the coat SF of paint. Namely, when the partition member 132 is in the first contraction state, the end part 134 is away from the coat SF of paint toward the +Z side. Note that a configuration for switching the state of the partition member 132 between the first expansion state in which the end part 134 of the partition member 132 is allowed to contact with the coat SF of paint and the first contraction state in which the end part 134 is away from the coat SF of paint is not limited to a configuration that allows the partition member 132 to extend and contract. For example, the state of the partition member 132 may be switched between the first expansion state and the first contraction state by means of the housing apparatus 13 itself being configured to move along the ±Z direction.

The housing apparatus 13 is further provided with the detection apparatus 135. The detection apparatus 135 detects the unnecessary substance (namely, the substance that is generated by the irradiation of the processing light EL) in the containing space SP. A detected result of the detection apparatus 135 is used by the control apparatus 18 when the state of the partition member 132 is changed from the first expansion state to the first contraction state, as described later in detail.

The support apparatus 14 supports the housing apparatus 13. Since the housing apparatus 13 supports the driving system 12 and the light irradiation apparatus 11, the support apparatus 14 substantially supports the driving system 12 and the light irradiation apparatus 11 through the housing apparatus 13. In order to support the housing apparatus 13, the support apparatus 14 is provided with a beam member 141 and a plurality of leg members 142. The beam member 141 is disposed at the +Z side than the housing apparatus 13. The beam member 141 is a beam-like member that extends along the XY plane. The beam member 141 supports the housing member 13 through supporting members 143. The plurality of leg members 142 are disposed at the beam member 141. The leg member 142 is a bar-like member that extends from the beam member 141 toward the −Z side.

An end part (specifically, an end part at the coat SF of paint side and an end part at the −Z side in the example illustrated in FIG. 1) 144 of the leg member 142 is allowed to contact with the surface of the coat SF of paint. As a result, the support apparatus 14 is supported by the coat SF of paint (namely, by the processing target object S). Namely, the support apparatus 14 supports the housing apparatus 13 in a state where the end part 144 contacts with the coat SF of paint (in other words, in a state where the support apparatus 14 is supported by the coat SF of paint). The end part 144 is configured to change a shape thereof (especially, a shape of a contact surface (the surface at the −Z side in the example illustrated in FIG. 1) of the end part 144 that contacts with the coat SF of paint, the same applies to the below described description) in accordance with the shape of the surface of the coat SF of paint when the it contacts with the coat SF of paint, as with the end part 134 of the housing apparatus 13. The end part 144 is configured to adhere to the coat SF of paint in a state where it contacts with the coat SF of paint. For example, the end part 144 may be provided with a suction mechanism that is configured to suck the coat SF of paint. When the end part 144 adheres to the coat SF of paint, a stability of the support apparatus 14 improves more, compared to the case where the end part 144 does not adhere to the coat SF of paint. However, the end part 144 may not be configured to adhere to the coat SF of paint.

The beam member 141 is a member that is configured to extend and contract along at least one of the X axis and the Y axis (alternatively, along any direction along the XY plane) by the driving system 15 that operates under the control of the control apparatus 18. For example, the beam member 141 may be provided with a telescopic pipe in which a plurality of hollow cylindrical members having different diameters, respectively, are combined, for example. In this case, the beam member 141 is configured to extend and contract due to a relative movement of the plurality of cylindrical members.

The leg member 142 is a member that is configured to extend and contract along the Z axis by the driving system 15 that operates under the control of the control apparatus 18. For example, the leg member 142 may be provided with a telescopic pipe in which a plurality of hollow cylindrical members having different diameters, respectively, are combined, for example. In this case, the leg member 142 is configured to extend and contract due to a relative movement of the plurality of cylindrical members. A state of the leg member 142 is allowed to be set to at least a second expansion state in which the leg member 142 extends along the Z axis and a size thereof in the Z axis direction is relatively long and a second contraction state in which the leg member 142 contracts along the Z axis and the size thereof in the Z axis direction is relatively short. When the leg member 142 is in the second expansion state, the end part 144 is allowed to contact with the coat SF of paint. On the other hand, when the leg member 142 is in the second contraction state, the end part 144 does not contact with the coat SF of paint. Namely, when the leg member 142 is in the second contraction state, the end part 144 is away from the coat SF of paint toward the +Z side.

The driving system 15 moves the support apparatus 14 relative to the coat SF of paint (namely, relative to the processing target object S on the surface of which the coat SF of paint is formed) under the control of the control apparatus 18. Namely, the driving system 15 moves the support apparatus 14 relative to the coat SF of paint so as to change a relative positional relationship between the support apparatus 14 and the coat SF of paint. Since the support apparatus 14 supports the housing apparatus 13, the driving system 15 substantially moves the housing apparatus 13 relative to the coat SF of paint by moving the support apparatus 14. Namely, the driving system 15 moves the support apparatus 14 relative to the coat SF of paint so as to substantially change a relative positional relationship between the housing apparatus 13 and the coat SF of paint. Moreover, the housing apparatus 13 supports the light irradiation apparatus 11 through the driving system 12. Thus, the driving system 15 is allowed to substantially move the light irradiation apparatus 11 relative to the coat SF of paint by moving the support apparatus 14. Namely, the driving system 15 is allowed to move the support apparatus 14 relative to the coat SF of paint so as to substantially change the relative positional relationship between the light irradiation apparatus 14 and the coat SF of paint. In other words, the driving system 15 is allowed to move the support apparatus 14 relative to the coat SF of paint so as to substantially change the relative positional relationship between the plurality of irradiation areas EA and the coat SF of paint.

The driving system 15 extends and contracts the beam member 141 in order to move the support apparatus 14 under the control of the control apparatus 18. Moreover, the driving system 15 extends and contracts the plurality of leg members 142 in order to move the support apparatus 14 under the control of the control apparatus 18. Note that a moving aspect of the support apparatus 14 by the driving system 15 will be described later in detail with reference to FIG. 7 to FIG. 17.

The exhaust apparatus 16 is coupled to the containing space SP through an exhaust pipe 161. The exhaust apparatus 16 is configured to exhaust gas in the containing space SP. Especially, the exhaust apparatus 16 is configured to suck the unnecessary substance that is generated by the irradiation of the processing light EL outside the containing space SP from the containing space SP by exhausting the gas in the containing space SP. Especially, when the unnecessary substance is on the optical path of the processing lights EL, there is a possibility that the irradiation of the processing lights EL to the coat SF of paint is affected. Thus, the exhaust apparatus 16 especially sucks, from a space including the optical path of the processing lights EL between the terminal optical element of the optical system 112 and the coat SF of paint, the unnecessary substance with the gas in this space. The unnecessary substance sucked by the exhaust apparatus 16 from the containing space SP is discharged outside the processing apparatus 1 through a filter 162. The filter 162 sorbs the unnecessary substance. Note that the filter 162 may be attachable and detachable and may be replaceable.

The gas supply apparatus 17 is coupled to the containing space SP through an intake pipe 171. The gas supply apparatus 17 is configured to supply gas to the containing space SP. The gas that is supplied to the containing space SP includes at least one of an air, a CDA (Clean Dry Air) and an inert gas. The inert gas includes a nitrogen gas. In the present example, the gas supply apparatus 17 supplies the CDA. Thus, the containing space SP is a space that is purged by the CDA. At least a part of the CDA supplied to the containing space SP is sucked by the exhaust apparatus 16. The CDA sucked by the exhaust apparatus 16 from the containing space SP is discharged outside the processing apparatus 1 through the filter 162.

The gas supply apparatus 17 especially supplies the gas such as the CDA to an optical surface 1124 at the containing space SP side of the fθ lens 1123 (namely, an optical surface at the containing space SP side of the terminal optical element of the optical system 112) illustrated in FIG. 3. There is a possibility that the optical surface 1124 is exposed to the unnecessary substance that is generated by the irradiation of the processing light EL, because the optical surface 1124 faces the containing space SP. As a result, there is a possibility that the unnecessary substance adheres to the optical surface 1124. Moreover, there is a possibility that the unnecessary substance adhered to the optical surface 1124 is backed (namely, is firmly fixed) by the processing light EL passing through the optical surface 1124, because the processing lights EL pass through the optical surface 1124. The unnecessary substance adhered (moreover, firmly fixed) to the optical surface 1124 becomes a dust to be likely to affect a characteristic of the processing lights EL. However, when the gas such as the CDA is supplied to the optical surface 1124, a contact between the optical surface 1124 and the unnecessary substance is prevented. Thus, an adherence of the dust to the optical surface 1124 is prevented. Therefore, the gas supply apparatus 17 also serves as an adherence prevention apparatus that prevents the adherence of the dust to the optical surface 1124. Moreover, even when the dust is adhered (moreover, firmly fixed) to the optical surface 1124, there is a possibility that the dust is removed (for example, is blown) by the CDA supplied to the optical surface 1124. Therefore, the gas supply apparatus 17 also serves as an adherence prevention apparatus that removes the dust adhered to the optical surface 1124.

The control apparatus 18 controls an entire operation of the processing apparatus 1. Especially, the control apparatus 18 controls the light irradiation apparatus 11, the driving system 12, the housing apparatus 13 and the driving system 15 so that the concave part C having a desired shape is formed at a desired position, as described later in detail.

(2) SPECIFIC EXAMPLE OF PROCESSING OPERATION BY PROCESSING APPARATUS 1

(2-1) Specific Example of Structure formed by Processing Operation

As described above by using FIG. 2, the processing apparatus 1 forms the concave part C at the coat SF of paint in the present embodiment. The concave part C is formed at a part of the coat SF of paint that is actually irradiated with the processing light EL (namely, a part at which the irradiation area EA that is actually irradiated with the processing light EL is set). Thus, the concave part C is formable at a desired position of the coat SF of paint by properly setting a position on the coat SF of paint that is actually irradiated with the processing light EL (namely, a position at which the irradiation area EA that is actually irradiated with the processing light EL is set). Namely, a structure of the coat SF of paint is formable on the processing target object S.

In the present embodiment, the processing apparatus 1 forms a riblet structure that is one example of the structure of the coat SF of paint on the processing target object S under the control of the control apparatus 15. The riblet structure is a structure by which a resistance (especially, a frictional resistance, a turbulent frictional resistance) of the surface of the coat SF of paint to a fluid is reducible. A resistance of the processing target object S on which the riblet structure is formed to the fluid is smaller than a resistance of the processing target object S on which the riblet structure is not formed to the fluid. Thus, it can be said that the riblet structure is a structure by which the resistance of the surface of the processing target object S to the fluid is reducible. Note that the fluid here may be any medium (gas, liquid) that flows relative to the surface of the coat SF of paint, and the medium may be referred to as the fluid when the surface of the coat SF of paint moves although the medium itself is static.

One example of the riblet structure is illustrated in FIG. 5A and FIG. 5B. As illustrated in FIG. 5A and FIG. 5B, the riblet structure is a structure in which a plurality of concave structures CP1 each of which is formed by sequentially forming the concave part C along a first direction (the Y axis direction in an example illustrated in FIG. 5A and FIG. 5B) (namely, a plurality of concave structures CP1 each of which is linearly formed to extend along the first direction) are arranged along a second direction (the X axis direction in the example illustrated in FIG. 5A and FIG. 5B) that intersects with the first direction, for example. A convex structure CP2 that protrudes from a surrounding area substantially exists between two adjacent concave structures CP1. Therefore, it can be said that the riblet structure is a structure in which a plurality of convex structures CP2 each of which linearly extends along the first direction (for example, the Y axis direction) are arranged along the second direction (for example, the X axis direction) that intersects with the first direction, for example. The riblet structure illustrated in FIG. 5A and FIG. 5B is a periodical structure.

An interval between the two adjacent concave structures CP1 (namely, an arrangement pitch P1 of the concave structure CP1) is several microns to several hundred microns, for example, however, may be different size. Moreover, a depth (namely, a depth in the Z axis direction) D of each concave structure CP1 is several microns to several hundred microns, for example, however, may be different size. The depth D of each concave structure CP1 may be equal to or smaller than the arrangement pitch P1 of the concave structure CP1. The depth D of each concave structure CP1 may be equal to or smaller than a half of the arrangement pitch P1 of the concave structure CP1. A shape of a cross-sectional surface including the Z axis (specifically, a cross-sectional surface along the XZ plane) of each concave structure CP1 is a bowl-shaped curved shape, however, may be a triangle shape, may be a quadrangular shape, may be a polygonal shape more than a pentagonal shape. Similarly, an interval between the two adjacent convex structures CP2 (namely, an arrangement pitch P2 of the convex structure CP2) is several microns to several hundred microns, for example, however, may be different size. Moreover, a height (namely, a height in the Z axis direction) H of each convex structure CP2 is several microns to several hundred microns, for example, however, may be different size. The height H of each convex structure CP2 may be equal to or smaller than the arrangement pitch P2 of the convex structure CP2. The height H of each convex structure CP2 may be equal to or smaller than a half of the arrangement pitch P2 of the convex structure CP2. A shape of a cross-sectional surface including the Z axis (specifically, a cross-sectional surface along the XZ plane) of each convex structure CP2 is a chevron shape having a curved slope, however, may be a triangle shape, may be a quadrangular shape, may be a polygonal shape more than a pentagonal shape. Note that the riblet structure itself formed by the processing apparatus 1 may be an existing riblet structure disclosed in "Mechanical Engineers' Handbook, Basic Edition, a4 Fluids Engineering", Chapter 5, edited by The Japan Society of Mechanical Engineers, for example, and a detailed description of the riblet structure itself is omitted.

As described above, the resistance of the surface of the processing target object S to the fluid is reducible by the riblet structure like this, as described above. Thus, the processing target object S may be an object an object (for example, a structural object) the resistance of which to the fluid is desired to be reduced. For example, the processing target object S may be an object (namely, a movable body) that is movable so that at least a part thereof travels in the fluid (for example, at least one of the gas and the liquid). Specifically, for example, the processing target object S may include an airframe (for example, at least one of a body PL1, a main wing PL2, a vertical tail PL3 and a horizontal tail PL4) of an airplane PL as illustrated in FIG. 6A to FIG. 6C. In this case, as illustrated in FIG. 6A to FIG. 6C, the processing apparatus 1 may self-stands on the airframe of the airplane PL by the support apparatus 14. Alternatively, the processing apparatus 1 may be attached to the airframe of the airplane PL to suspend (namely, hang) from the airframe of the airplane PL by the support apparatus 14 as illustrated in FIG. 6B, because the end part 144 of the leg member 142 of the support apparatus 14 is configured to attach to the coat SF of paint. Moreover, the processing apparatus 1 is capable of self-standing on the coat SF of paint even when the surface of the coat SF of paint is inclined with respect to the horizontal plane in a state where the surface of the coat SF of paint faces upwardly, because the end part 144 of the leg member 142 of the support apparatus 14 is configured to attach to the coat SF of paint and the end part 134 of the partition member 132 of the housing apparatus 13 is configured to adhere to the coat SF of paint. Moreover, the processing apparatus 1 is capable of attaching to the coat SF of paint to suspend from the coat SF of paint even when the surface of the coat SF of paint is inclined with respect to the horizontal plane in a state where the surface of the coat SF of paint faces downwardly. Even in both cases, the light irradiation apparatus 11 is movable along the surface of the airplane PL by the driving system 12 and/or the movement of the support apparatus 14. Therefore, the processing apparatus 1 is capable of forming the riblet structure of the coat SF of paint at the processing target object S such as the airframe of the airplane (namely, the processing target object S the surface of which is a curved surface, the surface of which is inclined with respect to the horizontal plane or the surface of which faces downwardly).

Beyond that, for example, the processing target object S may include a vehicle body of a vehicle. For example, the processing target object S may include a ship hull of a ship. For example, the processing target object S may include a body of a rocket. For example, the processing target object S may include a turbine (for example, at least one of a hydraulic turbine, a wind turbine and the like, especially a turbine blade thereof). Alternatively, for example, the processing target object S may include a component that constitutes the object at least a part of which travels in the fluid. Alternatively, for example, the processing target object S may include an object at least a part of which is fixed in the flowing fluid. Specifically, for example, the processing target object S may include a bridge column built in a river or a sea.

Note that one example of the processing target object S described here is a relatively large object (for example, an object having a size of an order of several meters to several hundred meters). In this case, as illustrated in FIG. 6A to FIG. 6C, a size of the light irradiation apparatus 11 is smaller than a size of the processing target object S. However, the processing target object S may be an object having any size. For example, the processing target object S may be an object having a size of an order of kilometer, centimeter, millimeter or micrometer.

A size of the above described riblet structure (for example, at least one of the arrangement pitch P1 of the concave structure CP1, the depth D of each concave structure CP1, the arrangement pitch P2 of the convex structure CP2, the height H of each convex structure CP2 and the like) may be set to a proper size by which an effect of a reduction of the resistance is properly achieved based on what object the processing target object S is. More specifically, the size of the riblet structure may be set to a proper size by which the effect of the reduction of the resistance is properly achieved based on a type of the fluid that distributes around the used (namely, operated) processing target object S, a relative velocity of the processing target object S relative to the fluid, a shape of the processing target object S and the like. For example, when the processing target object S is the airframe of the airplane that flies at a 1000 kilometer per hour at an altitude of 10 kilometer in cruising, the arrangement pitch P1 of the concave structure CP1 (namely, the arrangement pitch P2 of the convex structure CP2) may be set to about 78 micrometers, for example.

Moreover, the size of the above described riblet structure may be set to a proper size by which an effect of a reduction of the resistance is properly achieved based on what object the processing target object S is and where the riblet structure is formed at the object. For example, when the processing target object S is the airframe of the airplane PL, the size of the riblet structure formed at the body PL1 may be different from the size of the riblet structure formed at the main wing PL2.

(2-2) Flow of Processing Operation

Next, with reference to FIG. 7 to FIG. 17, a flow of a processing operation for forming the riblet structure will be described.

Firstly, as described above, the plurality of processing lights EL are deflected by the Galvano mirror 1122. In order to form the riblet structure, the Galvano mirror 1122 deflects the plurality of processing lights EL to alternately repeat a scan operation for sweeping the surface of the coat SF of paint with the plurality of processing lights EL along the Y axis (namely, for moving the plurality of irradiation areas EA along the Y axis on the surface of the coat SF of paint) and a step operation for moving the plurality of irradiation areas EA along the X axis on the surface of the coat SF of paint by a predetermined amount. In this case, a size of an area on the surface of the coat SF of paint that is swept with the plurality of processing lights EL by controlling the Galvano mirror 1122 without moving the light irradiation apparatus 11 relative to the coat SF of paint is limited. Therefore, in the present embodiment, as illustrated in FIG. 7, the control apparatus 18 sets a plurality of unit processing areas SA on the surface of the coat SF of paint (especially, an area of the coat SF of paint at which the riblet structure should be formed). Each unit processing area SA corresponds to an area that is sweepable with the plurality of processing lights EL by controlling the Galvano mirror 1122 without moving the light irradiation apparatus 11 relative to the coat SF of paint. A shape of each unit processing area SA is a quadrangular shape, however, may be any shape.

The control apparatus 18 forms the riblet structure at one unit processing area SA (for example, SA1) by controlling the light irradiation apparatus 11 to irradiate the one unit processing area SA (SA1) with the plurality of processing lights EL deflected by the Galvano mirror 1122. Then, the control apparatus 18 disposes the light irradiation apparatus 11 on a position from which another unit processing area SA (for example, SA2) is irradiated with the plurality of processing lights EL by controlling at least one of the driving systems 12 and 15 to move the light irradiation apparatus 11 relative to the coat SF of paint. Then, the control apparatus 18 forms the riblet structure at the another unit processing area SA (SA2) by controlling the light irradiation apparatus 11 to irradiate the another unit processing area SA (SA2) with the plurality of processing lights EL deflected by the Galvano mirror 1122. The control apparatus 18 repeats forms the riblet structure by repeating the following operation at all unit processing areas SA1 to SA16.

Next, an operation for forming the riblet structure at the unit processing areas SA1 to SA4 illustrated in FIG. 7 will be described as one example. Incidentally, in the below described description, an example in which two unit processing areas SA that are adjacent to each other along the X axis are located in the containing space SP will be described. However, the fact remains that same operation is performed even when any number of unit processing area SA is located in the containing space SP.

As illustrated in FIG. 8, firstly, the control apparatus 18 controls the driving system 15 to move the support apparatus 14 relative to the coat SF of paint so that the housing apparatus 13 is disposed at a first housing position at which the unit processing areas SA1 and SA2 are located in the containing space SP. Namely, the control apparatus 18 moves the housing apparatus 13 supported by the support apparatus 14 so that the unit processing areas SA1 and SA2 are covered by the housing apparatus 13. Moreover, the control apparatus 18 controls the driving system 12 to move the light irradiation apparatus 11 relative to the coat SF of paint so that the light irradiation apparatus 11 is disposed at a first irradiation position from which the unit processing area SA1 is irradiated with the plurality of processing lights EL. After the housing apparatus 13 is disposed at the first housing position and the light irradiation apparatus 11 is disposed at the first irradiation position, the partition member 132 becomes to be the first expansion state. Therefore, the end part 134 of the partition member 132 contacts with and adheres to the coat SF of paint. Similarly, the plurality of leg members 142 becomes to be the second expansion state. Therefore, the end parts 144 of the plurality of leg members 142 contact with and adhere to the coat SF of paint.

Then, as illustrated in FIG. 9A and FIG. 9B, the control apparatus 18 controls the light irradiation apparatus 11 (especially, the Galvano mirror 1122) to sweep the unit processing area SA1 with the plurality of processing lights EL. Specifically, the control apparatus 18 controls the Y scanning mirror 1122Y of the Galvano mirror 1122 to sweep a certain area in the unit processing area SA1 with the plurality of processing lights EL along the Y axis direction, in order to perform the above described scan operation. During a period when the scan operation is performed, the light source system 111 emits the plurality of processing lights EL. Then, the control apparatus 18 rotates the X scanning mirror 1122X of the Galvano mirror 1122 by a unit step amount, in order to perform the above described step operation. During a period when the step operation is performed, the light source system 111 does not emit the plurality of processing lights EL. Then, the control apparatus 18 controls the Y scanning mirror 1122Y of the Galvano mirror 1122 to sweep a certain area in the unit processing area SA1 with the plurality of processing lights EL along the Y axis direction, in order to perform the above described scan operation. In this manner, the control apparatus 18 controls the Galvano mirror 1122 to sweep whole of the unit processing area SA1 (alternatively, a partial area at which the riblet structure should be formed in the unit processing area SA1) with the plurality of processing lights EL by alternately repeating the scan operation and the step operation. As a result, the riblet structure is formed in the unit processing area SA1. Note that a width of an area that is swept by the processing lights EL (namely, a width of the unit processing area SA, especially, a width in the X axis direction) is wider than a width (especially, a width in the X axis direction) of the light irradiation apparatus 11, as illustrated in FIG. 9A and FIG. 9B.

The control apparatus 18 controls the driving system 15 so that the plurality of leg members 142 continue to be in the second expansion state during a period when the light irradiation apparatus 11 emits the processing lights EL. As a result, the end parts 144 of the plurality of leg members 142 continue to adhere to the coat SF of paint. As a result, the stability of the support apparatus 14 improves, and thus, there is a low possibility that the irradiation areas EA of the processing lights EL are shifted on the coat SF of paint accidentally due to an instability of the support apparatus 14. However, a part of the plurality of leg members 142 may be in the second contraction state as long as the support apparatus 14 is capable of self-standing on the coat SF of paint (alternatively, is capable of adhering to the coat SF of paint to suspend from the coat SF of paint) during at least a part of the period when the light irradiation apparatus 11 emits the lights EL.

The control apparatus 18 controls the non-illustrated driving system that extends and contracts the partition member 132 so that the partition member 132 continues to be in the first expansion state during the period when the light irradiation apparatus 11 emits the processing lights EL. As a result, the end part 134 of the partition member 132 continues to attach to the coat SF of paint. As a result, the sealability of the containing space SP is maintained, and thus, the processing light EL propagating in the containing space SP does not leak outside the containing space SP (namely, outside the housing apparatus 13). Moreover, the unnecessary substance that is generated in the containing space SP does not leak outside the containing space SP (namely, outside the housing apparatus 13).

Note that there is a possibility that at least a part of the end part 134 that should attach to the coat SF of paint is away from the coat SF of paint due to any factor. If the light irradiation apparatus 11 continues to emit the processing lights EL in this situation, there is a possibility that at least one of the processing light EL and the unnecessary substance leaks outside the housing apparatus 13. Thus, the control apparatus 18 may control the light irradiation apparatus 11 to stop the irradiation of the processing lights EL when it is detected that at least a part of the end part 134 is away from the coat SF of paint during the period when the light irradiation apparatus 11 emits the processing lights EL.

Then, as illustrated in FIG. 10, the control apparatus 18 controls the driving system 12 so that the light irradiation apparatus 11 moves from the first irradiation position to a second irradiation position at which the light irradiation apparatus 11 irradiates the unit processing area SA2 with the plurality of processing lights EL. During a period when the light irradiation apparatus 11 moves, the control apparatus 18 controls the light irradiation apparatus 11 so that the light irradiation apparatus 11 does not emit the processing lights EL.

Then, as illustrated in FIG. 11A and FIG. 9B, the control apparatus 18 controls the light irradiation apparatus 11 (especially, the Galvano mirror 1122) to sweep the unit processing area SA2 with the plurality of processing lights EL. Specifically, the control apparatus 18 controls the light irradiation apparatus 11 (especially, the Galvano mirror 1122) to sweep whole of the unit processing area SA2 (alternatively, a partial area at which the riblet structure should be formed in the unit processing area SA2) with the plurality of processing lights EL by alternately repeating the above described scan operation and the above described step operation. As a result, the riblet structure is formed in the unit processing area SA2. Note that the concave parts CP1 constituting the riblet structure in the unit processing area SA1 may be sequentially connected to or may not be connected to the concave parts CP1 constituting the riblet structure in the unit processing area SA2 (alternatively, other unit processing area SA) one by one. Because the size of about 10 centimeter or more can be secured as the size of the unit processing size SA, and thus, a sequential length of one concave part CP1 formed by sweeping the unit processing area SA with the processing lights EL is about 10 centimeter or more, and this size is sufficiently longer than a sequential length (about several millimeters) that is calculated on the basis of an air speed and a frequency of turbulence phenomenon when the airplane is used (namely, cruises) to fulfill a function of the riblet structure.

After the riblet structure is formed in the unit processing area SA2, there is no unit processing area SA in which the riblet structure is not formed yet in the containing space SP. Thus, it is difficult for the light irradiation apparatus 11 to irradiate the unit processing area SA in which the riblet structure is not formed yet with the plurality of processing lights EL to form therein only by moving the light irradiation apparatus 11 in the containing space SP by the driving system 12. Thus, when there is no unit processing area SA in which the riblet structure is not formed yet in the containing space SP, the control apparatus 18 controls the driving system 15 to move the support apparatus 14 (namely, to move the housing apparatus 13) so that the unit processing area SA in which the riblet structure is not formed yet is located in the containing space SP.

Specifically, firstly, as illustrated in FIG. 12, the control apparatus 18 controls the non-illustrated driving system that extends and contracts the partition member 132 so that the state of the partition member 132 is switched from the first expansion state to the first contraction state. As a result, the end part 134 of the partition member 132 is away from the coat SF of paint. Note that the control apparatus 18 controls the light irradiation apparatus 11 so that the light irradiation apparatus 11 does not emit the processing lights EL during a period when the support apparatus 14 moves. Thus, even when the end part 134 is away from the coat SF of paint, at least one of the processing light EL and the unnecessary substance does not leak outside the housing apparatus 13.

However, although the unnecessary substance existing in the containing space SP is sucked outside the containing space SP by the above described exhaust apparatus 16, there is a possibility that all of the unnecessary substance existing in the containing space SP is not sucked by the exhaust apparatus 16 (namely, the unnecessary substance remains in the containing space SP) due to any factor. In this, if the end part 134 is away from the coat SF of paint, there is a possibility that the unnecessary substance leaks outside the housing apparatus 13. Thus, the control apparatus 18 determines on the basis of the detected result of the detection apparatus 135 that detects the unnecessary substance in the containing space SP whether or not the partition member 132 is switched from the first expansion state to the first contraction state. When the unnecessary substance remains in the containing space SP, the control apparatus 18 does not switch the partition member 132 from the first expansion state to the first contraction state. In this case, the exhaust apparatus 16 continues to suck the unnecessary substance remaining in the containing space SP. On the other hand, when the unnecessary substance does not remain in the containing space SP, the control apparatus 18 switches the partition member 132 from the first expansion state to the first contraction state.

Moreover, the control apparatus 18 controls the driving system 15 so that the state of at least one leg member 142 that moves relative to the coat SF of paint due to the movement of the support apparatus 14 (especially, the expansion of the contracted beam member 141 described later) among the plurality of leg members 142 is switched from the second expansion state to the second contraction state. The leg member 142 that moves relative to coat SF of paint due to the expansion of the contracted beam member 141 is typically the leg member 142 that is disposed at a front side along a moving direction of the support apparatus 14 (namely, a moving direction of the housing apparatus 13) among the plurality of leg members 142. In an example illustrated in FIG. 12, the support apparatus 14 moves toward the +X side and the leg member 142 that is disposed at the front side along the moving direction of the support apparatus 14 is the leg member 142 at the +X side. Hereinafter, the leg member 142 that is disposed at the front side along the moving direction of the support apparatus 14 is referred to as a "front leg member 142". As a result, the end part 144 of the front leg member 142 is away from the coat SF of paint.

Then, as illustrated in FIG. 13, the control apparatus 18 controls the driving system 15 so that the housing apparatus 13 moves from the first housing position to a second housing position at which the unit processing areas SA3 and SA4 are located in the containing space SP. Specifically, the control apparatus 18 controls the driving system 15 so that the beam member 141 extends along the moving direction of the support apparatus 14. As a result, the beam member 141 extends while supporting the housing apparatus 13 (moreover, while supporting the light irradiation apparatus 11 supported by the housing apparatus 13). In parallel with the movement of the support apparatus 14, the control apparatus 18 controls the driving system 12 so that the light irradiation apparatus 11 moves from the second irradiation position to a third irradiation position at which the light irradiation apparatus 11 irradiates the unit processing area SA3 with the plurality of processing lights EL.

The control apparatus 18 controls the non-illustrated driving system that extends and contracts the partition member 132 so that the partition member 132 continues to be in the first contraction state during the period when the support apparatus 14 moves (namely, the contracted beam member 141 extends). As a result, the movement of the support apparatus 14 (namely, the movement of the housing apparatus 13) is not prevented by a contact between the end part 134 of the partition member 132 and the coat SF of paint. Moreover, the coat SF of paint is not scratched by the contact between the end part 134 and the coat SF of paint when the support apparatus 14 moves. However, when the contact between the end part 134 and the coat SF of paint does not prevent movement of the support apparatus 14, at least a part of the end part 134 may contact with the coat SF of paint during at least a part of the period when the support apparatus 14 moves. When the contact between the end part 134 and the coat SF of paint does not scratch the coat SF of paint during the period when the support apparatus 14 moves, at least a part of the end part 134 may contact with the coat SF of paint during at least a part of the period when the support apparatus 14 moves.

Moreover, the control apparatus 18 controls the driving system 15 so that the front leg member 142 continues to be in the second contraction state during the period when the support apparatus 14 moves. As a result, the movement of the support apparatus 14 (namely, the movement of the housing apparatus 13) is not prevented by a contact between the end part 144 of the front leg member 142 and the coat SF of paint. Moreover, the coat SF of paint is not scratched by the contact between the end part 144 and the coat SF of paint when the support apparatus 14 moves. However, when the contact between the end part 144 and the coat SF of paint does not prevent movement of the support apparatus 14, at least a part of the end part 144 may contact with the coat SF of paint during at least a part of the period when the support apparatus 14 moves. When the contact between the end part 144 and the coat SF of paint does not scratch the coat SF of paint during the period when the support apparatus 14 moves, at least a part of the end part 144 may contact with the coat SF of paint during at least a part of the period when the support apparatus 14 moves.

Moreover, the control apparatus 18 controls the driving system 15 so that the other leg member 142 of the plurality of leg members 142 other than the front leg member 142 continues to be in the first expansion state during the period when the support apparatus 14 moves. As a result, the movement of the support apparatus 14 (namely, the movement of the housing apparatus 14) is not prevented by the contact between the end part 144 of the front leg member 142 and the coat SF of paint. Moreover, the coat SF of paint is not scratched by the contact between the end part 144 and the coat SF of paint when the support apparatus 14 moves. Even when the end part 144 of the front leg member 142 is away from the coat SF of paint, the end part 144 of the other leg member other than the front leg member 142 contacts with the coat SF of paint. Thus, the fact remains that the processing apparatus 1 is capable of self-standing on the coat SF of paint (alternatively, is capable of adhering to the coat SF of paint to suspend from the coat SF of paint), as with the case where all end parts 144 of the plurality of leg members 142 contact with the coat SF of paint.

Moreover, during the period when the support apparatus 14 moves, the control apparatus 18 controls the light irradiation apparatus 11 so that the light irradiation apparatus 11 does not emit the processing lights EL.

After the housing apparatus 13 is disposed at the second housing position, as illustrated in FIG. 14, the control apparatus 18 controls the non-illustrated driving system that extends and contracts the partition member 132 so that the partition member 132 is switched from the first contraction state to the first expansion state. As a result, the end part 134 of the partition member 132 contacts with and adheres to the coat SF of paint. Moreover, the control apparatus 18 controls the driving system 15 so that the front leg member 142 is switched from the second contraction state to the second expansion state. As a result, the end part 144 of the front leg member 142 contacts with and adheres to the coat SF of paint. Here, an operation for extending the partition member 132 and an operation for extending the front leg member 142 may be performed at the same time or may be performed at different times.

Then, as illustrated in FIG. 15, the control apparatus 18 controls the driving system 15 so that the state of at least one leg member 142 that moves relative to the coat SF of paint due to the movement of the support apparatus 14 (especially, the contraction of the extended beam member 141 described later) among the plurality of leg members 142 is switched from the second expansion state to the second contraction state. The leg member 142 that moves relative to coat SF of paint due to the contraction of the extended beam member 141 is typically the leg member 142 that is disposed at a rear side along the moving direction of the support apparatus 14 among the plurality of leg members 142. In an example illustrated in FIG. 15, the leg member 142 that is disposed at the rear side along the moving direction of the support apparatus 14 is the leg member 142 at the −X side. Hereinafter, the leg member 142 that is disposed at the rear side along the moving direction of the support apparatus 14 is referred to as a "rear leg member 142". As a result, the end part 144 of the rear leg member 142 is away from the coat SF of paint.

Then, as illustrated in FIG. 16, the control apparatus 18 controls the driving system 15 to contract the beam member 141 extending along the moving direction of the support apparatus 14.

After the beam member 141 finishes contracting, as illustrated in FIG. 17, the control apparatus 18 controls the driving system 15 so that the second leg member 142 is switched from the second contraction state to the second expansion state. As a result, the end part 144 of the rear leg member 142 contacts with and adheres to the coat SF of paint.

Then, the control apparatus 18 controls the light irradiation apparatus 11 to sweep the unit processing areas SA3 and SA4 with the plurality of processing lights EL, as with the case where the unit processing areas SA1 and SA2 are swept with the plurality of processing lights EL. Then, same operation is repeated, and thus, the surface of the coat SF of paint (especially, the area of the coat SF of paint at which the riblet structure should be formed) is irradiated with the plurality of processing lights EL. As a result, the riblet structure of the coat SF of paint is formed on the processing target object S.

(3) TECHNICAL EFFECT OF PROCESSING APPARATUS 1

As described above, the processing apparatus 1 in the present embodiment forms the riblet structure of the coat SF of paint on the surface of the processing target object S by irradiating the processing target object S (especially, the coat SF of paint formed on the surface thereof) with the processing lights EL. Thus, the processing apparatus 1 forms the riblet structure relatively easily in a relatively short time, compared to a processing apparatus that forms the riblet structure by cutting the surface of the processing target object S by a cutting tool such as an end mill.

Moreover, the processing apparatus 1 forms the plurality of concave structures CP1 at the same time by emitting the plurality of processing lights EL at the same time. Thus, the throughput relating to the formation of the riblet structure improves, compared to a processing apparatus that forms only single concave structure CP1 at a time by emitting the single processing light EL.

Moreover, the processing apparatus 1 sweeps the coat SF of paint relatively fast by deflecting the plurality of processing lights EL by the Galvano mirror 1122. Thus, the throughput relating to the formation of the riblet structure improves.

Moreover, the processing apparatus 1 forms the riblet structure on the surface of the processing target object S by processing the coat SF of paint formed on the surface of the processing target object S instead of directly processing the processing target object S. Thus, an increase of a weight of the processing target object S duet to the formation of the riblet structure is prevented, compared to a processing apparatus that forms the riblet structure by newly adding (for example, pasting), on the surface of the processing target object S (namely, the surface of the coat SF of paint), a special material for forming the riblet structure.

Moreover, the riblet structure is formable again relatively easily, because the processing apparatus 1 does not directly process the processing target object S. Specifically, when the riblet structure is formed again, firstly, the riblet structure of the coat SF of paint is removed and then new coat SF of paint is coated. Then, the processing apparatus 1 forms new riblet structure by processing the newly coated coat SF of paint. Therefore, a deterioration (for example, a breakage) of the riblet structure is handled relatively easily by forming the riblet structure again.

Moreover, the processing apparatus 1 is allowed to form the riblet structure on the surface of the processing target object S that is difficult to be directly processed or at which the riblet structure is not formed from the beginning, because the processing apparatus 1 does not directly process the processing target object S. Namely, the riblet structure is formable relatively easily by processing the coat SF of paint by the processing apparatus 1 after coating the coat SF of paint on the surface of the processing target object.

Moreover, the processing apparatus 1 forms the riblet structure of the coat SF of paint. The coat SF of paint usually has relatively strong durability to an external environment (for example, at least one of heat, light, wind and the like). Thus, the processing apparatus 1 is capable of forming the riblet structure relatively having the strong durability relatively easily.

Moreover, in the present embodiment, the optical path of the processing lights EL between the terminal optical element of the optical system 112 and the coat SF of paint is included in the containing space SP. Thus, it is possible to properly prevent the processing light EL with which the coat SF of paint is irradiated (alternatively, scattered light, reflected light or the like of the processing light EL from the coat SF of paint) from propagating (in other words, scattering) toward the surrounding environment of the processing apparatus 1, compared to a processing apparatus in which the optical path of the processing lights EL is not included in the containing space SP (namely, is exposed to an opened space). Moreover, it is possible to properly prevent the unnecessary substance generated by the irradiation of the processing light EL from flying (in other words, scattering) toward the surrounding environment of the processing apparatus 1.

Moreover, in the present embodiment, the light irradiation apparatus 11 is supported by the support apparatus 14 that is movable on the coat SF of paint. Thus, the processing apparatus is capable of relatively easily processing the coat SF of paint that relatively widely spreads. Namely, the processing apparatus 1 is capable of forming the riblet structure of the coat SF of paint in a relatively wide area on the surface of the processing target object S. Moreover, the processing apparatus 1 is capable of forming the riblet structure on the surface of the relatively large or heavy processing target object S relatively easily, because it does necessarily move the processing target object S.

Moreover, the processing apparatus 1 sucks the unnecessary substance generated by the irradiation of the processing light EL outside the containing space SP by using the exhaust apparatus 16. Thus, the unnecessary substance rarely prevents the irradiation of the processing lights EL to the coat SF of paint. Thus, an irradiation accuracy of the processing lights EL improves, compared to a processing apparatus that is not provided with the exhaust apparatus 16 (namely, in which there is a possibility that the unnecessary substance prevents the irradiation of the processing lights EL to the coat SF of paint).

Moreover, the processing apparatus 1 prevents the adherence of the dust to the optical surface 1124 (namely, the optical surface at the containing space SP side of the terminal optical element of the optical system 112) by using the gas supply apparatus 17. Thus, there is lower possibility that the irradiation of the processing lights EL to the coat SF of paint is prevented by the dust that adheres to the optical surface 1124, compared to a processing apparatus that is not provided with the gas supply apparatus 17. Thus, the irradiation accuracy of the processing lights EL improves. As a result, the forming accuracy of a riblet structure improves.

(4) MODIFIED EXAMPLE

Next, modified examples of the processing apparatus 1 will be described.

(4-1) First Modified Example

The above described structure of the light irradiation apparatus 11 illustrated in FIG. 3 is one example, and the processing apparatus 1 may be provided with another light irradiation apparatus having a structure that is different from the light irradiation apparatus 11 illustrated in FIG. 3. Next, as one example of another light irradiation apparatus having the structure that is different from the light irradiation apparatus 11, a light irradiation apparatus 21a, a light irradiation apparatus 22a, a light irradiation apparatus 23a, a light irradiation apparatus 24a, a light irradiation apparatus 25a, a light irradiation apparatus 26a and a light irradiation apparatus 27a will be described.

(4-1-1) Structure of Light Irradiation Apparatus 21a

In order to irradiate the coat SF of paint with the processing light EL, the light irradiation apparatus 21a is provided with a light source system 211a that is configured to emit the processing light EL and an optical system 212a that guides the processing light EL emitted from the light source system 211a to the coat SF of paint as illustrated in FIG. 18.

The light source system 211a is provided with a single light source 2111a. The light source 2111a may be same as the above described light source 1111, and thus, the detailed description thereof is omitted.

The optical system 212a divides the processing light EL emitted from the light source 2111a into a plurality of (typically, two) lights and forms interference fringes that are formed by an interference of two divided processing lights EL on the surface of the coat SF of paint. In order to form the interference fringes, the optical system 212a is provided with an optical divide device 2121a, a light emitting port 2123a, a light emitting port 2124a, a collecting optical system 2125a and a collecting optical system 2126a. The light divide device 2121a divides the processing light EL emitted from the light source 2111a into a first divided light EL1 and a second divided light EL2. The first divided light EL1 is emitted from the light emitting port 2123a through a non-illustrated light guiding path (for example, an optical fiber and the like). The second divided light EL2 is emitted from the light emitting port 2124a through a non-illustrated light guiding path (for example, an optical fiber and the like). The first divided light EL1 emitted from the light emitting port 2123a is converted into parallel light by the collecting optical system 2125a and the surface of the coat SF of paint is irradiated with it. The second divided light EL2 emitted from the light emitting port 2124a is converted into parallel light by the collecting optical system 2126a and the surface of the coat SF of paint is irradiated with it. The first divided light EL1 emitted from the collecting optical system 2125a and the second divided light EL2 emitted from the collecting optical system 2126a interfere with each other and form, on the surface of the coat SF of paint, interference fringes having an interference pattern that is a fringe pattern in a periodical direction along the X direction in the drawing and that corresponds to the above described riblet structure (alternatively, the concave structure CP1). Namely, the coat SF of paint is irradiated with, as the processing light for forming the riblet structure, interference light having an intensity distribution on the surface of the coat SF of paint. As a result, a part of the coat SF of paint evaporates in accordance with the interference fringes, and thus, the riblet structure of the coat SF of paint is formed on the surface of the surface of the processing target object S.

The irradiation area EA that is irradiated with the first divided light EL1 and the second divided light EL2 by the light irradiation apparatus 21a (namely, the irradiation area EA in which the interference fringes are formed) is an area that spread two-dimensionally along the surface of the coat SF of paint. Therefore, the processing apparatus 1a having the light irradiation apparatus 21a forms the riblet structure of the coat SF of paint by alternately repeating an operation for forming the interference fringes on the surface of the coat SF of paint and the step operation for moving the irradiation area EA in which the interference fringes are formed along at least one of the X axis and the Y axis on the surface of the coat SF of paint by a predetermined amount. Namely, the processing apparatus 1a having the light irradiation apparatus 21a repeats an operation for forming the interference fringes on a certain area on the surface of the coat SF of paint, then moving the light irradiation apparatus 21a relative to the coat SF of paint and then forming the interference fringes on another area on the surface of the coat SF of paint. Note that the light irradiation apparatus 21a is not capable of moving the irradiation area EA by deflecting the first divided light EL1 and the second divided light EL2. Thus, the processing apparatus 1a having the light irradiation apparatus 21a moves the irradiation area EA relative to the coat SF of paint by moving the light irradiation apparatus 21a by the driving system 12. Note that the irradiation area EA may be moved by disposing a Galvano mirror between the collecting optical systems 2125a and 2126a and the coat SF of paint in the light irradiation apparatus 21a. Moreover, a pitch of the fringe pattern of the interference fringes may be changed by changing an angle at which the first divided light EL1 from the collecting optical system 2125a and the second divided light EL2 from the collecting optical system 2126a are intercrossed. In this case, the angle at which the first divided light EL1 and the second divided light EL2 reaching the irradiation area EA are intercrossed may be changed by configuring the light emitting port 2123a and the collecting optical system 2125a to be movable as an integrated one and configuring the light emitting port 2124a and the collecting optical system 2126a to be movable as an integrated one.

(4-1-2) Structure of Light Irradiation Apparatus 22a

In order to irradiate the coat SF of paint with the processing light EL, the light irradiation apparatus 22a is provided with a light source system 221a that is configured to emit the processing light EL and an optical system 222a that guides the processing light EL emitted from the light source system 221a to the coat SF of paint as illustrated in FIG. 19.

The light source system 221a is provided with a single light source 2211a. The light source 2211a may be same as the above described light source 1111, and thus, the detailed description thereof is omitted.

The optical system 222a converts the processing light EL emitted from the light source 2211a into a plurality of processing lights EL0 and projects the plurality of processing lights EL0 on the coat SF of paint. The optical system 222a is provided with a mirror array 2221a. The mirror array 2221a is provided with a plurality of mirrors M that are arranged in a matrix. Each mirror M is configured to change an inclination angle thereof. As one example of an operation, it is switched between a state where the processing light EL entering each mirror M is reflected to the coat SF of paint and a state where the processing light EL entering each mirror M is not reflected to the coat SF of paint. Note that the inclination angle of each mirror M may be controlled to change a position of the processing light EL from each mirror M on the coat SF of paint. The control apparatus 18 controls a digital mirror device 2221a so that the plurality of processing lights EL0 that forms the above described riblet structure (especially, the plurality of concave structures CP1 that are a part of the riblet structure) are emitted from the mirror array 2221a. As a result, the light irradiation apparatus 22a irradiates the surface of the coat SF of paint with the plurality of processing lights EL at the same time, as with the above described light irradiation apparatus 11. Namely, the plurality of irradiation areas EA that are irradiated with the plurality of processing lights EL0, respectively, are set on the surface of the coat SF of paint at the same time. As a result, the light irradiation apparatus 22a is capable of forming the riblet structure of the coat SF of paint on the surface of the processing target object S, as with the above described light irradiation apparatus 11.

The optical system 222a of the light irradiation apparatus 22a may be provided with the Galvano mirror 1122 and the fθ lens 1123, as with the light irradiation apparatus 11. In this case, the light irradiation apparatus 22a may sweep the surface of the coat SF of paint with the plurality of processing lights EL by controlling the Galvano mirror 1122. Alternatively, when the optical system 222a is not provided with the Galvano mirror 1122 and the fθ lens 1123, the surface of the coat SF of paint may be swept with the plurality of processing lights EL by moving the light irradiation apparatus 22a by the driving system 12. Note that the surface of the coat SF of paint may be swept with the plurality of processing lights EL by controlling the inclination angle of each mirror M of the mirror array 2221a to change a position of a reflected surface of each mirror M.

(4-1-3) Structure of Light Irradiation Apparatus 23a

In order to irradiate the coat SF of paint with the processing light EL, the light irradiation apparatus 23a is provided with a light source system 231a that is configured to emit the processing light EL and an optical system 232a that guides the processing light EL emitted from the light source system 231a to the coat SF of paint as illustrated in FIG. 20.

The light source system 231a may be same as the above described light source system 111, and thus, the detailed description thereof is omitted. Note that the light source system 231a having the plurality of light sources 1111 (namely, the light source system 231a having the structure illustrated in FIG. 3B) is used for the description in FIG. 20.

The optical system 232a reduces the plurality of processing lights EL emitted from the plurality of light sources 1111, respectively, and projects them on the coat SF of paint. The optical system 232a is provided with a plurality of collimator lenses 2321a and a projection optical system 2322a. The plurality of collimator lenses 2321a convert the plurality of processing lights EL emitted from the plurality of light sources 1111, respectively, into parallel lights, respectively. The projection optical system 2322a projects the plurality of processing lights EL each of which is converted to the parallel light on the coat SF of paint by a predetermined reduction magnification (for example, a projection magnification of 1/10). Note that the projection optical system 2322a may be configured to form a light source image on the coat SF of paint or may be configured to the light source image at a position that is away from the coat SF of paint along the optical axis direction. As a result, the light irradiation apparatus 23a irradiates the surface of the coat SF of paint with the plurality of processing lights EL at the same time, as with the above described light irradiation apparatus 11. Namely, the plurality of irradiation areas EA that are irradiated with the plurality of processing lights EL, respectively, are set on the surface of the coat SF of paint at the same time. As a result, the light irradiation apparatus 23a is capable of forming the riblet structure of the coat SF of paint on the surface of the processing target object S, as with the above described light irradiation apparatus 11. Here, the projection magnification of the projection optical system 2322a is not limited to the reduction magnification, and may be an equal magnification or may be an enlargement magnification. Moreover, one or more optical element of the projection optical system 2322a may be configured to be movable (typically, movable along the optical axis direction) to change the projection magnification. In this case, intervals at which the plurality of irradiation areas EA are formed is changeable, and thus, the pitch of the riblet structure is changeable. Note that each of the plurality of collimator lenses 2321a may be disposed on the light source 1111. Moreover, the traveling directions of the plurality of processing lights EL emitted from the projection optical system 2322a are not limited to be parallel to each other, and intervals therebetween may be configured to increase or decrease as the plurality of processing lights EL propagates more.

The optical system 232a of the light irradiation apparatus 23a may be provided with the Galvano mirror 1122, as with the light irradiation apparatus 11. In this case, the light irradiation apparatus 23a may sweep the surface of the coat SF of paint with the plurality of processing lights EL by controlling the Galvano mirror 1122. Alternatively, when the optical system 232a is not provided with the Galvano mirror 1122, the surface of the coat SF of paint may be swept with the plurality of processing lights EL by moving the light irradiation apparatus 23a by the driving system 12. Moreover, it may be configured that the surface of the coat SF of paint may be swept with the plurality of processing lights EL by moving the light sources 1111.

(4-1-4) Structure of Light Irradiation Apparatus 24a

In order to irradiate the coat SF of paint with the processing light EL, the light irradiation apparatus 24a is provided with a light source system 241a that is configured to emit the processing light EL and an optical system 242a that guides the processing light EL emitted from the light source system 241a to the coat SF of paint as illustrated in FIG. 21.

The light source system 241a is provided with a single light source 2411a and an illumination optical system 2412a. The light source 2411a may be same as the above described light source 1111, and thus, the detailed description thereof is omitted. The illumination optical system 2412a uniforms a light amount of the processing light EL from the light source 2411a in a cross-sectional surface of a flux of the processing light EL.

The optical system 242a is provided with a mask 2421a and a projection optical system 2422a. The mask 242a is a photo mask (in other words, a reticle) at which a mask pattern having a light transmittance distribution corresponding to the riblet structure (alternatively, the structure that should be formed) (for example, a pattern in which a transmittance pattern through which the processing light EL is allowed to pass and a light shield pattern that shields the processing light EL are arranged in the X axis direction in a periodical manner) is formed. The processing light EL passing through the illumination optical system 2412a passes through the mask 2421a to be the processing light EL having an intensity distribution the corresponds to the riblet structure and that changes in a periodical manner. The projection optical system 2422a projects the processing light EL passing through the mask 2421a on the coat SF of paint by a predetermined reduction magnification (for example, a projection magnification of 1/10). In other words, the projection optical system forms a reduction image of the mask 2421a on the coat SF of paint. As a result, the light irradiation apparatus 24a irradiates the surface of the coat SF of paint with the processing light EL having the intensity distribution corresponding to the above described riblet structure (alternatively, the concave structure CP1). Namely, the surface of the coat SF of paint is irradiated with the processing light EL having the intensity distribution corresponding to the riblet structure on the surface of the coat SF of paint. As a result, a part of the coat SF of paint evaporates based on the intensity distribution of the processing light EL and thus the riblet structure of the coat SF of paint is formed on the surface of the processing target object S. Here, the projection magnification of the projection optical system 2322a is not limited to the reduction magnification, and may be an equal magnification or may be an enlargement magnification. Moreover, one or more optical element of the projection optical system 2322a may be configured to be movable (typically, movable along the optical axis direction) to change the projection magnification. In this case, period of the intensity distribution in periodical manner is changeable, and thus, the pitch of the riblet structure is changeable.

The irradiation area EA that is irradiated with the processing light EL by the light irradiation apparatus 24a is an area that spreads two-dimensionally along the surface of the coat SF of paint. Therefore, the processing apparatus 1a having the light irradiation apparatus 24a forms the riblet structure of the coat SF of paint by alternately repeating an operation for irradiating the surface of the coat SF of paint with the processing light EL through the mask 2421a and the step operation for moving the irradiation area EA along at least one of the X axis and the Y axis on the surface of the coat SF of paint by a predetermined amount. Note that the light irradiation apparatus 24a is not capable of moving the irradiation area EA by deflecting the processing light EL. Thus, the processing apparatus 1a having the light irradiation apparatus 24a moves the irradiation area EA relative to the coat SF of paint by moving the light irradiation apparatus 24a by the driving system 12.

The optical system 242a of the light irradiation apparatus 24a may be provided with the Galvano mirror 1122, as with the light irradiation apparatus 11. In this case, the light irradiation apparatus 24a may sweep the surface of the coat SF of paint with the plurality of processing lights EL by controlling the Galvano mirror 1122. Moreover, the mask 2421a and the light source system 241a may be moved relative to the projection optical system 2422a.

Note that the light irradiation apparatus 24a may be provided with a spatial light modulator that is configured to spatial-modulate the processing light EL by a modulation pattern based on the riblet structure. "Spatially-modulating the processing light EL" means changing a characteristic of the light that is at least one of an amplitude (an intensity) of the processing light EL in a cross-sectional surface of the processing light EL that intersects with the traveling direction, a phase of the light, a polarization state of the light, the wavelength of the light and the traveling direction (in other words, a deflected state). The spatial light modulator may be a transmission type of spatial light modulator that is transparent to the processing light EL to space-modulate it, or may be a reflection type of spatial light modulator that reflect the processing light EL to spatially-modulate it.

(4-1-5) Structure of Light Irradiation Apparatus 25a

In order to irradiate the coat SF of paint with the processing light EL, the light irradiation apparatus 25a is provided with a light source system 251a that is configured to emit the processing light EL, a lens array 2513a that divides the processing light EL emitted from the light source system 251a into a plurality of beams and an optical system 252a that guides the plurality of beams from the lens array 2513a to the coat SF of paint as illustrated in FIG. 22.

The light source system 245a is provided with a single light source 2511a and a beam expander 2512a that shapes, typically expands and emits an entering beam from the light source 2511a. The beam expander 2512a may have an optical member for uniforms the intensity distribution in a beam cross-sectional surface of the entering beam from the light source 2511a.

The lens array 2513a is provided with a plurality of lens elements that are arranged in a direction intersecting the entering beam, typically in the YZ plane in the drawing and each of which focuses the entering beam. The light source image that are arranged two-dimensionally is formed at an emitting side of the lens array 2513a.

The optical system 252a is provided with an aforcal zoom lens 2522a for setting an interval between a plurality of entering beams to a predetermined interval, a condensing optical system 2523a that condenses the plurality of beams from the aforcal zoom lens 2522a on a predetermined position and a fθ lens 2524a that focuses the plurality of beams from the condensing optical system 2523a on the coat SF of paint as the plurality of processing lights EL0.

The plurality of processing lights EL0 from the optical system 252a (the plurality of processing lights EL0 from the fθ lens 2524a) forms the plurality of irradiation areas EA on the coat SF of paint. In other words, the coat SF of paint is irradiated with the plurality of processing lights EL0.

Here, the aforcal zoom lens 2522a may be regarded as a zoom lens that is telecentric on both sides. In this case, a position at which the plurality of light source images are formed by the lens array 2513a, an optical path between the aforcal zoom lens 2522a and the condensing optical system 2523a and the coat SF of paint are optically conjugate to one another. Since the optical path between the aforcal zoom lens 2522a and the condensing optical system 2523a, namely, the optical path at an emitting side of the aforcal zoom lens 2522a and the coat SF of paint are optically conjugate to each other, it is clear that the interval between the processing lights EL0 reaching the coat SF of paint is changed when the interval between the plurality of beams emitted from the aforcal zoom lens 2522a is changed. Therefore, the interval between the processing lights EL0 reaching the coat SF of paint may be changed by changing a magnification (an angular magnification) of the aforcal zoom lens 2522a by a non-illustrated driving part.

Moreover, a part of a plurality of lenses of the condensing optical system 2523a may be used as a focusing lens by configuring it to be movable along the optical axis direction.

Note that the lens array 2513a may be referred to as a light divide element in the above described description. A reflection type of mirror array may be used instead of the lens array 2513a.

(4-1-6) Structure of Light Irradiation Apparatus 26a

In order to irradiate the coat SF of paint with the processing light EL, the light irradiation apparatus 26a is provided with a light source system 261a that is configured to emit the processing light EL, a lens array 2613a that divides the processing light EL emitted from the light source system 261a into a plurality of beams and an optical system 262a that guides the plurality of beams from the lens array 2613a to the coat SF of paint as illustrated in FIG. 23.

The light irradiation apparatus 26a illustrated in FIG. 23 is different from the light irradiation apparatus 25a illustrated in FIG. 22 in that a position of a Galvano mirror 2624a is disposed between a condensing optical system 2623a (a focusing lens) and a fθ lens 2625a. Another structure of the light irradiation apparatus 26a may be same as another structure of the light irradiation apparatus 25a. Even when the arrangement of the Galvano mirror 2624a is different as described above, the light irradiation apparatus 26a illustrated in FIG. 23 achieves an effect that is same as the light irradiation apparatus 25a illustrated in FIG. 22.

Note that the fθ lens 2625a may be an optical system that is telecentric on the coat SF of paint side, or may be an optical system that is non-telecentric on the coat SF of paint side. When the fθ lens 2625a is the optical system that is non-telecentric on the coat SF of paint side, an area that is larger than a size of the fθ lens 2625a is allowed to be irradiated with the processing light EL.

Moreover, when at least one partial lens of the condensing optical system 2523a or 2623a is used as the focusing lens to move it along the optical axis direction in each of the above described light irradiation apparatuses 26a and 26b illustrated in FIG. 22 and FIG. 23, respectively, there is a possibility that the magnification of the optical system 252a or 262a is changed due to a movement of the focusing lens. In this case, a fluctuation of the magnification due to the movement of the focusing lens may be modified by changing the magnification of the aforcal zoom lens 2522a or 2622a.

Note that the Galvano mirror 2624a may be a biaxial Galvano mirror that is movable around two axis that are perpendicular to each other, however, it is not limited to this and a mirror having two combined single-axial mirrors may be used.

(4-1-7) Structure of Light Irradiation Apparatus 27a

In order to irradiate the coat SF of paint with the processing light EL, the light irradiation apparatus 27a is provided with a light source system 271a that is configured to emit the processing light EL, a light divide part having a light divide member 2713a that divides the processing light EL emitted from the light source system 271a into a plurality of beams and an optical system 272a that guides the plurality of beams from the light divide part to the coat SF of paint as illustrated in FIG. 24. Here, the structures of the light source system 271a and the optical system 272a are same as the structure of the light source system 251a and the optical system 252a illustrated in FIG. 22, and thus the description about them is omitted here.

A reflective type of diffractive optical element may be used as the light divide member 2713a. An entering beam entering the light divide member 2713a is divided into a plurality of diffracted beams that travel toward directions that are different from each other by a diffraction action, for example. A collimator optical system 2714a having a front focal point located at a position of the light divide member 2713a is disposed at an emitting side of the light divide member 2713a, and directions of the plurality of beams traveling toward directions that are different from each other are changed to be parallel to each other and they travel to the optical system 272a as the plurality of beams that are parallel to each other.

Note that the light divide member 2713a is not limited to the reflective type of diffractive optical element, and a reflective type of spatial light modulator may be used. Various spatial light modulator such as a mirror array having a plurality of mirrors positions and/or attitudes of which are changeable each other, a LCOS (Liquid Crystal On Silicon) type of spatial light modulator or the like may be used as the reflective type of spatial light modulator. Here, when the spatial light modulator that is configured to actively change a state of a reflected light is used as the light divide member 2713a, at least one of the position, a shape, a distribution and the like of the irradiation area EA on the coat SF of paint is adjustable by changing a state (the intensity distribution, the traveling direction and the like) of the light from the spatial light modulator. Moreover, at least one of a transmission type of diffractive optical element and a transmission type of spatial light modulator may be used as the light divide member 2713a.

Note that the optical system 262a illustrated in FIG. 25 may be used as the optical system 272a illustrated in FIG. 24.

(4-1-8) Modified Example of Light Irradiation Apparatus 11 Illustrated in FIG. 3

In the light source system 111 illustrated in FIG. 3B, the plurality of light sources 1111 are arranged in a line at regular intervals. However, the plurality of light sources 1111 may not be arranged at regular intervals and may not be arranged in a line. Namely, the plurality of light sources 1111 may be arranged in another arrangement pattern that is different from the arrangement pattern illustrated in FIG. 3B. For example, the plurality of light sources 1111 may be arranged in a matrix at regular intervals. For example, the plurality of light sources 1111 may be arranged in a staggered arrangement pattern. For example, the plurality of light sources 1111 may be arranged in a line or in rows at random intervals.

In the light source system 111 illustrated in FIG. 3C, the plurality of emitting ports from which the plurality of processing lights EL divided by the divide device 1112, respectively, are arranged in a line at regular intervals. However, the plurality of emitting ports may not be arranged at regular intervals and may not be arranged in a line. Namely, the plurality of emitting ports may be arranged in another arrangement pattern that is different from the arrangement pattern illustrated in FIG. 3C. For example, the plurality of emitting ports may be arranged in a matrix at regular intervals. For example, the plurality of emitting ports may be arranged in a staggered arrangement pattern. For example, the plurality of emitting ports may be arranged in a line or in rows at random intervals. Alternatively, the light source system 111 may be provided with single emitting port. Namely, the light source system 111 may emit single processing light EL. In this case, the light source system 111 may not be provided with the divide device 1112.

The coat SF of paint is irradiated with the plurality of processing lights EL at the same time by the light irradiation apparatus 11 illustrated in FIG. 3. The coat SF of paint may not be irradiated with the plurality of processing lights EL at the same time. For example, the coat SF of paint may not be irradiated with other part of the plurality of processing lights EL during a period when the coat SF of paint is irradiated with a part of the plurality of processing lights EL. For example, the coat SF of paint may be irradiated with a part of the plurality of processing lights EL at a first timing and then the coat SF of paint may be irradiated with other part of the plurality of processing lights EL at a second timing that is different from the first timing. For example, the coat SF of paint may be irradiated with the plurality of processing lights EL in order.

In the light irradiation apparatus 11 illustrated in FIG. 3, the Galvano mirror 1122 is the biaxial Galvano mirror having both of the X scanning mirror 1122X and the Y scanning mirror 1122Y. However, the Galvano mirror 1122 may be a single-axial Galvano mirror having at least one of the X scanning mirror 1122X and the Y scanning mirror 1122Y. The processing apparatus having the single-axial Galvano mirror may sweep the surface of the coat SF of paint with the plurality of processing lights EL along either one of the X axis direction and the Y axis direction by controlling the Galvano mirror and may sweep the surface of the coat SF of paint with the plurality of processing lights EL along the other one of the X axis direction and the Y axis direction by moving the light irradiation apparatus having the single-axial Galvano mirror along the other one of the X axis direction and the Y axis direction by using the driving system 12.

Note that a Galvano mirror having one mirror that is rotatable around two perpendicular axes may be used as the Galvano mirror 1122.

(4-2) Second Modified Example

Next, with reference to FIG. 25, a processing apparatus 1b in a second modified example will be described. As illustrated in FIG. 25, the processing apparatus 1b in the second modified example is different from the above described processing apparatus 1 in that it is further provided with a surface characteristic measurement apparatus 19b. The surface characteristic measurement apparatus 19b measures a characteristic of the surface of the coat SF of paint (especially, a partial surface part of the surface of the coat SF of paint that will be irradiated with the plurality of processing lights EL by the light irradiation apparatus 11) before the surface of the coat SF of paint is irradiated with the plurality of processing lights EL by the light irradiation apparatus 11. The surface characteristic measurement apparatus 19b is supported by the housing apparatus 13 through a supporting member 136b. Therefore, a positional relationship between the light irradiation apparatus 11 and the surface characteristic measurement apparatus 19b is fixed in the containing space SP. Moreover, the processing apparatus 1b in the second modified example is different from the above described processing apparatus 1 in that it controls the light irradiation apparatus 11 on the basis of a measured result of the surface characteristic measurement apparatus 19b. Another feature of the processing apparatus 1b may be same as another feature of the processing apparatus 1.

Next, specific examples of an advance measurement control operation for controlling the light irradiation apparatus 11 on the basis of the measured result of the surface characteristic measurement apparatus 19b will be described.

(4-2-1) First Specific Example of Advance Measurement Control Operation

In the first specific example, the surface characteristic measurement apparatus 19b measures a shape of the surface of the coat SF of paint as the characteristic of the surface of the coat SF of paint. The surface characteristic measurement apparatus 19b irradiates the coat SF of paint with a measurement light MLb (hereinafter, the measurement light MLb used in the first modified example is referred to as a "measurement light MLb1"). Thus, the surface characteristic measurement apparatus 19b is provided with a projection apparatus 191b that emits the measurement light MLb1. Moreover, the surface characteristic measurement apparatus 19b measures a reflected light of the measurement light MLb1 from the coat SF of paint. Thus, the surface characteristic measurement apparatus 19b is provided with a detection apparatus 192b that detects the reflected light of the measurement light MLb1. The reflected light is the measurement light EL reflected by the surface of the coat SF of paint, and thus, the measured result of the reflected light (namely, an output of the surface characteristic measurement apparatus 19b) includes an information relating to the shape of the surface of the coat SF of paint. Thus, the control apparatus 18 is capable of determining the shape of the surface of the coat SF of paint on the basis of the measured result of the surface characteristic measurement apparatus 19b. Note that an measurement apparatus that emits the measurement light MLb1 having a predetermined light pattern (for example, a liner light pattern or a grid-like light pattern) on the surface of the coat SF of paint and that measures the shape of the surface by measuring a pattern image from a direction that is different from an irradiation direction of the measurement light MLb1 (for example, a measurement apparatus using an optical cutting method and the like) is one example of the surface characteristic measurement apparatus 19b that measures the shape of the surface of the coat SF of paint. Moreover, an optical measurement apparatus using various methods such as a moire topography method using a grid irradiation method or a grid projection method, a holography interference method, an auto collimation method, a stereo method, an astigmatism method, a critical angle method or a knife edge method may be used as one example of the surface characteristic measurement apparatus 19b

In the first specific example, the control apparatus 18 sets an irradiation condition (namely, an irradiation state) of the plurality of processing lights EL on the basis of the shape of the surface of the coat SF of paint. In the first specific example, the irradiation condition of the plurality of processing lights EL is light concentration positions FP of the plurality of processing lights EL. Specifically, the control apparatus 18 sets the light concentration positions FP of the plurality of processing lights EL to positions that allow the coat SF of paint to be processed by the irradiation of the plurality of processing lights EL, for example. Here, as described above, the coat SF of paint is processed so that a part of the coat SF of paint evaporates by the irradiation of the processing lights EL. The coat SF of paint evaporates by the energy that is transmitted from the processing lights EL to the coat SF of paint by the irradiation of the processing lights EL (namely, the energy of the processing lights EL absorbed by the coat SF of paint). The energy that is transmitted from the processing light EL to the coat SF of paint becomes larger as the intensity of the processing light EL on the surface of the coat SF of paint becomes higher. Thus, when the intensity of the processing light EL on the surface of the coat SF of paint is equal to or higher than an intensity that allows the coat SF of paint to evaporate, the coat SF of paint evaporates by the irradiation of the processing light EL. Therefore, the control apparatus 18 sets the light concentration positions FP of the plurality of processing lights EL to the positions that allow the coat SF of paint to be processed by the irradiation of the plurality of processing lights EL on the basis of a relationship between a relative position of the light concentration positions FP of the processing lights EL relative to the surface of the coat SF of paint and the intensity of the processing lights EL on the surface of the coat SF of paint. Moreover, although a part of the coat SF of paint in the irradiation area EL that is irradiated with the processing light EL is processed to evaporate, there is a possibility that the irradiation area EA that is irradiated with the processing light EL becomes large and a desired riblet structure is not formed when the light concentration position of the processing light EL is away from (namely, away along the Z axis direction) surface of the coat SF of paint too much. Therefore, the control apparatus 18 sets the light concentration positions FP of the plurality of processing lights EL so that the sizes of the irradiation areas EA of the processing lights EL become desired sizes.

Considering this premise, when the surface of the coat SF of paint is located within a range of a depth of focus (namely, DOF: Depth Of Focus, and an area that extends from the light concentration positions FP of the plurality of processing lights EL toward an object plane side and an image plane side) of the optical system 112, the intensity of the processing lights EL becomes high to some extent (namely, becomes equal to or higher than an intensity that allows the coat SF of paint to evaporate) on the surface of the coat SF of paint. Moreover, when the surface of the coat SF of paint is positioned within the range of the depth of focus of the optical system 112, the sizes of the irradiation areas of the processing lights EL on the surface of the coat SF of paint become desired sizes. A state where the surface of the coat SF of paint is positioned within the range of the depth of focus of the optical system 112 may mean a state where the size of the irradiation area EA of the processing light EL formed on the surface of the coat SF of paint is within a desired range. Therefore, as illustrated in FIG. 26A to FIG. 26D, the control apparatus 18 may set the light concentration positions FP of the plurality of processing lights EL so that the surface of the coat SF of paint (especially, a partial surface part of the surface of the coat SF of paint that is irradiated with the plurality of processing lights EL) is located within the range of the depth of focus of the optical system 112. FIG. 26A is a cross-sectional view that illustrates an aspect in which the surface of the coat SF of paint is positioned within the range of the depth of focus of the optical system 112 when the surface of the coat SF of paint is a flat surface. FIG. 26B is a cross-sectional view that illustrates an aspect in which the surface of the coat SF of paint is positioned within the range of the depth of focus of the optical system 112 when the surface of the coat SF of paint is a curved surface. FIG. 26C is a cross-sectional view that illustrates an aspect in which the surface of the coat SF of paint is positioned within the range of the depth of focus of the optical system 112 when there is a concavity and/or convexity at the surface of the coat SF of paint. FIG. 26D is a cross-sectional view that illustrates an aspect in which the surface of the coat SF of paint is positioned within the range of the depth of focus of the optical system 112 when the surface of the coat SF of paint is inclined with respect to the optical axis AX (namely, the optical axis AX along the Z axis) of the optical system 112.

When the light concentration positions FP of the plurality of processing lights EL moves relative to the coat SF of paint along the Z axis, a relative positional relationship (especially, a positional relationship along the Z axis direction) between the coat SF of paint and the range of the depth of focus of the optical system 112 changes. Thus, it can be said that the control apparatus 18 substantially sets the relative positional relationship between the coat SF of paint and the range of the depth of focus of the optical system 112 by setting the light concentration positions FP of the plurality of processing lights EL.

After setting the light concentration positions FP like this, the control apparatus 18 controls the focusing lens 1121 of the light irradiation apparatus 11 so that the plurality of processing lights EL are focused on the set light concentration positions FP. Namely, the control apparatus 18 controls the focusing lens 1121 to collectively control (namely, adjust) the light concentration positions FP of the plurality of processing lights EL so that the plurality of processing lights EL are focused on the set light concentration positions FP. In other words, the control apparatus 18 controls the focusing lens 1121 to control at the same time (change at the same time) the light concentration positions FP of the plurality of processing lights EL so that the plurality of processing lights EL are focused on the set light concentration positions FP. Incidentally, even in the light irradiation apparatuses 21a to 24a described in the first modified example, if the optical systems 212a to 242a are provided with the focusing lens 1121, the light irradiation apparatuses 21a to 24a are controllable by the control apparatus 18 so that the plurality of processing lights EL are focused on the set light concentration positions FP. As a result, the surface of the coat SF of paint is positioned within the range of the depth of focus of the optical system 112. Therefore, the surface of the coat SF of paint is irradiated with the processing lights EL the intensity of which is equal to or higher than the intensity that allows the coat SF of paint to evaporate. Thus, the coat SF of paint is properly processed by the plurality of processing lights EL.

According to the first specific example of the advance measurement control operation, the processing apparatus 1b is capable of processing the coat SF of paint without being subjected to a restraint of the shape of the surface of the coat SF of paint while achieving an effect that is same as an effect achievable by the above described processing apparatus 1.

Note that the relative positions on the surface of the coat SF of paint (especially, the positions in a direction along the surface of the coat SF of paint) of the plurality of irradiation areas EA that are irradiated with the plurality of processing lights EL, respectively, change due to the sweep with the plurality of the processing lights EL. Namely, the plurality of processing lights moves relative to the coat SF of paint along the surface of the coat SF of paint. When the relative positions on the surface of the coat SF of paint of the plurality of irradiation areas EA change, there is a possibility that shapes of parts of the surface of the coat of paint at which the plurality of irradiation areas EA are formed also change during a period when the plurality of processing lights EL are emitted. Thus, the control apparatus 18 may set the light concentration positions FP appropriately on the basis of the shapes of the parts of the surface of the coat of paint at which the plurality of irradiation areas EA are formed and control the focusing lens 1121 so that the plurality of processing lights EL are focused on the set light concentration positions FP during the period when the plurality of processing lights EL are emitted (namely, the plurality of processing lights EL relatively moves relative to the coat SF of paint).

Moreover, depending on the shape of the surface of the coat SF of paint, a part of the surface of the coat SF of paint (especially, a partial surface part of the surface of the coat SF of paint that is irradiated with the plurality of processing lights EL) is not positioned within the range of the depth of focus of the optical system 112 in some cases even when the light concentration positions FP of the plurality of processing lights EL are set. Namely, a part of the surface of the coat SF of paint is positioned within the range of the depth of focus of the optical system 112 and other part of the surface of the coat SF of paint is not positioned within the range of the depth of focus of the optical system 112 in some cases. In this case, the processing apparatus 1b may irradiate the coat SF of paint with only a part of the plurality of processing lights EL selectively so that a part of the coat SF of paint the surface of which is positioned within the range of the depth of focus of the optical system 112 is irradiated with the processing light EL and other part of the coat SF of paint the surface of which is not positioned within the range of the depth of focus of the optical system 112 is not irradiated with the processing light EL.

Moreover, a control of the light concentration positions FP of the plurality of processing lights EL by the focusing lens 1121 is equivalent to a control of a relative positional relationship between the surface of the coat SF of paint and the light concentration positions FP of the plurality of processing lights EL along the Z axis direction. Thus, the control apparatus 18 may control the driving system 12 to control the relative position of the light irradiation apparatus 11 relative to the coat SF of paint in the Z axis direction, in addition to or instead of controlling the focusing lens 1121 to control the light concentration positions FP of the plurality of processing lights EL. Even in this case, the processing apparatus 1b is capable of processing the coat SF of paint without being subjected to the restraint of the shape of the surface of the coat SF of paint.

Moreover, when the light concentration positions FP change, the intensity distribution of the plurality of processing lights EL in a plane (for example, the XZ plane in examples illustrated in FIG. 26A to FIG. 26D) including an axis that intersects with the surface of the coat SF of paint change. Thus, the control of the light concentration positions FP of the plurality of processing lights EL by the focusing lens 1121 is equivalent to a control of the intensity distribution of the plurality of processing lights EL in the plane including the axis that intersects with the surface of the coat SF of paint. In other words, the control apparatus 18 may control the intensity distribution of the plurality of processing lights EL in the plane including the axis that intersects with the surface of the coat SF of paint so that the coat SF of paint is processed by the irradiation of the plurality of processing lights EL. In this case, the optical system 112 may be provided with an intensity distribution adjusting element for adjusting the intensity distribution of the plurality of processing lights EL under the control of the control apparatus 18. A filter having a desired density distribution in a plane intersecting the optical path, an aspherical (refractive or reflective) optical member having a desired surface shape in the plane intersecting the optical path, a diffractive optical element, a spatial light modulator and the like may be used as the intensity distribution adjusting element, for example. Alternatively, when the shapes of the plurality of processing lights EL in the plane including the axis that intersects with the surface of the coat SF of paint change, the intensity distribution of the plurality of processing lights EL also change. Thus, the control apparatus 18*b* may control the shapes of the plurality of processing lights EL in the plane including the axis that intersects with the surface of the coat SF of paint so that the coat SF of paint is processed by the irradiation of the plurality of processing lights EL. In this case, the optical system 112 may be provided with an optical shape adjusting element for adjusting the shapes of the plurality of processing lights EL under the control of the control apparatus 18. A diaphragm having a predetermined shape of an aperture, a filter having a desired density distribution in the plane intersecting the optical path, an aspherical (refractive or reflective) optical member having a desired surface shape in the plane intersecting the optical path, a diffractive optical element, a spatial light modulator and the like may be used as the optical shape adjusting element as the intensity distribution adjusting element, for example. Note that the control apparatus 18 may control or may not control the light concentration positions of the plurality of processing lights EL when controlling at least one of the intensity distribution and the shapes of the plurality of processing lights EL.

Moreover, when the light concentration positions FP change, sizes of the irradiation areas EA on the surface of the coat SF of paint change. Specifically, the size of the irradiation area EA becomes smaller as the light concentration position FP is closer to the surface of the coat SF of paint in a direction along the surface of the coat SF of paint. The size of the irradiation area EA becomes larger as the light concentration position FP is farther from the surface of the coat SF of paint in a direction along the surface of the coat SF of paint. Thus, the control of the light concentration positions FP of the plurality of processing lights EL by the focusing lens 1121 is equivalent to a control of the sizes of the plurality of irradiation areas EA on the coat SF of paint. Therefore, it can be said that the control apparatus 18 substantially controls the sizes of the plurality of irradiation areas EA on the coat SF of paint on the basis of the positional relationship between the coat SF of paint and the plurality of irradiation areas EA. For example, in the example illustrated in FIG. 26C, it can be said that the control apparatus 18 controls the sizes of the plurality of irradiation areas EA so that (i) the size of the irradiation area EA formed at a first part (a part that is located at the left side illustrated in FIG. 26C) on the coat SF of paint becomes relatively small and (ii) the sizes of the irradiation areas EA formed at a second part (a part that is located at a center illustrated in FIG. 26C) and a third part (a part that is located at a right side illustrated in FIG. 26C) on the coat SF of paint becomes relatively large. Namely, it can be said that the control apparatus 18 sets the size of the irradiation area EA formed at the first part on the coat SF of paint to a desired first size, sets the size of the irradiation area EA formed at the second part on the coat SF of paint to a desired second size and sets the size of the irradiation area EA formed at the third part on the coat SF of paint to a desired third size, Moreover, in the above described description, the control apparatus 18 is allowed to collectively control (control at the same time) the light concentration positions FP of the plurality of processing lights EL by controlling the focusing lens 1121. However, the control apparatus 18 may control the light concentration positions FP of the plurality of processing lights EL individually or independently. However, when the light concentration positions FP of the plurality of processing lights EL are controlled individually or independently, the processing apparatus 1*b* is provided with a light irradiation apparatus 11*b*-1 having a plurality of focusing lenses 1121 for adjusting the light concentration positions FP of the plurality of processing lights EL, respectively, instead of the light irradiation apparatus 11. One example of the light irradiation apparatus 11*b*-1 having the plurality of focusing lenses 1121 is illustrated in FIG. 27. As illustrated in FIG. 27*b*, the light irradiation apparatus 11*b*-1 is provided with a plurality of irradiation units 110*b*-1. Each irradiation unit 110*b*-1 is provided with a light source system 111*b*-1 and the above described optical system 112. The light source system 111*b*-1 is provided with the single light source 1111. According to the light irradiation apparatus 110*b*-1, the light concentration positions FP of the plurality of processing lights EL are controllable individually or independently, because the plurality of irradiation units 110*b*-1 that emit the plurality of processing lights EL, respectively, are provided with the plurality of focusing lenses 1121, respectively. Note that each irradiation unit 110*b*-1 is not limited to the unit that irradiates the coat SF of paint with the plurality of processing lights EL and may be a unit that irradiates the coat SF of paint with the single processing light EL.

Incidentally, in the case where each irradiation unit 110*b*-1 emits the single processing light EL, when the optical system 112 of each irradiation unit 110*b*-1 is the non-telecentric on the coat SF of paint side, a distance between the optical system 112 and the light concentration position FP changes depending on the position on the coat of paint even when the surface of the coat SF of paint is the flat surface, as illustrated in FIG. 28. In this case, the focusing lens 1121 may be controlled on the basis of the position of the processing light EL on the coat SF of paint.

Even when the light concentration positions FP of the plurality of processing lights EL are controlled individually or independently, the control apparatus 18 may set the light concentration positions FP of the plurality of processing lights EL so that the surface of the coat SF of paint is located within the range of the depth of focus of the optical system 112. Alternatively, as illustrated in FIG. 29A to FIG. 29D, the control apparatus 18 may set the light concentration positions FP of the plurality of processing lights EL so that the light concentration positions FP of the plurality of processing lights EL are positioned at the surface of the coat SF of paint. FIG. 29A is a cross-sectional view that illustrates an aspect in which the light concentration positions FP of the plurality of processing lights EL are positioned at the surface of the coat SF of paint when the surface of the coat SF of paint is a flat surface. FIG. 29B is a cross-sectional view that illustrates an aspect in which the light concentration positions FP of the plurality of processing lights EL are positioned at the surface of the coat SF of paint when the surface of the coat SF of paint is a curved surface. FIG. 29C is a cross-sectional view that illustrates an aspect in which the light concentration positions FP of the plurality of processing lights EL are positioned at the surface of the coat SF of paint when there is a concavity and/or convexity at the surface of the coat SF of paint. FIG. 29D is a cross-sectional view that illustrates an aspect in which the light concentration positions FP of the plurality of processing lights EL are positioned at the surface of the coat SF of paint when the surface of the coat SF of paint is inclined with respect to the optical axis AX of the optical system 112.

Moreover, depending on the shape of the surface of the coat SF of paint, the light concentration position FP of a part of the plurality of processing lights EL is not positioned at the surface of the coat SF of paint in some cases even when the light concentration positions FP of the plurality of processing lights EL are set individually or independently. Namely, the light concentration position FP of a part of the plurality of processing lights EL is located at the surface of the coat SF of paint and the light concentration position FP of other part of the plurality of processing lights EL is not positioned at the surface of the coat SF of paint in some cases. In this case, the processing apparatus 1b may irradiate the coat SF of paint with only a part of the plurality of processing lights EL selectively so that the coat SF of paint is irradiated with the processing light EL the light concentration position FP of which is positioned at the surface of the coat SF of paint and the coat SF of paint is not irradiated with the processing light EL the light concentration position FP of which is not positioned at the surface of the coat SF of paint. Alternatively, the surface of the painted fil SF is not located within the range of the depth of focus of the optical system 112 for emitting the processing light EL that is a part of the plurality of processing lights EL in some cases even when the light concentration positions FP of the plurality of processing lights EL are set individually or independently. Namely, the surface of the coat SF of paint is positioned within the range of the depth of focus of one optical system 112 for emitting one processing light EL of the plurality of processing lights EL and the surface of the coat SF of paint is not positioned within the range of the depth of focus of other one optical system 112 for emitting other one processing light EL of the plurality of processing lights EL in some cases. In this case, the processing apparatus 1b may irradiate the coat SF of paint with only a part of the plurality of processing lights EL selectively so that the processing light EL is emitted through the optical system 112 having the depth of focus within which the surface of the coat SF of paint is included and the processing light EL is not emitted through the optical system 112 having the depth of focus within which the surface of the coat SF of paint is not included Note that an individual control of the light concentration positions FP of the plurality of processing lights EL is substantially equivalent to a change of the relative positional relationship between the coat SF of paint and the light concentration positions FP of the plurality of processing lights EL in the Z axis direction (alternatively, a direction intersecting with the surface of the coat SF of paint). Thus, the control apparatus 18 may control a non-illustrated driving system by which the plurality of irradiation units 110b-1 are movable individually to control the relative position of each of the plurality of irradiation units 110b-1 relative to the coat SF of paint in the Z axis direction, in addition to or instead of controlling the plurality of focusing lenses 1121 to control the light concentration positions FP of the plurality of processing lights EL. Controlling the relative position of each of the plurality of irradiation units 110b-1 in the Z axis direction results in the change of the relative positional relationship between the surface of the coat SF of paint and the light concentration positions FP of the plurality of processing lights EL in the Z axis direction. Thus, the processing apparatus 1b is capable of processing the coat SF of paint without being subjected to the restraint of the shape of the surface of the coat SF of paint even when controlling the relative position of each of the plurality of irradiation units 110b-1 in the Z axis direction.

Alternatively, when an attitude (for example, an tilt amount, and relative position in at least one of the θX direction and the θY direction) of each of the plurality of irradiation units 110b-1 relative to the coat SF of paint changes, the relative positional relationship between the light concentration positions FP of the plurality of processing lights EL emitted from the plurality of irradiation units 110b-1, respectively, changes. Thus, the control apparatus 18 may control a non-illustrated driving system by which the plurality of irradiation units 110b-1 are movable individually to control the attitude of each of the plurality of irradiation units 110b-1 relative to the coat SF of paint. Even in this case, the processing apparatus 1b is capable of processing the coat SF of paint without being subjected to the restraint of the shape of the surface of the coat SF of paint. Note that the control apparatus 18 may control the attitude of the light irradiation apparatus 11 relative to the coat SF of paint even when the processing apparatus 1b is provided with the light irradiation apparatus 11 that is not provided with the plurality of irradiation units 110b-1. Even in this case, the relative position of the light concentration positions FP of the plurality of processing lights EL relative to the coat SF of paint is controllable.

(4-2-2) Second Specific Example of Advance Measurement Control Operation

A second specific example of the advance measurement control operation is different from the above described first specific example of the advance measurement control operation in that a condition relating to the depth of focus of the optical system 112 (in the below described description, the range of the depth of focus is used) is used as the irradiation condition of the plurality of processing lights EL instead of the light concentration positions FP of the plurality of processing lights EL. Another feature of the second specific example of the advance measurement control operation may be same as the first specific example of the advance measurement control operation.

In the second specific example, the control apparatus 18 sets the light concentration positions FP of the plurality of processing lights EL to positions that allow the coat SF of paint to be processed by the irradiation of the plurality of processing lights EL, as with the first specific example. For example, as illustrated in FIG. 30A to FIG. 30D, the control apparatus 18 may set the range of the depth of focus of the optical system 112 so that the surface of the coat SF of paint (especially, a partial surface part of the surface of the coat SF of paint that is irradiated with the plurality of processing lights EL) is positioned within the range of the depth of focus of the optical system 112. In other words, control apparatus 18 may set the range of the depth of focus of the optical system 112 so that the sizes of the irradiation areas EA of the processing lights EL formed on the surface of the coat SF of paint is within the desired range. FIG. 30A is a cross-sectional view that illustrates the range of the depth of focus of the optical system 112 that is set to include the surface of the coat SF of paint when the surface of the coat SF of paint is a flat surface. FIG. 30B is a cross-sectional view that illustrates the range of the depth of focus of the optical system 112 that is set to include the surface of the coat SF of paint when the surface of the coat SF of paint is a curved surface. FIG. 30C is a cross-sectional view that illustrates the range of the depth of focus of the optical system 112 that is set to include the surface of the coat SF of paint when there is a concavity and/or convexity at the surface of the coat SF of paint. FIG. 30D is a cross-sectional view that illustrates the range of the depth of focus of the optical system 112 that is set to include the surface of the coat SF of paint when the surface of the coat SF of paint is inclined with respect to the optical axis AX of the optical system 112.

In the second specific example, the optical system 112 is provided with an optical element for adjusting the range of the depth of focus of the optical system 112 (hereinafter, this optical element is referred to as a "focus depth adjusting element"). For example, the focusing lens 1121 may be used as the focus depth adjusting element. The range of the depth of focus may be positions of a lower limit and an upper limit of the range of the depth of focus in the traveling direction of the light. The control apparatus 18 controls the focus depth adjusting element so that the range of the depth of focus of the optical system 112 becomes the set range of the depth of focus. As a result, the surface of the coat SF of paint is located within the range of the depth of focus of the optical system 112. Therefore, the surface of the coat SF of paint is irradiated with the processing lights EL the intensity of which is equal to or higher than the intensity that allows the coat SF of paint to evaporate and the coat SF of paint is removed in a desired range. Thus, the coat SF of paint is properly processed by the plurality of processing lights EL. Incidentally, although a size of the range of the depth of focus is fixed in the second specific example, the size of the range of the depth of focus may be changed. When the size of the range of the depth of focus is changed, numerical apertures of the optical system 112 at the coat SF of paint side may be changed.

According to the second specific example of the advance measurement control operation, the processing apparatus 1b achieves an effect that is same as the effect achievable by the above described first specific example of the advance measurement control operation.

Incidentally, depending on the shape of the surface of the coat SF of paint, a part of the surface of the coat SF of paint (especially, a partial surface part of the surface of the coat SF of paint that is irradiated with the plurality of processing lights EL) is not located within the range of the depth of focus of the optical system 112 even when the range of the depth of focus of the optical system 112 is set in the second specific example, as with the first specific example. In this case, the processing apparatus 1b may irradiate the coat SF of paint with only a part of the plurality of processing lights EL selectively so that a part of the coat SF of paint the surface of which is located within the range of the depth of focus of the optical system 112 is irradiated with the processing light EL and other part of the coat SF of paint the surface of which is not located within the range of the depth of focus of the optical system 112 is not irradiated with the processing light EL.

(4-2-3) Third Specific Example of Advance Measurement Control Operation

A third specific example of the advance measurement control operation is different from the above described first specific example of the advance measurement control operation in that the control apparatus 18 sets a state of an image plane of the optical system 112 (namely, an optical plane on which the processing lights EL form an image through the optical system 112) on the basis of the shape of the surface of the coat SF of paint. Moreover, the third specific example of the advance measurement control operation is different from the above described first specific example of the advance measurement control operation in that the control apparatus 18 controls the optical system 112 so that the state of the image plane of the optical system 112 becomes the set state. Another feature of the third specific example of the advance measurement control operation may be same as the first specific example of the advance measurement control operation. Here, a virtual plane that fits the plurality of light concentration positions FP may be used as the image plane of the optical system 112. Moreover, in the modified example illustrated in FIG. 21, a plane on which the image of the mask 2421a is formed may be used.

The control apparatus 18 may set a size of the image plane on the basis of the shape of the surface of the coat SF of paint. For example, the control apparatus 18 may set the size of the image plane to a predetermined size based on the shape of the surface of the coat SF of paint. The control apparatus 18 may set a relative position (for example, a relative position along at least one of the X axis direction, the Y axis direction and the Z axis direction) of the image plane relative to the coat SF of paint (especially, the surface of the coat SF of paint) on the basis of the shape of the surface of the coat SF of paint. For example, the control apparatus 18 may set the position of the image plane to a predetermined position based on the shape of the surface of the coat SF of paint. The control apparatus 18 may set a shape of the image plane on the basis of the shape of the surface of the coat SF of paint. For example, the control apparatus 18 may set the shape of the image plane to a predetermined shape based on the shape of the surface of the coat SF of paint.

When the state of the image plane is set, the control apparatus 18 may set the state of the image plane so that the image plane is coincident with the surface of the coat SF of paint as illustrated in FIG. 31A to FIG. 31D. FIG. 31A is a cross-sectional view that illustrates the image plane that is set to be coincident with the surface of the coat SF of paint when the surface of the coat SF of paint is a flat surface. FIG. 31B is a cross-sectional view that illustrates the image plane that is set to be coincident with the surface of the coat SF of paint when the surface of the coat SF of paint is a curved surface. As illustrated in FIG. 31B, when the surface of the coat SF of paint is the curved surface (namely, is bent), the image plane is set so that the set image plane is also the curved plane (namely, is bent). FIG. 31C is a cross-sectional view that illustrates the image plane that is set to be coincident with the surface of the coat SF of paint when there is a concavity and/or convexity at the surface of the coat SF of paint. As illustrated in FIG. 31C, depending on the shape of the surface of the coat SF of paint, it is difficult to make the single image plane be coincident with the surface of the coat SF of paint in some cases. In this case, the surface of the coat of paint may be divided into a plurality of divided areas (in an example illustrated in FIG. 31C, three divided areas #1 to #3) and the state (especially, at least one of the size and the position) of the image plane may be set so that the image planes (in the example illustrated in FIG. 31C, three image plane #1 to #3) that are coincident with the divided areas, respectively, are obtained. Moreover, in this case, the plurality of divided areas are irradiated with the processing lights EL in order. Namely, the processing apparatus 1b processes the divided area #1 by emitting the processing light EL when the image plane of the optical system 12 is set to the image plane #1, then, processes the divided area #2 by emitting the processing light EL when the image plane of the optical system 12 is set to the image plane #2, and then, processes the divided area #3 by emitting the processing light EL when the image plane of the optical system 12 is set to the image plane #3. FIG. 31D is a cross-sectional view that illustrates the image plane that is set to be coincident with the surface of the coat SF of paint when the surface of the coat SF of paint is inclined with respect to the optical axis AX of the optical system 112. As illustrated in FIG. 31D, when the surface of the coat SF of paint is inclined, the state of the image plane is set so that the set image plane is also inclined.

In the third specific example, the optical system 112 that guides the processing lights EL to the coat SF of paint is provided with an optical element for adjusting the state of the image plane (hereinafter, this optical element is referred to as a "image plane adjusting element"). The control apparatus 18 controls the image plane adjusting element so that the image plane on which the processing lights EL actually form the image becomes the set image plane. Alternatively, the control apparatus 18 may control at least one of the relative position and the attitude of the light irradiation apparatus 11 relative to the coat SF of paint so that the image plane on which the processing lights EL actually form the image becomes the set image plane. As a result, the image plane on which the processing lights EL form the image is coincident with the surface of the coat SF of paint. Therefore, the coat SF of paint is properly processed by the plurality of processing lights EL. Note that a movable or deformable optical member among the optical member(s) constituting the optical system 112 may be used as the image plane adjusting element, for example. For example, a pair of wedge-shaped prisms that are rotatable around an optical axis may be disposed and the image plane may be inclined by changing a vertex angle of whole of the pair of the wedge-shaped prisms. Moreover, as the image plane adjusting element, the image plane may be inclined by decentering or inclining at least one of the optical member(s) constituting the optical system 112 with respect to the optical axis. Moreover, a pair of cylindrical lenses that are rotatable around an optical axis may be disposed as the image plane adjusting element and a degree of curvature of the image plane may be adjusted by changing their relative angle around the optical axis. Moreover, a deformable optical member may be disposed as the image plane adjusting element and the degree of the curvature of the image plane of the optical system 112 may be adjusted by a deformation of this optical member. Note that the focusing lens 1121 may be the image plane adjusting element when the processing light EL is the single processing light.

According to the third specific example of the advance measurement control operation, the processing apparatus 1b achieves an effect that is same as the effect achievable by the above described first specific example of the advance measurement control operation.

(4-2-4) Fourth Specific Example of Advance Measurement Control Operation

A fourth specific example of the advance measurement control operation is different from the above described first specific example of the advance measurement control operation in that the control apparatus 18 sets, on the surface of the coat SF of paint, a non-processing area at which the coat SF of paint should not be processed by the irradiation of the processing light EL on the basis of the shape of the surface of the coat SF of paint. Moreover, the fourth specific example of the advance measurement control operation is different from the above described first specific example of the advance measurement control operation in that the control apparatus 18 controls the light irradiation apparatus 11 so that the non-processing area is not irradiated with the processing light EL. Another feature of the fourth specific example of the advance measurement control operation may be same as the first specific example of the advance measurement control operation.

The control apparatus 18 sets an area at which a structural object having a size that is equal to or larger than an allowable size exists on the surface of the coat SF of paint to the non-processing area, as illustrated in FIG. 32A. Specifically, for example, the control apparatus 18 sets an area at which a convex structural object exists on the surface of the coat SF of paint to the non-processing area, wherein the convex structural object protrudes from a surrounding area and a protruding amount T1 of the convex structural object from the surrounding area is larger than a predetermined protruding threshold value (for example, several millimeters, several centimeters and the like) based on the allowable size. For example, the control apparatus 18 sets an area at which a concave structural object exists on the surface of the coat SF of paint to the non-processing area in addition to or instead of the area at which the convex structural object exists, wherein the concave structural object hollows from a surrounding area and a hollowing amount T2 of the concave structural object from the surrounding area is larger than a predetermined hollowing threshold value (for example, several millimeters, several centimeters and the like) based on the allowable size. The convex structural object or the concave structural object typically exists at a part at which the processing target object S itself protrudes or hollows, as illustrated in FIG. 32A.

As described above, the airframe of the airplane PL is one example of the processing target object S. In this case, the structural object having the size that is equal to or larger than the allowable size includes an operational structural object that is formed at a surface of the airframe for an operation of the airplane PL, for example. An antenna structural object relating to an antenna is one example of the operational structural object. The antenna structural object includes at least one of the antenna itself and an accessory that is provided with the antenna, for example. At least one of an ELT (Emergency Locator Transmitter) antenna, a VHF (Very High Frequency) antenna, an ADF (Automatic Direction Finder) antenna, an ATC (Air Traffic Control) transponder antenna, a TCAS (Traffic alert and Collision Avoidance System) antenna, a meteorological radar antenna and the like is one example of the antenna. A sensor structural object relating to a sensor is one example of the operational structural object. The sensor structural object includes at least one of the sensor itself and an accessory that is disposed with the sensor, for example. An ice detection sensor, a pitot tube, an AOA (Angle Of Attack) sensor, an altitude sensor and the like is one example of the sensor. A flow structural object relating to an inflow and an outflow of the fluid (typically, the gas) is one example of the operational structural object. At least one of an inflow port into which the fluid flows (for example, at least one of an air intake, a cooling port and the like) and an outflow port from which the fluid flows (for example, at least one of a drain discharge port, an exhaust port and the like). Beyond that, at least one of a window of a monitoring camera, a wiper, a retract door and the like is one example of the operational structural object.

After setting the non-processing area, the control apparatus 18 controls the light control apparatus 11 to sweep the surface of the coat of paint with the plurality of processing lights EL. In this period, the control apparatus 18 controls the light irradiation apparatus 11 not to irradiate the non-processing area with the processing light EL as illustrated in FIG. 32A and FIG. 32B. Namely, the control apparatus 18 may turn off the processing light EL with which a certain irradiation area EA is irradiated when this certain irradiation area EA overlaps with the non-processing area. Turning off the processing light EL is realizable by at least one of turning off the light source 1111, inserting a light shielding member into the optical path of the processing light EL and the like. On the other hand, the control apparatus 18 controls the light irradiation apparatus 11 to irradiate an area that is not set as the non-processing area with the processing light EL. Note that a control of setting a sweeping area of the processing light EL to only a processing area other than the non-processing area may be performed when the processing light EL is single.

According to the fourth specific example of the advance measurement control operation, the processing apparatus 1b achieves an effect that is same as the effect achievable by the above described first specific example of the advance measurement control operation. Moreover, in the fourth specific example, the processing apparatus 1b does not irradiate the part at which the coat SF of paint should not be processed with the processing light EL. Thus, the processing apparatus 1b is capable of processing the coat SF of paint while preventing the irradiation of the processing light EL from adversely affecting any structural object such as the operational structural object.

Note that the area at which the structural object having the size that is equal to or larger than the allowable size exists on the surface of the coat SF of paint is set to the non-processing area in the above described description. However, the riblet structural may be desired to be formed at the area at which the structural object having the size that is equal to or larger than the allowable size exists in some cases. For example, there is a possibility that the area at which the structural object having the size that is equal to or larger than the allowable size exists arises on the surface of the coat SF of paint due to at least one of a distortion of the processing target object S and unevenness of the thickness of the coat SF of paint, although the above described operational structural object does not exist. In this case, there is a possibility that the area at which the structural object having the size that is equal to or larger than the allowable size exists is the area at which the riblet structure should be formed, because it is not the area at which the operational structural object does not exist. Thus, the control apparatus 18 may not set, to the non-processing area, an area (hereinafter, this area is referred to as a "processing desired area" for the purpose of description) at which the riblet structure is desired to be formed although the structural object having the size that is equal to or larger than the allowable size exists and may irradiate the processing desired area with the processing light EL. Alternatively, the control apparatus 18 may temporarily set the processing desired area to the non-processing area and may irradiate the processing desired area with the processing light EL after or before irradiating the area on the surface of the coat SF of paint other than the processing desired area with the processing light EL. However, the area at which the structural object having the size that is equal to or larger than the allowable size exists corresponds to an area that protrudes from an area at which the structural object having the size that is equal to or larger than the allowable size does not exist (namely, the area at which there is the concavity and/or convexity). Thus, in order to irradiate the area at which the structural object having the size that is equal to or larger than the allowable size exists with the processing light EL, the control apparatus 18 may adjust the light concentration positions FP of the plurality of processing lights EL (see the above described first specific example), may control the driving system 12 to move the light irradiation apparatus 11 along the Z axis (see the above described first specific example) and may adjust the depth of focus of the optical system 112 (see the above described second specific example).

Moreover, the control apparatus 18 may set, to the non-processing area, an area at which the riblet structure is already formed (namely, the concave structure CP1 and/or the convex structure CP2 is already formed) in addition to or instead of the area at which the structural object having the size that is equal to or larger than the allowable size exists on the surface of the coat SF of paint. In this case, the riblet structure that is already formed is not processed so that a characteristic deteriorates (for example, the shape becomes an undesired shape) due to the second irradiation of the processing light EL.

Moreover, the control apparatus 18 may control the light irradiation apparatus 11 so that the irradiation areas EA do not overlap with the non-processing area (namely, the irradiation areas EA move to avoid the non-processing area on the surface of the coat SF of paint. For example, the control apparatus 18 may control the driving system 12 to move the light irradiation apparatus 11 relative to the coat SF of paint so that the irradiation areas EA do not overlap with the non-processing area during the period when the light irradiation apparatus 11 emits the processing lights EL. Even in this case, the processing apparatus 1b is capable of processing the coat SF of paint while preventing the irradiation of the processing light EL from adversely affecting any structural object such as the operational structural object, because it does not irradiate the part at which the coat SF of paint should not be processed with the processing light EL.

(4-2-5) Fifth Specific Example of Advance Measurement Control Operation

In the fifth specific example, the surface characteristic measurement apparatus 19b measures, as the characteristic of the surface of the coat SF of paint, a reflectance R of the coat SF of paint to the processing light EL. In order to measure the reflectance R, the projection apparatus 191b of the surface characteristic measurement apparatus 19b irradiates the coat SF of paint with the measurement light MLb (hereinafter, the measurement light MLb used in the fifth modified example is referred to as a "measurement light MLb2"). The measurement light MLb2 is a light having a wavelength that is same as the wavelength of the processing light EL. Alternatively, the measurement light MLb2 may be a light including a light component a wavelength of which is same as the wavelength of the processing light EL. In this case, if an intensity of the measurement light MLb2 is equal to or higher than the intensity allows the coat SF of paint to evaporate, there is a possibility that the coat SF of paint evaporates due to the irradiation of the measurement light MLb2. Thus, the projection apparatus 191$b$ emits the measurement light MLb2 having the intensity lower than the intensity that allows the coat SF of paint to evaporate. Namely, the projection apparatus 191$b$ emits the measurement light MLb2 having the intensity that is too low to evaporate the coat SF of paint.

The detection apparatus 192$b$ of the surface characteristic measurement apparatus 19$b$ measures a reflected light (especially, an intensity thereof) of the measurement light MLb2 from the coat SF of paint. Since the measurement light MLb2 is the light having the wavelength that is same as the wavelength of the processing light EL, the intensity of the reflected light of the measurement light MLb2 becomes larger as the reflectance R of the coat SF of paint to the processing light EL becomes higher. Therefore, a measured result of the reflected light (namely, the output of the surface characteristic measurement apparatus 19$b$) includes an information relating to the reflectance R. Thus, the reflectance R is determined on the basis of the measured result of the surface characteristic measurement apparatus 19$b$ by the control apparatus 18.

In the fifth specific example, the control apparatus 18 sets the intensity of the plurality of processing lights EL on the basis of the reflectance R. Specifically, as illustrated in FIG. 33A, the control apparatus 18 sets the intensity of the plurality of processing lights EL so that the intensity of the plurality of processing lights EL becomes higher as the reflectance R becomes higher. After setting the intensity of the plurality of processing lights EL in this manner, the control apparatus 18 controls the light irradiation apparatus 11 to emit the plurality of processing lights EL having the set intensity. Note that a relationship between the reflectance R and the intensity of the processing lights EL is not limited to a liner relationship illustrated in FIG. 33A, and may be a non-liner relationship illustrated in FIG. 33B and FIG. 33C.

According to the fifth specific example of the advance measurement control operation, the processing apparatus 1$b$ achieves an effect that is same as the effect achievable by the above described first specific example of the advance measurement control operation. Moreover, in the fifth specific example, the processing apparatus 1$b$ irradiates the coat SF of paint with the processing lights EL the intensity of which becomes higher as the reflectance R of the coat SF of paint to the processing light EL becomes higher. Thus, the processing apparatus 1$b$ is capable of properly processing the coat SF of paint without being affected by a difference of the reflectance R of the coat SF of paint. Namely, the processing apparatus 1$b$ is capable of processing the coat SF of paint having the relatively high reflectance R and the coat SF of paint having the relatively low reflectance R to form the same riblet structure. The reason will be described below.

Firstly, as described above, the coat SF of paint evaporates by the energy that is transmitted from the processing lights EL to the coat SF of paint by the irradiation of the processing lights EL. Thus, if the intensity of the processing lights EL with which the coat SF of paint having the relatively high reflectance R is same as the intensity of the processing lights EL with which the coat SF of paint having the relatively low reflectance R, the energy that is transmitted from the processing lights EL to the coat SF of paint having the relatively high reflectance R is smaller than the energy that is transmitted from the processing lights EL to the coat SF of paint having the relatively low reflectance R. The reason is that the coat SF of paint having the relatively high reflectance R reflects a larger amount of the processing lights EL than the coat SF of paint having the relatively low reflectance R and thus a ratio of the processing lights EL absorbed by the coat SF of paint as the energy becomes smaller. Namely, the reason is that a degree of an absorption of the processing lights EL by the coat SF of paint having the relatively high reflectance R (namely, the absorptance of the coat SF of paint to the processing light EL) is lower than a degree of an absorption of the processing lights EL by the coat SF of paint having the relatively low reflectance R (namely, the absorptance of the coat SF of paint to the processing light EL). As a result, there is a possibility that the coat SF of paint having the relatively high reflectance R is not processed in a same manner as the coat SF of paint having the relatively low reflectance R is processed. Namely, there is a possibility that the riblet structure formed by processing the coat SF of paint having the relatively high reflectance R is different from the riblet structure formed by processing the coat SF of paint having the relatively low reflectance R.

However, in the fifth specific example, the intensity of the processing lights EL with which the coat SF of paint having the relatively high reflectance R is irradiated is higher than the intensity of the processing lights EL with which the coat SF of paint having the relatively low reflectance R is irradiated, and thus, the energy that is transmitted from the processing lights EL to the coat SF of paint having the relatively high reflectance R is likely to be same as the energy that is transmitted from the processing lights EL to the coat SF of paint having the relatively low reflectance R. In other words, the control apparatus 18 sets the intensity of the plurality of processing lights EL on the basis of the reflectance R so that the energy that is transmitted from the processing lights EL to the coat SF of paint having the relatively high reflectance R is same as the energy that is transmitted from the processing lights EL to the coat SF of paint having the relatively low reflectance R. As a result, the coat SF of paint having the relatively high reflectance R is processed in a same manner as the coat SF of paint having the relatively low reflectance R is processed. Namely, the riblet structure formed by processing the coat SF of paint having the relatively high reflectance R is same as the riblet structure formed by processing the coat SF of paint having the relatively low reflectance R. Therefore, the processing apparatus 1$b$ is capable of preventing a fluctuation of the forming accuracy of the riblet structure caused by the difference of the reflectance R of the coat SF of paint. Note that there is a possibility that a processing range of the riblet go beyond the coat SF of paint and thereby the processing target object S is affected when the coat SF of paint having the relatively low reflectance R is irradiated with the processing lights EL having the high intensity. In the present example, since the intensity of the plurality of processing lights EL is set on the basis of the reflectance R, there is small possibility that the processing target object S is adversely affected.

Note that the relative positions on the surface of the coat SF of paint (especially, the positions in the direction along the surface of the coat SF of paint) of the plurality of irradiation areas EA that are irradiated with the plurality of processing lights EL, respectively, change due to the sweep with the plurality of the processing lights EL, as described above. When the relative positions on the surface of the coat SF of paint of the plurality of irradiation areas EA change, there is a possibility that the reflectance R at a part of the surface of the coat SF of paint at which the plurality of irradiation areas EA are set also changes during the period when the plurality of processing lights EL are emitted. Thus, the control apparatus 18 may set the intensity of the plurality of processing lights EL on the basis of the reflectance R at the part of the surface of the coat SF of paint at which the plurality of irradiation areas EA are set and may control the light irradiation apparatus 11 to emit the plurality of processing lights EL having the set intensity during the period when the plurality of processing lights EL are emitted (namely, when the plurality of processing lights EL relatively moves relative to the coat SF of paint). Incidentally, depending on the shape of the surface of the coat SF of paint, there is a possibility that an incident angle of the processing light EL relative to the coat SF of paint changes when the relative positions on the surface of the coat SF of paint of the plurality of irradiation areas EA change. Alternatively, there is a possibility that the incident angle of the processing light EL relative to the coat SF of paint changes due to any factor although the relative positions on the surface of the coat SF of paint of the plurality of irradiation areas EA do not change. When the incident angle of the processing light EL relative to the coat SF of paint changes, there is a possibility that the reflectance R changes. Even in this case, the control apparatus 18 may set the intensity of the processing lights EL to a proper intensity by using an information of the shape of the surface of the coat SF of paint that is measured or that is prepared in advance.

Moreover, the energy that is transmitted from the processing lights EL to the coat SF of paint changes depending on not only the intensity of the processing lights EL but also an irradiation time of the processing lights EL. Specifically, the energy that is transmitted from the processing lights EL to the coat SF of paint becomes larger as the irradiation time of the processing lights EL becomes longer. The "irradiation time of the processing light EL" here means a time during which same area on the surface of the coat SF of paint is irradiated with the processing light EL. Thus, the control apparatus 18 may set the irradiation time of the plurality of processing lights EL on the basis of the reflectance R in addition to or instead of the intensity of the plurality of processing lights EL. Specifically, as illustrated in FIG. 34A to FIG. 34C, the control apparatus 18 sets the irradiation time of the plurality of processing lights EL so that the irradiation time of the plurality of processing lights EL becomes longer as the reflectance R becomes higher. Not that FIG. 34A illustrates a case where a relationship between the reflectance R and the irradiation time of the processing lights EL changes linearly and FIG. 34B and FIG. 34C illustrate a case where a relationship between the reflectance R and the irradiation time of the processing lights EL changes non-linearly. After setting the irradiation time of the plurality of processing lights EL in this manner, the control apparatus 18 controls the light irradiation apparatus 11 to emit the plurality of processing lights EL on the basis of the set irradiation time. Specifically, the control apparatus 18 controls a scanning speed of the plurality of processing lights EL (namely, a relative moving speed of the plurality of irradiation areas EA relative to the coat SF of paint) on the basis of the set irradiation time. More specifically, the control apparatus 18 controls the scanning speed so that the scanning speed of the processing lights EL becomes slower as the irradiation time becomes longer. In order to control the scanning speed, the control apparatus 18 may control a rotational frequency or a swinging frequency of the Galvano mirror 1122. Specifically, the control apparatus 18 may control a rotational frequency or a swinging frequency of the Galvano mirror 1122 so that so that the control a rotational frequency or a swinging frequency of the Galvano mirror 1122 becomes lower as the irradiation time becomes longer. As a result, the scanning speed of the processing lights EL becomes slower as the irradiation time becomes longer. Even in the case where the irradiation time of the plurality of processing lights EL is set on the basis of the reflectance R in this manner, an effect that is same as an effect achievable in the case where the intensity of the plurality of processing lights EL is set on the basis of the reflectance R is achievable. Incidentally, depending on the shape of the surface of the coat SF of paint, there is a possibility that the incident angle of the processing light EL relative to the coat SF of paint changes when the relative positions on the surface of the coat SF of paint of the plurality of irradiation areas EA change. Alternatively, there is a possibility that the incident angle of the processing light EL relative to the coat SF of paint changes due to any factor although the relative positions on the surface of the coat SF of paint of the plurality of irradiation areas EA do not change. When the incident angle of the processing light EL relative to the coat SF of paint changes, there is a possibility that the reflectance R changes. Even in this case, the control apparatus 18 may set the irradiation time of the processing lights EL to a proper time by using the information of the shape of the surface of the coat SF of paint that is measured or that is prepared in advance.

Note that the processing apparatus $1b$ is provided with the surface characteristic measurement apparatus $19b$-1 that measures the shape of the surface of the coat SF of paint and the surface characteristic measurement apparatus $19b$-2 that measures the reflectance of the coat SF of paint individually when the processing apparatus $1b$ performs not only the fifth specific example of the advance measurement control operation but also at least one of the first specific example to the fourth specific example of the advance measurement control operation. In this case, the surface characteristic measurement apparatuses $19b$-1 and $19b$-2 emit the measurement lights MLb1 and MLb2, respectively, and they may share a light source of the measurement lights MLb1 and MLb2. Namely, the surface characteristic measurement apparatuses $19b$-1 and $19b$-2 may share a single light source that emits the measurement light MLb that is usable as the measurement lights MLb1 and MLb2.

In the above described description, the measurement light MLb2 for measuring the reflectance R is the light having the wavelength that is same as the wavelength of the processing light EL (alternatively, the light including the light component the wavelength of which is same as the wavelength of the processing light EL). However, the measurement light MLb2 may be a light having the wavelength that is different from the wavelength of the processing light EL (alternatively, a light that does not includes the light component the wavelength of which is same as the wavelength of the processing light EL). Even in this case, the reflectance R is determined on the basis of the measured result of the surface characteristic measurement apparatus $19b$ by the control apparatus 18, as long as the measurement light MLb that has any correlation between the reflectance of the coat SF of paint to the measurement light MLb and the reflectance R of the coat SF of paint to the processing light EL is used.

In the above described description, the surface characteristic measurement apparatus $19b$ measures the reflectance R of the coat SF of paint to the processing light EL. However, the absorptance of the coat SF of paint to the processing light EL becomes lower as the reflectance R of the coat SF of paint to the processing light EL becomes higher. Thus, it can be said that the surface characteristic measurement apparatus 19b substantially measures the absorptance of the coat SF of paint to the processing light EL. In this case, it can be said that the control apparatus 18 sets the intensity of the plurality of processing lights EL so that the intensity of the plurality of processing lights EL becomes lower as the absorptance of the coat SF of paint to the processing light EL becomes higher. Moreover, it can be said that the control apparatus 18 sets the irradiation time of the plurality of processing lights EL so that the irradiation time of the plurality of processing lights EL becomes shorter as the absorptance of the coat SF of paint to the processing light EL becomes higher.

(4-2-6) Sixth Specific Example of Advance Measurement Control Operation

In the sixth specific example, the surface characteristic measurement apparatus 19b measures, as the characteristic of the surface of the coat SF of paint, reflectances Ra of the coat SF of paint to the plurality of measurement lights MLb having different wavelengths, respectively (hereinafter, the measurement light MLb used in the sixth modified example is referred to as a "measurement light MLb3"). In order to measure the reflectances Ra, the projection apparatus 191b of the surface characteristic measurement apparatus 19b irradiates the coat SF of paint with the plurality of measurement lights MLb3 having the different wavelengths, respectively. The plurality of measurement lights MLb3 may include or may not include the light having the wavelength that is same as the wavelength of the processing light EL. The plurality of measurement lights MLb3 may include or may not include the light including the light component the wavelength of which is same as the wavelength of the processing light EL. The intensity of the plurality of measurement lights MLb3 are set to the intensity lower than the intensity that allows the coat SF of paint to evaporate, as with the fifth specific example. Moreover, the detection apparatus 192b of the surface characteristic measurement apparatus 19b measures reflected lights (especially, an intensity thereof) of the plurality of measurement lights MLb3 from the coat SF of paint. Thus, the reflectance Ra of the coat SF of paint to each of the plurality of measurement lights MLb3 is determined on the basis of the measured result of the surface characteristic measurement apparatus 19b by the control apparatus 18. Note that FIG. 35 is a graph that illustrates an example of the plurality of determined reflectances Ra.

Then, the control apparatus 18 sets the wavelength of at least one of the plurality of measurement lights MLb3 to the wavelength of the processing light EL. Specifically, the control apparatus 18 sets the wavelength of one measurement light MLb3 to which the reflectance Ra is minimum among the plurality of measurement lights MLb3 to the wavelength of the processing light EL. Namely, the control apparatus 18 sets the wavelength of one measurement light MLb3 to which the absorptance of the coat SF of paint is maximum among the plurality of measurement lights MLb3 to the wavelength of the processing light EL. In an example illustrated in FIG. 35, the reflectance Ra corresponding to a measurement light MLb3 (#3) is minimum among five measurement lights MLb3 (namely, a measurement light MLb3 (#1) to a measurement light MLb3 (#5)). Thus, the control apparatus 18 sets the wavelength of the measurement lights MLb3 (#3) to the wavelength of the processing light EL Then, the control apparatus 18 controls the light irradiation apparatus 11 to irradiate the coat SF of paint with the processing light EL having the set wavelength. Specifically, the processing apparatus 1b that performs the sixth specific example of the advance measurement control operation is provided with a light irradiation apparatus 11b-6 having the plurality of light source systems 111 that emit the processing lights EL having different wavelengths, respectively, instead of the above described light irradiation apparatus 11, as illustrated in FIG. 36. The wavelengths of the plurality of processing lights EL emitted from the plurality of light source systems 111 are same as the wavelengths of the plurality of measurement lights MLb3, respectively. The control apparatus 18 controls one optical system 111 that is configured to emit the processing light EL having the set wavelength among the plurality of light source systems 111 so that the one light source system 111 emits the plurality of processing lights EL having the set wavelength. On the other hand, the control apparatus 18 controls the other optical system 111 other than the one optical system 111 among the plurality of light source systems 111 so that the other light source system 111 does not emit the processing lights EL. As a result, the light irradiation apparatus 111 irradiates the coat SF of paint with the processing lights EL having the set wavelength.

Note that the light irradiation apparatus 11b-6 is provided with the plurality of light source systems 111 that emit the processing lights EL having different wavelengths, respectively, in the above described example, however, may be provided with the light source system 111 including a wavelength changeable light source that is configured to sequentially change the emitting wavelength in addition to or instead of this.

According to the sixth specific example of the advance measurement control operation, the processing apparatus 1b achieves an effect that is same as the effect achievable by the above described first specific example of the advance measurement control operation. Moreover, in the sixth specific example, the processing apparatus 1b irradiates the coat SF of paint with the processing lights EL having the wavelength that is same as the one measurement light MLb3 corresponding to the minimum reflectance Ra among the plurality of measurement lights MLb3. Thus, the processing apparatus 1b is capable of irradiating the coat SF of paint with the processing light EL to which the reflectance R of the coat of paint is relatively high (namely, to which the absorptance of the coat SF of paint is relatively low). Thus, the processing apparatus 1b is capable of properly processing the coat SF of paint without being affected by the difference of the characteristic of the coat SF of paint.

Note that there is a possibility that the reflectance Ra at the part of the surface of the coat SF of paint at which the plurality of irradiation areas EA are set also changes during the period when the plurality of processing lights EL are emitted, as described in the fifth specific example. Thus, the control apparatus 18 may set the wavelength of the processing lights EL on the basis of the reflectance Ra at the part of the surface of the coat SF of paint at which the plurality of irradiation areas EA are set and may control the light irradiation apparatus 11 to emit the plurality of processing lights EL having the set wavelength during the period when the plurality of processing lights EL are emitted (namely, when the plurality of processing lights EL relatively moves relative to the coat SF of paint). Note that there is a possibility that the reflectance R changes when the incident angle of the processing light EL relative to the coat SF of paint changes, as described in the fifth specific example. In this case, the control apparatus 18 may set the wavelength of the processing lights EL to a proper wavelength by using the information of the shape of the surface of the coat SF of paint that is measured or that is prepared in advance.

Moreover, the control apparatus 18 may set the wavelength of one measurement light MLb3 to which the reflectance Ra is equal to or lower than a predetermined reflection threshold value (namely, to which the absorptance of the coat SF of paint is equal to or higher than a predetermined absorption threshold value) among the plurality of measurement lights MLb3 to the wavelength of the processing light EL. The reflection threshold value is set to satisfy a condition that the coat SF of paint evaporates by the processing lights EL even when a part of the processing lights EL with which the coat SF of paint is irradiated is reflected by the coat SF of paint having the reflectance R that is equal to or higher than the reflection threshold value. The absorpotion threshold value is also set from a same viewpoint. Even in this case, the processing apparatus 1b is capable of properly processing the coat SF of paint without being affected by the difference of the characteristic of the coat SF of paint.

(4-2-7) Seventh Specific Example of Advance Measurement Control Operation

A seventh specific example of the advance measurement control operation is different from the above described first specific example of the advance measurement control operation in that control apparatus 18 controls the relative positional relationship between the coat SF of paint and the plurality of irradiation areas EA on the basis of the shape of the surface of the coat SF of paint. Another feature of the seventh specific example of the advance measurement control operation may be same as the first specific example of the advance measurement control operation.

Specifically, in the seventh specific example, the surface characteristic measurement apparatus 19b measures the shape of the surface of the coat SF of paint before the light irradiation apparatus 11 moves and measures the shape of the surface of the coat SF of paint after the light irradiation apparatus 11 moves (alternatively, when the light irradiation apparatus 11 moves), in a situation where the light irradiation apparatus 11 relatively moves relative to the coat SF of paint (moreover, the surface characteristic measurement apparatus 19b a relative position of which is fixed to the light irradiation apparatus 11 also relatively moves). In this case, the surface characteristic measurement apparatus 19b measures the shape of the coat SF of paint so that an area 31b on the surface of the coat SF of paint that is a measurement target of the surface characteristic measurement apparatus 19b before the light irradiation apparatus 11 moves is partially overlapped with an area 32b on the surface of the coat SF of paint that is the measurement target of the surface characteristic measurement apparatus 19b after the light irradiation apparatus 11 moves, as illustrated in FIG. 37. Namely, the surface characteristic measurement apparatus 19b performs the measurement in accordance with the movement of the light irradiation apparatus 11 to measure the shape of the surface of an overlapped area 33b that is included in both of the areas 31b and 32b. As a result, the measured result of the overlapped area 33b that is included in both of the areas 31b and 32b is included in both of the measured result of the area 31b and the measured result of the area 32b.

The control apparatus 18 determines on the basis of the measured result of the area 31b and the measured result of the area 32b how the overlapped area 33b moves. Specifically, the control apparatus 18 determines a specific area at which the shape of the surface is some sort of shape that is uniquely distinguishable in the area 31b on the basis of the measured result of the area 31b. Moreover, the control apparatus 18 determines on the basis of the measured result of the area 32b by a pattern matching using the shape of the surface of the specific area as a template whether or not the specific area exists in the area 32b. When the specific area does not exist in the area 32b, the control apparatus 18 determines new specific area in the area 31b and determines whether or not the new specific area exists in the area 32b. When the specific area exists in the area 32b, the specific area corresponds to the overlapped area 33b. The control apparatus 18 determines how a relative position of the surface characteristic measurement apparatus 19b relative to the overlapped area 33b changes in accordance with the movement of the light irradiation apparatus 11 by comparing the position of the overlapped area 33b in the area 31b and the position of the overlapped area 33b in the area 32b. Specifically, the control apparatus 18 determines how long the surface characteristic measurement apparatus 19b moves relative to the overlapped area 33b along each of the X axis direction and the Y axis direction. Note that the light irradiation apparatus 11 may irradiate the surface of the coat SF of paint with the processing light EL to form the specific area at which the shape of the surface is some sort of shape that is uniquely distinguishable in the area 31b. For example, the processing is performed so that the riblet structure has a shape in which a part of the convex structure or the concave structure linearly extending along a predetermined direction is cut, and the riblet structure in which the shape of the cross-sectional surface changes in an extending direction of the riblet as illustrated in FIG. 58 and FIG. 59 described later.

A relative moving distance of the surface characteristic measurement apparatus 19b relative to the overlapped area 33b is same as a relative moving distance of the light irradiation apparatus 11 relative to the overlapped area 33b. A relative moving direction of the surface characteristic measurement apparatus 19b relative to the overlapped area 33b is same as a relative moving direction of the light irradiation apparatus 11 relative to the overlapped area 33b. Therefore, the control apparatus 18 is capable of determining how long the light irradiation apparatus 11 moves relative to the coat SF of paint along each of the X axis direction and the Y axis direction. Namely, the control apparatus 18 is capable of determining the relative position of the light irradiation apparatus 11 relative to the coat SF of paint by determining the relative position of the surface characteristic measurement apparatus 19b relative to the overlapped area 33b Since the light irradiation apparatus 11 irradiates the coat SF of paint with the processing lights EL, determining the relative position of the light irradiation apparatus 11 relative to the coat SF of paint is substantially equivalent to determining the relative positions of the plurality of irradiation areas EA relative to the coat SF of paint. Therefore, the control apparatus 18 is capable of determining the relative positions (especially, the positions along each of the X axis direction and the Y axis direction) of the plurality of irradiation areas EA relative to the coat SF of paint on the basis of the shape of the surface of the coat SF of paint. Then, when the determined positions of the plurality of irradiation areas EA are away from positions of the plurality of irradiation areas EA that are required to form the riblet structure (alternatively, the structure to be formed by processing the coat SF of paint), the control apparatus 18 controls the light irradiation apparatus 11 so that the plurality of irradiation areas EA relatively move relative to the coat SF of paint. Namely, the control apparatus 18 controls the positional relationship between the coat SF of paint and the plurality of irradiation areas EA. For example, the control apparatus 18 may relatively move the plurality of irradiation areas EA by controlling the driving system 12 to move the light irradiation apparatus 11 relative to the coat SF of paint.

According to the seventh specific example of the advance measurement control operation, the processing apparatus 1b achieves an effect that is same as the effect achievable by the above described first specific example of the advance measurement control operation. Moreover, in the seventh specific example, the processing apparatus 1b is capable of properly adjusting the relative positions of the plurality of irradiation areas EA on the surface of the coat SF of paint and thus is capable of forming the riblet structure more properly (for example, with higher accuracy).

(4-2-8) Eighth Specific Example of Advance Measurement Control Operation

In the above described description, the processing apparatus 1b is provided with the surface characteristic measurement apparatus 19b. However, the processing apparatus 1b may not be provided with the surface characteristic measurement apparatus 19b. Even in this case, the processing apparatus 1b is allowed to perform the above described advance measurement control operation, as long as the information relating to the shape of the surface of the coat SF of paint is available by the control apparatus 18. For example, the shape of the surface of the coat SF of paint is allowed to be estimated from a design data such as a three-dimensional model of the processing target object S. Thus, the control apparatus 18 may collect the design data of the processing target object S, may estimate the shape of the surface of the coat SF of paint from the design data and may perform the first specific example to the fourth specific example of the above described advance measurement control operation on the basis of the estimated shape of the surface of the coat SF of paint. Alternatively, the control apparatus 18 may collect a data in which an information of a processing area and the non-processing area is added to the design data. Alternatively, for example, the reflectance R of the coat SF of paint is allowed to be estimated from a specification of the coat SF of paint. Thus, the control apparatus 18 may collect an information relating to the specification of the coat SF of paint, may estimate the reflectance R of the coat SF of paint from the information relating to the specification and may perform the fifth specific example to the sixth specific example of the above described advance measurement control operation on the basis of the estimated reflectance R of the coat SF of paint. Alternatively, the control apparatus 18 may collect a data in which a reflectance information of a painting (generally, an information relating to a color) is added to the design data. As a result, the measurement by the surface characteristic measurement apparatus 19b is not necessary, and thus, a time required to process the coat SF of paint is reducible. Note that the operation performed in this case may not be referred to as the advance measurement control operation, because it does not need the measurement by the surface characteristic measurement apparatus 19b. Note that the non-processing area may be masked by a masking tape.

In the above described description, the control apparatus 18 controls at least one of the light concentration positions FP of the processing lights EL, the intensity distribution of the processing lights EL, the shapes of the processing lights EL and the depth of focus of the optical system 112 on the basis of the shape of the surface of the coat SF of paint. The control apparatus 18 controls at least one of the intensity of the plurality of processing lights EL, the irradiation time of the plurality of processing lights EL and the wavelength of the plurality of processing lights EL on the basis of the reflectance of the coat SF of paint. However, the control apparatus 18 may control any characteristic of the processing lights EL on the basis of any characteristic of the coat SF of paint so that the coat SF of paint is processed by the irradiation of the plurality of processing lights EL. At least one of the shapes of the plurality of irradiation areas EA, the sizes of the plurality of irradiation areas EA, the positions of the plurality of irradiation areas EA, the relative position between the plurality of processing lights EL, the relative angle between the plurality of processing lights EL, the polarization state of the plurality of processing lights EL, the intensity of the plurality of processing lights EL, the irradiation time of the plurality of processing lights EL and the wavelengths of the plurality of processing lights EL is one example of any characteristic of the processing lights EL.

In the above described description, the surface characteristic measurement apparatus 19b measures the characteristic of the surface of the coat SF of paint before the light irradiation apparatus 11 irradiates the surface of the coat SF of paint with the plurality of processing lights EL. Namely, the light irradiation apparatus 11 does not emit the plurality of processing lights EL during a period when the surface characteristic measurement apparatus 19b measures the characteristic of the surface of the coat SF of paint, and the surface characteristic measurement apparatus 19b does not measure the characteristic of the surface of the coat SF of paint during the period when the light irradiation apparatus 11 emits the plurality of processing lights EL. However, the surface characteristic measurement apparatus 19b may measure the characteristic of the surface of the coat SF of paint in at least a part of the period when the light irradiation apparatus 11 irradiates the surface of the coat SF of paint with the plurality of processing lights EL. The light irradiation apparatus 11 may irradiate the surface of the coat SF of paint with the plurality of processing lights EL in at least a part of the period when the surface characteristic measurement apparatus 19b measures the characteristic of the surface of the coat SF of paint. Namely, an operation for measuring the characteristic of the surface of the coat SF of paint by the surface characteristic measurement apparatus 19b and an operation for irradiating the surface of the coat SF of paint with the plurality of processing lights EL (namely, an operation for processing the coat SF of paint) by the light irradiation apparatus 11 may be performed in parallel. For example, the surface characteristic measurement apparatus 19b may measure the characteristic of other area of the coat SF of paint that is different from one area in at least a part of the period when the light irradiation apparatus 11 irradiates the one area of the coat SF of paint the characteristic of which is already measured by the surface characteristic measurement apparatus 19b with the plurality of processing lights EL. For example, the light irradiation apparatus 11 may irradiate the one area of the coat SF of paint the characteristic of which is already measured by the surface characteristic measurement apparatus 19b with the plurality of processing lights EL in at least a part of the period when the surface characteristic measurement apparatus 19b measures other area of the coat SF of paint. In this case, it is expected that a throughput relating to the formation of the riblet structure improves.

(4-3) Third Modified Example

Next, with reference to FIG. 38, a processing apparatus 1c in a third modified example will be described. As illustrated in FIG. 38A, the processing apparatus 1c in the third modified example is different from the above described processing apparatus 1 in that it is further provided with a structure measurement apparatus 19c. Another feature of the processing apparatus 1c may be same as another feature of the processing apparatus 1.

The structure measurement apparatus 19c measures a characteristic of the riblet structure (alternatively, any structure, the same applies to this modified example) formed by the irradiation of the processing lights EL from the light irradiation apparatus 11. A presence or absence of the riblet structure, a shape of the riblet structure (for example, at least one of a shape of the cross-sectional surface of the concave structure CP1, a shape of the cross-sectional surface of the convex structure CP2 and the like), a size of the riblet structure (for example, at least one of the depth D of the concave structure CP1, a width of the concave structure CP1, the arrangement pitch P1 of the concave structure CP1, the height H of the convex structure CP2, the width of the convex structure CP2, the arrangement pitch P2 of the convex structure CP2, and the like) and a position of the riblet structure (for example, the position of at least one of the concave structure CP1 and the convex structure CP2) is one example of the characteristic of the riblet structure.

In order to measure the characteristic of the riblet structure, the structure measurement apparatus 19c is provided with a lighting apparatus 191c and a detection apparatus 192c. The lighting apparatus 191c and the detection apparatus 192c are supported by the housing apparatus 13 through a supporting member 136c. The lighting apparatus 191c irradiates the riblet structure (namely, the coat SF of paint) with a measurement light MLc1. When the riblet is irradiate with the measurement light MLc1, the measurement light MLc1 is reflected or scattered by the riblet structure. As a result, a measurement light MLc2 including at least one of a reflected light or a scattered light of the measurement light MLc1 is emitted from the riblet structure. The detection apparatus 192c detects the measurement light MLc2.

When the part at which the riblet structure is formed is irradiated with the measurement light MLc1, the measurement light MLc2 includes at least one of the reflected light and the scattered light that propagate in a traveling direction that intersects with a traveling direction of the measurement light MLc1. On the other hand, when the part at which the riblet structure is not formed is irradiated with the measurement light MLc1, the measurement light MLc2 does not include at least one of the reflected light and the scattered light that propagate in the traveling direction that intersects with the traveling direction of the measurement light MLc1. Namely, the traveling direction of the measurement light MLc2 is nearly parallel with the traveling direction of the measurement light MLc1. Thus, as illustrated in FIG. 39, when the lighting apparatus 191c and the detection apparatus 192c are disposed to detect the measurement light MLc2 traveling in the direction that intersects with the traveling direction of the measurement light MLc1, the control apparatus 18 is capable of determining the presence or absence of the riblet structure at a part that is irradiated with the measurement light MLc1 on the basis of a detected result of the detection apparatus 192c. Moreover, the characteristic (for example, the intensity and the like) of the measurement light MLc2 changes depending on at least one of the shape and the size of the riblet structure. Therefore, the control apparatus 18 is capable of determining at least one of the shape of the riblet structure, the size of the riblet structure, a position of the concave structure CP1 that constitutes the riblet structure and a position of the convex structure CP2 that constitutes the riblet structure on the basis of the detected result of the detection apparatus 192c.

The structure measurement apparatus 19c is configured to change the traveling direction of the measurement light MLc1. For example, when the lighting apparatus 191c is provided with an optical element that optically changes the traveling direction of the measurement light MLc1, the traveling direction of the measurement light MLc1 may be changed by this optical element. For example, when the lighting apparatus 191c is relatively movable relative to the coat SF of paint, the traveling direction of the measurement light MLc1 may be changed by a relative movement of the lighting apparatus 191c. Here, if the measurement light MLc1 is allowed to be emitted to the riblet structure from only one direction, there is a possibility that the measurement light MLc2 is not generated even if the riblet structure is irradiated with the measurement light MLc1, depending on the extending direction of the riblet structure. However, when the traveling direction of the measurement light MLc1 is changeable, the lighting apparatus 191c is allowed to emit the measurement light MLc1 from various directions to the riblet structure extending in a certain direction. Thus, the structure measurement apparatus 19c is capable of measuring the characteristic of the riblet structure without being affected by the difference of the extending direction of the riblet structure. Note that the structure measurement apparatus 19c itself may be rotated around the Z axis in order to change the traveling direction of the measurement light MLc1. Moreover, a plurality of structure measurement apparatus 19c from which the traveling directions of the measurement lights MLc1 are different from each other may be disposed.

The structure measurement apparatus 19c may be configured to change the traveling direction of the measurement light MLc2 that is detectable by the detection apparatus 192c, in addition to or instead of changing the traveling direction of the measurement light MLc1. For example, when the detection apparatus 192c is relatively movable relative to the coat SF of paint, the traveling direction of the measurement light MLc2 that is detectable by the detection apparatus 192c may be changed by a relative movement of the detection apparatus 192c. Here, if the detection apparatus 192c is allowed to detect the measurement light MLc2 that travels in only one direction, there is a possibility that the measurement light MLc2 does not travel toward the detection apparatus 192c and thus the measurement light MLc2 is not detectable by the detection apparatus 192c, depending on the extending direction of the riblet structure. However, when the traveling direction of the measurement light MLc2 that is detectable by the detection apparatus 192c is changeable, the detection apparatus 192c is allowed to detect the measurement light MLc2 traveling in various directions from the riblet structure extending in a certain direction. Thus, the structure measurement apparatus 19c is capable of measuring the characteristic of the riblet structure without being affected by the difference of the extending direction of the riblet structure.

The structure measurement apparatus 19c may measure the characteristic of all riblet structure formed by the processing apparatus 1c. However, if the characteristic of all riblet structure formed by the processing apparatus 1c is measured, a time required to measure the characteristic of the riblet structure is too large. Thus, in the third modified example, the structure measurement apparatus 19c selectively measures the characteristic of the riblet structure formed in a sample area DAc that is a part of a processed area in which the processing apparatus 1c forms the riblet structure, as illustrated in FIG. 40. The structure measurement apparatus 19c selectively measures the characteristic of the riblet structure formed in a plurality of sample areas DAc that evenly distribute in the processed area. However, the structure measurement apparatus 19c may selectively measure the characteristic of the riblet structure formed in a plurality of (alternatively, one) sample areas DAc that randomly distribute in the processed area.

The structure measurement apparatus 19c may selectively measure the characteristic of the riblet structure formed in the sample area DAc in a certain area in which the riblet structure should be formed after the processing apparatus 1c forms the riblet structure in this certain area. For example, the structure measurement apparatus 19c may set the sample are DAc in a certain unit processing area SA and selectively measure the characteristic of the riblet structure formed in the set sample area DAc after the processing apparatus 1c forms the riblet structure in this certain unit processing area SA. Then, when the processing apparatus 1c forms the riblet structure in another unit processing area SA, the structure measurement apparatus 19c may set the sample are DAc in another unit processing area SA and selectively measure the characteristic of the riblet structure formed in the set sample area DAc. Namely, the formation of the riblet structure by the processing apparatus 1c and the measurement of the characteristic of the riblet structure by the structure measurement apparatus 19c may be alternately repeated.

Alternatively, the structure measurement apparatus 19c may selectively measure the characteristic of the riblet structure that is already formed by the processing apparatus 1c in another area that is different from one area during a period when the processing apparatus 1c irradiates the one area on the surface of the coat SF of paint with the plurality of processing lights EL (namely, the riblet structure is formed in the one area). For example, the structure measurement apparatus 19c may selectively measure the characteristic of the riblet structure formed in the sample area DAc in another unit processing area SA that is different from one unit processing area SA and in which the processing apparatus 1c already forms the riblet structure during a period when the processing apparatus 1c forms the riblet structure in the one unit processing area SA. Namely, the formation of the riblet structure by the processing apparatus 1c and the measurement of the characteristic of the riblet structure by the structure measurement apparatus 19c may be performed in parallel. In this case, it is expected that a throughput relating to the formation of the riblet structure improves.

After the structure measurement apparatus 19c finishes the measurement, the measured result of the structure measurement apparatus 19c is outputted to the control apparatus 18. The control apparatus 18 determines the characteristic of the riblet structure on the basis of the measured result of the structure measurement apparatus 19c, as described above. The control apparatus 18 determines on the basis of the determined characteristic of the riblet structure whether or not the characteristic of the riblet structure is good. Moreover, the control apparatus 18 notifies an operator of the processing apparatus 1c of a determined result of the goodness of the characteristic of the riblet structure through an output including at least one of a display and a speaker.

For example, the control apparatus 18 may determine whether or not the size of the riblet structure in the direction intersecting with the surface of the coat SF of paint (namely, the width D of the concave structure CP1 or the height H of the convex structure CP2) is good. FIG. 41A is a cross-sectional view that illustrates an ideal riblet structure that should be formed by the processing apparatus 1c. When the determined size of the riblet structure is same as the size of the ideal riblet structure as illustrated in FIG. 41B, the control apparatus 18 determines that the size of the riblet structure is normal (namely, the riblet structure is good one). In this case, the control apparatus 18 notifies that the size of the riblet structure is normal. On the other hand, when the determined size of the riblet structure is smaller than the size of the ideal riblet structure as illustrated in FIG. 41C, the control apparatus 18 determines that the size of the riblet structure is abnormal (namely, the riblet structure is defective one). In this case, the control apparatus 18 notifies that the size of the riblet structure is abnormal (especially, the size is small). On the other hand, when the determined size of the riblet structure is larger than the size of the ideal riblet structure as illustrated in FIG. 41D, the control apparatus 18 determines that the size of the riblet structure is abnormal (namely, the riblet structure is defective one). In this case, the control apparatus 18 notifies that the size of the riblet structure is abnormal (especially, the size is large).

For example, the control apparatus 18 may determine whether or not the shape of the riblet structure is good. When the determined shape of the riblet structure is same as the shape of the ideal riblet structure as illustrated in FIG. 42A, the control apparatus 18 determines that the shape of the riblet structure is normal (namely, the riblet structure is good one). In this case, the control apparatus 18 notifies that the shape of the riblet structure is normal. On the other hand, when the determined shape of the riblet structure is different from the shape of the ideal riblet structure as illustrated in FIG. 42B, the control apparatus 18 determines that the shape of the riblet structure is abnormal (namely, the riblet structure is defective one). In this case, the control apparatus 18 notifies that the shape of the riblet structure is abnormal.

For example, the control apparatus 18 may determine whether or not the position of the concave structure CP1 (furthermore, the convex structure CP2, the same applies to the below described description) constituting the riblet structure is good. When the determined position of the concave structure CP1 is same as the position of the concave structure CP1 constituting the ideal riblet structure as illustrated in an upper part of FIG. 43, the control apparatus 18 determines that the position of the concave structure CP1 constituting the riblet structure is normal (namely, the riblet structure is good one). In this case, the control apparatus 18 notifies that the position of the concave structure CP1 constituting the riblet structure is normal. On the other hand, when the determined position of the concave structure CP1 is different from the position of the concave structure CP1 constituting the ideal riblet structure as illustrated in an lower part of FIG. 43, the control apparatus 18 determines that the position of the concave structure CP1 constituting the riblet structure is abnormal (namely, the riblet structure is defective one). In this case, the control apparatus 18 notifies that the position of the concave structure CP1 constituting the riblet structure is wrong.

For example, the control apparatus 18 may determine the goodness of the presence or absence of the riblet structure. When the riblet structure exists in the sample area DA as illustrated in FIG. 44A, the control apparatus 18 determines that the riblet structure is formed (namely, the riblet structure is good one). In this case, the control apparatus 18 notifies that the riblet structure is formed. On the other hand, when the riblet structure does not exist in the sample area DA as illustrated in FIG. 44B, the control apparatus 18 determines that the riblet structure is not formed (namely, the riblet structure is defective one). In this case, the control apparatus 18 notifies that the riblet structure is not formed.

When it is determined that the riblet structure is defective one, the control apparatus 18 may control the light irradiation apparatus 18 to modify the riblet structure that is already formed. Specifically, when it is determined that the riblet structure is defective one, there is a possibility that not only the riblet structure in the sample area DA in which the defective riblet structure exists but also the riblet structure in a wider area on the coat SF of paint including this sample area DA are defective. Thus, the control apparatus 18 controls the light irradiation apparatus 11 to irradiate the wider area on the coat SF of paint including the sample area DA (hereinafter, this area is referred to as a "modification target area") with the processing light EL to modify the riblet structure in the modification target area. For example, when the size (here, the depth D) of the concave structure CP1 constituting the riblet structure is smaller than the size of the concave structure CP1 constituting the ideal riblet structure as illustrated in FIG. 45A, the control apparatus 18 may control the light irradiation apparatus 11 so that the concave structure CP1 is enlarged by irradiating the concave structure CP1 with the processing light EL to remove the coat SF of paint more (namely, reducing the thickness of the coat SF of paint more). As a result, as illustrated in FIG. 45B, the size of the riblet structure in the modification target area is modified to be same as the size of the ideal riblet structure. Note that a processing condition of the processing apparatus 1c may be changed by using the measured result of the characteristic of the riblet structure by the structure measurement apparatus 19c. For example, when it is measured that the shape, the formed position or the size of the riblet structure almost goes beyond the upper/lower limit of a predetermined range (a standard), the shape, the formed position or the size of the riblet structure may be brought close to a center value of the standard by changing the processing condition of the processing apparatus 1c.

The processing apparatus 1c in the third modified example achieves an effect that is same as the effect achievable by the above described processing apparatus 1. Moreover, the processing apparatus 1c is capable of evaluating the goodness of the actually formed riblet structure properly.

(4-4) Fourth Modified Example

Next, a processing apparatus 1d in a fourth modified example will be described. The processing apparatus 1d in the fourth modified example is configured to change the arrangement pitch P1 of the concave structure CP1. When the arrangement pitch P1 of the concave structure CP1 changes, the arrangement pitch P2 of the convex structure CP2 also changes. Thus, it can be said that the processing apparatus 1d is configured to change the arrangement pitch P2 of the convex structure CP2.

In order to change the arrangement pitch P1, the processing apparatus 1d is provided with a light irradiation apparatus 11d instead of the above described light irradiation apparatus 11. The light irradiation apparatus 11d is different from the light irradiation apparatus 11 in that it is provided with an optical system 112d having a zoom lens 1124d, as illustrated in FIG. 46. Another feature of the light irradiation apparatus 11d may be same as another feature of the light irradiation apparatus 11. The zoom lens 1124d is configured to change a projection magnification of the optical system 112d under the control of the control apparatus 18. The zoom lens 1124d is configured to change an interval between the plurality of emitted processing lights EL under the control of the control apparatus 18.

When the projection magnification of the optical system 112d changes, the relative positional relationship between the plurality of irradiation areas EA in the direction along the surface of the coat SF of paint changes. Specifically, as illustrated in FIG. 47A, when the magnification of the optical system 112d is a first magnification (namely, the interval between the plurality of emitted processing lights EL is a first interval), an arrangement pitch of the plurality of irradiation areas EA is a first pitch Pe1. Note that the arrangement pitch of the plurality of irradiation areas EA means an arrangement pitch along a direction (the X axis direction in an example illustrated in FIG. 47A) in which the plurality of irradiation areas EA move on the surface of the coat SF of paint during the step operation. On the other hand, as illustrated in FIG. 47B, when the magnification of the optical system 112d is a second magnification that is larger than the first magnification (namely, the interval between the plurality of emitted processing lights EL is a second interval that is larger than the first interval), the arrangement pitch of the plurality of irradiation areas EA is a second pitch Pe2 that is larger than first pitch Pe1. Namely, the control apparatus 18 changes the relative positional relationship between the plurality of irradiation areas EA in the direction along the surface of the coat SF of paint (especially, the arrangement pitch of the plurality of irradiation areas EA) by changing the projection magnification of the optical system 112d.

When the arrangement pitch of the plurality of irradiation areas EA changes, the arrangement pitch P1 of the plurality of concave structures CP1 formed by the plurality of processing lights EL with which the plurality of irradiation areas EA are irradiated, respectively, also changes. Specifically, as illustrated in FIG. 47C, the arrangement pitch P1 of the plurality of concave structures CP1 formed by the plurality of processing lights EL with which the plurality of irradiation areas EA the arrangement pitch of which is the first pitch Pe1 are irradiated, respectively, is a first pitch Pp1 corresponding to the first pitch Pe1. On the other hand, as illustrated in FIG. 47D, the arrangement pitch P1 of the plurality of concave structures CP1 formed by the plurality of processing lights EL with which the plurality of irradiation areas EA the arrangement pitch of which is the second pitch Pe2 are irradiated, respectively, is a second pitch Pp2 corresponding to the second pitch Pe2. Since the second pitch Pe2 is larger than the first pitch Pe1, the second pitch Pp2 is also larger than the first pitch Pp1.

Note that the relative positional relationship between the plurality of processing lights EL changes when the arrangement pitch of the plurality of irradiation areas EA changes, because the light irradiation apparatus 11d emits the plurality of processing lights EL that are parallel with each other. Namely, as illustrated in FIG. 47C and FIG. 47D, the relative positional relationship between the plurality of processing lights EL changes so that the interval (especially, the interval in the direction along the surface of the coat SF of paint) between the plurality of processing lights EL becomes larger as the arrangement pitch of the plurality of irradiation areas EA becomes larger. Thus, controlling the arrangement pitch of the plurality of irradiation areas EA is equivalent to controlling the relative positional relationship between the plurality of processing lights EL. Therefore, it can be said that the control apparatus 18 substantially changes the arrangement pitch of the concave structure CP1 by changing the relative positional relationship between the plurality of processing lights EL The control apparatus 18 may changes the arrangement pitch P1 of the concave structure CP1 on the basis of which part of the processing target object S corresponds to an area in which the riblet structure will be formed. For example, when the processing target object S is the airplane PL as described above, the arrangement pitch P1 of the concave structure CP1 that effectively achieves the effect of the reduction of the resistance of the body PL1 is not necessarily same as the arrangement pitch P1 of the concave structure CP1 that effectively achieves the effect of the reduction of the resistance of the main wing PL2. Thus, the control apparatus 18 may change the arrangement pitch P1 of the concave structure CP1 so that the arrangement pitch P1 of the concave structure CP1 formed by processing the coat SF of paint on the body PL1 is different from the arrangement pitch P1 of the concave structure CP1 formed by processing the coat SF of paint on the main wing PL2.

The control apparatus 18 may change the arrangement pitch P1 of the concave structure CP1 on the basis of the shape of the surface of the coat SF of paint. Specifically, as described above, there is a high possibility that the shape of the surface of the coat SF of paint depends on the surface of the processing target object S under the coat SF of paint. Namely, there is a high possibility that the surface of the coat SF of paint coated on the processing target object S having the flat surface is a flat surface and there is a high possibility that the surface of the coat SF of paint coated on the processing target object S having the curved surface is a curved surface. In this case, the arrangement pitch P1 of the concave structure CP1 that effectively achieves the effect of the reduction of the resistance of the surface of the processing target object S having a first shape is not necessarily same as the arrangement pitch P1 of the concave structure CP1 that effectively achieves the effect of the reduction of the resistance of the surface of the processing target object S having a second shape that is different from the first shape. Thus, the control apparatus 18 may change the arrangement pitch P1 of the concave structure CP1 so that the arrangement pitch P1 of the concave structure CP1 formed by processing the coat SF of paint the shape of the surface of which is the first shape is different from the arrangement pitch P1 of the concave structure CP1 formed by processing the coat SF of paint the shape of the surface of which is the second shape. Incidentally, in this case, in order to change the arrangement pitch P1 of the concave structure CP1 on the basis of the shape of the surface of the coat SF of paint, the processing apparatus 1*d* may be provided with the surface characteristic measurement apparatus 19*b* that is configured to measure the shape of the surface of the coat SF of paint as with the processing apparatus 1*b*, or may collect the information relating to the shape of the surface of the coat SF of paint (for example, the above described design data). Moreover, when the light irradiation apparatus 11*d* irradiates the coat SF of paint with the plurality of processing lights EL that are parallel with each other, the interval between (the pitch of) the plurality of processing lights EL is not necessarily same as the arrangement pitch P1 of the formed concave structure CP1 in the situation where the shape of the processing target object S is not the flat surface. In this case, the interval between the plurality of processing lights EL may be changed so that the arrangement pitch P1 of the formed concave structure CP1 is a predetermined pitch. Note that the interval between the plurality of processing lights EL may be changed even when the light irradiation apparatus 11*d* irradiates the coat SF of paint with the plurality of processing lights EL that are not parallel with each other, because the interval between (the pitch of) the plurality of processing lights EL is not necessarily same as the arrangement pitch P1 of the formed concave structure CP1 in the situation where the shape of the processing target object S is not the flat surface.

The relative positions on the surface of the coat SF of paint (especially, the positions in the direction along the surface of the coat SF of paint) of the plurality of irradiation areas EA that are irradiated with the plurality of processing lights EL, respectively, change due to the sweep with the plurality of processing lights EL. When the relative positions on the surface of the coat SF of paint of the plurality of irradiation areas EA change, there is a possibility that an area at which the plurality of irradiation areas EA are formed moves from an area corresponding to one part of the processing target object S (for example, an area corresponding to the body PL1) an area corresponding to another part of the processing target object S (for example, an area corresponding to the main wing PL2) during the period when the plurality of processing lights EL are emitted. Alternatively, when the relative positions on the surface of the coat SF of paint of the plurality of irradiation areas EA change, there is a possibility that a shape of a part of the surface of the coat SF of paint at which the plurality of irradiation areas EA are formed also changes during the period when the plurality of processing lights EL are emitted. Thus, the control apparatus 18 may change the arrangement pitch P1 of the concave structure CP1 when the coat SF of paint is irradiated with the plurality of processing lights EL (namely, the plurality of processing lights EL relatively move relative to the coat SF of paint). As described above, there is a possibility that the arrangement pitch of the formed concave structure CP1 changes even when the interval between the processing lights EL is constant, when the shape of the processing target object S changes. In this case, the interval between (the pitch of) the plurality of processing lights EL may be changed on the basis of the shape of the shape of the coat SF of paint.

The processing apparatus 1*d* in the fourth modified example achieves an effect that is same as the effect achievable by the above described processing apparatus 1 and is allowed to change the arrangement pitches of the concave structure CP1 and the convex structure CP2. Therefore, more proper riblet structure is formable compared to the case where the arrangement pitches of the concave structure CP1 and the convex structure CP2 are not allowed to be changed. Specifically, the riblet structure having the proper arrangement pitch that properly achieves the effect of the reduction of the resistance is formable Note that at least one of the above described light irradiation apparatuses 21*a* to 27*a* that are described with reference to FIG. 18 to FIG. 24 may be provided with the zoom lens 1124*d*. In this case, the arrangement pitches of the concave structure CP1 and the convex structure CP2 that constitute the riblet structure are changeable.

Moreover, in the above described description, the control apparatus 18 changes the arrangement pitch P1 of the concave structure CP1 (namely, the arrangement pitch of the plurality of irradiation areas EA) and/or the interval between the plurality of processing lights EL by changing the projection magnification of the optical system 112*d* by using the zoom lens 1124*d*. However, the control apparatus 18 may change the arrangement pitch P1 of the concave structure CP1 (namely, the arrangement pitch of the plurality of irradiation areas EA) and/or the interval between the plurality of processing lights EL by using another method. Even when the processing apparatus 1*d* is provided with the above described light irradiation apparatuses 21*a* to 27*a* instead of the light irradiation apparatus 11*d*, the control apparatus 18 may change the arrangement pitch P1 of the concave structure CP1 (namely, the arrangement pitch of the plurality of irradiation areas EA) and/or the interval between the plurality of processing lights EL by using another method.

For example, plane parallel plates each of which is configured to change an inclination angle relative to an optical axis may be disposed in the optical paths of the plurality of processing lights EL emitted from the light source system 111, respectively, and the arrangement pitch of the plurality of irradiation areas EA and/or the interval between the plurality of processing lights EL may be changed by setting the angle of the plane parallel plates to predetermined angles, respectively. At least one of the above described light irradiation apparatuses 22*a* to 23*a* and 25*a* to 27*a* each of which is configured to emit the plurality of processing lights EL may be provided with the plane parallel plates too.

For example, when the processing apparatus 1*d* is provide with the plurality of above described irradiation units 110*b*-1 illustrated in FIG. 27, the control apparatus 18 may change the arrangement pitch of the plurality of irradiation areas EA and/or the interval between the plurality of processing lights EL by moving the plurality of irradiation units 110*b*-1 in the direction along the surface of the coat SF of paint. Specifically, the control apparatus 18 may change the arrangement pitch of the plurality of irradiation areas EA and/or the interval between the plurality of processing lights EL by moving the plurality of irradiation units 110*b*-1 to change an arrangement interval between the plurality of irradiation units 110*b*-1. As a result, the arrangement pitch P1 of the concave structure CP1 changes. The same applies to the case where the processing apparatus 1*d* is provided with either one of the above described light irradiation apparatuses 22*a* to 23*a* and 25*a* to 27*a* each of which is configured to emit the plurality of processing lights EL and either one of the light irradiation apparatuses 22*a* to 23*a* and 25*a* to 27*a* is provided with the plurality of irradiation units 110*b*-1 in order to emits the plurality of processing lights EL.

For example, when the processing apparatus 1*d* is provided with the plurality of above described light sources 1111 illustrated in FIG. 3B, the control apparatus 18 may change the arrangement pitch of the plurality of irradiation areas EA and/or the interval between the plurality of processing lights EL by moving the plurality of light sources 1111 in the direction along the surface of the coat SF of paint. Specifically, the control apparatus 18 may change the arrangement pitch of the plurality of irradiation areas EA and/or the interval between the plurality of processing lights EL by moving the plurality of irradiation units 110*b*-1 to change an arrangement interval between the plurality of light sources 1111. As a result, the arrangement pitch P1 of the concave structure CP1 changes. The same applies to the case where the processing apparatus 1*d* is provided with either one of the above described light irradiation apparatuses 22*a* to 23*a* and 25*a* to 27*a* each of which is configured to emit the plurality of processing lights EL and either one of the light irradiation apparatuses 22*a* to 23*a* and 25*a* to 27*a* is provided with the plurality of light sources 1111 in order to emits the plurality of processing lights EL.

For example, when the processing apparatus 1*d* divides the processing light EL from the above described single light source 1111 illustrated in FIG. 3B and then emits from the plurality of emitting ports, the control apparatus 18 may change the arrangement pitch of the plurality of irradiation areas EA and/or the interval between the plurality of processing lights EL by changing positions of the plurality of emitting ports. Specifically, the control apparatus 18 may change the arrangement pitch of the plurality of irradiation areas EA and/or the interval between the plurality of processing lights EL by changing an arrangement interval between the plurality of emitting ports. As a result, the arrangement pitch P1 of the concave structure CP1 changes. The same applies to the case where the processing apparatus 1*d* is provided with either one of the above described light irradiation apparatuses 22*a* to 23*a* and 25*a* to 27*a* each of which is configured to emit the plurality of processing lights EL and either one of the light irradiation apparatuses 22*a* to 23*a* and 25*a* to 27*a* divides the processing light EL from the single light source 1111 in order to emits the plurality of processing lights EL.

For example, when the processing apparatus 1*d* is provided with the light irradiation apparatus 22*a* having the mirror array 2221*a*, the control apparatus 18 may change the arrangement pitch of the plurality of irradiation areas EA and/or the interval between the plurality of processing lights EL by controlling the inclination angle of each mirror M of the mirror array 2221*a* to change the position (especially, the position around the Y axis) of the reflected surface of each mirror M. For example, when the mirror array 2221*a* is provided with the plurality of mirrors M that are arranged in a matrix on the XY plane, the control apparatus 18 may change the arrangement pitch of the plurality of irradiation areas EA and/or the interval between the plurality of processing lights EL that are arranged along the X axis direction by controlling the inclination angle of each mirror M in a unit of one group of mirrors M that are arranged along the Y axis direction.

For example, when the processing apparatus 1*d* is provided with a light irradiation apparatus 11*d*-1 that is configured to change the relative angle between the plurality of processing lights EL, the control apparatus 18 may change the arrangement pitch of the plurality of irradiation areas EA and/or the interval between the plurality of processing lights EL by changing the relative angle between the plurality of processing lights EL. Specifically, FIG. 48A illustrates an aspect in which the relative angle between the plurality of processing lights EL is in a first angle state and FIG. 48B illustrates an aspect in which the relative angle between the plurality of processing lights EL is in a second angle state that is different from the first angle state. As illustrated in FIG. 48A and FIG. 48B, when the relative angle between the plurality of processing lights EL changes, angles at which the plurality of processing lights EL enters the coat SF of paint also change. On the other hand, eve when the relative angle between the plurality of processing lights EL changes, points from which the plurality of processing lights EL emit do not change from the optical system of the light irradiation apparatus 11*d*-1. As a result, as illustrated in FIG. 48C and FIG. 48D, when the relative angle between the plurality of processing lights EL changes, the arrangement pitch of the plurality of irradiation areas EA changes. Specifically, as illustrated in FIG. 48C, when the relative angle between the plurality of processing lights EL is in the first angle, the arrangement pitch of the plurality of irradiation areas EA is a third pitch Pe3. On the other hand, as illustrated in FIG. 48D, when the relative angle between the plurality of processing lights EL is in the second angle, the arrangement pitch of the plurality of irradiation areas EA is a fourth pitch Pe4 that is larger than the third pitch Pe3. As a result, as a result, the arrangement pitch P1 of the concave structure CP1 changes. Note that the light irradiation apparatus 11d-1 may be a light irradiation apparatus obtained by adding an optical member for changing the relative angle between the plurality of processing lights EL to the above described light irradiation apparatus 11 and light irradiation apparatuses 22a to 23a and 25a to 27a each of which is configured to emit the plurality of processing lights EL.

For example, when the processing apparatus 1d is provided with a light irradiation apparatus 11d-2 that is configured to irradiate the coat SF of paint with the plurality of processing lights EL that are not parallel with each other, the control apparatus 18 may change the arrangement pitch of the plurality of irradiation areas EA and/or the interval between the plurality of processing lights EL by changing the relative positional relationship between the light irradiation apparatus 11d-2 and the coat SF of paint (a distance between the light irradiation apparatus 11d-2 and the coat SF of paint) along the direction intersecting with the surface of the coat SF of paint (the Z axis direction in an example illustrated in FIG. 49A and FIG. 49B). Specifically, as illustrated in FIG. 49A, when the distance between the light irradiation apparatus 11d-2 and the coat SF of paint in the Z axis direction is D5, the arrangement pitch of the plurality of irradiation areas EA is a fifth pitch Pe5. Then, as illustrated in FIG. 49B, when the distance between the light irradiation apparatus 11d-2 and the coat SF of paint in the Z axis direction changes to D6 (note that D5<D6) as a result of the light irradiation apparatus 11d-2 moving along the Z axis direction to be farther from the coat SF of paint by the driving system 12, the arrangement pitch of the plurality of irradiation areas EA changes to a sixth pitch Pe6 that is larger than the fifth pitch Pe5. As a result, the arrangement pitch P1 of the concave structure CP1 changes. Note that the light irradiation apparatus 11d-2 may be a light irradiation apparatus obtained by adding an optical member for emitting the plurality of processing lights EL that are not parallel with each other to the above described light irradiation apparatus 11 and light irradiation apparatuses 22a to 23a and 25a to 27a each of which is configured to emit the plurality of processing lights EL.

For example, when the processing apparatus 1d is provided with the plurality of light sources 1111 each of which is configured to emit the processing light EL, the control apparatus 18 may change the arrangement pitch of the plurality of irradiation areas EA and/or the interval between the plurality of processing lights EL by changing the number of the light source 1111 that actually emits the processing light EL among the plurality of light sources 1111. Specifically, in an example illustrated in FIG. 50A, six light sources 1111 among the plurality of light sources 1111 are selected as the light source that emits the processing light EL. In this case, the six light sources 1111 emit the processing lights EL and the other light source 1111 does not emit the processing light EL. Alternatively, although the other light source 1111 may emit the processing light EL, the emitted processing light EL is shielded and the coat SF of paint is not irradiated with it. In this case, as illustrated in FIG. 50B, the arrangement pitch of the plurality of irradiation areas EA is a seventh pitch Pe7. On the other hand, in an example illustrated in FIG. 50C, three light sources 1111 (especially, three light sources 1111 selected every other one from the six light sources 1111 selected in the example illustrated in FIG. 50A) among the plurality of light sources 1111 are selected as the light source that emits the processing light EL. In this case, as illustrated in FIG. 50D, the arrangement pitch of the plurality of irradiation areas EA is an eighth pitch Pe8 that is larger than (for example twice as large as) the seventh pitch Pe7. As a result, the arrangement pitch P1 of the concave structure CP1 changes. The same applies to the case where the processing apparatus 1d is provided with either one of the above described light irradiation apparatuses 22a to 23a and 25a to 27a each of which is configured to emit the plurality of processing lights EL and either one of the light irradiation apparatuses 22a to 23a and 25a to 27a is provided with the plurality of light sources 1111 in order to emits the plurality of processing lights EL.

Alternatively, the control apparatus 18 may change the arrangement pitch P1 of the concave structure CP1 and/or the interval between the plurality of processing lights EL by using another method in addition to or instead of changing the arrangement pitch of the plurality of irradiation areas EA (namely, changing the relative positional relationship between the plurality of irradiation areas EA). For example a shutter may be disposed in the optical path of each of the plurality of processing lights EL emitted from the light source system 111.

For example, when the processing apparatus 1d is provide with the light irradiation apparatus 21a that forms, on the surface of the coat SF of paint, the interference fringe that is formed by interfering the first divided light EL1 and the second divided light EL2 illustrated in above described FIG. 18, the control apparatus 18 may change the arrangement pitch P1 of the concave structure CP1 by changing the angle at which the first divided light EL1 and the second divided light EL2 are intercrossed (namely, a relative angle between the first divided light EL1 and the second divided light EL2). Specifically, in an example illustrated in FIG. 51A, the angle at which the first divided light EL1 and the second divided light EL2 are intercrossed is a first angle θ1. In this case, as illustrated in FIG. 51B, a pitch of the interference fringe formed on the surface of the coat SF of paint is a ninth pitch Pe9. On the other hand, in an example illustrated in FIG. 51C, the angle at which the first divided light EL1 and the second divided light EL2 are intercrossed is a second angle θ2 that is different from the first angle θ1. In this case, as illustrated in FIG. 51D, the pitch of the interference fringe formed on the surface of the coat SF of paint is a tenth pitch Pe10 that is different from the ninth pitch Pe9. As a result, the arrangement pitch P1 of the concave structure CP1 changes.

Note that the processing apparatus 1d is provided with a light irradiation apparatus 11d-3 having an angle adjusting element 2127d for adjusting the angle at which the first divided light EL1 and the second divided light EL2 are intercrossed as illustrated in FIG. 52, instead of the light irradiation apparatus 21a, in order to change the angle at which the first divided light EL1 and the second divided light EL2 are intercrossed. The angle adjusting element 2127d is configured to change a relative angle of the first divided light EL1 to the second divided light EL2 by synchronously moving the light emitting port 2123a and the projection optical system 2125a. Moreover, the angle adjusting element 2127d may be configured to change a relative angle of the second divided light EL2 to the first divided light EL1 by synchronously moving the light emitting port 2124a and the collecting optical system 2126a in addition to or instead of synchronously moving the light emitting port 2123a and the projection optical system 2125a. therefore, the angle at which the first divided light EL1 and the second divided light EL2 are intercrossed is changeable by the angle adjusting element 2127d.

For example, when the above described arrangement pitch of the plurality of irradiation areas EA and/or the interval between the plurality of processing lights EL is changed, the intensity distribution of the plurality of processing lights EL on the surface of the coat SF of paint changes. Therefore, changing the arrangement pitch of the plurality of irradiation areas EA and/or the interval between the plurality of processing lights EL is equivalent to controlling the intensity distribution of the plurality of processing lights EL on the surface of the coat SF of paint. Similarly, when the pitch of the interference fringe formed on the surface of the coat SF of paint by interfering the above described first divided light EL1 and the second divided light EL2 is changed, the intensity distribution of the plurality of processing lights EL on the surface of the coat SF of paint changes. Therefore, changing the angle at which the first divided light EL1 and the second divided light EL2 are intercrossed is equivalent to controlling the intensity distribution of the plurality of processing lights EL on the surface of the coat SF of paint. Thus, the control apparatus 18 may control the intensity distribution of the plurality of processing lights EL on the surface of the coat SF of paint (alternatively, the intensity distribution of the plurality of processing lights EL in a plane along the surface of the coat SF of paint) in addition to or instead of changing the arrangement pitch P1 of the concave structure CP1 and/or the interval between the plurality of processing lights EL. In this case, the optical system 112 may be provided with the intensity distribution adjusting element for adjusting the intensity distribution of the plurality of processing lights EL under the control of the control apparatus 18. The intensity distribution adjusting element may be a spatial light modulator that is configured to space-modulate the processing light, for example. Therefore, the processing apparatus 1d is provided with the light irradiation apparatus 24a having the spatial light modulator (see FIG. 21), the control apparatus 18 may control the spatial light modulator to change the intensity distribution of the plurality of processing lights EL.

Moreover, in the above described description, the control apparatus 18 performs at least one of changing the arrangement pitch of the plurality of irradiation areas EA and/or the interval between the plurality of processing lights EL, changing the angle at which the first divided light EL1 and the second divided light EL2 are intercrossed and changing the intensity distribution of the plurality of processing lights EL on the surface of the coat SF of paint for the purpose of changing the arrangement pitch P1 of the concave structure CP1. However, the control apparatus 18 performs at least one of changing the arrangement pitch of the plurality of irradiation areas EA and/or the interval between the plurality of processing lights EL, changing the angle at which the first divided light EL1 and the second divided light EL2 are intercrossed and changing the intensity distribution of the plurality of processing lights EL on the surface of the coat SF of paint for the purpose of maintaining the arrangement pitch P1 of the concave structure CP1 (namely, preventing the variation of the arrangement pitch P1). Specifically, as described above, the processing apparatus 1d sweep the unit processing area SA with the plurality of processing lights EL through the Galvano mirror 1122. Here, a length of the optical path of the processing light EL from the Galvano mirror 1122 to a center part of the unit processing area SA is different from a length of the optical path of the processing light EL from the Galvano mirror 1122 to an edge part of the unit processing area SA in a strict sense. Thus, there is a possibility that the arrangement pitch of the plurality of irradiation areas EA at the center part of the unit processing area SA is not same as the arrangement pitch of the plurality of irradiation areas EA at the edge part of the unit processing area SA. Alternatively, there is a high possibility that the surface of the coat SF of paint is the curved surface, has a concavity and/or convexity, or is inclined, because the processing target object S is the airframe of the airplane PL and the like. Even in this case, a length of the optical path of the processing light EL from the Galvano mirror 1122 to a one part of the unit processing area SA is different from a length of the optical path of the processing light EL from the Galvano mirror 1122 to another part of the unit processing area SA in a strict sense. Thus, there is a possibility that the arrangement pitch of the plurality of irradiation areas EA at one part of the unit processing area SA is not same as the arrangement pitch of the plurality of irradiation areas EA at another part of the unit processing area SA. As a result, there is a possibility that the arrangement pitch P1 of the concave structure CP1 formed at one part of the unit processing area SA is not same as the arrangement pitch P1 of the concave structure CP1 at another part of the unit processing area SA undesirably, although the concave structures CP1 should be formed in the unit processing area SA at constant arrangement pitch P1. Thus, the control apparatus 18 may perform at least one of changing the arrangement pitch of the plurality of irradiation areas EA and/or the interval between the plurality of processing lights EL, changing the angle at which the first divided light EL1 and the second divided light EL2 are intercrossed and changing the intensity distribution of the plurality of processing lights EL on the surface of the coat SF of paint so as to cancel this undesired variation of the arrangement pitch P1 of the concave structure CP1. As a result, the undesired variation of the arrangement pitch P1 of the concave structure CP1 is canceled and the concave structures CP1 are formable at constant arrangement pitch P1

(4-5) Fifth Modified Example

The above described processing apparatus 1d in the fourth modified example changes the characteristic of the processing lights EL (for example, at least one of the relative positional relationship between the plurality of irradiation areas EA, the angle at which the first divided light EL1 and the second divided light EL2 are intercrossed and the intensity distribution of the plurality of processing lights EL on the surface of the coat SF of paint) for the purpose of changing the arrangement pitch P1 of the concave structure CP1 constituting the riblet structure. On the other hand, a processing apparatus 1e in the fifth modified example changes any characteristic of the processing lights EL for the purpose of changing any characteristic of the riblet structure. The presence or absence of the riblet structure, the shape of the riblet structure (for example, at least one of the shape of the cross-sectional surface of the concave structure CP1, the shape of the cross-sectional surface of the convex structure CP2 and the like), the size of the riblet structure (for example, at least one of the depth D of the concave structure CP1, a width of the concave structure CP1, the arrangement pitch P1 of the concave structure CP1, the height H of the convex structure CP2, the width of the convex structure CP2, the arrangement pitch P2 of the convex structure CP2, and the like) and the position of the riblet structure (for example, the position of at least one of the concave structure CP1 and the convex structure CP2) is one example of "any characteristic of the riblet structure" in the fifth modified example, as described in the third modified example. Thus, the processing apparatus 1e is different from the above described processing apparatus 1 in that it is provided with a characteristic adjustment apparatus 41e for adjusting the characteristic of the processing lights EL. Note that the processing apparatus 1e may be provided with the characteristic adjustment apparatus 41e separately from the light irradiation apparatus 11 or may be provided with the characteristic adjustment apparatus 41e that is combined with the light irradiation apparatus 11 (namely, that constitutes a part of the light irradiation apparatus 11). Another feature of the processing apparatus 1e may be same as another feature of the processing apparatus 1.

The control apparatus 18 may change any characteristic of the processing lights EL so that any characteristic of the riblet structure is changed to form more proper riblet structure. For example, the control apparatus 18 may change any characteristic of the processing lights EL so that any characteristic of the riblet structure is changed to form the proper riblet structure that properly achieves the effect of the reduction of the resistance.

The characteristic of the processing lights EL may include the intensity distribution of the plurality of processing lights EL on the surface of the coat SF of paint. Namely, the control apparatus 18 may control the characteristic adjustment apparatus 41e to change the intensity distribution of the plurality of processing lights EL on the surface of the coat SF of paint. When the intensity distribution of the plurality of processing lights EL on the surface of the coat SF of paint is changed, the characteristic (especially, at least one of the shape, the position and the like) of the concave structure CP1 changes. As a result, the characteristic (especially, at least one of the shape, the position and the like) of the riblet structure formed by the concave structure CP1 also changes. For example, the surface of the coat SF of paint is irradiated with the plurality of processing lights EL having a first intensity distribution illustrated in FIG. 54A, the concave structure CP1 illustrated in FIG. 54B is formed. On the other hand, for example, the surface of the coat SF of paint is irradiated with the plurality of processing lights EL having a second intensity distribution that is different from the first intensity distribution illustrated in FIG. 54C, the concave structure CP1 illustrated in FIG. 54D having the characteristic that is different from the concave structure CP1 illustrated in FIG. 54B is formed.

The characteristic of the processing lights EL may include the shapes of the plurality of irradiation areas EA. Namely, the control apparatus 18 may control the characteristic adjustment apparatus 41e to change the shapes of the plurality of irradiation areas EA. When the shapes of the plurality of irradiation areas EA are changed, the characteristic (especially, at least one of the shape, the position and the like) of the concave structure CP1 changes. As a result, the characteristic (especially, at least one of the shape, the position and the like) of the riblet structure formed by the concave structure CP1 also changes. For example, the plurality of irradiation areas EA having first shapes illustrated in FIG. 55A are irradiated with the plurality of processing lights EL, the concave structure CP1 illustrated in FIG. 55B is formed. On the other hand, for example, the plurality of irradiation areas EA having second shapes that are different from the first shapes illustrated in FIG. 55C are irradiated with the plurality of processing lights EL, the concave structure CP1 illustrated in FIG. 55D having the characteristic that is different from the concave structure CP1 illustrated in FIG. 55B is formed.

The characteristic of the processing lights EL may include the sizes of the plurality of irradiation areas EA. Namely, the control apparatus 18 may control the characteristic adjustment apparatus 41e to change the sizes of the plurality of irradiation areas EA. When the sizes of the plurality of irradiation areas EA are changed, the characteristic (especially, at least one of the shape, the position and the like) of the concave structure CP1 changes. As a result, the characteristic (especially, at least one of the shape, the position and the like) of the riblet structure formed by the concave structure CP1 also changes. For example, the plurality of irradiation areas EA having first sizes illustrated in FIG. 56A are irradiated with the plurality of processing lights EL, the concave structure CP1 illustrated in FIG. 56B is formed. On the other hand, for example, the plurality of irradiation areas EA having second sizes that are smaller than the first sizes illustrated in FIG. 56C are irradiated with the plurality of processing lights EL, the concave structure CP1 illustrated in FIG. 56D having the width that is narrower than the concave structure CP1 illustrated in FIG. 56B is formed.

The characteristic of the processing lights EL may include the intensity of the plurality of processing lights EL. Namely, the control apparatus 18 may control the characteristic adjustment apparatus 41e to change the intensity of the plurality of processing lights EL. When the intensity of the plurality of processing lights EL is changed, the characteristic (especially, the shape and the like) of the concave structure CP1 changes. Specifically, the energy transmitted to the coat SF of paint by the irradiation of the plurality of processing lights EL becomes larger as the intensity of the plurality of processing lights EL becomes higher, and thus, the coat SF of paint is removed more. Therefore, the depth of the formed concave structure CP1 becomes larger as the intensity of the plurality of processing lights EL becomes higher. As a result, the characteristic (especially, the shape and the like) of the riblet structure formed by the concave structure CP1 also changes. For example, the plurality of processing lights EL having a first intensity illustrated in FIG. 57A are emitted, the concave structure CP1 illustrated in FIG. 57B is formed. On the other hand, for example, the plurality of processing lights EL having a second intensity that is higher than the first intensity illustrated in FIG. 57C are emitted, the concave structure CP1 illustrated in FIG. 57D that is deeper than the concave structure CP1 illustrated in FIG. 57B is formed.

The characteristic of the processing lights EL may include the irradiation time of the plurality of processing lights EL. Namely, the control apparatus 18 may control the characteristic adjustment apparatus 41e to change the irradiation time of the plurality of processing lights EL. When the irradiation time of the plurality of processing lights EL is changed, the characteristic (especially, the shape and the like) of the concave structure CP1 changes. Specifically, the energy transmitted to the coat SF of paint by the irradiation of the plurality of processing lights EL becomes larger as the irradiation time of the plurality of processing lights EL becomes longer, and thus, the coat SF of paint is removed more. Therefore, the depth of the formed concave structure CP1 becomes larger as the irradiation time of the plurality of processing lights EL becomes longer. As a result, the characteristic (especially, the shape and the like) of the riblet structure formed by the concave structure CP1 also changes. For example, the plurality of processing lights EL having a first intensity illustrated in FIG. 57A are emitted, the concave structure CP1 illustrated in FIG. 57B is formed. On the other hand, for example, the plurality of processing lights EL having a second intensity that is higher than the first intensity illustrated in FIG. 57C are emitted, the concave structure CP1 illustrated in FIG. 57D that is deeper than the concave structure CP1 illustrated in FIG. 57B is formed.

The characteristic of the processing lights EL may include the polarization state (for example, at least one of a difference between s-polarized light or p-polarized light, a difference among circular polarized light, a liner polarized light and elliptic polarized light and the like) of the plurality of processing lights EL. Namely, the control apparatus 18 may control the characteristic adjustment apparatus 41e to change the polarization state of the plurality of processing lights EL. When the polarization state of the plurality of processing lights EL is changed, a degree of absorption of the plurality of processing lights EL by the coat SF of paint is likely to change. As a result, the energy added to the coat SF of paint by the irradiation of the plurality of processing lights EL is likely to change, and thus, the characteristic (especially, the shape and the like) of the plurality of concave structures CP1 is likely to change. As a result, the characteristic (especially, the shape and the like) of the riblet structure formed by the concave structure CP1 also changes.

The characteristic of the processing lights EL may include the wavelength of the plurality of processing lights EL. Namely, the control apparatus 18 may control the characteristic adjustment apparatus 41e to change the wavelength of the plurality of processing lights EL. When the wavelength of the plurality of processing lights EL is changed, a degree of absorption of the plurality of processing lights EL by the coat SF of paint is likely to change. As a result, the energy added to the coat SF of paint by the irradiation of the plurality of processing lights EL is likely to change, and thus, the characteristic (especially, the shape and the like) of the plurality of concave structures CP1 is likely to change. As a result, the characteristic (especially, the shape and the like) of the riblet structure formed by the concave structure CP1 also changes.

The control apparatus 18 the control apparatus 18 may change the characteristic of the plurality of processing lights EL when the coat SF of paint is irradiated with the plurality of processing lights EL (namely, the plurality of processing lights EL relatively move relative to the coat SF of paint). As a result, a series of concave structure CP1 extending in a certain direction includes a part having a first characteristic and a part having a second characteristic that is different from the first characteristic. For example, as illustrated in FIG. 58A to FIG. 58C, a series of concave structure CP1 extending in a certain direction includes a part having a first shape (see FIG. 53B that is a I-I' cross sectional surface in FIG. 58A) and a part having a second shape (see FIG. 58C that is a II-IF cross sectional surface in FIG. 58A) that is different from the first shape. Namely, the shape of the cross-sectional surface of the concave structure CP1 changes along the extending direction of the concave structure CP1. Alternatively, as illustrated in FIG. 59A to FIG. 59C, a series of concave structure CP1 extending in a certain direction includes a part having a first width (see FIG. 54B that is a I-I' cross sectional surface in FIG. 59A) and a part having a second width (see FIG. 59C that is a II-II' cross sectional surface in FIG. 59A) that is different from the first width. Namely, the width of the concave structure CP1 changes along the extending direction of the concave structure CP1.

The processing apparatus 1e in the fifth modified example achieves an effect that is same as the effect achievable by the above described processing apparatus 1 and is allowed to change the characteristic of the riblet structure. Therefore, more proper riblet structure is formable compared to the case where the characteristic of the riblet structure is not allowed to be changed. Specifically, the riblet structure having the proper characteristic that properly achieves the effect of the reduction of the resistance is formable.

(4-6) Sixth Modified Example

Next, with reference to FIG. 60, a processing apparatus 1f in a sixth modified example will be described. In the above described description, the end part 144 of the support apparatus 14 is allowed to contact with the surface of the coat SF of paint. Namely, the support apparatus 14 supports the housing apparatus 13 (moreover, the light irradiation apparatus 11 supported by the housing apparatus 13) in a state where it contacts with the coat SF of paint. On the other hand, as illustrated in FIG. 60, the processing apparatus if in the sixth modified example is different from the above described processing apparatus 1 in that it is provided with a support apparatus 14f that does not contact with the surface of the coat SF of paint instead of the support apparatus 14. Another feature of the processing apparatus if may be same as another feature of the processing apparatus 1.

Since the support apparatus 14f does not contact with the surface of the coat SF of paint, the support apparatus 14f support the housing apparatus 13 (moreover, the light irradiation apparatus 11 supported by the housing apparatus 13, the same applies to the sixth modified example) without contacting with the coat SF of paint. The support apparatus 14f is supported by a supporting frame (alternatively, any supporting member and the like) Ff that is separated from the coat SF of paint (moreover, the processing target object S). The support apparatus 14f supports the housing apparatus 13 in a state where it contacts with the supporting frame Ff.

The support apparatus 14f is provided with the beam member 141, as with the support apparatus 14. Moreover, the support apparatus 14f is provided with a plurality of column members 142f disposed at the beam member 141, instead of the plurality of leg members 142 of the support apparatus 14. The column member 142f is a bar-like member that extends from the beam member 141 toward the +Z size. An end part (an end part at the +Z side in the example illustrated in FIG. 60) 144f of the column member 142f is allowed to contact with the supporting frame Ff. The end part 144f is configured to adhere to the supporting frame Ff in a state where it contacts with the supporting frame Ff, as with the end part 144 of the leg member 142.

The column member 142f is a member that is configured to extend and contract along the Z axis by the driving system 15, as with the leg member 142. Namely, a state of the column member 142f is switchable between a third expansion state in which the column member 142f extends along the Z axis and a size thereof in the Z axis direction is relatively long and a third contraction state in which the column member 142f contracts along the Z axis and the size thereof in the Z axis direction is relatively short. The state of the column member 142f is switched between the third expansion state and the third contraction state when the support apparatus 14f moves, as with the leg member 142. When the column member 142f is in the third expansion state, the end part 144f of the column member 142f is allowed to contact with the supporting frame Ff. On the other hand, when the column member 142f is in the third contraction state, the end part 144f does not contact with the supporting frame Ff. Namely, when the column member 142*f* is in the third contraction state, the end part 144*f* is away from the support frame Ff toward the −Z side. Therefore, the movement of the support apparatus 14*f* is not prevented by a contact between the end part 144*f* of the column member 142*f* and the supporting frame Ff. Note that the column member 142*f* may be attachable to an overhead crane that is movable along at least one of the X axis and the Y axis. Moreover, the support apparatus 14*f* may be at least one of a crane and a robot arm.

The processing apparatus if in the sixth modified example achieves an effect that is same as the effect achievable by the above described processing apparatus 1.

Note that the support apparatus 14 is vibrationally separated from the coat SF of paint in the processing apparatus if, because the support apparatus 14*f* does not contact with the coat SF of paint. The light irradiation apparatus 11 is vibrationally separated from the coat SF of paint in the processing apparatus 1*f*, because the support apparatus 14*f* supports the light irradiation apparatus 11. Therefore, there is a possibility that the irradiation position (namely, the position of the irradiation area EA) of the processing light EL by the light irradiation apparatus 11 is shifted from a desired irradiation position on the surface of the coat SF of paint, if the coat SF of paint relatively moves relative to the light irradiation apparatus 11 due to the vibration and the like. Namely, there is a possibility that the relative positional relationship between the coat SF of paint and the light irradiation apparatus 11. Thus, in the sixth modified example, the control apparatus 18 relatively moves the irradiation area EA relative to the support apparatus 14*f* on the basis of at least one of a vibration state of the coat SF of paint relative to the support apparatus 14*f* and the relative positional relationship between the coat SF of paint and the support apparatus 14*f* so that the relative position of the irradiation area EA relative to the coat SF of paint does not change. The relative positional relationship between the coat SF of paint and the irradiation area EA changes if the coat SF of paint vibrates (alternatively, moves) relative to the support apparatus 14*f*, and thus, the control apparatus 18 changes the relative position of the irradiation area EA relative to the coat SF of paint on the basis of the relative positional relationship between the coat SF of paint and the irradiation area EA so that the relative position of the irradiation area EA relative to the coat SF of paint is maintained.

Thus, the processing apparatus 14*f* is provide with a vibration measurement apparatus 51*f* that measures the relative vibration state of the coat SF of paint relative to the support apparatus 14*f*. An optical measurement apparatus using various measurement basis such as a moire topography method using a grid irradiation method or a grid projection method, a holography interference method, an auto collimation method, a stereo method, an astigmatism method, a critical angle method or a knife edge method may be used as the vibration measurement apparatus, for example. Note that the processing apparatus 14*f* may be provided with a vibration measurement apparatus having a displacement sensor, a speed sensor or an acceleration sensor that measures the vibration state thereof.

The control apparatus 18 changes the position of the irradiation area EA relative to the support apparatus 14*f* on the basis of a measured result of the vibration measurement apparatus 51*f* so that the position of the irradiation area EA relative to the coat SF of paint does not change even when the coat SF of paint vibrates relative to the support apparatus 14*f*. Here, when the coat SF of paint moves relative to the support apparatus 14*f* in one moving direction by one moving distance due to the vibration and the irradiation area EA does not move relative to the support apparatus 14*f*, the coat SF of paint moves relative to the irradiation area EA in one moving direction by one moving distance. Namely, the irradiation area EA moves on the surface of the coat SF of paint in another moving direction that is opposite to one moving direction by one moving distance. Thus, it is necessary to move the irradiation area EA in a same manner as the coat SF of paint in order not to change the relative position of the irradiation area EA relative to the coat SF of paint. Namely, the relative position of the irradiation area EA relative to the coat SF of paint does not change if the irradiation area EA moves in one moving direction by one moving distance in accordance with the movement of the coat SF of paint. More specifically, the relative position of the irradiation area EA relative to the coat SF of paint does not change if the irradiation area EA moves relative to the support apparatus 14*f* in one moving direction by one moving distance. Thus, the control apparatus 18 moves the irradiation area EA relative to the support apparatus 14*f* toward a direction that is same as the moving direction of the coat SF of paint relative to the support apparatus 14*f* by a moving distance that is same as the moving distance of the coat SF of paint relative to the support apparatus 14*f*. Note that irradiation area EA may be moved by moving the light irradiation apparatus 11 by the driving system 12, by moving and/or by controlling the attitude of at least one optical member of the optical member(s) of the light irradiation apparatus 11 (for example, controlling the rotational state of the Galvano mirror M), or by another method.

Note that there is a possibility that the vibration state of the support member 14 is not same as the vibration state of the coat SF of paint even in the above described processing apparatus 1 and the like in which the support apparatus 14 is allowed to contact with the coat SF of paint. Thus, even in the above described processing apparatus 1 and the like, the control apparatus 18 may relatively move the irradiation area EA relative to the support apparatus 14*f* on the basis of the vibration state of the coat SF of paint relative to the support apparatus 14*f* (namely, the relative position of the coat SF of paint relative to the support apparatus 14*f*) so that the relative position of the irradiation area EA relative to the coat SF of paint does not change.

(4-7) Seventh Modified Example

Next, with reference to FIG. 61, a processing apparatus 1*g* in a seventh modified example will be described. The above described processing apparatus 1 is configured to move the light irradiation apparatus 11 relative to the coat SF of paint by the driving systems 12 and 15 without moving the processing target object S. On the other hand, the processing apparatus 1*g* in the seventh modified example is different from the above described processing apparatus 1 in that it is configured to move the coat SF of paint (namely, the processing target object S) relative to the light irradiation apparatus 11 without moving the light irradiation apparatus 11. Another feature of the processing apparatus 1*g* may be same as another feature of the processing apparatus 1.

In order to move the processing target object S, the processing apparatus 1*g* is provided with a stage 61*g*. The stage 61*g* is supported by a surface plate 62*g* from the −Z side. The stage 61*g* is housed in the containing space SP. The state 61*g* is disposed to face the light irradiation apparatus 11. The stage 61*g* is configured to hold the processing target object S so that the coat SF of paint faces the light irradiation apparatus 11. The stage 61*g* is configured to hold the processing target object S so that the coat SF of paint is irradiated with the plurality of processing lights EL from the light irradiation apparatus 11. The stage 61g is configured to release the held processing target object S.

The stage 61g is movable by a driving system 63g. The stage 63g is movable while holding the processing target object S. The stage 61g is movable relative to the light irradiation apparatus 11. The stage 61g is movable relative to the irradiation areas EA that are irradiated with the plurality of processing lights EL from the light irradiation apparatus 11. The driving system 63g moves the stage to change the relative positional relationship between the light irradiation apparatus 11 and the coat SF of paint (namely, the relative positional relationship between the irradiation areas EA and the coat SF of paint) under the control of the control apparatus 18. The driving system 63g may move the stage 61g along at least one of the X axis and the Y axis. As a result, the irradiation areas EA moves on the coat SF of paint along at least one of the X axis and the Y axis. The driving system 63g may move the stage 61g along the Z axis. The driving system 63g may move the stage 61g along at least one of the $\theta X$ direction, the $\theta Y$ direction and the $\theta Z$ direction in addition to at least one of the X axis, the Y axis and the Z axis.

The processing target object S moves relative to the light irradiation apparatus 11 due to the movement of the stage 61g, the coat SF of paint moves relative to the housing apparatus 13 (especially, the end part 134 of the partition member 132) and the support apparatus 14 (especially, the end part 144 of the leg member 142). Thus, if the stage 61g moves in a state where at least one of the end parts 134 and 144 contacts with the coat SF of paint, there is a possibility that the movement of the stage 61g (namely, the movement of the processing target object S) is prevented by the contact between the coat SF of paint and at least one of the end parts 134 and 144. Thus, in the seventh modified example, the end parts 134 and 144 do not contact with the coat SF of paint. In this case, the end part 134 contacts with the surface plate 62g, for example. As a result, the housing apparatus 13 maintains the sealability of the containing space SP with the surface plate 62g. Moreover, the end part 144 also contacts with the surface plate 62g, for example. The support apparatus 14 self-stands on the surface plate 62g. Namely, the support apparatus 14 supports the containing space 13 in a state where the end parts 144 contacts with the surface plate 62g.

In the seventh modified example, the light irradiation apparatus 11 is not necessarily moved, the processing apparatus 1g is not necessarily provided with the driving system 12 that moves the light irradiation apparatus 11 and the driving system 15 that moves the support apparatus 15. However, the processing apparatus 1g may move the light irradiation apparatus 11 as with the above described processing apparatus 1 and may be provided with at least one of the driving systems 12 and 15 in this case.

The processing apparatus 1g in the seventh modified example is configured to change the relative position between the coat SF of paint and the irradiation areas EA by moving the stage 61g (namely, moving the processing target object S), although the above described apparatus 1 realized it by moving the light irradiation apparatus 11. Moreover, the processing apparatus 1g is configured to change the relative position between the coat SF of paint and the irradiation areas EA by moving the stage 61g (namely, moving the processing target object S), although the above described apparatus 1 realized it by rotating the Galvano mirror 1122. Thus, the processing apparatus 1g also achieves an effect that is same as the effect achievable by the above described processing apparatus 1. Namely, the processing apparatus 1g is allowed to alternately repeat the scan operation for sweeping the surface of the coat SF of paint with the plurality of processing lights EL along the Y axis (namely, for moving the plurality of irradiation areas EA along the Y axis) and the step operation for moving the plurality of irradiation areas EA along the X axis by the predetermined amount by moving the processing target object S by the movement of the stage 61g. As a result, the plurality of unit processing areas SA are sweepable with the plurality of processing lights EL and thus the above described riblet structure is formable by the processing apparatus 1g.

(4-8) Eighth Modified Example

Next, with reference to FIG. 62, a processing apparatus 1h in an eighth modified example will be described. The above described processing apparatus 1 moves the light irradiation apparatus 11 by the driving system 12 in a state where the light irradiation apparatus 11 is supported by the housing apparatus 13. Namely, the processing apparatus 1 moves the light irradiation apparatus 11 without contacting with the coat SF of paint. On the other hand, the processing apparatus 1h in the eighth modified example is different from the above described processing apparatus 1 in that it moves a light irradiation apparatus 11h in a state where the light irradiation apparatus 11h is not supported by the housing apparatus 13. Thus, the processing apparatus 1h in the eighth modified example is different from the above described processing apparatus 1 in that the housing apparatus 13 does not necessarily support the light irradiation apparatus 11. Namely, the processing apparatus 1h in the eighth modified example is different from the above described processing apparatus 1 in that it is provided with the light irradiation apparatus 11 that is not supported by the housing apparatus 13. Moreover, the processing apparatus 1h in the eighth modified example is different from the above described processing apparatus 1 in that it is provided with a driving system 12h for moving the light irradiation apparatus 11 that is not supported by the housing apparatus 13 instead of the above described driving system 12. Another feature of the processing apparatus 1h may be same as another feature of the processing apparatus 1.

Since the housing apparatus does not support the light irradiation apparatus 11h, the light irradiation apparatus 11h is placed on the surface of the coat SF of paint. The light irradiation apparatus 11h is different from the above described light irradiation apparatus 11 in that it is provided with a contacting part 113h that is allowed to contact with the surface of the coat SF of paint. Another feature of the light irradiation apparatus 11h may be same as another feature of the light irradiation apparatus 11. The light irradiation apparatus 11h is placed on the surface of the coat SF of paint in a state where it contacts with the surface of the coat SF of paint through the contacting part 113h. Thus, the light irradiation apparatus 11h is supported by the coat SF of paint.

The driving system 12h moves the light irradiation apparatus 11h relative to the coat SF of paint (namely, relative to the processing target object S) under the control of the control apparatus 18. More specifically, the driving system 12h moves the light irradiation apparatus 11h along the surface of the coat SF of paint. In this case, the driving system 12h moves the light irradiation apparatus 11h in the state where the light irradiation apparatus 11h contacts with the surface of the coat SF of paint through the contacting part 113*h*. Thus, the contacting part 113*h* is a member having a relatively small friction resistance to the coat SF of paint. Alternatively, the contacting part 113*h* is a member having a relatively small rolling resistance (for example, at least one of a tire, a ball and the like). Thus, the light irradiation apparatus 11*h* is movable along the surface of the coat SF of paint as if it self-run on the surface of the coat SF of paint.

The light irradiation apparatus 11*h* emits the processing lights EL in the state where the light irradiation apparatus 11*h* contacts with the surface of the coat SF of paint through the contacting part 113*h*. The light irradiation apparatus 11*h* may emits the processing lights EL during a period when the light irradiation apparatus 11*h* moves along the surface of the coat SF of paint. As a result, the irradiation areas EA moves relative to the coat SF of paint, and thus, the scan operation for sweeping the surface of the coat SF of paint with the plurality of processing lights EL along the Y axis (namely, for moving the plurality of irradiation areas EA along the Y axis) is performable. Namely, the light irradiation apparatus 1*h* is allowed to form the riblet structure by alternately repeating the scan operation and the above described step operation by the movement of the light irradiation apparatus 11*h* without rotating the Galvano mirror 1122. However, the light irradiation apparatus 1*h* may alternately repeat the scan operation and the above described step operation by rotating the Galvano mirror 1122.

As described above, the processing apparatus 1*h* is disposed relative to the coat SF of paint to be suspended from the coat SF of paint by the support apparatus 14 (for example, to be suspended from the airframe of the airplane PL that is one example of the processing target object S) in some cases (see the above described FIG. 6A). When the processing apparatus 1*h* is suspended from the coat SF of paint in this manner, there is a possibility that the light irradiation apparatus 11*h* drops, because the light irradiation apparatus 11*h* is not supported by the housing apparatus 13. Thus, the light irradiation apparatus 11 itself may be configured to contact to the coat SF of paint. For example, the contacting part 113*h* may be configured to contact to the coat SF of paint. For example, the contacting part 113*h* may be provided with a suction mechanism that is configured to suck the coat SF of paint. Alternatively, as illustrated in FIG. 63, a suction part 114*h* that makes the light irradiation apparatus 11*h* be disposed above the coat SF of paint may be used. In FIG. 63, the light irradiation apparatus 11*h* is supported by a frame 115*h*. Wheels 113*h* that are the contacting parts and suction nozzles 114*h*1 that constitute a part of the suction part 114*h* are disposed at the frame 115*h*. The suction nozzles 114*h*1 are connected to suction pumps 114*h*3 through suction pipes 114*h*2. The suction pumps 114*h*3 makes the light irradiation apparatus 11*h* be sucked to the coat SF of paint by depressurizing a space between the suction nozzles 114*h*1 and the coat SF of paint through the suction pipes 114*h*2. Note that the wheels 113*h* are configured to drive by the driving apparatus 12*h*. Note that the suction part 114*h* is not limited to an above described negative pressure suction type, and may be a magnetic attraction type, for example.

The processing apparatus 1*h* in the eights modified example achieves an effect that is same as the effect achievable by the above described processing apparatus 1. Moreover, the processing apparatus 1*h* is movable along the surface of the coat SF of paint in the state where the light irradiation apparatus 11*h* contacts with the surface of the coat SF of paint. Therefore, the light irradiation apparatus 11 is movable along the surface of the coat SF of paint whatever the shape of the surface of the coat SF of paint is. Thus, the processing apparatus 1*h* processes the coat SF of paint without being much subjected to a restraint of the shape of the surface of the coat SF of paint.

(4-9) Ninth Modified Example

Next, with reference to FIG. 64, a processing apparatus 1*i* in a ninth modified example will be described. As illustrated in FIG. 64, the processing apparatus 1*i* is different from the above described processing apparatus 1 in that it is further provided with a position measurement apparatus 71*i*. Another feature of the processing apparatus 1*i* may be same as another feature of the processing apparatus 1.

The position measurement apparatus 71*i* measures the positions of the plurality of irradiation areas EA relative to the coat SF of paint (namely, relative to the processing target object S). In the ninth modified example, in order to measure the positions of the plurality of irradiation areas EA, the position measurement apparatus 71*i* includes an imaging device (for example, a camera) 72*i* that is configured to capture an image of both of at least a part of the coat SF of paint and at least a part of the light irradiation apparatus 11 at the same time, and indirectly measures the positions of the irradiation areas EA relative to the coat SF of paint by measuring the position of the light irradiation apparatus 11 relative to the coat SF of paint. In order to capture the image of both of at least a part of the coat SF of paint and at least a part of the light irradiation apparatus 11 at the same time, the imaging device 72*i* is aligned with respect to at least one of the coat SF of paint (namely, the processing target object S) and the light irradiation apparatus 11 so that both of at least a part of the coat SF of paint and at least a part of the light irradiation apparatus 11 are included in an imaging range of the imaging device 72*i*. In this case, the imaging device 72*i* is typically disposed at a position that is away from the coat SF of paint and the light irradiation apparatus 11 by a predetermined distance or more. In this case, the imaging device 72*i* captures the image of at least a part of the coat SF of paint and at least a part of the light irradiation apparatus 11 from the position that is away from the coat SF of paint and the light irradiation apparatus 11 by the predetermined distance or more. Namely, the imaging device 72*i* captures the image of at least a part of the coat SF of paint and at least a part of the light irradiation apparatus 11 in a state where it overviews the coat SF of paint and the light irradiation apparatus 11.

Since the imaging device 72*i* captures the image of both of at least a part of the coat SF of paint and at least a part of the light irradiation apparatus 11 at the same time, an imaged result of the imaging device 72*i* (namely, a measured result of the position measurement apparatus 71*i*) includes information relating to the position of the light irradiation apparatus 11 relative to the coat SF of paint.

Here, as described above, the light irradiation apparatus 11 is housed in the containing space SP surrounded by the partition member 132. When the partition member 132 is a member through which the visible light is allowed to pass through, the imaging device 72*i* is allowed to directly capture the image of the light irradiation apparatus 11 housed in the containing space SP. As a result, the measured result of the position measurement apparatus 71*i* includes the information relating to the position of the light irradiation apparatus 11 relative to the coat SF of paint. Thus, the partition member 132 may be the member through which the visible light is allowed to pass through. Even in this case, the fact remains that the processing light EL is shielded by the partition member 132 as long as the processing light EL is the invisible light.

Alternatively, when the partition member 132 is a member that shields the visible light, there is a possibility that it is difficult for the imaging device 72*i* to directly capture the image of the light irradiation apparatus 11. However, even in this case, it is possible for the device 72*i* to capture the image of the housing apparatus 13 that supports the light irradiation apparatus 11 and the support apparatus 14 that supports the housing apparatus 13. Therefore, in this case, the measured result of the position measurement apparatus 71*i* includes information relating to a position of at least one of the housing apparatus 13 and the support apparatus 14 relative to the coat SF of paint. Moreover, when the position of at least one of the housing apparatus 13 and the support apparatus 14 relative to the coat SF of paint changes, the position of the light irradiation apparatus 11 supported by the housing apparatus 13 and the support apparatus 14 relative to the coat SF of paint also changes. Namely, the position of the light irradiation apparatus 11 relative to the coat SF of paint depends on the position of at least one of the housing apparatus 13 and the support apparatus 14 relative to the coat SF of paint. Therefore, when a positional relationship between at least one of the housing apparatus 13 and the support apparatus 14 and the light irradiation apparatus 11 is known, the information relating to the position of at least one of the housing apparatus 13 and the support apparatus 14 relative to the coat SF of paint is convertible to the information relating to the position of the light irradiation apparatus 11 relative to the coat SF of paint. Therefore, even when the partition member 132 is the member that shields the visible light, the measured result of the position measurement apparatus 71*i* substantially includes the information relating to the position of the light irradiation apparatus 11 relative to the coat SF of paint. Note that the positional relationship between at least one of the housing apparatus 13 and the support apparatus 14 and the light irradiation apparatus 11 is known information to the control apparatus 18, because the control apparatus 18 controls the driving systems 12 and 15 to move the light irradiation apparatus 11 and the support apparatus 14, respectively. Therefore, the information relating to the position of the light irradiation apparatus 11 relative to the coat SF of paint is collectable by the control apparatus 18 from the measured result of the position measurement apparatus 71*i*, even when the partition member 132 is the member that shields the visible light.

Alternatively, when the imaging device 72*i* is a device that captures the image of at least a part of the coat SF of paint and at least a part of the light irradiation apparatus 11 by using illumination light that is the invisible light, the imaging device 72*i* is capable of directly capturing the light irradiation apparatus 11 even when the partition member 132 is the member that shields the visible light. Therefore, the imaging device 72*i* may capture the image of at least a part of the coat SF of paint and at least a part of the light irradiation apparatus 11 by using the illumination light that is the invisible light that is allowed to pass through the partition member 132. However, there is a possibility that the coat SF of paint evaporates by the irradiation of the illumination light when the invisible light having the wavelength that is absorbed by the coat SF of paint to a certain degree and an intensity of the illumination light is equal to or higher than an intensity that allows the coat SF of paint to evaporate. Thus, the intensity of the illumination light used by the imaging device 72*i* is set to an intensity lower than the intensity that allows the coat SF of paint to evaporate. Namely, the intensity of the illumination light is too low to evaporate the coat SF of paint.

The measured result of the position measurement apparatus 71*i* is outputted from the position measurement apparatus 71*i* to the control apparatus 18 through a wired or wireless communication line. The control apparatus 18 receives the measured result of the position measurement apparatus 71*i*. The control apparatus 18 determines the position of the light irradiation apparatus 11 relative to the coat SF of paint from the measured result of the position measurement apparatus 71*i*, and eventually determines the positions of the plurality of irradiation areas EA relative to the coat SF of paint. Specifically, the measured result of the position measurement apparatus 71*i* includes the information relating to the position of the light irradiation apparatus 11 relative to the coat SF of paint, as described above. Here, the position of the light irradiation apparatus 11 relative to the coat SF of paint changes, the positions of the plurality of irradiation areas EA relative to the coat SF of paint also change. Namely, the positions of the plurality of irradiation areas EA relative to the coat SF of paint depends on the position of light irradiation apparatus 11 relative to the coat SF of paint. Therefore, when a positional relationship between the light irradiation apparatus 11 and the plurality of irradiation areas EA is known, the information relating to the position of the light irradiation apparatus 11 relative to the coat SF of paint is convertible to the information relating to the positions of the plurality of irradiation areas EA relative to the coat SF of paint. Moreover, the control apparatus 18 controls the light irradiation apparatus 11 (especially, the Galvano mirror 1122) to change the positions of the plurality of irradiation areas EA on the painted surface SF. Thus, the positional relationship between the light irradiation apparatus 11 and the plurality of irradiation areas EA is known information to the control apparatus 18. Therefore, the control apparatus 18 is capable of determining the positions of the plurality of irradiation areas EA relative to the coat SF of paint on the basis of the measured result of the position measurement apparatus 71*i* and the positional relationship between the light irradiation apparatus 11 and the plurality of irradiation areas EA (in other words, a controlled state of the Galvano mirror 1122).

The control apparatus 18 controls at least one of the light irradiation apparatus 11, the driving system 12 and driving system 15 to form the riblet structure on the basis of the determined positions of the plurality of irradiation areas EA. For example, the control apparatus 18 may control the light irradiation apparatus 11, the driving system 12 and driving system 15 so that the irradiation areas EA are set at desired positions on the coat SF of paint. Alternatively, for example, the control apparatus 18 may associate the determined positions of the plurality of irradiation areas EA (alternatively, the position of the light irradiation apparatus 11 relative to the coat SF of paint) with the characteristic of the surface (for example, at least one of the shape, the reflectance and the like of the surface) of the coat SF of paint described in the second modified example and may perform the advance measurement control operation in the above described second modified example on the basis of the associated information.

The processing apparatus 1*i* in the ninth modified example achieves an effect that is same as the effect achievable by the above described processing apparatus 1. Moreover, the processing apparatus 1*i* properly determines the positions of the irradiation areas EA relative to the coat SF of paint. Therefore, the processing apparatus 1*i* processes the coat SF of paint properly (namely, with a relatively high accuracy) while setting the plurality of irradiation areas EA to proper positions on the surface of the coat SF of paint.

Note that the position measurement apparatus 71*i* captures the image of the surface of the coat SF of paint as described above. Thus, the control apparatus 18 may determine at least one of the shape of the surface of the coat SF of paint and a position at which the determined shape exists on the surface of the coat SF of paint from the image of the surface of the coat SF of paint that is captured by the position measurement apparatus 71. Thus, the position measurement apparatus 71*i* may be used as the surface characteristic measurement apparatus 19*b* for measuring the shape of the surface of the coat SF of paint that is used in the above described second modified example. In this case, the control apparatus 18 may determine the "shape of the surface of the coat SF of paint" that is used in the first specific example to the third specific example of the advance measurement control operation in the second modified example from the measured result of the position measurement apparatus 71*i*, for example. Alternatively, the control apparatus 18 may determine at least one of the shape of "the structural object having the size that is equal to or larger than the allowable size that exists on the surface of the coat SF of paint" that is used in the fourth specific example of the advance measurement control operation in the second modified example and the position of an area on the surface of the coat SF of paint at which this structural object exists from the measured result of the position measurement apparatus 71*i*, for example.

Note that the position measurement 71*i* may directly measure the positions of the irradiation areas EA relative to the coat SF of paint, although the position measurement 71*i* indirectly measures the positions of the irradiation areas EA in the above described example. For example, the light irradiation apparatus 11 irradiates the coat SF of paint with the processing lights EL having a weak intensity (an intensity that does not evaporate the coat SF of paint and that is detectable by the imaging device 72*i*) to form the irradiation areas EA on the coat SF of paint. The positions of the irradiation areas EA relative to the coat SF of paint may be directly measured by imaging the positions of the irradiation areas EA by the imaging device 72*i*. Note that the positions of the irradiation areas EA may be directly measured during a period when the coat SF of paint is processed.

Moreover, in the above described description, an example in which the processing apparatus 1*i* itself is provided with the position measurement apparatus 71*i* is described. However, since the position measurement apparatus 71*i* (especially, the imaging device 72*i*) is disposed at the position that is away from the light irradiation apparatus 11 by the predetermined distance as described above, the position measurement apparatus 71*i* may be an apparatus that is different from the processing apparatus 1*i*. Namely, not only the processing apparatus 1*i* but also a processing system that is provided with the processing apparatus 1 and the position measurement apparatus 71*i* between which information is transmittable through a wired or wireless communication line achieves an effect that is same as the effect achievable by the above described processing apparatus 1*i* in the ninth modified example.

(4-10) Tenth Modified Example

Next, with reference to FIG. 65, a processing apparatus 1*j* in a tenth modified example will be described. The processing apparatus 1*j* in the tenth modified example is same as the above described processing apparatus 1*j* in the ninth modified example in that it measures the positions of the plurality of irradiation areas EA relative to the coat SF of paint and controls at least one of the light irradiation apparatus 11, the driving system 12 and driving system 15 to form the riblet structure on the basis of the measured result. The processing apparatus 1*j* is different from the above described processing apparatus 1*i* in that it is provided with a position measurement apparatus 71*j* instead of the position measurement apparatus 71*i*. Another feature of the processing apparatus 1*j* may be same as another feature of the processing apparatus 1*i*.

The position measurement apparatus 71*j* is same as the position measurement apparatus 71*i* in that it measures the positions of the plurality of irradiation areas EA relative to the coat SF of paint (namely, relative to the processing target object S). In the tenth modified example, in order to measure the positions of the plurality of irradiation areas EA, the position measurement apparatus 71*j* is provided with a first measurement apparatus 711*j* and a second measurement apparatus 712*j*. The first measurement apparatus 711*j* and the second measurement apparatus 712*j* measure the positions of the plurality of irradiation areas EA relative to the coat SF of paint in cooperation.

The first measurement apparatus 711*j* is disposed at a first position that has a predetermined first positional relationship with the coat SF of paint. The predetermined first positional relationship is known to the control apparatus 18. Namely, the control apparatus 18 has information relating to the predetermined first positional relationship. In an example illustrated in FIG. 65, the first measurement apparatus 711*j* is disposed at the surface of the coat SF of paint. However, the first measurement apparatus 711*j* may be disposed at a position other than the surface of the coat SF of paint. For example, the first measurement apparatus 711*j* may be disposed in the coat SF of paint, may be disposed at the processing target object S or may be disposed at another position.

The second measurement apparatus 712*j* is disposed at a second position that has a predetermined second positional relationship with the light irradiation apparatus 11. The predetermined second positional relationship is known to the control apparatus 18. Namely, the control apparatus 18 has information relating to the predetermined second positional relationship. In an example illustrated in FIG. 65, the second measurement apparatus 712*j* is disposed at the light irradiation apparatus 11. However, the second measurement apparatus 712*j* may be disposed at a part of the processing apparatus 1*j* other than the light irradiation apparatus 11. Alternatively, the second measurement apparatus 712*j* may be disposed at a position other than the processing apparatus 1*j*.

The first measurement apparatus 711*j* includes a signal output apparatus that is configured to output (namely, transmit) a signal toward a surrounding area. In this case, the position measurement apparatus 71*j* is provided with a plurality of (for example, two or three or more) first measurement apparatuses 711*j* at different disposed positions. Moreover, in this case, the second measurement apparatus 712*j* includes a signal detection apparatus that detects the signals outputted from the plurality of first measurement apparatuses 711*j*. A measured result of the second measurement apparatus 712*j* (namely, a detected result of the signal detection apparatus) is outputted to the control apparatus 18. The control apparatus 18 determines a position of the second measurement apparatus 712*j* relative to each of the plurality of first measurement apparatuses 711*j* from the measured result of the second measurement apparatus 712*j*. The control apparatus 18 may determine the position of the second measurement apparatus 712*j* relative to each of the plurality of first measurement apparatuses 711*j* by using an existing method (for example, a three-dimensional positioning method and the like such as a GPS (Global Positioning System) for determining the position of the signal detection apparatus relative to the plurality of signal output apparatuses.

Then, the control apparatus 18 determines the position of the light irradiation apparatus 11 relative to the coat SF of paint on the basis of the position of the second measurement apparatus 712*j* relative to each of the plurality of first measurement apparatuses 711*j*. Specifically, a positional relationship between the second measurement apparatus 712*j* and each of the plurality of first measurement apparatuses 711*j* is equivalent to the positional relationship between the light irradiation apparatus 11 and the coat SF of paint, because the first positional relationship between each of the plurality of first measurement apparatuses 711*j* and the coat SF of paint and the second positional relationship between the second measurement apparatus 712*j* and the light irradiation apparatus 11 are known to the control apparatus 18. Thus, the control apparatus 18 determines the position of the light irradiation apparatus 11 relative to the coat SF of paint on the basis of not only the position of the second measurement apparatus 712*j* relative to each of the plurality of first measurement apparatuses 711*j* but also the first positional relationship between each of the plurality of first measurement apparatuses 711*j* and the coat SF of paint and the second positional relationship between the second measurement apparatus 712*j* and the light irradiation apparatus 11 that are known to the control apparatus 18. An operation after the position of the light irradiation apparatus 11 relative to the coat SF of paint is determined in the tenth modified example is same as that of the second modified example. Namely, the control apparatus 18 determines the positions of the plurality of irradiation areas EA relative to the coat SF of paint on the basis of the determined position of the light irradiation apparatus 11 relative to the coat SF of paint The processing apparatus 1*j* in the tenth modified example achieves an effect that is same as the effect achievable by the above described processing apparatus 1*i* in the ninth modified example.

Note that the first measurement apparatus 711*j* may not include the signal output apparatus that is configured to output (namely, transmit) the signal toward the surrounding area. For example, the first measurement apparatus 711*j* may include any detected apparatus that is detectable by the second measurement apparatus 712*j*. A marker is one example of any detected apparatus. Moreover, in this case, the second measurement apparatus 712*j* may include a detection apparatus that is configured to detect any detected apparatus. An imaging device such as a camera is one example of any detection apparatus. Even in this case, the position of the second measurement apparatus 712*j* relative to the first measurement apparatus 711*j* is determined by the control apparatus 18 from the measured result of the second measurement apparatus 712*j*. Thus, the positions of the plurality of irradiation areas EA relative to the coat SF of paint is determined by the control apparatus 18

(4-11) Eleventh Modified Example

Next, a processing apparatus 1*k* in an eleventh modified example will be described. The processing apparatus 1*k* sets the plurality of unit processing areas SA on the surface of the coat SF of paint and irradiates the plurality of unit processing areas SA with the plurality of processing lights EL in order, as with the above described processing apparatus 1. In the eleventh modified example, each unit processing area SA partially overlaps with adjacent another unit processing area SA. Namely, each unit processing area SA includes an overlapped area SAa that overlaps with anther unit processing area SA and a non-overlapped area Sab that does not overlap with anther unit processing area SA. For example, as illustrated in FIG. 66A, a unit processing area SA1 includes an overlapped area SAa1-2 that partially overlaps with a unit processing area SA2 adjacent to the +X side of the unit processing area SA1 (however, that does not overlap with a unit processing area SA6), an overlapped area SAa1-5 that partially overlaps with a unit processing area SA5 adjacent to the +Y side of the unit processing area SA1 (however, that does not overlap with the unit processing area SA6), an overlapped area SAa1-256 that partially overlaps with the unit processing areas SA2 and SA5 and that partially overlaps with the unit processing area SA6 adjacent to the unit processing area SA1 in an oblique direction, and a non-overlapped area Sab1 that does not overlap with the other unit processing areas SA. For example, as illustrated in FIG. 66B, the unit processing area SA2 includes an overlapped area SAa2-1 that partially overlaps with the unit processing area SA1 adjacent to the –X side of the unit processing area SA2 (however, that does not overlap with the unit processing area SA5), an overlapped area SAa2-3 that partially overlaps with a unit processing area SA3 adjacent to the +X side of the unit processing area SA2 (however, that does not overlap with a unit processing area SA7), an overlapped area SAa2-6 that partially overlaps with the unit processing area SA6 adjacent to the +Y side of the unit processing area SA2 (however, that does not overlap with the unit processing areas SA5 and SA7), an overlapped area SAa2-156 that partially overlaps with the unit processing areas SA1 and SA6 and that partially overlaps with the unit processing area SA5 adjacent to the unit processing area SA2 in an oblique direction, an overlapped area SAa2-367 that partially overlaps with the unit processing areas SA3 and SA6 and that partially overlaps with the unit processing area SA7 adjacent to the unit processing area SA2 in an oblique direction, and a non-overlapped area Sab2 that does not overlap with the other unit processing areas SA.

The processing apparatus 1*k* is different from the above described processing apparatus 1 in that it emits the plurality of processing lights EL so that the characteristic of the processing lights EL with which the overlapped area SAa is irradiated is different from the characteristic of the processing lights EL with which the non-overlapped area SAb, compared to the processing apparatus 1. This is because there is a possibility that the overlapped area SAa at which one unit processing area SA partially overlaps with another unit processing area SA is irradiated redundantly with the processing light EL with which one unit processing area SA is irradiated and the processing light EL with which another unit processing area SA is irradiated. On the other hand, the non-overlapped area Sab included in one unit processing area SA is irradiated with the processing light EL with which one unit processing area SA is irradiated, but is not irradiated with the processing light EL with which another unit processing area SA is irradiated. Thus, there is a possibility that the characteristic of the concave structure CP1 formed in the overlapped area SAa is different from the characteristic of the concave structure CP1 formed in the non-overlapped area SAb, if the characteristic of the processing lights EL with which the overlapped area SAa is irradiated is same as the characteristic of the processing lights EL with which the non-overlapped area SAb is irradiated. As a result, there is a possibility that the characteristic of the riblet structure is different from a necessary characteristic. Thus, in the eleventh modified example, the processing apparatus 1k emits the plurality of processing lights EL so that the characteristic of the processing lights EL with which the overlapped area SAa is irradiated is different from the characteristic of the processing lights EL with which the non-overlapped area SAb is irradiated. Next, three examples in each of which the characteristic of the processing lights EL with which the overlapped area SAa is irradiated is different from the characteristic of the processing lights EL with which the non-overlapped area Sab is irradiated will be described. Note that another feature of the processing apparatus 1k may be same as another feature of the processing apparatus 1.

(4-11-1) First Specific Example in which Characteristic of Processing Light EL with which Overlapped Area SAa is Irradiated is Different from Characteristic of Processing Light EL with which Non-Overlapped Area SAb is Irradiated In a first specific example, as illustrated in FIG. 67, the control apparatus 18 controls the light irradiation apparatus 11 so that the overlapped area SAa that is not yet irradiated with the processing lights EL (namely, the overlapped area SAa in which the concave structure CP1 is not yet formed) is irradiated with the processing lights EL. On the other hand, the control apparatus 18 controls the light irradiation apparatus 11 so that the overlapped area SAa that is already irradiated with the processing lights EL (namely, the overlapped area SAa in which the concave structure CP1 is already formed) is not irradiated with the processing lights EL. Moreover, the control apparatus 18 controls the light irradiation apparatus 11 so that the non-overlapped area SAb is irradiated with the processing lights EL. Namely, the control apparatus 18 sets the intensity of the processing lights EL with which the overlapped area SAa that is already irradiated with the processing lights EL is irradiated to zero and sets the intensity of the processing lights EL with which each of the overlapped area SAa that is not yet irradiated with the processing lights EL and the non-overlapped area SAb is irradiated to an intensity higher than zero. In other words, the control apparatus 18 sets the irradiation time of the processing lights EL with which the overlapped area SAa that is already irradiated with the processing lights EL is irradiated to zero and sets the irradiation time of the processing lights EL with which each of the overlapped area SAa that is not yet irradiated with the processing lights EL and the non-overlapped area SAb is irradiated to a time larger than zero. Note that FIG. 67 illustrates an example in which the overlapped area SAa1-2 that is not yet irradiated with the processing lights EL is irradiated with the processing lights EL at a timing when the unit processing area SA1 is irradiated with the processing lights EL and then the overlapped area SAa2-1 that is already irradiated with the processing lights EL is not irradiated with the processing lights EL at a timing when the unit processing area SA2 is irradiated with the processing lights EL subsequent to the unit processing area SA1 in a situation where the unit processing area SA1 is irradiated with the processing lights EL and then the unit processing area SA2 that partially overlaps with the unit processing area SA1 is irradiated with the processing lights EL.

When the intensity of the processing lights EL with which the overlapped area SAa that is already irradiated with the processing lights EL is irradiated is set to zero in this manner, the riblet structure that is already formed in the overlapped area SAa is not processed so that the characteristic thereof deteriorates (for example, the shape thereof becomes an undesired shape) by the second irradiation of the processing lights EL. Thus, the processing apparatus 1k achieves an effect that is same as the effect achievable by the above described processing apparatus 1 and properly forms the riblet structure even when the adjacent unit processing areas SA partially overlap with each other.

(4-11-2) Second Specific Example in which Characteristic of Processing Light EL with which Overlapped Area SAa is Irradiated is Different from Characteristic of Processing Light EL with which Non-Overlapped Area SAb is Irradiated In a second specific example, as illustrated in FIG. 68, the control apparatus 18 controls the light irradiation apparatus 11 so that the overlapped area SAa that is not yet irradiated with the processing lights EL is irradiated with the processing lights EL the intensity of which is high enough to evaporate the coat SF of paint. On the other hand, the control apparatus 18 controls the light irradiation apparatus 11 so that the overlapped area SAa that is already irradiated with the processing lights EL is irradiated with the processing lights EL the intensity of which is too low to evaporate the coat SF of paint. Moreover, the control apparatus 18 controls the light irradiation apparatus 11 so that the non-overlapped area SAb is irradiated with the processing lights EL the intensity of which is high enough to evaporate the coat SF of paint. Namely, the control apparatus 18 sets the intensity of the processing lights EL with which the overlapped area SAa that is already irradiated with the processing lights EL is irradiated to a non-processable intensity that does not allow the coat SF of paint to evaporate and sets the intensity of the processing lights EL with which each of the overlapped area SAa that is not yet irradiated with the processing lights EL and the non-overlapped area SAb is irradiated to an intensity higher than the non-processable intensity (namely, a processable intensity that allows the coat SF of paint to evaporate). Note that FIG. 68 illustrates an example in which the overlapped area SAa1-2 that is not yet irradiated with the processing lights EL is irradiated with the processing lights EL having the processable intensity at the timing when the unit processing area SA1 is irradiated with the processing lights EL and then the overlapped area SAa2-1 that is already irradiated with the processing lights EL is irradiated with the processing lights EL having the non-processable intensity at the timing when the unit processing area SA2 is irradiated with the processing lights EL subsequent to the unit processing area SA1 in the situation where the unit processing area SA1 is irradiated with the processing lights EL and then the unit processing area SA2 that partially overlaps with the unit processing area SA1 is irradiated with the processing lights EL.

When the intensity of the processing lights EL with which the overlapped area SAa that is already irradiated with the processing lights EL is irradiated is set to the non-processable intensity, the riblet structure that is already formed in the overlapped area SAa is not processed so that the characteristic thereof deteriorates by the second irradiation of the processing lights EL, as with the case where the intensity of the processing lights EL with which the overlapped area SAa that is already irradiated with the processing lights EL is irradiated is set to zero. Thus, the processing apparatus 1k achieves the effect that is same as the effect achievable by the above described processing apparatus 1 and properly forms the riblet structure even when the adjacent unit processing areas SA partially overlap with each other.

Note that the coat SF of paint evaporates by the energy added from the emitted processing lights EL to the coat SF of paint as described above.

Moreover, the energy added from the emitted processing lights EL to the coat SF of paint varies depending on not only the intensity of the processing lights EL but also the irradiation time of the processing lights EL. Thus, the control apparatus 18 may control the light irradiation apparatus 11 so that the overlapped area SAa that is not yet irradiated with the processing lights EL is irradiated with the processing lights EL for an irradiation time that is long enough to evaporate the coat SF of paint. On the other hand, the control apparatus 18 may control the light irradiation apparatus 11 so that the overlapped area SAa that is already irradiated with the processing lights EL is irradiated with the processing lights EL for an irradiation time that too short to evaporate the coat SF of paint. Moreover, the control apparatus 18 may control the light irradiation apparatus 11 so that the non-overlapped area SAb is irradiated with the processing lights EL for an irradiation time that is long enough to evaporate the coat SF of paint. Namely, the control apparatus 18 may set the irradiation time of the processing lights EL with which the overlapped area SAa that is already irradiated with the processing lights EL is irradiated to a non-processable time that does not allow the coat SF of paint to evaporate and may set the irradiation time of the processing lights EL with which the overlapped area SAa that is not yet irradiated with the processing lights EL and the non-overlapped area SAb are irradiated to an irradiation time longer than the non-processable time (namely, a processable time that allows the coat SF of paint to evaporate).

(4-11-3) Third Specific Example in which Characteristic of Processing Light EL with which Overlapped Area SAa is Irradiated is Different from Characteristic of Processing Light EL with which Non-Overlapped Area SAb is Irradiated In a third specific example, as illustrated in FIG. 69, the control apparatus 18 controls the light irradiation apparatus 11 so that each of the overlapped area SAa and the non-overlapped area SAb is irradiated with the processing lights EL having the processable intensity. However, in this case, the control apparatus 18 controls the light irradiation apparatus 11 so that the intensity of the processing lights EL with which the overlapped area SAa is irradiated is lower than the intensity of the processing lights EL with which the non-overlapped area SAb is irradiated. More specifically, the control apparatus 18 controls the light irradiation apparatus 11 so that the intensity of the processing lights EL with which the overlapped area SAa is irradiated is 1/n (note that n is an integer equal to or larger than 2) times as much as the intensity of the processing lights EL with which the non-overlapped area SAb is irradiated when the overlapped area SAa is an area in which the n unit processing areas SA areas partially overlap with each other. For example, in an example illustrated in FIG. 69, the overlapped area SAa1-2 (namely, the overlapped area SAa2-1) is an area in which two unit processing areas SA1 and SA2 partially overlap with each other. Thus, each of the intensity of the processing light EL with which the overlapped area SAa1-2 is irradiated at the timing when the unit processing area SA1 is irradiated with the processing lights EL and the intensity of the processing light EL with which the overlapped area SAa2-1 is irradiated at the timing when the unit processing area SA2 is irradiated with the processing lights EL is ½ times (namely, half) as much as the intensity of the processing lights EL with which each of the non-overlapped areas SAb1 and SAb2 is irradiated.

When the intensity of the processing lights EL with which the overlapped area SAa is irradiated is 1/n times as much as the intensity of the processing lights EL with which the non-overlapped area SAb is irradiated in this manner, the characteristic of the concave structure CP1 formed in the overlapped area SAa is not greatly different from the characteristic of the concave structure CP1 formed in the non-overlapped area SAb. This is because the overlapped area SAa is irradiated with the processing lights EL the intensity of which is 1/n times as much as the intensity of the processing lights EL with which the non-overlapped area SAb is irradiated every time each of the n unit processing area SA including the overlapped area SAa is irradiated with the plurality of processing lights EL. Namely, the overlapped area SAa is irradiated with the processing lights EL the intensity of which is 1/n times as much as the intensity of the processing lights EL with which the non-overlapped area SAb is irradiated in n times. As a result, a total amount of the energy added to the overlapped area SAa by the n times irradiations of the processing lights EL is same as a total amount of the energy added to the non-overlapped area SAb by one time irradiation of the processing lights EL. Therefore, the characteristic (for example, the depth) of the concave structure CP1 formed in the overlapped area SAa by the n times irradiations of the processing lights EL is nearly same as the characteristic (for example, the depth) of the concave structure CP1 formed in the non-overlapped area SAb by one time irradiation of the processing lights EL. Namely, in the third specific example, the concave structure CP1 is formed so that it is gradually deepened. Thus, the processing apparatus 1k achieves the effect that is same as the effect achievable by the above described processing apparatus 1 and properly forms the riblet structure even when the adjacent unit processing areas SA partially overlap with each other.

Note that the intensity of the processing lights EL with which the overlapped area SAa is irradiated may not be set to be 1/n times as much as the intensity of the processing lights EL with which the non-overlapped area SAb is irradiated, as long as the total amount of the energy added to the overlapped area SAa by the n times irradiations of the processing lights EL is same as the total amount of the energy added to the non-overlapped area SAb by one time irradiation of the processing lights EL. For example, in the example illustrated in FIG. 69, the intensity of the processing lights EL is fixed to the intensity that is 1/n times as much as the intensity of the processing lights EL with which the non-overlapped area SAb is irradiated during a period when the overlapped area SAa is irradiated with the processing lights EL. However, as illustrated in FIG. 70, the control apparatus 18 may change the intensity of the processing lights EL continuously (alternatively, discontinuously) during the period when the overlapped area SAa is irradiated with the processing lights EL.

Moreover, as described above, the energy added from the processing lights EL to the coat SF of paint varies depending on not only the intensity of the processing lights EL but also the irradiation time of the processing lights EL. Thus, the control apparatus 18 may control the light irradiation apparatus 11 so that the irradiation time of the processing lights EL with which the overlapped area SAa is irradiated is shorter than the irradiation time of the processing lights EL with which the non-overlapped area SAb is irradiated. More specifically, the control apparatus 18 may control the light irradiation apparatus 11 so that the irradiation time of the processing lights EL with which the overlapped area SAa is irradiated is 1/n times as long as the irradiation time of the processing lights EL with which the non-overlapped area SAb is irradiated when the overlapped area SAa is the area in which the n unit processing areas SA areas partially overlap with each other. Note that an energy amount of the processing lights EL with which the overlapped area SAa is irradiated may be different from an amount that is 1/n times as much as an energy amount of the processing lights EL with which the non-overlapped area SAb is irradiated, when the thickness of the evaporated part of the coat SF of paint does not vary linearly to the energy amount (the intensity of the processing lights EL×irradiation time) added from the emitted processing lights EL to the coat SF of paint.

Note that an example in which the processing apparatus 1k emits the plurality of processing lights EL so that the characteristic of the processing lights EL with which the overlapped area SAa is irradiated is different from the characteristic of the processing lights EL with which the non-overlapped area Sab is irradiated is described in the eleventh modified example. However, the processing apparatus 1a that is provided with the light irradiation apparatus 21a (see FIG. 18) or the light irradiation apparatus 24a (see FIG. 21) that irradiates the irradiation area EA spreading on the surface of the coat SF of paint two-dimensionally with the processing light EL may also emit the processing light EL so that an intensity (alternatively, any characteristic, the same applies to this paragraph) of light component of the processing light EL with which the overlapped area SAa is irradiated is different from an intensity of light component of the processing light EL with which the non-overlapped area SAb is irradiated. Namely, the processing apparatus 1a that is provided with the light irradiation apparatus 21a or 24a may emit the processing light EL so that the intensity of the processing light EL with which the overlapped area SAa is irradiated is different from the intensity of the processing light EL with which the non-overlapped area SAb is irradiated. In this case, the processing apparatus 1a that is provided with the light irradiation apparatus 21a or 24a may adjust the intensity distribution of the processing light EL on the surface of the coat SF of paint so that the intensity of the processing light EL with which the overlapped area SAa is irradiated is different from the intensity of the processing light EL with which the non-overlapped area SAb is irradiated, for example. Even in this case, the above described effect is achievable.

(4-12) Twelfth Modified Example

Next, a processing apparatus 11 in a twelfth modified example will be described. The processing apparatus 11 emits the plurality of processing lights EL to alternately repeat the scan operation and the step operation in each unit processing area SA, as with the above described processing apparatus 1. Namely, the processing apparatus 11 emits the plurality of processing lights EL to repeat the scan operation for moving the for moving the plurality of irradiation areas EA on the surface of the coat SF of paint along the Y axis while performing the step operation every time each scan operation completes. In the twelfth modified example, an area on the surface of the coat SF of paint on which at least one of the plurality of irradiation areas EA moves by a first scan operation overlaps with an area on the surface of the coat SF of paint on which at least another one of the plurality of irradiation areas EA moves by a second scan operation that is performed subsequent to the first scan operation. Namely, the surface of the coat SF of paint includes an overlapped area SAc at which the irradiation area EA is set in the first scan operation and the irradiation area EA is also set in the second scan operation and a non-overlapped area SAd at which the irradiation area EA is set in the first scan operation but the irradiation area EA is not set in the second scan operation. in other words, the plurality of irradiation areas EA include an overlapped irradiation area EAc that is set at a position at which another irradiation area EA is set during a period when the scan operation is performed in a plurality of times and a non-overlapped irradiation area EAd that is not set at the position at which another irradiation area EA is set during the period when the scan operation is performed in a plurality of times.

For example, FIG. 71A illustrates an area on the surface of the coat SF of paint in which an irradiation area EA #1 to an irradiation area EA #4 move during a period when m-th (note that n is an integer equal to or larger than 1) scan operation is performed. FIG. 71B illustrates an area on the surface of the coat SF of paint in which an irradiation area EA #1 to an irradiation area EA #4 move during a period when (m+1)-th scan operation is performed. FIG. 71C illustrates an area on the surface of the coat SF of paint in which an irradiation area EA #1 to an irradiation area EA #4 move during a period when (m+2)-th scan operation is performed. In an example illustrated in FIG. 71A to FIG. 71C, an area in which the irradiation area EA #4 move during the period when the m-th scan operation is performed is coincident with an area in which the irradiation area EA #1 move during the period when the (m+1)-th scan operation is performed. Similarly, an area in which the irradiation area EA #4 move during the period when the (m+1)-th scan operation is performed is coincident with an area in which the irradiation area EA #1 move during the period when the (m+2)-th scan operation is performed. Therefore, in the example illustrated in FIG. 71A to FIG. 71C, each of the irradiation areas EA #1 and EA #4 corresponds to the overlapped irradiation area EAc and each of the irradiation areas EA #2 and EA #3 corresponds to the overlapped irradiation area EAd.

Note that the plurality of irradiation areas EA are arranged on the coat SF of paint along the X axis direction that intersects with the Y axis direction along which the plurality of irradiation areas EA move in the scan operation, as illustrated in FIG. 71A to FIG. 71C. In this case, the overlapped irradiation area EAc includes at least the irradiation areas EA at both end sides in the X axis direction among the plurality of irradiation areas EA. Namely, the non-overlapped irradiation area EAd includes the other irradiation area EA except for at least the irradiation areas EA at both end sides in the X axis direction among the plurality of irradiation areas EA.

The processing apparatus 11 is different from the above described processing apparatus 1 in that it emits the plurality of processing lights EL so that the characteristic of the processing lights EL with which the overlapped area SAc is irradiated is different from the characteristic of the processing lights EL with which the non-overlapped area SAd, compared to the processing apparatus 1k in the eleventh modified example. This is because there is a possibility that the area on the surface of the coat SF of paint at which the overlapped irradiation area EAc is set (namely, the overlapped area SAc) is irradiated redundantly with the processing light EL in not only one scan operation but also another scan operation. On the other hand, the area on the surface of the coat SF of paint at which the non-overlapped irradiation area EAd is set (namely, the non-overlapped area SAd) is irradiated with the processing light EL in one scan operation but is not irradiated with the processing light EL in another scan operation. Thus, there is a possibility that the characteristic of the concave structure CP1 formed by the processing lights EL with which the overlapped irradiation area EAc is irradiated is different from the characteristic of the concave structure CP1 formed by the processing lights EL with which the non-overlapped irradiation area EAd is irradiated, if the characteristic of the processing lights EL with which the overlapped irradiation area EAc is irradiated is same as the characteristic of the processing lights EL with which the non-overlapped irradiation area EAd is irradiated. As a result, there is a possibility that the characteristic of the riblet structure is different from a necessary characteristic. Thus, in the twelfth modified example, the processing apparatus 11 emits the plurality of processing lights EL so that the characteristic of the processing lights EL with which the overlapped irradiation area EAc is irradiated is different from the characteristic of the processing lights EL with which the non-overlapped irradiation area EAd is irradiated. Note that another feature of the processing apparatus 11 may be same as another feature of the processing apparatus 1k.

A technical subject in the twelfth modified example that is caused by an existence of the overlapped irradiation area EAc and the non-overlapped irradiation area EAd is substantially same as a technical subject in the eleventh modified example that is caused by an existence of the overlapped area SAc and the non-overlapped area SAd. Therefore, the processing apparatus 11 may emits the plurality of processing lights EL from a same viewpoint of the processing apparatus 1k under the control of the control apparatus 18 so that the characteristic of the processing lights EL with which the overlapped irradiation area EAc is irradiated is different from the characteristic of the processing lights EL with which the non-overlapped irradiation area EAd is irradiated. For example, the control apparatus 18 may set the intensity of the processing lights EL with which the overlapped irradiation area EAc being set at the area of the coat SF of paint that is already irradiated with the processing lights EL is irradiated to zero or the non-processable intensity and may set the intensity of the processing lights EL with which each of the overlapped irradiation area EAc being set at the area of the coat SF of paint that is not yet irradiated with the processing lights EL and the non-overlapped irradiation area EAd is irradiated to the intensity higher than zero or the processable intensity. For example, the control apparatus 18 may set the irradiation time of the processing lights EL with which the overlapped irradiation area EAc being set at the area of the coat SF of paint that is already irradiated with the processing lights EL is irradiated to zero or the non-processable time and may set the irradiation time of the processing lights EL with which each of the overlapped irradiation area EAc being set at the area of the coat SF of paint that is not yet irradiated with the processing lights EL and the non-overlapped irradiation area EAd is irradiated to the irradiation time longer than zero or the processable time. For example, the control apparatus 18 may control the light irradiation apparatus 11 so that the intensity of the processing lights EL with which the overlapped irradiation area EAc is irradiated is lower than (for example, ½ times as much as) the intensity of the processing lights EL with which the non-overlapped irradiation area EAd is irradiated. For example, the control apparatus 18 may control the light irradiation apparatus 11 so that the irradiation time of the processing lights EL with which the overlapped irradiation area EAc is irradiated is shorter than (for example, ½ times as long as) the irradiation time of the processing lights EL with which the non-overlapped irradiation area EAd is irradiated.

The processing apparatus 11 in the twelfth modified example achieves the effect that is same as the effect achievable by the above described processing apparatus 1 and properly forms the riblet structure even when the area EAc that is set at a position at which another irradiation area EA is set during the period when the scan operation is performed in a plurality of times is set on the coat SF of paint.

Incidentally, even in the twelfth modified example, the processing apparatus 1a that is provided with the light irradiation apparatus 21a (see FIG. 18) or the light irradiation apparatus 24a (see FIG. 21) that irradiates the irradiation area EA spreading on the surface of the coat SF of paint two-dimensionally with the processing light EL may also emit the processing light EL so that an intensity (alternatively, any characteristic, the same applies to this paragraph) of light component with which the overlapped area SAc that is irradiated with the processing light EL in a plurality of times by the plurality of times of scan operation is irradiated is different from an intensity of light component with which the non-overlapped area EAd that is irradiated with the processing light EL in only one time by the plurality of times of scan operation is irradiated.

(4-13) Other Modified Example

In the above described description, the plurality of the concave parts C are formed by the irradiation of the plurality of processing lights EL, respectively. Namely, one concave part C is formed by the irradiation of one processing light EL. However, one concave part C may be formed by the irradiation of two or more processing lights EL. In this case, the control apparatus 18 may control a characteristic (for example, at least one of the shape, the depth, a formed position and the like) by adjusting a characteristic (for example, the intensity distribution and the like) of two or more processing lights EL.

In the above described description, the processing apparatus 1 deflects the processing lights EL by the Galvano mirror 1122 in order to sweep the surface of the coat SF of paint with the plurality of processing lights EL. However, the processing apparatus 1 may sweep the surface of the coat SF of paint with the plurality of processing lights EL by relatively moving the light irradiation apparatus 11 relative to the coat SF of paint in addition to or instead of deflecting the processing lights EL by the Galvano mirror 1122. Namely, the control apparatus 18 may control the driving system 12 to relatively move the light irradiation apparatus 11 relative to the coat SF of paint so that the surface of the coat SF of paint is swept with the processing lights EL.

One of a purpose of relatively moving the light irradiation apparatus 11 relative to the coat SF of paint is to sweep the surface of the coat SF of paint with the processing lights EL as described above. Thus, when the sweep of the coat SF of paint with the plurality of the processing lights EL is realized without moving the light irradiation apparatus 11, the light irradiation apparatus 11 may not move. Namely, the processing apparatus 1 may not be provided with the driving system 12.

One of the purpose of relatively moving the light irradiation apparatus 11 relative to the coat SF of paint by the driving system 12 is to sweep the plurality of unit processing areas SA with the processing lights EL in order without moving the housing apparatus 13 and the support apparatus 14 when the plurality of unit processing areas SA are housed in the containing space SP of the housing apparatus 13. Thus, when the single unit processing area SA is housed in the containing space SP, the light irradiation apparatus 11 may not move. Namely, the processing apparatus 1 may not be provided with the driving system 12.

In the above described description, the housing apparatus 13 supports the driving system 12 (moreover, the light irradiation apparatus 11) through the supporting member 133. However, at least one of the driving system 12 and the light irradiation apparatus 11 may be supported by a member other than the housing apparatus 13 (for example, the support apparatus 14).

In the above described description, the housing apparatus 13 is provided with the plate-like top member 131 and the pipe-like partition member 132 that extends from the top member 131 toward the −Z side. However, a shape, a disposed position and the like of the top member 131 and a shape, a disposed position and the like of the partition member 132 may be any, as long as the containing space SP surrounded by the top member 131 and the partition member 132 are secured.

In the above described description, the housing apparatus 13 is provided with the single partition member 132. However, the housing apparatus 13 may be provided with a plurality of partition members that extend from the top member 131 toward the −Z side and that are arranged to surround the optical path of the processing lights EL. In this case, the plurality of partition members may be arranged so that adjacent two partition members partially overlap with each other along an arrangement direction thereof (for example, a circumferential direction). At least a part of the plurality of partition members may be movable relative to the top member 131. End parts (specifically, end parts at the coat SF of paint side) of all of the plurality of partition members may be allowed to contact with the surface of the coat SF of paint. The end parts of all of the plurality of partition members may be configured to attach to the surface of the coat SF of paint. Alternatively, the end part of a part of the plurality of partition members may be allowed to contact with the surface of the coat SF of paint and the end part of another part of the plurality of partition members may not be allowed to contact with the surface of the coat SF of paint. The end part of a part of the plurality of partition members may be configured to attach to the surface of the coat SF of paint and the end part of another part of the plurality of partition members may not be configured to attach to the surface of the coat SF of paint.

In the above described description, each of the top member 131 and the partition member 132 is the member that is configured to shield or reduce the processing light EL. However, at least one of the top member 131 and the partition member 132 may not be the member that is configured to shield or reduce the processing light EL. At least a part of the top member 131 may not be the member that is configured to shield or reduce the processing light EL. At least a part of the partition member 132 may not be the member that is configured to shield or reduce the processing light EL.

In the above described description, each of the top member 131 and the partition member 132 is the member that does not allow the unnecessary substance that is generated by the irradiation of the processing light EL to pass therethrough. However, at least one of the top member 131 and the partition member 132 may not be the member that does not allow the unnecessary substance to pass therethrough. At least one of the top member 131 and the partition member 132 may be a member that allows the unnecessary substance to pass therethrough. At least a part of the top member 131 may not be the member that does not allow the unnecessary substance to pass therethrough. At least a part of the partition member 132 may not be the member that does not allow the unnecessary substance to pass therethrough.

In the above described description, the light irradiation apparatus 11 is disposed in the containing space SP of the housing apparatus 13. However, at least a part of the light irradiation apparatus 11 may be disposed outside the housing apparatus 13. Even in this case, the housing apparatus 13 may house the space including the optical path of the processing lights EL between the terminal optical element of the optical system 112 and the coat SF of paint. In this case, the housing apparatus 13 may not be provided with at least one of the top member 131 and the partition member 132, and may be provided with a member for housing the space including the optical path of the processing lights EL in addition to or instead of at least one of the top member 131 and the partition member 132. Alternatively, even when whole of the light irradiation apparatus 11 is disposed in the containing space SP, the housing apparatus 13 may not be provided with at least one of the top member 131 and the partition member 132, and may be provided with a member for forming the containing space SP in addition to or instead of at least one of the top member 131 and the partition member 132. Alternatively, whole of the light irradiation apparatus 11 may be disposed outside the housing apparatus 13. In this case, the housing apparatus 13 may not be provided with at least one of the top member 131 and the partition member 132. Alternatively, the processing apparatus 1 may not be provided with the housing apparatus 13 itself.

In the above described description, the end part 134 of the housing apparatus 13 is configured to change the shape thereof in accordance with the shape of the surface of the coat SF of paint. However, the end part 134 may not be configured to change the shape thereof in accordance with the shape of the surface of the coat SF of paint. In this case, the shape of the end part 134 may be a shape that is complementary to the shape of the surface of the coat SF of paint. For example, when the end part 134 contacts with the coat SF of paint the surface of which is a planar shape, the shape of the end part 134 becomes a planar shape as with the coat SF of paint. For example, when the end part 134 contacts with the coat SF of paint the surface of which is curved convexly to the end part 134, the shape of the end part 134 becomes a shape that is concave viewed from the coat SF of paint.

In the above described description, the housing apparatus 13 is provided with the detection apparatus 135 that detects the unnecessary substance (namely, the substance that is generated by the irradiation of the processing light EL) in the containing space SP. However, housing apparatus 13 may not be provided with the detection apparatus 135

In the above described description, the support apparatus 14 supports the housing apparatus 13 (moreover, the driving system 12 and the light irradiation apparatus 11) through the support member 143. However, at least one of the housing apparatus 13, the driving system 12 and the light irradiation apparatus 11 may be supported by a member other than the support apparatus 14.

In the above described description, the exhaust apparatus 16 is provided with the filter 162 that sorbs the unnecessary substance sucked from the containing space by the exhaust apparatus 16. However, the exhaust apparatus 16 may not be provided with the filter 162. For example, when the unnecessary substance is not generated by irradiating the coat SF of paint with the processing lights EL, the exhaust apparatus 16 may not be provided with the filter 162.

In the above described description, the processing apparatus 1 is provided with the exhaust apparatus 16. However, the processing apparatus 1 may not be provided with the exhaust apparatus 16. For example, when the unnecessary substance is not generated by irradiating the coat SF of paint with the processing lights EL, the exhaust apparatus 16 may not be provided with the exhaust apparatus 16. For example, when the gas supplied to the containing space SP from the gas supply apparatus 17 is not necessarily exhaust (namely, is not necessarily sucked outside the containing space SP), the exhaust apparatus 16 may not be provided with the exhaust apparatus 16. Alternatively, the processing apparatus 1 may be provided with any back-flow prevention apparatus that prevents the unnecessary substance generated by the irradiation of the processing light EL to return to the optical path of the processing lights EL (especially, the optical surface at the containing space SP side of the terminal optical element of the optical system 112) in addition to or instead of the exhaust apparatus 16. An adsorber apparatus that adsorbs the unnecessary substance in the containing space SP is one example of the back-flow prevention apparatus. Note that an air nozzle that blows air to the optical surface at the containing space SP side of the terminal optical element of the optical system 112 may be used in addition to or instead of the exhaust apparatus 16.

In the above described description, the gas supply apparatus 17 prevents the adherence of the dust to the optical surface 1124 by supplying the gas such as the inert gas to the optical surface 1124 of the fθ lens 1123 (namely, the optical surface at the containing space SP side of the terminal optical element of the optical system 112). However, the processing apparatus 1 may be provided with any adherence prevention apparatus that prevents the adherence of the dust to the optical surface 1124 in addition to or instead of the gas supply apparatus 17. For example, the processing apparatus 1 may be provided with an adherence prevention apparatus that prevents the adherence of the dust to the optical surface 1124 by ejecting liquid (for example, purified water) to the optical surface 1124. For example, the processing apparatus 1 may be provided with an adherence prevention apparatus that prevents the adherence of the dust to the optical surface 1124 by forming a liquid immersion space that is filled with liquid (for example, purified water) and that faces the optical surface 1124. In this case, the liquid in the liquid immersion space may be replaced if needed, because impurity enters the liquid immersion space.

In the above described description, the gas supply apparatus 17 removes the dust adhered to the optical surface 1124 or prevents the adherence of the dust to the optical surface 1124 by supplying the gas such as the inert gas to the optical surface 1124 of the fθ lens 1123. However, the processing apparatus 1 may be provided with any adherence prevention apparatus that removes the dust adhered to the optical surface 1124 in addition to or instead of the gas supply apparatus 17. For example, the processing apparatus 1 may be provided with an adherence prevention apparatus that removes the dust adhered to the optical surface 1124 by ejecting liquid (for example, purified water) to the optical surface 1124. For example, the processing apparatus 1 may be provided with an adherence prevention apparatus that removes the dust adhered to the optical surface 1124 by physically wiping the optical surface 1124.

In the above described description, the processing apparatus 1 forms the riblet structure of the coat SF of paint on the surface of the processing target object S. However, the processing apparatus 1 may form any structure of the coat SF of paint having any shape on the surface of the processing target object S. Even in this case, any structure having any shape is formable by means of the control apparatus 18 controlling the light irradiation apparatus 11 so that the surface of the coat SF of paint is swept with the processing lights EL along a scanning path based on the structure that should be formed.

In the above described description, the processing apparatus 1 removes the coat SF of paint by evaporating the coat SF of paint by the irradiation of the processing lights EL. However, the processing apparatus 1 may remove the coat SF of paint by changing the characteristic of the coat SF of paint by the irradiation of the processing lights EL, in addition to or instead of evaporating the coat SF of paint by the irradiation of the processing lights EL. For example, the processing apparatus 1 may remove the coat SF of paint by melting the coat SF of paint by the irradiation of the processing lights EL and removing the melted coat SF of paint. For example, the processing apparatus 1 may remove the coat SF of paint by making the coat SF of paint brittle by the irradiation of the processing lights EL and peeling the brittle coat SF of paint. In the above described description, the processing apparatus 1 processes the coat SF of paint formed on the surface of the processing target object S by the ablation. However, the processing apparatus 1 may remove a part of the coat SF of paint formed on the surface of the processing target object S by a heat processing.

In the above described description, the processing apparatus 1 forms the concave part C (alternatively, the concave structure CP1 or any structure by the concave structure CP1 such as the riblet structure) by removing the coat SF of paint. Namely, the processing apparatus 1 processes the coat SF of paint to partially reduce the thickness of the coat SF of paint. However, the processing apparatus may process the coat SF of paint to partially increase the thickness of the coat SF of paint in addition to or instead of partially reducing the thickness of the coat SF of paint. Namely, the processing apparatus 1 may form a convex part (alternatively, the convex structure CP2 or any structure by the convex structure CP2) by adding the coat SF of paint in addition to or instead of forming the concave part C by removing the coat SF of paint. For example, the processing apparatus 1 may irradiate a first part of the coat SF of paint with the processing light EL to remove the coat SF of paint at the first part and then may fix the removed coat SF of paint at a second part of the coat SF of paint to increase the thickness of the coat SF of paint at the second part (namely, to form the convex part at the second part).

In the above described description, the processing apparatus 1 processes the coat SF of paint formed on the surface of the processing target object S. However, the processing apparatus 1 may process any coat that is other than the coat SF of paint and that is formed on the surface of the processing target object S. Alternatively, the processing apparatus 1 may process a structural object in which a plurality of layers are laminated. Specifically, the processing apparatus 1 may process at least one layer (typically, at least one layer including a layer that is closest to the surface) of the plurality of layers that constitute the structural object. The processing apparatus 1 may process at least one layer of the plurality of layers that constitute the structural object to form a structure of this layer. In this case, at least one layer that is processed corresponds to the above described coat SF of paint and the other layer other than the at least one layer corresponds to the processing target object S. For example, FIG. 72A illustrates an example in which a layer S1 and a layer S2 are processed without exposing a layer S3 in a structural object in which the layer S1 to the layer S3 are layered. In the example illustrated in FIG. 72A, the layer S1 and the layer S2 are the layers that are processed by the irradiation of the processing light EL (namely, the layers that form the riblet structure and the like) and layers that correspond to the above described coat SF of paint. On the other hand, in the example illustrated in FIG. 72A, the layer S3 is a layer that is not processed by the irradiation of the processing light EL (namely, the layer on which the layer for forming the riblet structure and the like is formed) and a layer that corresponds to the above described processing target object S. Alternatively, for example, FIG. 72B illustrates an example in which the layer S1 is processed without exposing the layer S2 in the structural object in which the layer S1 to the layer S3 are laminated. In the example illustrated in FIG. 72B, the layer S1 is the layer that is processed by the irradiation of the processing light EL and the layer that corresponds to the above described coat SF of paint. On the other hand, in the example illustrated in FIG. 72B, the layer S2 and the layer S3 are the layers that are not processed by the irradiation of the processing light EL and the layers that correspond to the above described processing target object S. Alternatively, the processing apparatus 1 may process the processing target object S itself. Namely, the processing apparatus 1 may process the processing target object S on the surface of which the coat SF of paint or any coat is not formed.

Incidentally, although the processing apparatus 1 forms the riblet structure for reducing the resistance of the surface to the fluid is described in the above described embodiment, various structures such as a riblet structure for reducing noise generated when the fluid and the surface relatively move, a structure that generates swirl relative to a flow on the surface and a structure for adding hydrophobic property to the surface may be formed.

The feature of each embodiment described above is allowed to be combined appropriately. For example, the feature of one modified example among the above described first modified example to the eleventh modified example may be used in modified example among the above described first modified example to the eleventh modified example. As one example, for example, the advance measurement control operation using the surface characteristic measurement apparatus 19*b* in the above described second modified example may be performed by the processing apparatus 1*c* in the third modified example. In this case, the processing apparatus 1*c* may be provided with the surface characteristic measurement apparatus 19*b* in addition to the structure measurement apparatus 19*c*. In other combination of the modified example, the processing apparatus 1 and the like may be appropriately provided with the apparatus based on the pattern of the combination. One portion of the feature of each embodiment described above may not be used. The feature of each embodiment described above may be allowed to be replaced by the feature of other embodiment appropriately. Moreover, the disclosures of all publications and United States patents that are cited in each embodiment described above are incorporated in the disclosures of the present application by reference if it is legally permitted.

The present invention is allowed to be changed, if desired, without departing from the essence or spirit of the invention which can be read from the claims and the entire specification, and a processing apparatus, a processing method, a painting material, a processing system, a movable body and a manufacturing method of movable body that moves in a fluid each of which involves such changes, are also intended to be within the technical scope of the present invention.

DESCRIPTION OF REFERENCE CODES

1 processing apparatus
11 light irradiation apparatus
111 light source system
112 optical system
12 driving system
13 housing apparatus
132 partition member
14 support apparatus
15 driving system
16 exhaust apparatus
17 gas supply apparatus
18 control apparatus
C concave part
CP1 concave structure
CP2 convex structure
SP containing space
EA irradiation area
EL processing light
S processing target object
SF coat of paint

The invention claimed is:

1. A processing apparatus comprising:
a light irradiation apparatus that irradiates a surface of an object with a processing light to thereby change a shape of the surface of the object; and
a control apparatus that sets an irradiation position of the processing light and sets, as a non-processing area at which an irradiation of the processing light is prohibited, an area at which an operational structural object exists on the surface of the object by using an information relating to a shape of the surface of the object so as to form a riblet structure by which a frictional resistance of the surface of the object to a fluid is reduced, wherein
the control apparatus sets, as the irradiation position, a position in a plane intersecting with an irradiation direction of the processing light, and
the control apparatus controls the light irradiation apparatus so that the set irradiation position is irradiated with the processing light.

2. The processing apparatus according to claim 1, wherein the control apparatus sets, as the non-processing area, an area at which the operational structural object having a size that is equal to or larger than an allowable size exists on the surface of the object by using the information relating to the shape of the surface of the object.

3. The processing apparatus according to claim 1, wherein the control apparatus sets, as the non-processing area, an area at which the operational structural object having a height that is equal to or larger than an allowable height exists on the surface of the object by using the information relating to the shape of the surface of the object.

4. The processing apparatus according to claim 2, wherein the control apparatus sets, as the non-processing area, an area at which the operational structural object having a depth that is equal to or larger than an allowable depth exists on the surface of the object by using the information relating to the shape of the surface of the object.

5. The processing apparatus according to claim 2, wherein the control apparatus sets an irradiation state of the processing light.

6. The processing apparatus according to claim 5, wherein the control apparatus sets the irradiation state of the processing light so that the non-processing area is not irradiated with the processing light.

7. The processing apparatus according to claim 1, wherein the control apparatus sets, as the non-processing area, an area at which a structure exists that was formed by an irradiation of the processing light from the light irradiation apparatus.

8. The processing apparatus according to claim 1, further comprising a measurement apparatus that measures a position of the light irradiation apparatus relative to the object.

9. The processing apparatus according to claim 8, wherein the control apparatus controls the light irradiation apparatus by using the position measured by the measurement apparatus and the information relating to the shape of the surface of the object.

10. The processing apparatus according to claim 8, wherein
the measurement apparatus is a first measurement apparatus,
the processing apparatus further comprises a second measurement apparatus that measures the characteristic of the surface of the object, and
the control apparatus controls the light irradiation apparatus by using a measured result of the second measurement apparatus.

11. The processing apparatus according to claim 10, wherein
the second measurement apparatus includes a projection apparatus that irradiates the surface of the object with measurement light and a detection apparatus that detects an intensity of the measurement light through the surface of the object.

12. The processing apparatus according to claim 11, wherein
the projection apparatus emits the measurement light along a first direction that traverses the surface of the object, and
the detection apparatus detects the measurement light traveling along a second direction that traverses the surface of the object.

13. The processing apparatus according to claim 11, wherein
the measurement light includes a light component a wavelength of which is same as a wavelength of the processing light.

14. The processing apparatus according to claim 13, wherein
the second measurement apparatus measures a characteristic of a structure formed at the surface of the object by an irradiation of the processing light from the light irradiation apparatus.

15. The processing apparatus according to claim 1, wherein
the control apparatus changes a relative positional relationship between the object and an irradiation area based on the shape of the surface of the object.

16. The processing apparatus according to claim 15, wherein
the control apparatus determines the positional relationship based on the shape of the surface of the object, and changes the positional relationship based on the determined positional relationship.

17. The processing apparatus according to claim 15, wherein
the control apparatus changes the positional relationship so that the positional relationship is a predetermined relationship.

18. The processing apparatus according to claim 15, further comprising a position change apparatus that changes the positional relationship, wherein
the control apparatus controls the position change apparatus to change the positional relationship based on the shape of the surface of the object.

19. The processing apparatus according to claim 18, wherein
the position change apparatus changes the positional relationship by relatively moving the light irradiation apparatus relative to the object.

20. The processing apparatus according to claim 1, wherein
the control apparatus sets an irradiation state of the processing light.

21. The processing apparatus according to claim 1, wherein
the control apparatus sets a light concentration position of the processing light on the surface of the object.

22. The processing apparatus according to claim 1, wherein
the control apparatus performs a control so that the light irradiation apparatus changes the shape of the surface of the object based on a target shape.

23. The processing apparatus according to claim 1, wherein
the light irradiation apparatus performs an ablation of the surface of the object.

24. The processing apparatus according to claim 1, wherein
the light irradiation apparatus removes a part of the surface of the object.

25. The processing apparatus according to claim 1, further comprising a support member that supports the light irradiation apparatus.

26. The processing apparatus according to claim 25, wherein
the support member is fixed to the object in at least a part of a period during which the light irradiation apparatus changes the shape of the surface.

27. The processing apparatus according to claim 1, wherein
the processing light from the light irradiation apparatus vertically enters the surface of the object.

28. The processing apparatus according to claim 27, wherein
the light irradiation apparatus changes a condensing position of the processing light based on the shape of the surface of the object.

29. The processing apparatus according to claim 1, wherein
the light irradiation apparatus changes a condensing position of the processing light based on the shape of the surface of the object.

30. The processing apparatus according to claim 1, wherein
the object includes at least a part of an airframe of an airplane, and
the operational structural object is formed at a surface of the airframe for a flight of the airplane.

31. The processing apparatus according to claim 30, wherein
the operational structural object includes at least one of a first structural object relating to an antenna, a second structural object relating to a sensor and a third structural object relating to an inflow and an outflow of a fluid.

32. A processing apparatus comprising:
a light irradiation apparatus that irradiates a surface of an object with a processing light;
a measurement apparatus that measures a shape of the surface of the object; and
a control apparatus that sets an irradiation position of the processing light and sets, as a non-processing area at which an irradiation of the processing light is prohibited, an area at which an operational structural object exists on the surface of the object by using a measured result of the shape of the surface by the measurement apparatus, wherein
the set irradiation position is a position in a plane intersecting with an irradiation direction of the processing light, and
the set irradiation position is irradiated with the processing light.

33. The processing apparatus according to claim 32, wherein
the control apparatus sets, as the non-processing area, an area at which the operational structural object having a size that is equal to or larger than an allowable size exists on the surface of the object by using the measured result of the shape of the surface by the measurement apparatus.

34. The processing apparatus according to claim 33, wherein
the control apparatus sets, as the non-processing area, an area at which the operational structural object having a height that is equal to or larger than an allowable height exists on the surface of the object by using the measured result of the shape of the surface by the measurement apparatus.

35. The processing apparatus according to claim 33, wherein
the control apparatus sets, as the non-processing area, an area at which the operational structural object having a depth that is equal to or larger than an allowable depth exists on the surface of the object by using the measured result of the shape of the surface by the measurement apparatus.

36. The processing apparatus according to claim 33, wherein
the control apparatus sets an irradiation state of the processing light.

37. The processing apparatus according to claim 36, wherein
the control apparatus sets the irradiation state of the processing light so that the non-processing area is not irradiated with the processing light.

38. The processing apparatus according to claim 36, wherein
the irradiation state of the processing light includes a light concentration position of the processing light in a direction that intersects with the surface of the object.

39. The processing apparatus according to claim 38, wherein
the control apparatus sets the light concentration position of the processing light on the surface of the object.

40. The processing apparatus according to claim 38, wherein
the light irradiation apparatus emits the processing light through an optical system, and
the control apparatus sets the light concentration position of the processing light so that the surface of the object is located within a range of a depth of focus of the optical system.

41. The processing apparatus according to claim 38, wherein
the light irradiation apparatus irradiates the surface of the object with the processing light through an optical system, and
the irradiation state of the processing light includes a state of an image plane of the optical system.

42. The processing apparatus according to claim 41, wherein
the state of the image plane includes a size of the image plane, and
the control apparatus sets the size of the image plane to a predetermined size.

43. The processing apparatus according to claim 41, wherein
the state of the image plane includes a relative position of the image plane relative to the object, and
the control apparatus sets the relative position of the image plane relative to the object to a predetermined position.

44. The processing apparatus according to claim 41, wherein
the state of the image plane includes a shape of the image plane, and
the control apparatus sets the shape of the image plane to a predetermined shape.

45. The processing apparatus according to claim 41, wherein
the control apparatus sets the image plane so that at least a part of the image plane is curved or is inclined in accordance with the shape of the surface of the object.

46. The processing apparatus according to claim 32, wherein
the control apparatus sets, as the non-processing area, an area at which a structure exists that was formed by an irradiation of the processing light from the light irradiation apparatus.

47. The processing apparatus according to claim 32, further comprising a movement apparatus that moves the light irradiation apparatus, wherein
the control apparatus controls at least one of the movement apparatus and the light irradiation apparatus by using information relating to the measured result of the surface of the object.

48. The processing apparatus according to claim 32, wherein
the measurement apparatus measures a position of the light irradiation apparatus relative to the object.

49. The processing apparatus according to claim 48, wherein
the information relating to the measured result of the surface of the object relates to a position on the surface of the object.

50. The processing apparatus according to claim 49, wherein
the control apparatus controls the light irradiation apparatus by using the position measured by the measurement apparatus and the information relating to the measured result of the surface of the object.

51. The processing apparatus according to claim 32, wherein
the control apparatus sets, based on the shape of the surface of the object, an irradiation state of the processing light with which the surface is irradiated.

52. The processing apparatus according to claim 32, wherein
the measurement apparatus comprising a projection apparatus that irradiates the surface of the object with the measurement light and a detection apparatus that detects an intensity of the measurement light through the surface of the object.

53. The processing apparatus according to claim 32, wherein
the measurement apparatus irradiates the surface of the object with the measurement light to measure the reflectance or the absorptance of the object to the measurement light.

54. The processing apparatus according to claim 53, wherein
the measurement apparatus emits the measurement light having an intensity that is lower than the intensity of the processing light emitted by the light irradiation apparatus.

55. The processing apparatus according to claim 53, wherein
the measurement light irradiated by the measurement apparatus does not change a thickness of a part of the object.

56. The processing apparatus according to claim 47, wherein
the light irradiation apparatus forms, at the surface of the object, an irradiation area that is irradiated with the processing light, and
the control apparatus changes a relative positional relationship between the object and the irradiation area based on the shape of the surface of the object.

57. The processing apparatus according to claim 56, wherein
the control apparatus determines the positional relationship based on the shape of the surface of the object and changes the positional relationship based on the determined positional relationship.

58. The processing apparatus according to claim 47, wherein
the control apparatus changes the positional relationship so that the positional relationship is a predetermined relationship.

59. The processing apparatus according to claim 47, wherein
the control apparatus controls the movement apparatus to change the positional relationship based on the characteristic of the surface of the object.

60. The processing apparatus according to claim 59, wherein
the movement apparatus changes the positional relationship by relatively moving the light irradiation apparatus relative to the object.

61. The processing apparatus according to claim 32, wherein
the object includes at least a part of an airframe of an airplane, and
the operational structural object is formed at a surface of the airframe for a flight of the airplane.

62. The processing apparatus according to claim 61, wherein
the operational structural object includes at least one of a first structural object relating to an antenna, a second structural object relating to a sensor and a third structural object relating to an inflow and an outflow of a fluid.

63. The processing apparatus according to claim 32, wherein
the control apparatus sets, to the non-processing area, an area at which a structure formed by an irradiation of the processing light from the light irradiation apparatus exists.

64. The processing apparatus according to claim 32, wherein
the measurement apparatus measures a characteristic of a structure formed at the surface of the object by an irradiation of the processing light from the light irradiation apparatus.

65. The processing apparatus according to claim 64, wherein
the measurement apparatus comprises a projection apparatus that irradiates the surface of the object with the measurement light and a detection apparatus that detects an intensity of the measurement light through the surface of the object,
the projection apparatus emits the measurement light along a first direction that traverses the surface of the object, and
the detection apparatus detects the measurement light traveling along a second direction that traverses the surface of the object.

66. The processing apparatus according to claim 65, wherein
at least one of the first direction and the second direction is changeable.

67. The processing apparatus according to claim 32, further comprising a support member that supports the light irradiation apparatus.

68. The processing apparatus according to claim 67, wherein
the support member is fixed to the object in at least a part of a period during which the light irradiation apparatus changes the shape of the surface.

69. The processing apparatus according to claim 32, wherein
the processing light from the light irradiation apparatus vertically enters the surface of the object.

70. The processing apparatus according to claim 69, wherein
the light irradiation apparatus changes a condensing position of the processing light based on the shape of the surface of the object.

71. The processing apparatus according to claim 32, wherein
the light irradiation apparatus changes a condensing position of the processing light based on the shape of the surface of the object.

72. A manufacturing method of a movable body that moves in fluid, the method comprising:
irradiating a surface of an object that is part of the movable body with a processing light;
setting an irradiation position of the processing light and setting, as a non-processing area at which an irradiation of the processing light is prohibited, an area at which an operational structural object exists on the surface of the object by using an information relating to a shape of the surface of the object; and changing the shape of the surface of the object by irradiating the surface of the object with the processing light thereby forming a riblet structure, by which a frictional resistance of the surface of the object to a fluid is reduced, on the surface of the object, wherein the setting includes setting, as the irradiation position, a position in a plane intersecting with an irradiation direction of the processing light, and the forming the riblet structure includes irradiating the set irradiation position with the processing light.

73. The processing method according to claim 72, wherein
the movable body is an airplane and the object includes at least a part of an airframe of the airplane, and
the operational structural object is formed at a surface of the airframe for a flight of the airplane.

74. The processing method according to claim 73, wherein
the operational structural object includes at least one of a first structural object relating to an antenna, a second structural object relating to a sensor and a third structural object relating to an inflow and an outflow of a fluid.

75. A manufacturing method of a movable body that moves in fluid, the method comprising:
irradiating a surface of an object that is part of the movable body with a processing light from a light irradiation apparatus;
measuring a shape of the surface of the object;
setting an irradiation position of the processing light and setting, as a non-processing area at which an irradiation of the processing light is prohibited, an area at which an operational structural object exists on the surface of the object by using a measured result of the shape of the surface of the object; and
forming a riblet structure by which a frictional resistance of the surface of the object to a fluid is reduced by using information relating to the non-processing area, wherein
the setting includes setting, as the irradiation position, a position in a plane intersecting with an irradiation direction of the processing light, and
the forming the riblet structure includes irradiating the set irradiation position with the processing light.

76. The processing method according to claim 75, further comprising moving the light irradiation apparatus by using the measured result of the measuring.

77. The processing method according to claim 76, wherein
the movable body is an airplane and the object includes at least a part of an airframe of the airplane, and
the operational structural object is formed at a surface of the airframe for a flight of the airplane.

78. The processing method according to claim 77, wherein
the operational structural object includes at least one of a first structural object relating to an antenna, a second structural object relating to a sensor and a third structural object relating to an inflow and an outflow of a fluid.

* * * * *